(12) United States Patent
Verdine et al.

(10) Patent No.: US 11,377,476 B2
(45) Date of Patent: Jul. 5, 2022

(54) RAS INHIBITORY PEPTIDES AND USES THEREOF

(71) Applicant: President and Fellows of Harvard College, Cambridge, MA (US)

(72) Inventors: Gregory L. Verdine, Boston, MA (US); John Hanney McGee, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/696,027

(22) Filed: Nov. 26, 2019

(65) Prior Publication Data

US 2020/0239533 A1 Jul. 30, 2020

Related U.S. Application Data

(63) Continuation of application No. 15/312,958, filed as application No. PCT/US2015/031961 on May 21, 2015, now Pat. No. 10,533,039.

(60) Provisional application No. 62/001,587, filed on May 21, 2014.

(51) Int. Cl.

| | |
|---|---|
| *A61K 38/16* | (2006.01) |
| *A61K 38/22* | (2006.01) |
| *C07K 7/06* | (2006.01) |
| *C07K 7/08* | (2006.01) |
| *C07K 14/00* | (2006.01) |
| *C07K 14/575* | (2006.01) |
| *C07K 14/47* | (2006.01) |
| *C07K 14/82* | (2006.01) |
| *C12N 15/10* | (2006.01) |
| *A61K 38/00* | (2006.01) |

(52) U.S. Cl.
CPC .......... *C07K 14/4703* (2013.01); *A61K 38/16* (2013.01); *A61K 38/22* (2013.01); *C07K 7/06* (2013.01); *C07K 7/08* (2013.01); *C07K 14/00* (2013.01); *C07K 14/575* (2013.01); *C07K 14/82* (2013.01); *C12N 15/1037* (2013.01); *A61K 38/00* (2013.01)

(58) Field of Classification Search
CPC ........ A61K 38/08; A61K 38/10; A61K 38/16; A61K 38/1709; A61K 38/22; C07K 7/06; C07K 7/08; C07K 14/00; C07K 14/47; C07K 14/575

See application file for complete search history.

(56) References Cited

U.S. PATENT DOCUMENTS

| | | | |
|---|---|---|---|
| 4,270,537 A | 6/1981 | Romaine et al. | |
| 4,596,556 A | 6/1986 | Morrow et al. | |
| 4,730,006 A | 3/1988 | Bohme et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,120,859 A | 6/1992 | Webb | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,364,851 A | 11/1994 | Joran | |
| 5,383,851 A | 1/1995 | McKinnon, Jr. et al. | |
| 5,417,662 A | 5/1995 | Hjertman et al. | |
| 5,446,128 A | 8/1995 | Kahn | |
| 5,466,220 A | 11/1995 | Brenneman | |
| 5,480,381 A | 1/1996 | Weston | |

(Continued)

FOREIGN PATENT DOCUMENTS

| | | |
|---|---|---|
| WO | 1996/02642 A1 | 2/1996 |
| WO | 1996/20951 A1 | 7/1996 |

(Continued)

OTHER PUBLICATIONS

Andersson et al. CRS-peptides: unique defense peptides of mouse Paneth cells. Mucosal Immunology. Jul. 2012, vol. 5, No. 4, pp. 367-376. (Year: 2012).*
Hornef et al. Increased diversity of intestinal antimicrobial peptides by covalent dimer formation. Nature Immunology. Aug. 2004, vol. 5, No. 8, pp. 836-843. (Year: 2004).*
Scott et al., "Evidence of insulin-stimulated phosphorylation and activation of the mammalian target of rapamycin mediated by a protein kinase B signaling pathway," Proc Natl Acad Scui USA. 95(13):17772-7 (1998).
Smith et al., "Structural resolution of a tandem hormone-binding element in the insulin receptor and its implications for design of peptide agonists," Proc Natl Acad Sci USA. (107(15):16771-6 (2010).
Stafstrom et al., "Dormancy-associated gene expression in pea axillary buds. Cloning and expression of PsDRMI and PsDRM2," Planta. 205(4):1547-52 (1998).

(Continued)

*Primary Examiner* — Jeffrey E. Russel
(74) *Attorney, Agent, or Firm* — Hogan Lovells US LLP

(57) ABSTRACT

The present invention provides peptides comprising a sequence of $X_{-6}X_{-5}X_{-4}X_{-3}X_{-2}X_{-1}X_1PX_3X_4PX_6X_7PGX_{10}X_{11}AX_{13}X_{14}X_{15}X_{16}LX_{18}X_{19}X_{20}X_{21}X_{22}X_{23}LX_{25}X_{26}YLX_{29}X_{30}X_{31}X_{32}$ (SEQ ID NO: 13) wherein the amino acids $X_{-6}$, $X_{-5}$, $X_{-4}$, $X_{-3}$, $X_{-2}$, $X_{-1}$, $X_1$, $X_3$, $X_4$, $X_6$, $X_7$, $X_{10}$, $X_{11}$, $X_{13}$, $X_{14}$, $X_{15}$, $X_{16}$, $X_{18}$, $X_{19}$, $X_{20}$, $X_{21}$, $X_{22}$, $X_{25}$, $X_{26}$, $X_{29}$, $X_{30}$, $X_{31}$, and $X_{32}$ are as defined herein. The present invention further provides pharmaceutical compositions comprising the peptides and methods of using the peptides for treating proliferative diseases such as cancer which are associated with Ras. Also provided are methods of screening a library of peptide dimers using a peptide dimer display technology.

12 Claims, 48 Drawing Sheets

Specification includes a Sequence Listing.

(56) References Cited

U.S. PATENT DOCUMENTS

| | | | |
|---|---|---|---|
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,622,852 A | 7/1997 | Korsmeyer | |
| 5,649,912 A | 7/1997 | Peterson | |
| 5,663,316 A | 9/1997 | Xudong | |
| 5,704,911 A | 1/1998 | Parsons | |
| 5,708,136 A | 1/1998 | Burrell et al. | |
| 5,750,767 A | 5/1998 | Carpino et al. | |
| 5,811,515 A | 9/1998 | Grubbs et al. | |
| 5,824,483 A | 10/1998 | Houston et al. | |
| 5,834,209 A | 11/1998 | Korsmeyer | |
| 5,856,445 A | 1/1999 | Korsmeyer | |
| 5,874,529 A | 2/1999 | Gilon et al. | |
| 5,893,397 A | 4/1999 | Peterson et al. | |
| 5,922,863 A | 7/1999 | Grubbs et al. | |
| 5,955,593 A | 9/1999 | Korsmeyer | |
| 5,965,703 A | 10/1999 | Horne et al. | |
| 5,993,412 A | 11/1999 | Deily et al. | |
| 5,998,583 A | 12/1999 | Korsmeyer | |
| 6,051,554 A | 4/2000 | Hornik et al. | |
| 6,153,391 A | 11/2000 | Picksley et al. | |
| 6,184,344 B1 | 2/2001 | Kent et al. | |
| 6,271,198 B1 | 8/2001 | Braisted et al. | |
| 6,326,354 B1 | 12/2001 | Gross et al. | |
| 6,348,558 B1 | 2/2002 | Harris et al. | |
| 6,444,425 B1 | 9/2002 | Reed et al. | |
| 6,613,874 B1 | 2/2003 | Mazur et al. | |
| 6,610,657 B1 | 8/2003 | Goueli | |
| 6,703,382 B2 | 3/2004 | Wang et al. | |
| 6,713,280 B1 | 3/2004 | Huang et al. | |
| 6,849,428 B1 | 2/2005 | Evans et al. | |
| 6,875,594 B2 | 4/2005 | Muir et al. | |
| 6,936,428 B2 * | 8/2005 | Davis | C07K 14/43595 |
| | | | 435/7.1 |
| 7,064,193 B1 | 6/2006 | Cory et al. | |
| 7,083,983 B2 | 8/2006 | Lane et al. | |
| 7,084,244 B2 | 8/2006 | Gilon et al. | |
| 7,183,059 B2 | 2/2007 | Verdine et al. | |
| 7,192,713 B1 | 3/2007 | Verdine et al. | |
| 7,202,332 B2 | 4/2007 | Arora et al. | |
| 7,247,700 B2 | 7/2007 | Korsmeyer et al. | |
| 7,297,762 B2 * | 11/2007 | Shrader | C07K 14/00 |
| | | | 530/324 |
| 7,538,190 B2 | 5/2009 | Robinson et al. | |
| 7,705,118 B2 | 4/2010 | Arora et al. | |
| 7,723,469 B2 | 5/2010 | Walensky et al. | |
| 7,745,573 B2 | 6/2010 | Robinson et al. | |
| 7,786,072 B2 | 8/2010 | Verdine et al. | |
| 8,324,428 B2 | 12/2012 | Verdine et al. | |
| 8,592,377 B2 | 11/2013 | Verdine et al. | |
| 8,895,699 B2 | 11/2014 | Verdine et al. | |
| 8,957,026 B2 | 2/2015 | Verdine et al. | |
| 9,163,330 B2 | 10/2015 | Verdine et al. | |
| 9,458,189 B2 | 10/2016 | Verdine et al. | |
| 10,533,039 B2 * | 1/2020 | Verdine | A61K 38/22 |
| 2003/0109690 A1 * | 6/2003 | Ruben | A61P 35/00 |
| | | | 536/23.1 |
| 2004/0023887 A1 | 2/2004 | Pillutla et al. | |
| 2004/0038901 A1 | 2/2004 | Basler et al. | |
| 2004/0067503 A1 | 4/2004 | Tan et al. | |
| 2005/0250680 A1 | 11/2005 | Walensky et al. | |
| 2006/0008848 A1 | 1/2006 | Verdine et al. | |
| 2006/0014675 A1 | 1/2006 | Arora et al. | |
| 2006/0148715 A1 | 7/2006 | Tweardy | |
| 2006/0270003 A1 * | 11/2006 | Arnott | A61P 37/02 |
| | | | 435/69.52 |
| 2008/0220441 A1 | 9/2008 | Birnbaum et al. | |
| 2008/0262200 A1 | 10/2008 | Nash | |
| 2009/0047711 A1 | 2/2009 | Nash | |
| 2009/0088553 A1 | 4/2009 | Nash | |
| 2009/0092582 A1 * | 4/2009 | Bogin | A61P 5/00 |
| | | | 424/85.5 |
| 2009/0149630 A1 | 6/2009 | Walensky et al. | |
| 2009/0176964 A1 | 7/2009 | Walensky et al. | |
| 2009/0326192 A1 | 12/2009 | Nash et al. | |
| 2010/0029552 A1 | 2/2010 | Watt et al. | |
| 2010/0081611 A1 | 4/2010 | Bradner et al. | |
| 2010/0152103 A1 | 6/2010 | Phadke et al. | |
| 2010/0168388 A1 | 7/2010 | Bernal et al. | |
| 2010/0184628 A1 | 7/2010 | Nash | |
| 2010/0184645 A1 | 7/2010 | Verdine et al. | |
| 2010/0216688 A1 | 8/2010 | Nash et al. | |
| 2010/0298201 A1 | 11/2010 | Nash et al. | |
| 2011/0028753 A1 | 2/2011 | Verdine et al. | |
| 2011/0097376 A1 * | 4/2011 | Berlemann | A61L 27/52 |
| | | | 424/423 |
| 2011/0144303 A1 | 6/2011 | Nash et al. | |
| 2011/0144306 A1 | 6/2011 | Verdine et al. | |
| 2011/0223149 A1 | 9/2011 | Nash et al. | |
| 2011/0263815 A1 | 10/2011 | Nash | |
| 2011/0275559 A1 * | 11/2011 | Ostergaard | A61P 1/00 |
| | | | 514/5.2 |
| 2012/0046231 A1 * | 2/2012 | Palmer | A61K 38/38 |
| | | | 514/15.2 |
| 2012/0077272 A1 * | 3/2012 | Kharazi | A61L 27/3891 |
| | | | 435/395 |
| 2012/0082636 A1 | 7/2012 | Walensky et al. | |
| 2012/0172311 A1 | 7/2012 | Nash | |
| 2012/0190818 A1 | 7/2012 | Nash | |
| 2012/0270800 A1 | 10/2012 | Verdine et al. | |
| 2013/0005943 A1 | 1/2013 | Arora et al. | |
| 2013/0023646 A1 | 1/2013 | Nash et al. | |
| 2013/0177979 A1 | 7/2013 | Turkson | |
| 2013/0211046 A1 | 8/2013 | Verdine et al. | |
| 2014/0005118 A1 | 1/2014 | Verdine et al. | |
| 2014/0011979 A1 | 1/2014 | Verdine et al. | |
| 2014/0162339 A1 | 6/2014 | Verdine et al. | |
| 2014/0235549 A1 | 8/2014 | Moellering et al. | |
| 2014/0256912 A1 | 9/2014 | Moellering et al. | |
| 2014/0323701 A1 | 10/2014 | Nash et al. | |
| 2015/0225471 A1 | 8/2015 | Liang et al. | |
| 2015/0239937 A1 | 8/2015 | Verdine et al. | |
| 2015/0284437 A1 | 10/2015 | Verdine et al. | |
| 2015/0376227 A1 | 12/2015 | Verdine et al. | |
| 2016/0024153 A1 | 1/2016 | Verdine et al. | |
| 2018/0057565 A1 | 3/2018 | Liang et al. | |

FOREIGN PATENT DOCUMENTS

| | | |
|---|---|---|
| WO | 1996/34878 A1 | 11/1996 |
| WO | 1997/13537 A1 | 4/1997 |
| WO | 1997/26002 A1 | 7/1997 |
| WO | 1997/37705 A1 | 10/1997 |
| WO | 1999/14259 A1 | 3/1999 |
| WO | 1999/34833 A1 | 7/1999 |
| WO | 1999/34850 A1 | 7/1999 |
| WO | 1999/46367 A1 | 9/1999 |
| WO | 2000/06187 A2 | 2/2000 |
| WO | 2001/29247 A1 | 4/2001 |
| WO | 2002/064790 A2 | 8/2002 |
| WO | 2003/053996 A2 | 7/2003 |
| WO | 2003/106491 A2 | 12/2003 |
| WO | 2004/041275 A1 | 5/2004 |
| WO | 2004/058804 A1 | 7/2004 |
| WO | 2005/040202 A2 | 5/2005 |
| WO | 2005/044839 A2 | 5/2005 |
| WO | 2005/085457 A2 | 9/2005 |
| WO | 2005/090388 A1 | 9/2005 |
| WO | 2005/118620 A2 | 12/2005 |
| WO | 2005/118634 A2 | 12/2005 |
| WO | 2006/103666 A2 | 10/2006 |
| WO | 2007/013050 A1 | 2/2007 |
| WO | 2007/141533 A2 | 12/2007 |
| WO | 2008/061192 A2 | 5/2008 |
| WO | 2008/095063 A1 | 8/2008 |
| WO | 2008/121767 A2 | 10/2008 |
| WO | 2009/020477 A1 | 2/2009 |
| WO | 2009/042237 A2 | 4/2009 |

(56) References Cited

FOREIGN PATENT DOCUMENTS

| WO | 2009/046407 A2 | 4/2009 |
|---|---|---|
| WO | 2009/126292 A2 | 10/2009 |
| WO | 2010/011313 A2 | 1/2010 |
| WO | 2010/068684 A2 | 6/2010 |
| WO | 2010/121288 A1 | 10/2010 |
| WO | 2011/008260 A2 | 1/2011 |
| WO | 2011/146974 A1 | 12/2011 |
| WO | 2012/040459 A2 | 3/2012 |
| WO | 2012/065181 A2 | 5/2012 |
| WO | 2012/174423 A1 | 12/2012 |
| WO | 2014/047673 A1 | 4/2014 |
| WO | 2014/052647 A2 | 4/2014 |
| WO | 2014/055564 A1 | 4/2014 |
| WO | 2014/110420 A1 | 7/2014 |
| WO | 2010/034029 A1 | 3/2020 |

OTHER PUBLICATIONS

Supplementary Information for Menting et al., "How insulin engages its primary binding site on the insulin receptor," Nature. 493(7431):1241-5 (2013 (18 pages).
Surinya et al., "role of insulin receptor dimerization domains in ligand binding, cooperativity, and modulation by anti-receptor antibodies." J Biol Chem. 288(19):116718-25 (2002).
Tanaka, "Design and synthesis of non-proteinogenic amino acids and secondary structures of their peptides,", Yakugaku Zasshi, 126(10):1931-44 (2006). Japanese.
Toniolo, "Conformationally restricted peptides through short-range cyclizations," Int J Pept Protein Res. 335(4):298-300 (1990).
Tsuruzoe et al., "Insulin receptor substiate 3 (IRS-3) and IRS-4 impair IRS-1 and IRS-2-mediated signaling," Mol Cell Biol. 21(1):126-39 (2001).
Ueki et al., "Increased insulin sensitivity in mice lacking p85beta subunit of phosphoinositide 3-kinase," Proc Natl Acad Sci USA. 99(1):1419-24 (2002).
Williams et al., "Asymmetric Synthesis of Monosubstituted and alpha, alpha-Disubstituted alpha Amino Acids via Diastereoselective Glycine Enolate Alkylations," J Am Chem Soc. 113:19276-86 (1991).
Zhang et al., "A cell-penetrating helical peptide as a potential HIV-1 inhibitor," J Mol Biol. 378(3):1565-80 (2008).
International Preliminary Report on Patentability for International Patent Application No. PCT/US2015/031961, dated Nov. 22, 2016 (pages).
Hilpert et al., "Peptide arrays on cellulose support; SPOT synthesis, a time and cost efficient method for synthesis of large numbers of peptides in a parallel and addressable fashion," Nat Protoc. 2(6):11333-49 (2007).
International Preliminary Report on Patentability for PCT/US2015/031961, dated Dec. 1, 2016 (9 pages).
Becker et al., "Three-dimensional structure of the Stat3beta homodimer bound to DNA," Nature 394(6689):1145-51 (1998).
NCBI Blast for ID P40763. Dated Feb. 1, 1995 (39 pages).
Zhao et al., "A cell permeable Stat3 SH2 domain mimetic inhibits Stat3 SH2 domain mimetic inhibits Stat3 activation and induces antitumor cell effects in vitro," J Biol Chem. 285(46):135855-65 (2010).
Robinson, "Beta-hairpin peptidomimetics: design, structures and biological activities," Acc Chem Res. 41(10):11278-88 (2008).
Oh et al., "A convergent synthesis of new beta-turn mimics by click chemistry," Chem Commun (Camb). (29):13069-71 (2006).
Holland-Nell et al., "Maintaining biological activity by using triazoles as disulfide bond mimetics," Angew Chem Int Ed Engl. 50(22):15204-6 (2011).
Fujimoto et al., "Development of a series of cross-linking agents that effectively stabilize alpha-helical structures in various short peptides," Chemistry, 14(3):1857-63 (2008).
Anderson, "The process of structure-based drug design," Chem Biol. 10(9):1787-97 (2003).

Supplementary Partial European Search Report for European Application No. 15796407.3, dated Oct. 19, 2017 (17 pages).
Isidro-Liobet et al., "Amino acid-protecting groups," Chem Rev. 109(6):12455-2504 (2009).
McKay et al., The complete primary structure of pancreatic polypeptide from the European common frog *Rana temporaria*, Regulatory Peptides, 1990, vol. 31, pp. 187-198. (year: 1990).
Andrews et al., "Forming Stable Helical Peptides Using Natural and Artificial Amino Acids," Tetrahedron, 55:11711-43 (1999).
Biagini et al., "Cross-metathesis of Unsaturated alpha-amino Acid Derivatives," J Chem Soc Perkin Trans. 1:2485-99 (1998).
Bierzynski et al., "A salt bridge stabilizes the helix formed by isolated C-peptide of Rnase A," Proc Natl Acad Sci USA. 79(8):2470-4 (1982).
Blackwell et al., Highly Efficient Synthesis of Covalently Cross-Linked Peptide Helices by Ring Closing Metathesis, Angew Chem Int Ed. 37(23):3281-84 (1998).
Blackwell et al., "Ring-closing metathesis of olefinic peptides: design, synthesis, and structural characterization of macrocyclic helical peptides," J Org Chem. 66 (16):5291-302 (2001).
Blundell et al., "Atomic positions in rhombohedral 2-zincv insulin crystals," Nature, 231 (5304):506-11 (1971).
Bode et al., "Chemoselective amide ligations by decarboxylative condensations of N-alkylhydroxylamines and alpha-ketoacids," Angew Chem Int Ed Engl. 45(8):1248-52 (2006).
Brandt et al., "Dimeric fragment of the insulin receptor alpha-subunit binds insulin with full holoreceptor affinity." J. Biol Chem. 276(15): 12378-84 (2001).
Chang et al., "Insulin signaling and the regulation of glucose transport," Mol Med. 10(7-12):65-71 (2004).
Chen et al., "Determination of the helix and beta form of proteins in aqueous solution by circular dichroism," Biochemistry. 13 (16):3350-9 (1974).
Clark et al., "Supramolecular Design by Covalent Capture, Design of a Peptide Cylinder via Hydrogen-Bond-Promoted Intermolecular Olefin Metathesis," J Am Chem Soc. 117(49):12364-65 (1995).
Cox et al., "Insulin receptor expression by human prostate cancers," Prostate, 69(1):33-40 (2009).
De Meyts et al., "Insulin interactions with its receptors: experimental evidence for negative cooperativity," Biochem Biophys Res Commun. 55(1):154-61(1973).
De Meytis et al., "The structural basis of Insulin and Insulin-like growth factor-1 receptor binding and negative co-operativity, and its relevance to mitogenic versus metabolic signaling," Diabetologia. 37(Suppl 2):S135-48 (1994).
Duronio, "Insulin receptor is phosphorylated in response to treatment of HepG2 cells with insulin-like growth factor I," Biochem J. 270(1):27-32 (1990).
Ellis et al., "Design, Synthesis, and evaluation of a new generation of modular nucleophilic glycine equivalents for the efficient synthesis of sterically constrained alpha-amino acids," J Org Chem. 71 (22):8572-8 (2006).
Evans et al., "The Rise of Azide-Alkyne 1,3-Dipolar 'Click' Cycloaddition and its Application to Polymer Science and Surface Modification," Aust J Chem. 60:384-95 (2007).
Furstner et al., Alkyne Metathesis: Development of a Novel Molybdenum-Based Catalyst System and its Application to the Total Synthesis of Epothilone A and C,: Chem Euro J. 7(24):5299-5317 (2001).
Furstero et al., "Asymmetric synthesis of new beta,beta-difluorinated cyclic quaternary alpha-amino acid derivatves," Org Lett. 8(18):4129-32 (2006).
Giannis et al., "Peptidomimetrics for Recepor Ligands-Discovery, Development, and Medical Perspectives," Angew Chem In Ed Engl. 32:1244-67 (1993).
Greenfield et al., "Computed circular dichroism spectra for the evaluation of protein conformation," Biochemistry, 8 (10):4108-16 (1969).
Greenlee et al., "A General Synthesis of alpha-vinyl-alpha-amino acids," Tetrahedron Letters. 42:3999-4002 (1978).
Guo et al., "Probing the alpha-helical structural stability of stapled p53 peptides: molecular dynamics simulations and analysis," Chem Biol Drug Des. 75(4):348-59 (2010).

(56) References Cited

OTHER PUBLICATIONS

Huang et al., "How insulin binds; the B-chain alpha-helix contacts the L1 beta-helix of the insulin receptor," J Mol Biol. 341(2):529-50 (2004).
Jackson et al., "General Approach to the Synthesis of Short alpha-Helical Peptides," J Am Chem Soc. 113:9391-92 (1991).
Jensen, et al., "Activation of the insulin receptor (IR) by insulin and a synthetic peptide has different effects on gene expression in IR-transfected L6 myoblasts," Biochem J. 412(3);435-45 (2008).
Karle et al., "Structural characteristics of alpha-helical peptide molecules containing Alb residues," Biochemistry, 29 (29):6747-56 (1990).
Kaul et al., "Stereochemical control of peptide folding," Bioorg Med Chem. 7(1):105-17(1999).
Kazmaier, Synthesis of Quaternary Amino Acids Containing beta,gamma—as well as gamma,delta-Unsaturated Side Chains via Chelate-Enolate Claisen Rearrangement,: Tetrahedron Letters, 37(30):535:1-4 (1996).
Khalil et al., "An efficient and high yield method for the N-tert-butoxycarbonyl protection of sterically hindered amino acids," Tetrahedron Lett. 37(20):3441-44 (1996).
Kim et al., "Iutroduction of all-hydrocarbon i,i+3 staples into alpha-helices via ring-closing olefin metathesis," Org Lett. 12(13):3046-9 (2010).
Kim et al., "Stereochemical effects of all hydrocarbon tethers in i,i+4 stapled peptides," Bioorg Med Chem Lett. 19 (9):2533-6 (2009).
Kim et al., "Synthesis of all-hydrocarbon stapled alpha-helical peptides by ring-closing olefin metathesis," Nat Protoc. 6 (6):761-71 (2011).
Leduc et al., "Helix-stabilized cyclic peptides as selective inhibitors of steroid receptor-coactivator interactions," Proc Natl Acad Sci USA. 100(20):11273-78 (2003).
Liskamp, "Conformationally restricted amino acids and dipeptides, (non)peptidomimetics and secondary structure mimetics," Reel Travl Chim Pays-Bas. 113:1-19 (1994).
Lou et al., "The first three domains of the insulin receptor differ structurally from the insulin-like growth factor 1 receptor in the regions governing ligand specificity," Proc Natl Acad Sci USA. 103(33):12429-34 (2006).
McKern et al., "Structure of the insulin receptor ectodomain reveals a folded-over conformation," Nature. 443 (7108):218-21 (2006).
McNamana et al., "Peptides constrained by an aliphatic linkage between two C(alpha) sites: design, synthesis and unexpected conformational properties of an i,(i+4)-linked pepdide," J Org Chem. 66(13):4585-94 (2001).
Mellegaard-Waetzig et al., "Allylic amination via decarboxylative c—n bond formation," Synlett. 18:2759-62 (2005).
Menting et al., "A thermodynamic study of ligand binding to the first three domains of the human insulin receptor relationship between the receptor alpha-chain C0terminal peptide and the sitel insulin mimetic peptides," Biochemistry, 48(23):5492-500 (2009).
Menting et al., How insulin engages its primary binding site on the insulin receptor,: Nature. 493(7431):241-5 (2013).
Miller et al., "Application of Ring-Closing Metathesis to the Synthesis of Ridgidified Amino Acids and Peptides," J Am Chem Soc. 118(40):9606-9614 (1996).
Miller et al., "Synthesis of Conformationally Restricted Amino Acids and Peptides Employing Olefin Metathesis," J Am Chem Soc. 117(21);5855-5856 (1995).
Roos et al., "Synthesis of alpha-Substituted alpha-Amino Acids via Cationic Intermediates," J Org Chem. 58:3259-68 (1993).
Sali et al., "Stabilization of protein structure by interaction of alpha-helix dipole with a charged side chain," Nature. 335 (6192):840-3 (1988).
Schaffer et al., A novel high-affinity peptide antagonist to the insulin receptor,: Biochem Biophys Res Commun. 376 (2):380-3(2008).
Schafmeister et al., "An All-Hydrocarbon Cross-Linking System for Enhancing eh Helicty and Metabolic Stability of Peptides," J Am Chem Soc. 122:5859-92 (2000).
Schmiedeberg et al., "Reversible backbone protection enables combinatorial solid-phase ring closing metathesis reaction (RCM) in peptides," Org Lett. 4(1):59-62(2002).
Scholtz et al., "The mechanism of alpha-helix formation by peptides," Annu Rev Biophys Biomol Struct. 21:95-118 (1992).
Hodges et al., "Engineering a Monomeric Miniature Protein", J. Am. Chem. Soc. (2007) 129(36):11024-11025.

* cited by examiner

Flow Cytometry

| Library | Sequence |
|---|---|
| aPP | GPSQPTYPGDDAPVEDLIRFYNDLQQYLNVVA |
| aPP-M | GPRRPRYPGDDAPVEDLIRFYNDLQQYLNVVA |
| aPP Library | GPRRPRYPGDDAPVXDLXXFXAXLXXYLXVVA |

| | |
|---|---|
| aPP Library | GPRRPRYPGDDAPV<u>X</u>DL<u>XX</u>F<u>X</u>A<u>X</u>L<u>XX</u>YL<u>X</u>VVA |

*screening at 1 μM, then 1.8 μM, then 500 nM KRas:*

| | |
|---|---|
| 221-1 | GPRRPRYPGDDAPV<u>E</u>DL<u>HA</u>F<u>W</u>A<u>A</u>L<u>WN</u>YL<u>Y</u>VVA |
| 221-2 | GPRRPRYPGDDAPV<u>G</u>DL<u>HE</u>F<u>W</u>A<u>Q</u>L<u>WN</u>YL<u>Y</u>VVA |
| 221-3 | GPRRP<u>K</u>YPGDDAPV<u>E</u>DL<u>HW</u>F<u>W</u>A<u>A</u>L<u>WN</u>YL<u>Y</u>VVA |

*error-prone PCR; screening at 100 nM, then 50 nM KRas:*

| | |
|---|---|
| 223-1 | GPRRPRYPGDDA*S*VEDL*HEF*W*A*RL*WN*YL*Y*AVA |
| 223-2 | GPRRPRYPGDDA*SI*EDL*HAF*W*A*AL*WN*YL*Y*AVA |

*error-prone PCR; screening at 25 nM KRas:*

| | |
|---|---|
| 224-1 | GPRRPR<u>C</u>PGDDA*SV*EDL*HEY*W*A*RL*WN*YL*Y*AVA |
| 224-2 | GPRRPR<u>C</u>PGDDA*SI*EDL*HEF*W*A*RL*WN*YL*Y*AVA |
| 224-3 | GPRRPR<u>C</u>PGDDA*SV*EDL*HEF*W*A*RL*WN*YL*Y*AVA |
| 224-4 | G<u>PRR</u>PRRPRYPGDDA*SI*EDL*HAF*W*A*AL*WN*YL*Y*AVA |

*error-prone PCR of shuffled (Y7) template; screening at 100 nM KRas:*

| | |
|---|---|
| 225-1 | GPRRPRYPGDDA*SI*EDL*HEY*W*A*RL*WN*YL*Y*AVA |
| 225-5 | GPRRPRYPGDDA*SI*EDL*HAY*W*A*RL*WN*YL*Y*AVA |
| 225-6 | GPRRPRYPGDDA*SI*EDL*HEY*W*A*RL*WN*YL*<u>P</u>VA |

*error-prone PCR; screening at 100 nM, then 50 nM, then 20 nM KRas:*

| | | |
|---|---|---|
| 226-1 | | GPRRPRYPGDDA*SV*EDL*HEY*W*A*RL*WN*YL*Y*AVA |
| 226-2 | (225-1) | GPRRPRYPGDDA*SI*EDL*HEY*W*A*RL*WN*YL*Y*AVA |
| 226-3 | | GPRRPR*C*PGDDA*SI*EDL*HEY*W*A*RL*WN*YL*Y*AVA |
| 226-4 | (224-1) | GPRRPR*C*PGDDA*SV*EDL*HEY*W*A*RL*WN*YL*Y*AVA |
| 226-5 | | GPRRPR*C*PGDDA*ST*EDL*HAY*W*A*RL*WN*YL*Y*AVA |
| 226-6 | | GPRRPR*C*PGDDA*SV*EDL*HAY*W*A*<u>K</u>L*WN*YL*Y*AVA |
| 226-7 | | GPRRPR*C*PGDDA*ST*EDL*HAY*W*A*<u>K</u>L*WN*YL*Y*AVA |

Fig. 10

| Peptide | Sequence |
| --- | --- |
| 225-1 | GCGGPRRPRYPGDDASIEDLHEYWARLWNYLYAVA |
| 225-1 N26A | GCGGPRRPRYPGDDASIEDLHEYWARLWAYLYAVA |
| 225-3 | GCGGPRRPRRPRYPGDDASIEDLHEYWARLWNYLYAVA |
| 225-3 R3A | GCGGPRRPARPRYPGDDASIEDLHEYWARLWNYLYAVA |
| 225-3 R6A | GCGGPRRPRRPAYPGDDASIEDLHEYWARLWNYLYAVA |
| 225-3 D11A | GCGGPRRPRRPRYPGDAASIEDLHEYWARLWNYLYAVA |
| 225-3 I14A | GCGGPRRPRRPRYPGDDASAEDLHEYWARLWNYLYAVA |
| 225-3 H18A | GCGGPRRPRRPRYPGDDASIEDLAEYWARLWNYLYAVA |
| 225-3 W21A | GCGGPRRPRRPRYPGDDASIEDLHEYAARLWNYLYAVA |
| 225-3 W25A | GCGGPRRPRRPRYPGDDASIEDLHEYWARLANYLYAVA |
| 225-3 N26A | GCGGPRRPRRPRYPGDDASIEDLHEYWARLWAYLYAVA |
| 225-3 Y29A | GCGGPRRPRRPRYPGDDASIEDLHEYWARLWNYLAAVA |

Fig. 11

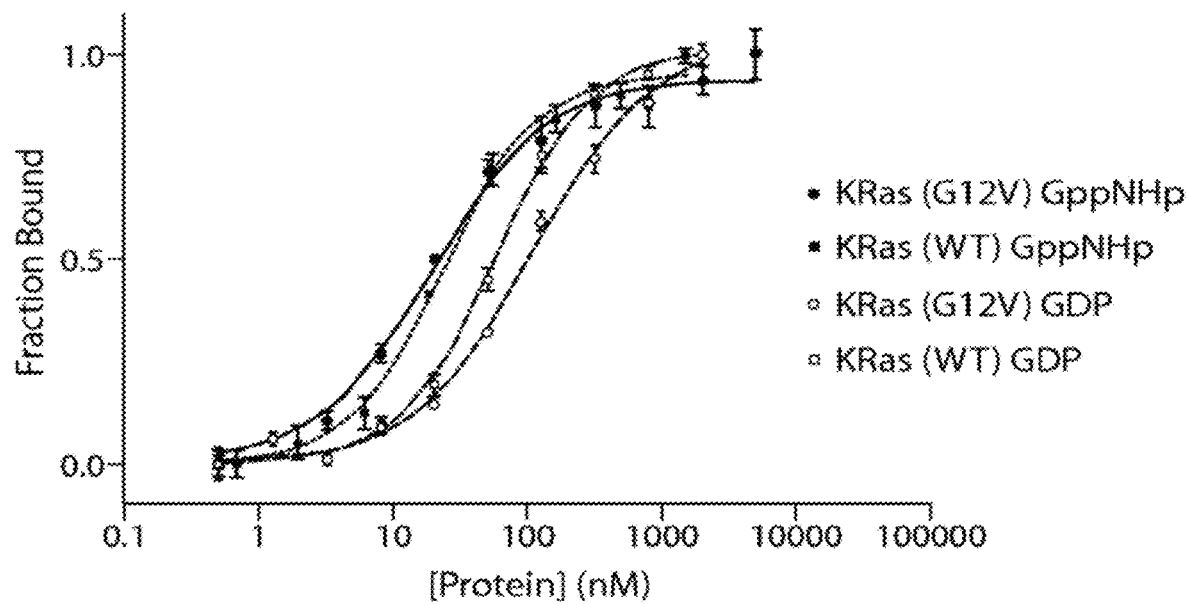
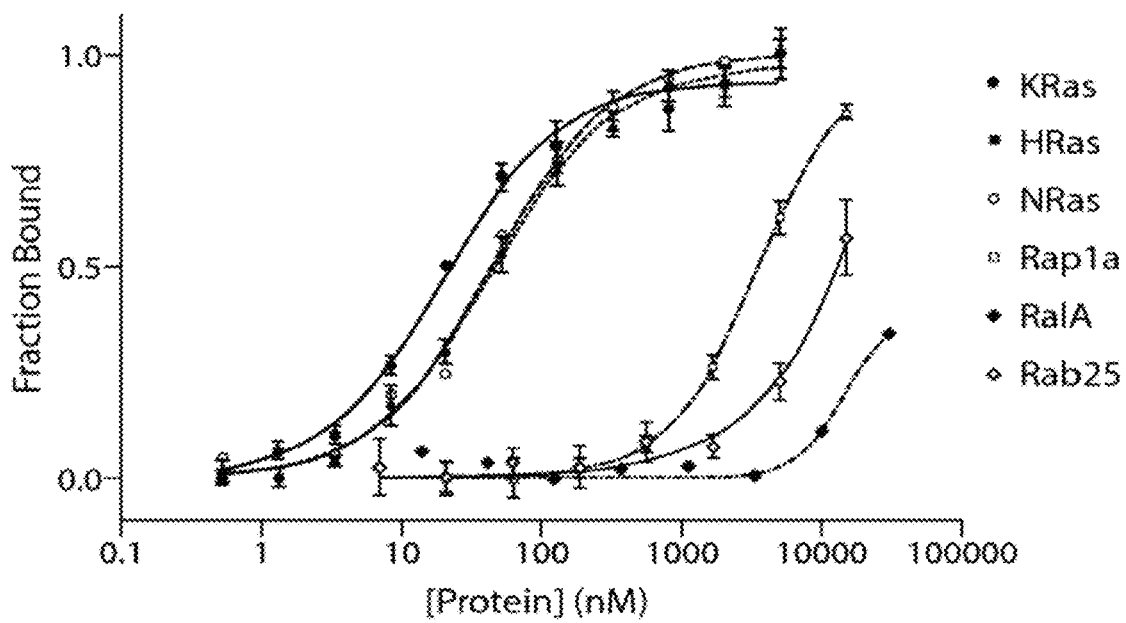
Fig. 14

| Protein | Kd (nM) | Hill coefficient |
|---|---|---|
| KRas (G12V) GppNHp | 20 | 1.0 |
| KRas (WT) GppNHp | 24 | 1.2 |
| KRas (G12V) GDP | 110 | 1.0 |
| KRas (WT) GDP | 38 | 1.0 |
| HRas (G12V) GppNHp | 45 | 1.0 |
| NRas (G12V) GppNHp | 45 | 1.0 |
| Rap1a (G12V) GppNHp | 3500 | 1.4 |
| RalA (WT) GppNHp | >5000 | n/a |
| Rab25 (WT) GppNHp | >5000 | n/a |

Fig. 14 (continued)

Fig. 20A
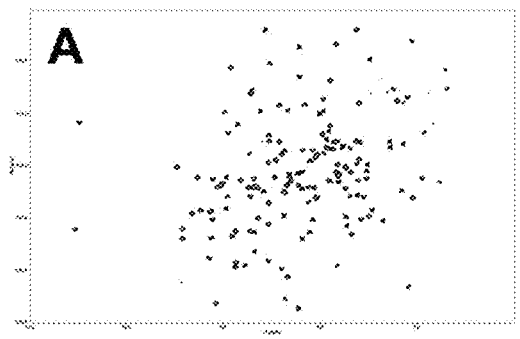
Fig. 20B
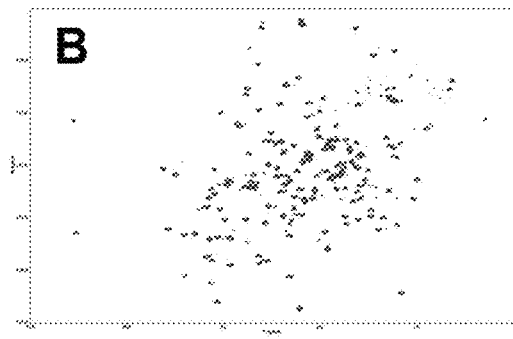
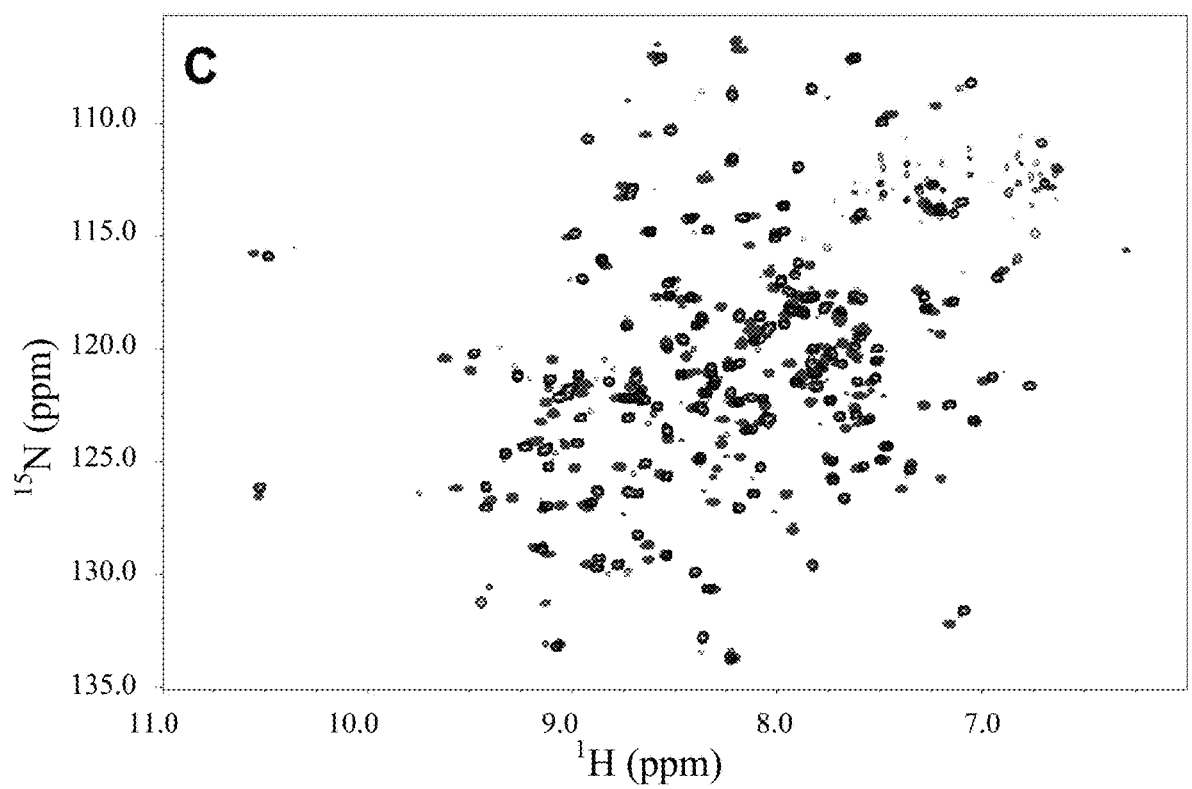
Fig. 20C

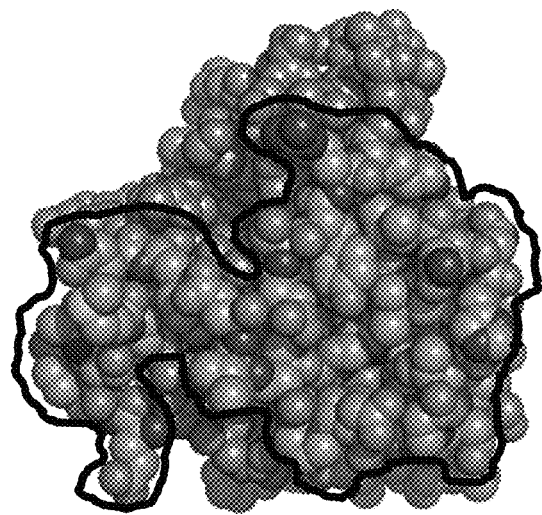 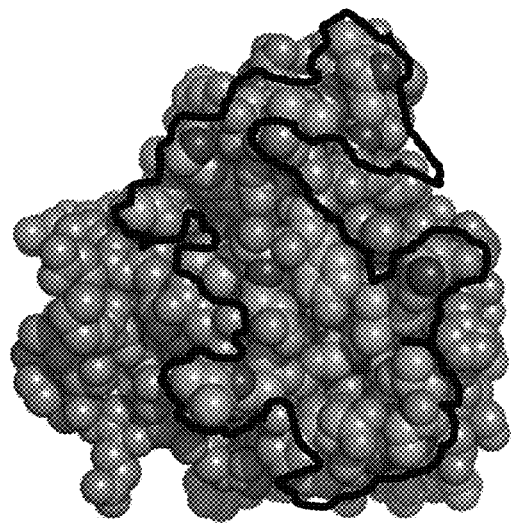
Ras effector domain  225-1 NMR footprint
Fig. 21

Fig. 22A
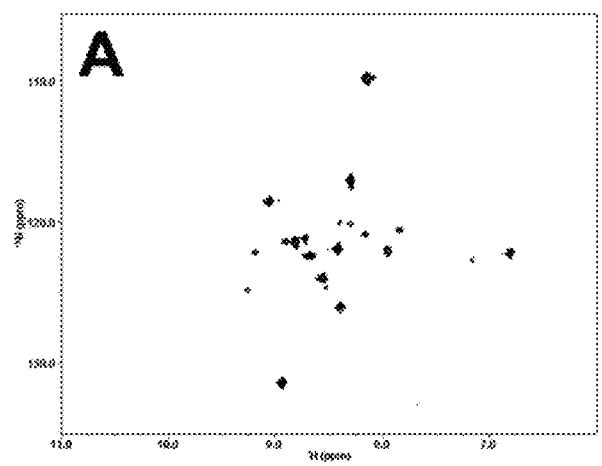
Fig. 22B
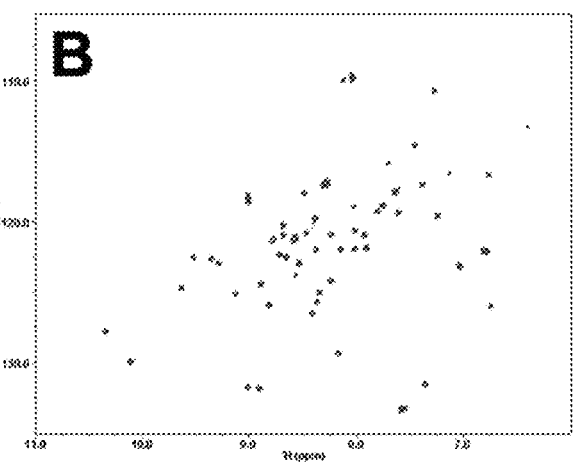
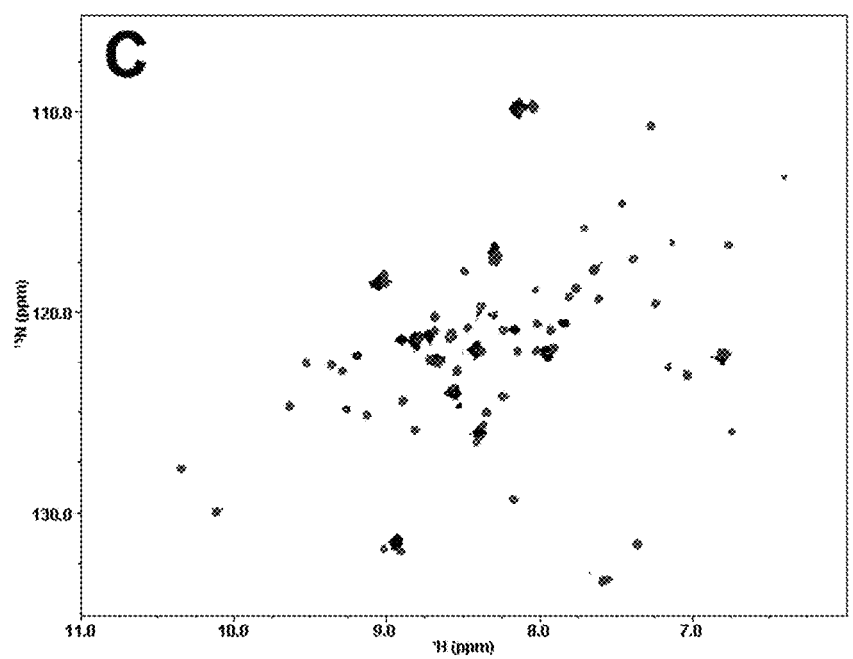
Fig. 22C 225-1  GPRRPRYPGDDASIEDLHEYWARLWNYLYAVA
       XXRRPRYPGDDASIEDLHEYWARLWNYLYAVA
       GXXRPRYPGDDASIEDLHEYWARLWNYLYAVA
       GPXXPRYPGDDASIEDLHEYWARLWNYLYAVA
       GPRXXRYPGDDASIEDLHEYWARLWNYLYAVA
       ...
       GPRRPRYPGDDASIEDLHEYWARLWNYLYAXX

Fig. 25

225 helices　　　IEDLHEYWARLWNYLYA　　EDLHEYWARLWNYLYAV
library　　　...CG$_{1-2}$IED<u>A</u>HE<u>A</u>WARLWNXLYAX$_{4-6}$EDXHE<u>A</u>WARLWN<u>A</u>LYAVG$_{1-2}$C

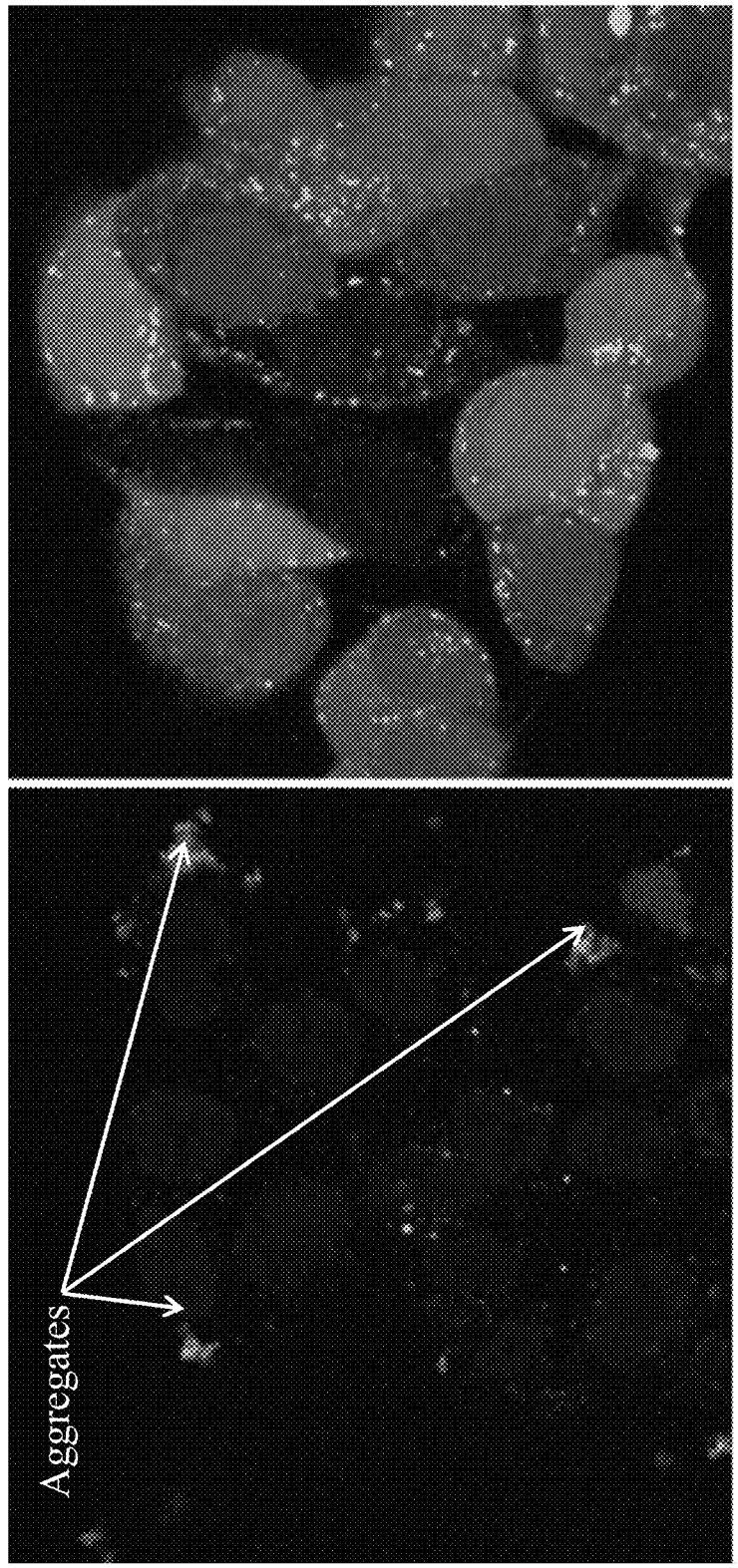

RAS INHIBITORY PEPTIDES AND USES THEREOF

RELATED APPLICATIONS

This application is a Continuation of U.S. patent application Ser. No. 15/312,958, filed Nov. 21, 2016, which is a U.S. National Stage of PCT/US2015/031961, filed May 21, 2015, which claims the benefit of U.S. Provisional Application No. 62/001,587, filed May 21, 2014. The entire teachings of the above applications are incorporated herein by reference.

GOVERNMENT SUPPORT

This invention was made with government support under [T32] GM007598 awarded by the National Institutes of Health [NIH]. The government has certain rights in the invention.

REFERENCE TO A SEQUENCE LISTING

This application contains a Sequence Listing in computer readable form. The computer readable form is incorporated herein by reference. Said ASCII copy, created on Sep. 20, 2021, is named 085298_000131_SL.txt and is 66,277 bytes in size.

BACKGROUND OF THE INVENTION

Conventional therapeutics can be broadly divided into two classes: small molecules and biologics. Small molecules typically have a mass of <1000 Da and bind with high affinity to hydrophobic pockets in proteins, and many are capable of penetrating cells. Biologics are biomolecules, usually proteins (such as antibodies or hormones) that can bind the surfaces of other biomolecules with high affinity and specificity, but are unable to efficiently enter cells. It has been estimated that only ~12% of human proteins contain a hydrophobic pocket capable of binding small molecules with high affinity, and that less than 10% of human proteins are secreted (i.e., transported outside of the cell). As these two groups are not mutually exclusive, more than 78% of human proteins are therefore inside the cell but lack a hydrophobic binding pocket. These proteins, along with others that are intracellular and contain intractable hydrophobic pockets, are often referred to as "undruggable." Therefore, there remains a need for the development and characterization of molecules that inhibit the interactions of protein targets.

SUMMARY OF THE INVENTION

While advances have been made in understanding the molecular causes of human disease, the ability to exploit these discoveries for therapeutic benefit is frequently limited by the inability to make drugs that target the processes responsible. Many diseases can be linked to the aberrant activity of proteins, and while the development of inhibitors for enzymes and extracellular targets is often feasible, these proteins account for only a small fraction of all the proteins in cells. The remaining proteins are, in most cases, considered therapeutically intractable and are sometimes referred to as "undruggable." The current invention solves the problem by providing peptides as described herein to inhibit the interactions of protein targets and for applications in methods and systems for screening peptide libraries for inhibiting the interactions of protein targets.

Many proteins, particularly in higher organisms, carry out their activity in part through interactions with other proteins and biomolecules. The ability to specifically disrupt these interactions could have great therapeutic benefit, as it may provide a means of targeting otherwise intractable processes. Therefore, there is a need for the development and characterization of molecules that inhibit the interactions of protein targets, such as Ras, which is linked to both the initiation and progression of a wide array of human cancers. Other protein targets include, but are not limited to, the Myc/Max heterodimer, RalA protein, Beta catenin, YAP/TEAD, and NEMO/IκB kinase. Through high-throughput screening, coupled with directed evolution and rational peptide design using crystal structures, small proteins (sometimes referred to as miniproteins) that bind various protein targets, including Ras, Myc/Max, RalA, Beta catenin, YAP/TEAD, and NEMO/IκB kinase, and block their ability to engage the effector proteins necessary for its oncogenic activity have been identified. The peptides described herein are useful for the treatment of proliferative diseases such as cancer and other diseases such as rasopathies.

The peptides provided herein are based on mutants of the pancreatic polypeptide family. In one aspect, provided herein are peptides comprising a sequence: $X_1PX_3X_4PX_6X_7PGDX_{11}AX_{13}X_{14}X_{15}DLX_{18}X_{19}YX_{21}X_{22}RLX_{25}X_{26}YLX_{29}X_{30}VA$ (SEQ ID NO: 96), wherein the amino acids $X_1$, $X_3$, $X_4$, $X_6$, $X_7$, $X_{11}$, $X_{13}$, $X_{14}$, $X_{15}$, $X_{18}$, $X_{19}$, $X_{21}$, $X_{22}$, $X_{25}$, $X_{26}$, $X_{29}$, and $X_{30}$ are as defined herein, and peptides at least 93% identical to SEQ ID NO: 1 or 96.

In another aspect, provided herein are peptide dimers comprising a first peptide associated with a second peptide, wherein the first and second peptides each independently comprise a peptide of SEQ ID NO: 1 or 96. The peptide dimers comprise peptide monomers which dimerize in a head-to-tail arrangement. The peptide dimers can be homodimers or heterodimers.

In one aspect, provided herein are peptides comprising a sequence: $X_1PX_3X_4PX_6X_7PGX_{10}X_{11}AX_{13}X_{14}X_{15}DLX_{18}X_{19}X_{20}X_{21}X_{22}X_{23}LX_{25}X_{26}YLX_{29}X_{30}VA$ (SEQ ID NO: 12), wherein the amino acids $X_1$, $X_3$, $X_4$, $X_6$, $X_7$, $X_{10}$, $X_{11}$, $X_{13}$, $X_{14}$, $X_{15}$, $X_{18}$, $X_{19}$, $X_{20}$, $X_{21}$, $X_{22}$, $X_{23}$, $X_{25}$, $X_{26}$, $X_{29}$, and $X_{30}$ are as defined herein, and peptides at least 93% identical to SEQ ID NO: 12.

In another aspect, provided herein are peptide dimers comprising a first peptide associated with a second peptide, wherein the first and second peptides each independently comprise a peptide of SEQ ID NO: 12. The peptide dimers comprise peptide monomers which dimerize in a head-to-tail arrangement. The peptide dimers can be homodimers or heterodimers.

In one aspect, provided herein are peptides comprising a sequence: $X_{-6}X_{-5}X_{-4}X_{-3}X_{-2}X_{-1}X_1PX_3X_4PX_6X_7PGX_{10}X_{11}A X_{13}X_{14}X_{15}X_{16}LX_{18}X_{19}X_{20}X_{21}X_{22}X_{23}LX_{25}X_{26}YLX_{29}X_{30} X_{31}X_{32}$ (SEQ ID NO: 13), wherein the amino acids $X_{-6}$, $X_{-5}$, $X_{-4}$, $X_{-3}$, $X_{-2}$, $X_{-1}$, $X_1$, $X_3$, $X_4$, $X_6$, $X_7$, $X_{10}$, $X_{11}$, $X_{13}$, $X_{14}$, $X_{15}$, $X_{16}$, $X_{18}$, $X_{19}$, $X_{20}$, $X_{21}$, $X_{22}$, $X_{25}$, $X_{26}$, $X_{29}$, $X_{30}$, $X_{31}$, and $X_{32}$ are as defined herein, and peptides at least 93% identical to SEQ ID NO: 13. In some embodiments, if $X_{-6}$ is present, then $X_{-6}$ is Gly and $X_{-5}$ to $X_1$ are present; if $X_{-5}$ is present, then $X_{-5}$ is Cys or Sec and $X_{-4}$ to $X_1$ are present; if $X_{-4}$ is present, then $X_{-4}$ is Gly and $X_{-3}$ to $X_1$ are present; if $X_{-3}$ is present, then $X_{-3}$ is Gly and $X_{-2}$ to $X_1$ are present;

if $X_{-2}$ is present, then $X_{-2}$ is Pro, Cys, Sec, or Gly and $X_{-1}$ and $X_1$ are present; if $X_{-1}$ is present, then $X_{-1}$ is Arg or Gly and $X_1$ is present; and if $X_1$ is present, $X_1$ is Gly, Arg, or an amino acid capable of cross-linking the peptide with another peptide (SEQ ID NO: 97). In other embodiments, $X_{-6}$ to $X_1$ are not present (SEQ ID NO: 98).

In another aspect, provided herein are peptide dimers comprising a first peptide associated with a second peptide, wherein the first and second peptides each independently comprise a peptide of SEQ ID NO: 13. The peptide dimers comprise peptide monomers which dimerize in a head-to-tail arrangement. The peptide dimers can be homodimers or heterodimers.

In one aspect, provided herein are peptides comprising a sequence: $X_1PX_3X_4PX_6X_7PGX_{10}AAX_{13}X_{14}AALHAYX_{21}AX_{23}LX_{25}NYLX_{29}X_{30}VX_{32}$ (SEQ ID NO: 48), wherein the amino acids $X_1$, $X_3$, $X_4$, $X_6$, $X_7$, $X_{10}$, $X_{13}$, $X_{14}$, $X_{21}$, $X_{23}$, $X_{25}$, $X_{29}$, $X_{30}$, and $X_{32}$ are as defined herein, and peptides at least 93% identical to SEQ ID NO: 48.

In another aspect, provided herein are peptide dimers comprising a first peptide associated with a second peptide, wherein the first and second peptides each independently comprise a peptide of SEQ ID NO: 48. The peptide dimers comprise peptide monomers which dimerize in a head-to-tail arrangement. The peptide dimers can be homodimers or heterodimers.

In another aspect, provided herein are peptides comprising a oligomerization domain comprising a sequence: $PX_aX_bPX_cX_bP$ (SEQ ID NO: 2), wherein each of $X_a$, $X_b$, and $X_c$ is independently any non-proline amino acid, and $X_d$ is an amino acid capable of cross-linking the peptide with another peptide (e.g., cysteine, selenocysteine). The oligomerization domain allows the peptide to associate with another peptide to form a dimer.

In certain embodiments, peptides comprising a oligomerization domain comprising a sequence: $PX_aX_bPX_cX_dP$ (SEQ ID NO: 2), wherein each of $X_a$ and $X_b$ is independently any non-proline amino acid, and each of $X_c$ and $X_d$ is independently any non-proline amino acid or an amino acid capable of cross-linking the peptide with another peptide (e.g., cysteine, selenocysteine, Phe, Trp, Tyr, or amino acid comprising an acrylamide moiety such as Dap- and Dab-conjugated acrylamide residues).

The peptide further comprises an alpha-helical domain comprising a sequence: $X_{13}X_{14}X_{15}DLX_{18}X_{19}YX_{21}X_{22}RLX_{25}X_{26}YLX_{29}X_{30}VA$ (SEQ ID NO: 3), wherein $X_{13}$, $X_{14}$, $X_{15}$, $X_{18}$, $X_{19}$, $X_{21}$, $X_{22}$, $X_{25}$, $X_{26}$, $X_{29}$, and $X_{30}$ are as defined herein. The alpha-helical domain is involved with protein-protein interactions and associates with the target protein (e.g., Ras, Myc/Max, RalA, Beta catenin, YAP/TEAD, and NEMO/IκB kinase).

In another aspect, provided herein are peptides comprising an alpha-helical domain comprising a sequence: $X_{13}X_{14}X_{15}DLX_{18}X_{19}YX_{21}X_{22}RLX_{25}X_{26}YLX_{29}X_{30}VA$ (SEQ ID NO: 3), wherein $X_{13}$, $X_{14}$, $X_{15}$, $X_{18}$, $X_{19}$, $X_{21}$, $X_{22}$, $X_{25}$, $X_{26}$, $X_{29}$, and $X_{30}$ are as defined herein.

Exemplary peptides of SEQ ID NO: 1 or 96, 12, and 13 include, but are not limited to

```
                                       (SEQ ID NO: 4)
    GPRRPRCPGDDASIEDLHEYWARLWNYLYAVA, (SEQ ID NO: 5)
    GPRRPRCPGDDASIEDLHEYWARLWNYLYRVA, (SEQ ID NO: 6)
    GRRPRRPRCPGDDASIEDLHEYWARLWNYLYAVA, (SEQ ID NO: 7)
    GPRRPRYPGDDAPVEDLIRFYNDLQQYLNVVA, (SEQ ID NO: 8)
    GCGGPRRPRYPGDDASIEDLHEYWARLWNYLYAVA, (SEQ ID NO: 9)
    GCGGPRRPRYPGDDACEEDLHEYWARLWNYLYAVA, (SEQ ID NO: 10)
    GCGGPRRPRYPGDDASIEDLHEYWARLWNYLYRVA,
    or
                                       (SEQ ID NO: 11)
    GCGGPRRPRRPRYPGDDASIEDLHEYWARLWNYLYAVA.
```

The peptides may comprise a sequence that is about 80% to about 99% homologous to the amino acid sequence of SEQ ID NO: 1 or 96 or SEQ ID NO: 4-11. The peptides may comprise a sequence that is about 80% to about 99% identical to the amino acid sequence of SEQ ID NO: 1 or 96 or SEQ ID NO: 4-11. The peptides may comprise a sequence that that contains the amino acid sequence of SEQ ID NO: 1 or 96 or SEQ ID NO: 4-11 with 1, 2, 3, 4, 5, 6, 7, 8, 9, or 10 amino acid changes (e.g., amino acid deletions and/or additions). Any of the exemplary peptides and peptides that are at least 80% homologous or identical to the exemplary peptides can form heterodimers or homodimers with one another.

Exemplary peptides of SEQ ID NO: 12, 13, and 48 include, but are not limited to

```
                                      (SEQ ID NO: 14)
    PRRPRCPGDDASIEDLHEYWARLWNYLYAVA, (SEQ ID NO: 15)
    PRRPRCPGDDASIEDLHEYWARLWNYLYRVA, (SEQ ID NO: 16)
    RRPRRPRCPGDDASIEDLHEYWARLWNYLYAVA, (SEQ ID NO: 17)
    PRRPRYPGDDAPVEDLIRFYNDLQQYLNVVA, (SEQ ID NO: 18)
    PRRPRYPGDDASIEDLHEYWARLWNYLYAVA, (SEQ ID NO: 19)
    CGGPRRPRYPGDDACEEDLHEYWARLWNYLYAVA, (SEQ ID NO: 20)
    PRRPRYPGDDASIEDLHEYWARLWNYLYRVA, (SEQ ID NO: 21)
    PRRPRRPRYPGDDASIEDLHEYWARLWNYLYAVA, (SEQ ID NO: 22)
    PRRPRCPGDDASIEDLHEYWARLWNYLYRVA, (SEQ ID NO: 23)
    PRRPRCPGDQASLEELHEYWARLWNYLYRVA, (SEQ ID NO: 24)
    PRRPRCPGDNASIKQLHAYWNRLYAYLAAVA, (SEQ ID NO: 25)
    PRRPRCPGDDASIEDLHEYWQRLYAYLAAVA, (SEQ ID NO: 26)
    PRRPRCPGDNASIKQLHAYWQRLYAYLAAVA, (SEQ ID NO: 27)
    PRRPRCPGDNASIRQLHAYWQRLYAYLAAVA,
```

-continued

```
                                  (SEQ ID NO: 28)
GCGGPRRPRYPGDAASIAALHAYWARLWNYLYRVA, (SEQ ID NO: 29)
PRRPRYPGDAASIAALHAYWARLWNYLYRVA,

225-H:
                                  (SEQ ID NO: 30)
PRRPKYPGDAASCAALHAYWARLWNYLYRVA,

225-I:
                                  (SEQ ID NO: 31)
PRRPRYPGDAASIAALHAYWARLWNYLYRXA,

225-J:
                                  (SEQ ID NO: 32)
PRRPRYPGDAASIAALHAYWARLWNYLYRZA,

225-K:
                                  (SEQ ID NO: 33)
PRRPCYPGDAASIAALHAYWARLWNYLYRVA,

225-L:
                                  (SEQ ID NO: 34)
PRRPKCPGDAASIAALHAYWARLWNYLYRVA,

225-M:
                                  (SEQ ID NO: 35)
PRRPRYPGXAASIAALHAYWARLWNYLYRVA,

225-N:
                                  (SEQ ID NO: 36)
PRRPRYPGZAASIAALHAYWARLWNYLYRVA, 225-4s1:
                                  (SEQ ID NO: 37)
PRRPKYPGDAASIAALHAYWARLWNYLYRVR,

291-A:
                                  (SEQ ID NO: 38)
PRRPKHPGHAASIAALHAYWARLWNYLYRVR, 291-1:
                                  (SEQ ID NO: 39)
PRRPRHPGPNATISQLHHYWARLWNYLYRVR,

291-H:
                                  (SEQ ID NO: 40)
PRRPHHPGHAASIAALHAYWARLWNYLYRVR,

291-I:
                                  (SEQ ID NO: 41)
PRRPHYPGHAASIAALHAYWARLWNYLYRVR,

291-Q3:
                                  (SEQ ID NO: 42)
PRRPRCPGHAASIAALHAYWARLWNYLYRVR,

MY01:
                                  (SEQ ID NO: 43)
GPRRPRCPGDDASIRDLLKYWWRLRLYLLAVA,

RL01:
                                  (SEQ ID NO: 44)
GPRRPRCPGDDASISDLLLYWLRLDRYLWAVA,

RR01:
                                  (SEQ ID NO: 45)
GPRRPRCPGDDASIRDLVMYWYRLYFYLEAVA, 225-1c:
                                  (SEQ ID NO: 46)
PRRPKYPGDAASIAALHAYWARLWNYLYRVS, 225-4d:
                                  (SEQ ID NO: 47)
RPRRPKYPGDAASIAALHAYWARLWNYLYRVS,

291-T:
                                  (SEQ ID NO: 49)
PRRPRYPGDAASIAALHAYWARLWNYLYRVS,

Q:
                                  (SEQ ID NO: 50)
PRRPRCPGDNASIRQLHAYWQRLYAYLAAVA,
and R:
                                  (SEQ ID NO: 51)
PRRPRCPGDAASIAALHAYWQRLYAYLAAVA.
```

The peptides may comprise a sequence that is about 80% to about 99% homologous to the amino acid sequence of SEQ ID NO: 12-51. The peptides may comprise a sequence that is about 80% to about 99% identical to the amino acid sequence of SEQ ID NO: 12-51. The peptides may comprise a sequence that that contains the amino acid sequence of SEQ ID NO: 12-51 with 1, 2, 3, 4, 5, 6, 7, 8, 9, or 10 amino acid changes (e.g., amino acid deletions and/or additions). Any of the exemplary peptides and peptides that are at least 80% homologous or identical to the exemplary peptides can form heterodimers or homodimers with one another.

In certain embodiments, a heterodimerized peptide comprises a primary peptide selected from SEQ ID NO: 22, 23, and 49. In certain embodiments, a heterodimerized peptide comprises a secondary peptide selected from SEQ ID NO: 24-27, 50, and 51. In certain embodiments, a heterodimerized peptide comprises a primary peptide selected from SEQ ID NO: 22, 23, and 49 and and a secondary peptide selected from SEQ ID NO: 24-27, 50, and 51.

In another aspect, provided herein are peptides comprising an alpha-helical domain comprising a sequence: $X_{13}X_{14}X_{15}DLX_{18}X_{19}YX_{21}X_{22}RLX_{25}X_{26}YLX_{29}X_{30}VA$ (SEQ ID NO: 100), wherein $X_{13}$ is Ser, Pro, Thr, or an amino acid capable of cross-linking the peptide with another peptide; $X_{14}$ is Ile, Glu, Val, Leu, or an amino acid capable of cross-linking the peptide with another peptide; $X_{15}$ is Glu, Lys, Arg, Ala, Ser, Asp, Gln, or Gly; $X_{18}$ is an aromatic or hydrophobic amino acid; $X_{19}$ is Glu, Lys, Leu, Met, His, Asp, Gln, Ala, Ser, Trp, or Arg; $X_{21}$ is Gln, Tyr, Phe, Trp, His, or an amino acid with a cyclohexyl side chain, wherein Tyr, Phe, Trp, or the cyclohexyl side chain can be substituted with one or more fluorines; $X_{22}$ is Ala, Gln, Trp, Leu, Tyr, Gly, Ser, Val, or Asn; $X_{25}$ is Gln, Tyr, Phe, Trp, His, Asp, or an amino acid with a cyclohexyl side chain, wherein Tyr, Phe, Trp, or the cyclohexyl side chain can be substituted with one or more fluorines; $X_{26}$ is Asn, Ala, Leu, Arg, Phe, Ile, His, or Gln; $X_{29}$ is Ala, Leu, Glu, Asn, Gln, Tyr, Phe, Trp, His, or an amino acid with a cyclohexyl side chain, wherein Tyr, Phe, Trp, or the cyclohexyl side chain can be substituted with one or more fluorines and $X_{30}$ is Ala, Arg or Val.

In one aspect, provided are peptides the can penetrate cells. In certain embodiments, the peptides comprise reduced number of negative charges. In certain embodiments, the number of negative charges of a peptide is reduced by 1, 2, 3, 4, 5, or 6 negative charges compared to the starting peptide. For example, introducing neutral or non-negatively charged amino acids, such as Ala or Ser, in place of anionic residues can help to increase cell penetration. Other residues that would be useful for increasing cell penetration are those that are known to decrease protein aggregation (residues that are generally not large, do not have high charges, and/or not too hydrophobic). In certain embodiments, the disclosed peptides comprise at least one, two, or three neutral or non-negatively charged amino acids at positions $X_{11}$, $X_{15}$, and/or $X_{16}$. In certain embodiments, the disclosed peptides comprise at least one, two, three, or four neutral or non-negatively charged amino acids at positions $X_{11}$, $X_{15}$, $X_{16}$, and/or $X_{19}$. In certain embodiments, the neutral or non-negatively charged amino acids are Ala or Ser. In certain embodiments, the peptides comprise Ala in place of anionic residues. In certain embodiments, the peptides comprise Ser in place of anionic residues. In certain embodiments, the disclosed peptides comprise at least one, two, three, or four Ala or Ser at positions $X_{11}$, $X_{15}$, $X_{16}$, and/or $X_{19}$ of any one of the peptides disclosed herein.

In one aspect, provided herein are peptides designed to prevent or minimize dimerization prior to cell penetration. The peptides disclosed herein can comprise Cys or Sec masked with small organic thiol moieties to prevent crosslinking. In certain embodiments, the small organic thiol moiety is —$SR^S$, wherein $R^S$ is a substituted or unsubstituted $C_{1-5}$ alkyl. In certain embodiments, the small organic thiol moiety is t-butyl thiol or ethanethiol. In certain embodiments, the peptide comprises a sequence selected from the group consisting of SEQ ID NO: 30, 33, and 34, wherein the Cys is disulfide bonded to small organic thiol moiety. In any of the foregoing embodiments or embodiments herein comprising Cys, Sec is also contemplated in place of Cys.

In another aspect, provided herein are peptides designed to crosslink to another peptide comprising electrophilic side chains after the peptides have penetrated the cells. In certain embodiments, peptides disclosed herein comprise residues modified with moieties capable of crosslinking to Cys or Sec. In certain embodiments, the peptides comprises an amino acid comprising an acrylamide moiety. In certain embodiments, the peptides comprise L-2,4-diaminobutyric acid (Dab) residues or L-2,3-diaminopropionic acid (Dap) residues. In certain embodiments, the peptides comprise L-2,4-diaminobutyric acid (Dab) residues or L-2,3-diaminopropionic acid (Dap) residues, wherein the Dab and Dap are modified with acrylic acid to form a side chain comprising acrylamide. In certain embodiments, the peptide comprises a sequence selected from the group consisting of SEQ ID NO: 31, 32, 35, and 36, wherein X is L-2,4-diaminobutyric acid (Dab) residue conjugated to acrylamide and Z is a L-2,3-diaminopropionic acid (Dap) residue conjugated to acrylamide. Dap and Dab residues conjugated to acrylamide are further described herein. Peptide dimers can be formed from any combination of SEQ ID NO: 30, 33, and 34 with SEQ ID NO: 31, 32, 35, and 36. It is understood that Cys can be replaced with Sec in any of the embodiments described herein. In certain embodiments, the disclosed peptides comprise Cys or Sec at positions $X_6$, $X_7$, and/or $X_{14}$ of any one of the peptides disclosed herein. In certain embodiments, the disclosed peptides comprise an amino acid comprising an acrylamide moiety at positions $X_{10}$, $X_{31}$, and/or $X_{32}$ of any one of the peptides disclosed herein. In certain embodiments, the disclosed peptides comprise Dap or Dab at positions $X_{10}$, $X_{31}$, and/or $X_{32}$ of any one of the peptides disclosed herein, wherein the Dap or Dab are modified with acrylic acid to form a side chain comprising acrylamide. In certain embodiments, provided is a first peptide monomer comprising Cys or Sec at positions $X_6$, $X_7$, or $X_{14}$ of the first peptide monomer, wherein the Cys or Sec are masked with a small organic thiol moiety as provided herein; and a second peptide monomer comprising Dap or Dab at positions $X_{10}$, $X_{31}$, or $X_{32}$ of the second peptide, wherein the Dap or Dab are modified with acrylic acid to form a side chain comprising acrylamide.

In yet another aspect, provided herein are selective dimer destabilization strategies to improve endosomal escape and cytosolic access of the dimer. Strategies provided herein include pH-induced destabilization or bulky residue destabilization. In certain embodiments, the peptides described herein comprise one or more His placed in amino acid positions such that they are spatially close to one or more cationic residues or one or more His on the opposing monomer peptide. In certain embodiments, the peptides comprise His placed at positions $X_6$, $X_7$, and/or $X_{10}$. His placed at one, two, or three of these positions is applicable to any of the peptides described herein. In certain embodiments, the peptide comprises a sequence selected from the group consisting of SEQ ID NO: 38 to 41.

In certain embodiments, dimer destabilization is achieved using residues comprising bulky moieties near the dimer interface to prevent dimerization. Such bulky moieties are removed after cell penetration and the corresponding residue is free to dimerize. Examples of bulky moieties useful for masking Cys or Sec include organic thiol molecules. In certain embodiments, the peptides described herein comprise Cys or Sec protected by reaction with organic thiol molecules. In certain embodiments, the organic thiol molecules are selected from aryl thiols, heteroaryl thiols, and aliphatic thiols. In certain embodiments, the organic thiol molecules are heteroaryl thiols. In certain embodiments, the peptides described herein comprise Cys or Sec protected by reaction with 2,2'-Dipyridyldisulfide, 4,4'-Dipyridyldisulfide, or 2,2'-Dithiobis(5-nitropyridine). In certain embodiments, the peptides comprise a sequence selected from SEQ ID NO: 30, 33, 34, and 42, wherein the Cys is protected by any of the foregoing organic thiol molecules. It is understood that Cys can be replaced with Sec in any of the embodiments described herein.

In certain embodiments, any of the peptides described herein comprise Cys or Sec at $X_7$ and Ala or Ser at one or more of $X_{11}$, $X_{15}$, $X_{16}$, and/or $X_{19}$. In certain embodiments, any of the peptides described herein comprise Tyr at $X_7$ and Ala or Ser at one or more of $X_{11}$, $X_{15}$, $X_{16}$, and/or $X_{19}$.

In certain embodiments, any of the peptides described herein comprise His at $X_6$ and Cys or Sec at $X_7$. In certain embodiments, any of the peptides described herein comprise Cys or Sec at $X_7$ and His at $X_{10}$.

It is understood that the peptides described herein can comprise an acetylated N-terminus and/or an amidated C-terminus.

In still another aspect, provided herein is a method of treating a disease or condition associated with Ras, Myc/Max, RalA, Beta catenin, YAP/TEAD, or NEMO/IκB kinase in a subject in need thereof comprising administering a peptide as described herein to the subject. In certain embodiments, the disease or condition is associated with Ras. Also provided herein is a method of treating a proliferative disease in a subject in need thereof comprising administering a peptide as described herein to the subject. Exemplary diseases or conditions include various cancers and rasopathies.

The peptides described herein are also useful in methods and systems for screening libraries of peptides. In one aspect, provided herein are methods and systems of screening a library of peptide dimers comprising the steps of transforming display cells with a vector encoding a first peptide and a second peptide, wherein the first and second peptides associate to form a peptide dimer fused to a cell wall protein, contacting the display cells with a first label, wherein the first label comprises a target protein and associates with a cell expressing the peptide dimer having enhanced binding to the target and does not associate with a cell which does not express the peptide dimer having enhanced binding to the target; isolating the display cells with which the first label is associated; and identifying the first and second peptides which exhibit enhanced binding to the target. Alternatively, the method can comprises transforming display cells with a first vector encoding a first peptide and second vector encoding a second peptide.

In a further aspect, provided herein are kits comprising the peptides and dimers described herein. Also provided are nucleic acids encoding the peptides and dimers described herein. In addition, host cells comprising the nucleic acids, peptides, and dimers are also contemplated.

BRIEF DESCRIPTION OF THE DRAWINGS

The accompanying drawings are not intended to be drawn to scale. In the Drawings, for purposes of clarity, not every component may be labeled in every drawing.

FIG. 2 adapted from Chao, G., et al. Isolating and engineering human antibodies using yeast surface display. *Nat Protoc* 1, 755-68 (2006).

FIG. 3A shows CD spectra of aPP and aPP-M. FIG. 3B shows the thermal melting profile at 222 nm.

FIG. 4B shows the amino acid sequences (SEQ ID NOS: 52, 7 and 54, respectively, in order of appearance) of the libraries. An underlined X designates any amino acid.

FIG. 7A shows gel filtration trace of His$_6$-tagged (SEQ ID NO: 55) KRas G12V following elution from cobalt resin. FIG. 7B shows reverse-phase HPLC analysis of Ras-bound nucleotides for GDP- and GTP-loaded proteins. GDP and GTP standards elute at 12 and 15 minutes, respectively. FIG. 7C shows the MALDI-MS spectrum of Ras before and after enzymatic biotinylation by Sfp.

FIG. 10 shows the directed evolution of aPP-scaffolded peptides. The hits of each round were diversified by error-prone PCR, then the resulting yeast libraries were selected by magnetic-activated cell sorting (MACS) and fluorescence-activated cell sorting (FACS) for the ability to bind KRas under increasingly stringent conditions (lower [KRas] and increased blocking agents). Mutations are underlined in the first round in which they appear; in subsequent rounds, they are indicated in italics. FIG. 10 discloses SEQ ID NOS 54, 56-68, 65, 4, 61 and 72-74, respectively, in order of appearance.

FIG. 11 shows the peptides used for in vitro studies. For consistency, residue numbers are reported using the positions in the wild-type aPP peptide. Alanine point mutations are underlined. FIG. 11 discloses SEQ ID NOS 8, 75, 11 and 77-85, respectively, in order of appearance.

FIG. 13A shows the UV CD spectra; FIG. 13B shows the melting profile at 222 nm. aPP-M and 225-1 were measured at pH 8.0; 225-3 was measured at pH 12 and pH 4.5 due to low solubility in the pH 5-10 range.

FIG. 14 shows fluorescence polarization measurements of the Ras-peptide interaction. FITC-labeled 225-3 peptide was mixed with increasing concentrations of Ras or Ras family proteins, then the fluorescence polarization was read and plotted. Error bars are standard error of the mean (SEM).

FIG. 17A shows fluorescence polarization experiments as were performed above with the indicated 225-3 alanine mutant peptides and KRas(G12V).GppNHp. FIG. 17B shows CD spectra of mutants at 25° C., FIG. 17C shows the melting profile at 222 nm. All CD experiments were carried out at pH 12. Error bars are SEM.

FIGS. 20A-C show $^1H$-$^{15}N$ HSQC (TROSY) NMR spectra of Ras in the presence and absence of 225-1. FIG. 20A shows the TROSY of $^{15}N$-labeled KRas (WT) GDP;

FIG. 20B shows the TROSY of $^{15}N$-labeled KRas with unlabeled 225-1, and FIG. 20C shows the overlay of spectra.

FIG. 21 shows that the 225 peptide binding site overlaps with the Ras effector domain. The residues in the effector domain were defined by co-crystal structures of HRas with effectors, and the peptide binding site was defined by the TROSY experiment with 225-1 in FIG. 20B. Residues are indicated with a black outline on the crystal structure of KRas(WT).GppNHp (PDB: 3GFT).

FIGS. 22A-C show $^1H$-$^{15}N$ HSQC (TROSY) NMR spectra of 225-1 in the presence and absence of Ras. FIG. 22A shows the TROSY of $^{15}N$-labeled 225-1; FIG. 22B shows the TROSY of $^{15}N$-labeled 225-1 with unlabeled KRas (G12V) GDP, and FIG. 22C shows the overlay of spectra.

FIG. 25 shows the design of scanning mutagenesis library based on 225-1. The library was prepared by overlap extension as for the original naïve libraries, using individual primers for each sublibrary. X was encoded by an NNK codon. FIG. 25 discloses SEQ ID NOS 65 and 86-90, respectively, in order of appearance.

FIG. 26A shows yeast displaying either 225-1 or 225-1 S13C/I14E were pre-incubated with 10 uM of (free) 225-1, 225-1 alk (alkylated 225-1), or 225-1 N26A, then pelleted and incubated with 5 nM KRas before FACS. FIG. 26B shows the alkylation of the cysteine sidechain by iodoacetamide.

FIG. 29 discloses SEQ ID NOS 91-93, respectively, in order of appearance.

FIG. 33A shows SPR measurements using a heterodimer peptide comprising SEQ ID NO: 23 and 26. FIG. 33B shows SPR measurements using a homodimer peptide comprising SEQ ID NO: 4.

FIGS. 34A-B show live-cell microscopy with labeled peptides, performed in H358 lung adenocarcinoma cells at 5 uM peptide concentration in DMEM media supplemented with 10% fetal calf serum. FIG. 34A shows cells treated with a peptide homodimer comprising SEQ ID NO: 10. FIG. 34B shows cells treated with the 4-residue mutant peptide homodimer comprising SEQ ID NO: 28. Both peptides were labeled with fluorescein. The 4-residue mutant peptide comprising SEQ ID NO: 28 entered cells better than the peptide comprising SEQ ID NO: 10. The aggregates in FIG. 34A were not present in FIG. 34B, which is a consequence of increased solubility imparted by the mutations found in SEQ ID NO: 28 compared to SEQ ID NO: 10.

FIG. 36A shows peptides of SEQ ID NO: 37, which lacks histidines. FIG. 36B shows peptides of SEQ ID NO: 38, which contains two histidines per monomer (four histidines per dimer; "His tetrad").

FIG. 38A shows RL01 peptide of SEQ ID NO: 44 binding data to KRas and to RalA. FIG. 38B shows RR01 peptide of SEQ ID NO: 45 binding data to KRas and to RalA. FIG. 38C shows MY01 peptide of SEQ ID NO: 43 binding data to Myc/Max.

DEFINITIONS

Figure 1:
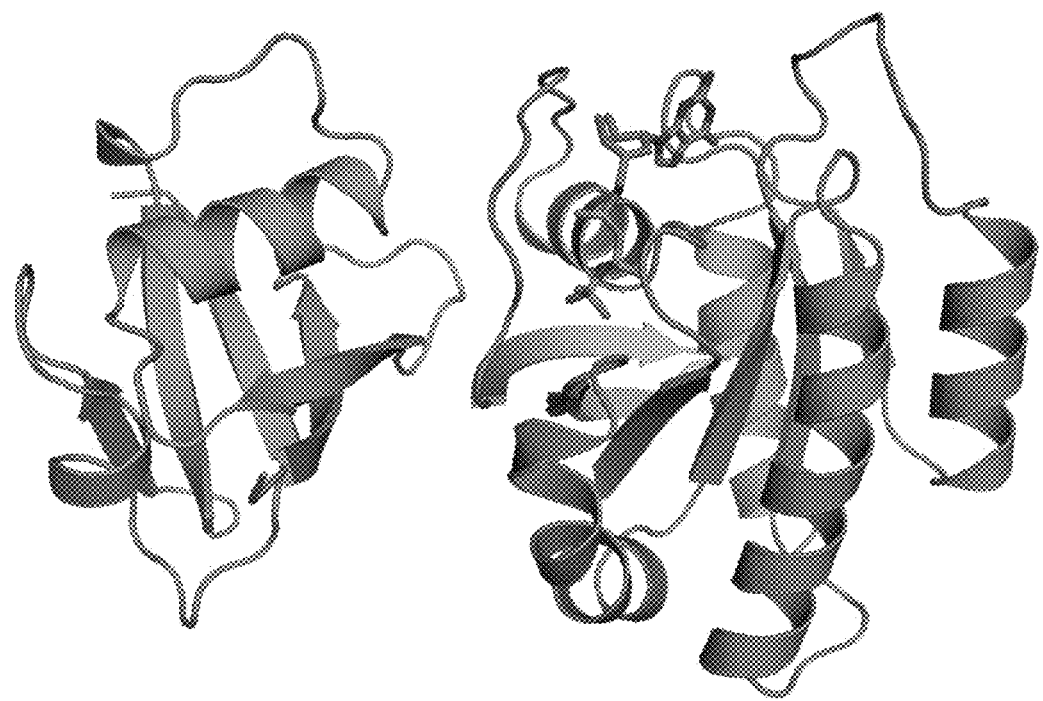
FIG. 1 shows a crystal structure of Ras bound to an effector. HRas.GppNHp is shown on the right, with nucleotide indicated in sticks; the Ras binding domain (RBD) of RalGDS is shown on the left. PDB: 1LFD.

A "peptide" comprises a polymer of amino acid residues linked together by peptide (amide) bonds. The term peptide is used herein to generally refer to both the peptide monomer and the peptide dimer. The terms, as used herein, refers to proteins, miniproteins, polypeptides, and peptides of any size, structure, or function. The terms may also refer to dimers or oligomers of peptides. The terms, as used herein, may include stapled, unstapled, stitched, and unstitched polypeptides. Typically, a peptide will be at least three amino acids long. A peptide may refer to an individual peptide or a collection of peptides. Inventive peptides preferably can comprises only natural amino acids or also non-natural amino acids (i.e., compounds that do not occur in nature but that can be incorporated into a peptide chain) and/or amino acid analogs as are known in the art may alternatively be employed. One or more of the amino acids in a peptide may be modified, for example, by the addition of a chemical entity such as a carbohydrate group, a hydroxyl group, a phosphate group, a farnesyl group, an isofarnesyl group, palmitoyl, geranylgeranyl, lauryl, a fatty acid group, a linker for conjugation, functionalization, or other modification. A peptide may be just a fragment of a naturally occurring protein or peptide. A peptide or polypeptide may be naturally occurring, recombinant, or synthetic, or any combination thereof.

The term "amino acid" refers to a molecule containing both an amino group and a carboxyl group. In certain embodiments, the amino acid is an alpha-amino acid. In certain embodiments, the amino acid is a natural amino acid. In certain embodiments, the amino acid is an non-amino acid. There are many known non-natural amino acids any of which may be included in the peptides of the present invention. See for example, S. Hunt, The Non-Protein Amino Acids: In Chemistry and Biochemistry of the Amino Acids, edited by G. C. Barrett, Chapman and Hall, 1985.

Exemplary amino acids include, without limitation, natural alpha-amino acids such as D- and L-isomers of the 20 common naturally occurring alpha amino acids found in peptides, natural amino acids which are not the 20 common naturally occurring amino acids, and unnatural alpha-amino acids. Amino acids used in the construction of peptides of the present invention may be prepared by organic synthesis, or obtained by other routes, such as, for example, degradation of or isolation from a natural source. Amino acids may be commercially available or may be synthesized. Amino acids with hydrophobic side chains include Gly, Pro, Ala, Ile, Leu, Val, Phe, Met, Trp, and Tyr. In certain embodiments, amino acids with hydrophobic side chains include Ala, Ile, Leu, and Val. Amino acids with polar neutral side chains include Asn, Cys, Gln, Met, Ser, and Thr. Amino acids with aromatic side chains include Phe, Trp, Tyr, and His. Amino acids with hydrophobic aromatic side chains include Phe, Typ, and Tyr. Amino acids with charged side chains include Asp, Glu, Arg, His, and Lys. Negatively charged side chains include Asp and Glu. Positively charged side chains include Arg, His, and Lys. Non-negatively charged amino acids are selected from the group consisting of Ala, Ser, Val, Leu, Ile, Pro, Phe, Trp, Met, Gly, Thr, Cys, Tyr, Asn, and Gln.

As used herein, "amino acids capable of cross-linking the peptide with another peptide" include amino acids that cross-link covalently and non-covalently. For example, residues capable of covalent cross-linking include, but are not limited to, Cys, Sec, amino acids comprising a acrylamide moiety such as Dap and Dab modified with acrylic acid to form a side chain with an acrylamide. Such Dab- and Dap-conjugated acrylamide residues can crosslink to Cys or Sec residues. Amino acid residues capable of non-covalently cross-linking the peptides include, but are not limited to, His, Phe, Trp, Tyr.

Amino acids can be cross-linked through a disulfide bond, diselenium bond, sulfide-selenium bond, carbon-carbon bond, amide bond, ester bond, hydrogen bond, salt bridge, pi stacking interaction, or non-polar hydrophobic interaction. In certain embodiments, two peptides are associated through a disulfide bond. In certain embodiments, two peptides are associated through a diselenium bond. In certain embodiments, two peptides are associated through a hydrogen bond, salt bridge, or non-polar hydrophobic interaction. In certain embodiments, two peptides are associated through pi stacking interaction. For example, a tyrosine on one peptide interacts with another tyrosine on another peptide through pi stacking.

The term "homologous", as used herein is an art-understood term that refers to nucleic acids or proteins that are highly related at the level of nucleotide or amino acid sequence. Nucleic acids or proteins that are homologous to each other are termed homologues. Homologous may refer to the degree of sequence similarity between two sequences (i.e., nucleotide sequence or amino acid). The homology percentage figures referred to herein reflect the maximal homology possible between two sequences, i.e., the percent homology when the two sequences are so aligned as to have the greatest number of matched (homologous) positions. Homology can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Methods commonly employed to determine homology between sequences include, but are not limited to those disclosed in Carillo, H., and Lipman, D., SIAM J Applied Math., 48:1073 (1988); incorporated herein by reference. Techniques for determining homology are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and PASTA Atschul, S. F. et al., J Molec. Biol., 215, 403 (1990)).

The term "homologous", as used herein is an art-understood term that refers to nucleic acids or polypeptides that are highly related at the level of nucleotide or amino acid sequence. Nucleic acids or polypeptides that are homologous to each other are termed "homologues."

The term "homologous" refers to a comparison between two sequences. Two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids.

As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

As used herein, "cross-linking" peptides refers to either covalently cross-linking peptides or non-covalently cross-linking peptides. In certain embodiments, the peptides are covalently associated. Covalent interaction is when two peptides are covalently connected through a linker group such as a natural or non-natural amino acid side chain. In other embodiments, the peptides are non-covalently associated. Non-covalent interactions include hydrogen bonding, van der Waals interactions, hydrophobic interactions, magnetic interactions, and electrostatic interactions. The peptides herein comprise an amino acid capable of cross-linking the peptide with another peptide (e.g., cysteine, selenocysteine, amino acids comprising a acrylamide moiety, Dap-conjugated acrylamide, Dab-conjugated acrylamide). In the case of peptide dimers, the peptide dimers comprise amino acids cross-linking the first peptide with the second peptide. The peptides may also comprise natural or non-natural amino acids capable of cross-linking the peptide with another peptide. The peptide dimers may comprise natural or non-natural amino acids cross-linking the first peptide with the second peptide.

"Peptide stapling" is one method for crosslinking within a peptide (intrapeptide) or between different peptides (interpeptide). Peptide stapling describes a synthetic methodology wherein two olefin-containing sidechains present in a peptide or different peptides are covalently joined ("stapled") using a ring-closing metathesis (RCM) reaction to form a crosslink (see, the cover art for *J. Org. Chem*. (2001) vol. 66, issue 16 describing metathesis-based crosslinking of alpha-helical peptides; Blackwell et al.; *Angew Chem. Int. Ed.* (1994) 37:3281; and U.S. Pat. No. 7,192,713). "Peptide stitching" involves multiple "stapling" events in a single polypeptide chain to provide a multiply stapled (also known as "stitched") polypeptide (see, for example, Walensky et al., *Science* (2004) 305:1466-1470; U.S. Pat. Nos. 7,192,713; 7,786,072; 8,592,377; 7,192,713; U.S. Patent Application Publication No. 2006/0008848; U.S. Patent Application Publication No. 2012/0270800; International Publication No. WO 2008/121767 and International Publication No. WO 2011/008260). Stapling of a peptide using all-hydrocarbon crosslinks has been shown to help maintain its native conformation and/or secondary structure, particularly under physiologically relevant disorders (see Schafmiester et al., *J. Am. Chem. Soc.* (2000) 122:5891-5892; Walensky et al., *Science* (2004) 305:1466-1470). In certain embodiments, the non-natural amino acids found in the peptides described herein comprise a side chain capable of being covalently joined using olefin moieties (i.e., "stapled together") using a cross-linking reaction such as a ring-closing metathesis (RCM) reaction. Additional description of the related peptide stapling or peptide stitching can be found in WO2010/011313, WO2012/040459, WO2012/174423, and PCT/US2013/062004, U.S. Ser. No. 61/478,845, 61/478,862, 61/705,950, 61/789,157, and 61/708,371, all of which are incorporated by reference herein.

The term "Ras" refers to the Ras protein family or mutants thereof. Ras proteins are small cytosolic GTPases that function in several signal transduction pathways, and that can activate a number of downstream proteins (effectors) by binding through the Ras effector domain. Ras proteins are switched by upstream factors between the guanosine triphosphate (GTP, "on") and guanosine diphosphate (GDP, "off") states. There are three Ras isoforms in humans: KRas, HRas, and NRas, with two splice variants of KRas, KRas4A and KRas4B. Active Ras proteins are localized to membranes by the post-translational attachment of lipids (typically famesyl or geranylgeranyl groups), and typically activate effector proteins by binding their Ras binding domains (RBDs) and thereby recruiting them to the membrane, where they are activated through a variety of mechanisms.

As used herein, the terms "disease" and "disorder" are used interchangeably.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from a disorder which reduces the severity of the disorder or retards or slows the progression of the disorder ("therapeutic treatment"), and also contemplates an action that occurs before a subject begins to suffer from the disorder and which inhibits or reduces the severity of the disorder ("prophylactic treatment").

In general, the "effective amount" of a peptide refers to an amount sufficient to elicit the desired biological response, i.e., treating the disorder. As will be appreciated by those of ordinary skill in this art, the effective amount of a peptide of the invention may vary depending on such factors as the desired biological endpoint, the pharmacokinetics of the compound, the disorder being treated, the mode of administration, and the age, health, and the subject. An effective amount encompasses therapeutic and prophylactic treatment.

As used herein, and unless otherwise specified, a "therapeutically effective amount" of a peptide is an amount sufficient to provide a therapeutic benefit in the treatment of the disorder or to delay or minimize one or more symptoms associated with the disorder. A therapeutically effective amount of a peptide means an amount of therapeutic agent, alone or in combination with other therapies, which provides a therapeutic benefit in the treatment of the disorder. The term "therapeutically effective amount" can encompass an amount that improves overall therapy, reduces or avoids symptoms or causes of the disorder, or enhances the therapeutic efficacy of another therapeutic agent.

As used herein, and unless otherwise specified, a "prophylactically effective amount" of a peptide is an amount sufficient to prevent the disorder, or one or more symptoms associated with the disorder or prevent its recurrence. A prophylactically effective amount of a peptide means an amount of a therapeutic agent, alone or in combination with other agents, which provides a prophylactic benefit in the prevention of the disorder. The term "prophylactically effective amount" can encompass an amount that improves overall prophylaxis or enhances the prophylactic efficacy of another prophylactic agent.

The term "RASopathy" or "RASopathies" are a clinically defined group of medical genetic syndromes caused by germline mutations in genes that encode components or regulators of the Ras/mitogen-activated protein kinase (MAPK) pathway. These disorders include neurofibromatosis type 1, Noonan syndrome, Noonan syndrome with multiple lentigines, capillary malformation-arteriovenous malformation syndrome, Costello syndrome, cardio-facio-cutaneous (CFC) syndrome, and Legius syndrome. Because of the common underlying Ras/MAPK pathway dysregulation, the RASopathies exhibit numerous overlapping phenotypic features. The Ras/MAPK pathway plays an essential role in regulating the cell cycle and cellular growth, differentiation, and senescence, all of which are critical to normal development. Therefore, Ras/MAPK pathway dysregulation has profound deleterious effects on both embryonic and later stages of development. The Ras/MAPK pathway has been studied in cancer and is a target for small-molecule inhibition to treat various malignancies.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "thiol" refers to the group —SH (e.g., found in Cys side chain), —$SR^S$, or a molecule comprising a —S—S— moiety. For example, an "organic thiol molecule" includes molecules such as 2,2'-Dipyridyldisulfide, 4,4'-Dipyridyldisulfide, or 2,2'-Dithiobis(5-nitropyridine). The phrase "small organic thiol moieties" include organic groups comprising a sulfur, such as —$SR^S$, wherein $R^S$ is a substituted or unsubstituted $C_{1-5}$ alkyl. Such moieties are able to bond to other thiol or selenium moieties through disulfide bonding or selenium-sulfide bonding, respectively. For example, a Cys side chain bonded to t-butyl thiol has the following structure:

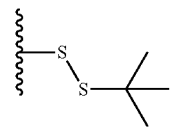

Provided below are a list of abbreviations that are used herein.
Dab L-2,4-diaminobutyric acid
Dap L-2,3-diaminopropionic acid
PPI Protein-protein interaction
RBD Ras binding domain
GAP GTPase activating protein
GRP Guanine nucleotide releasing proteins
bHLHZip Basic helix-loop-helix leucine zipper
PCR Polymerase chain reaction
FACS Fluorescence-activated cell sorting
NMR Nuclear magnetic resonance
aPP Avian pancreatic polypeptide PPII Polyproline type II
Tm Melting transition
CD Circular dichroism
PI3K Phosphatidylinositide 3-kinase
MACS Magnetic-activated cell sorting
NA-PE Neutravidin-phycoerythrin
SA-PE Streptavidin-allophycocyanin
IMAC Immobilized metal affinity chromatography
CoA Coenzyme A
GTP Guanosine triphosphate
GDP Guanosine diphosphate
GppNHp Guanosine 5'-[β,γ-imido]triphosphate
GppCp (β,γ-methyleneguanosine 5'-triphosphate
IPTG Isopropyl β-D-1-thiogalactopyranoside
LB Lysogeny Broth
MALDI-MS Matrix-assisted laser desorption/ionization mass spectrometry
HPLC High-performance liquid chromatography
TEV Tobacco etch protease
LC/MS Liquid chromatography-mass spectrometry
DMSO Dimethyl sulfoxide
TCEP Tris(2-carboxyethyl)phosphine
Kd Dissociation constant
FP Fluorescence polarization
FITC Fluorescein isothiocyanate
SPR Surface plasmon resonance
RU Resonance units
SDS-PAGE Sodium dodecyl sulfate-polyacrylamide gel electrophoresis
GST Glutathione-S-transferase
mantGppNHp N-methylanthraniloyl ester of GppNHp
HSQC Heteronuclear quantum spin correlation spectroscopy
NLS Nuclear localization signals
MBP Maltose binding protein
SEC selenocysteine

DETAILED DESCRIPTION OF CERTAIN EMBODIMENTS OF THE INVENTION

While advances have been made in understanding the molecular mechanisms of human disease, our ability to exploit these discoveries for therapeutic benefit is frequently limited by the inability to make drugs that target the processes which are responsible for the disease. Many diseases can be linked to the aberrant activity of proteins, and while the development of inhibitors of enzymes and extracellular targets is often feasible, these proteins account for only a small fraction of all proteins. The remaining proteins are, in most cases, considered therapeutically intractable and are sometimes referred to as "undruggable." An example of an "undruggable" protein target is Ras, which is linked to both the initiation and progression of a wide array of human diseases, such as cancers, yet remains out of the reach of contemporary therapeutics. This is primarily a consequence of the intracellular localization of Ras, which renders this protein inaccessible to biologics, and their intractability to small molecules, which are typically capable of entering cells. Attempts to target the one hydrophobic pocket (the nucleotide binding site) of Ras has not been successful, largely due to the extremely high (picomolar) affinity of the Ras proteins for guanine nucleotides, and the relatively high abundance of these nucleotides in cells. Many peptide therapeutics are limited by their ability to enter cells. However, certain small proteins (peptides) are capable of entering cells with the appropriate chemical modifications. Peptides are often large enough to engage protein surfaces, and if modified to possess high affinity and specificity for their protein targets, they have been shown to act as effective inhibitors of protein-protein interactions in vivo.

Provided herein are peptides that inhibit protein-protein interactions of protein targets that cannot currently be treated by conventional therapy. The peptides are based on a scaffold that includes an alpha-helical domain. The alpha-helix is the most common secondary structure in proteins, and alpha-helices are often involved in critical protein-protein interactions. Alpha-helices are therefore attractive as potential therapeutics, in particular because they might be used to disrupt protein-protein interactions responsible for disease.

In certain embodiments, the peptides provided herein comprise a polyproline type-II helix domain, a linker domain, and an alpha-helical domain. These proteins may bind protein targets and thereby disrupt protein-protein interactions. Examples of targets of the inventive proteins include the Ras oncoprotein. The peptides bind the surfaces of their targets and block key interactions with partner molecules that are required for the target's activity (e.g., the oncogenic activity of Ras). Other targets include the Myc/Max heterodimer and RalA protein.

Figure 23A:
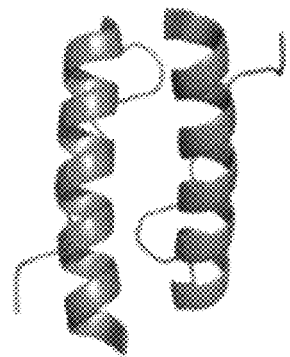
FIGS. 23A-C show the head-to-tail dimerization of aPP peptides. Crystal structure of aPP (PDB: 1PPT) shown in cartoon representation (FIG. 23A), with sticks (FIG. 23B), and with the Y7 pair shown (FIG. 23C).
Figures 23B, 23C:
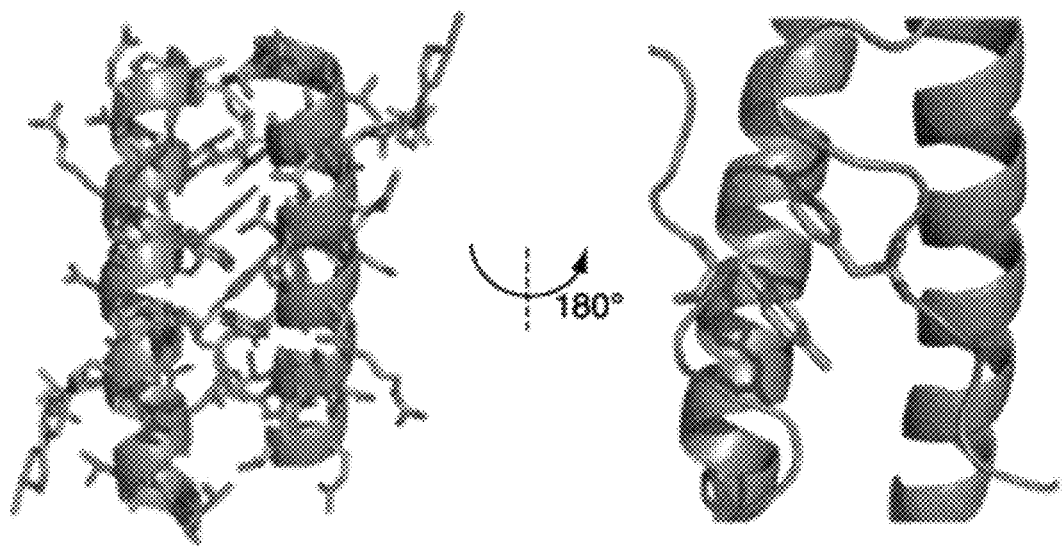

The peptides provided herein are based on the pancreatic polypeptide family. In certain embodiments, the peptides provided herein are based on avian, human, bovine, ovine, porcine, canine pancreatic polypeptides, and mutants thereof. In certain embodiments, the peptides provided herein are based on avian pancreatic polypeptide (aPP), and derivatives and mutants thereof. The peptides provided herein comprise a polyproline type-II helix domain, a linker domain, and a C-terminal alpha-helical domain, and the peptides include a moiety capable of cross-linking the peptide with another peptide. An example of a general peptide dimer is shown in FIGS. 23A-C. Also provided herein are peptide dimers of two peptides, each comprising a polyproline type-II helix domain, a linker domain, and a C-terminal alpha-helix domain, wherein each peptide includes a moiety capable of covalently or non-covalently cross-linking with another peptide monomer. The peptide dimers can be homodimers or heterodimers.

The term "peptide" is used herein to refer to both the peptide monomer and peptide dimer. In certain embodiments, the peptides are chemically stabilized and/or cell-permeable. Examples of chemical stabilization includes crosslinking as described herein, peptide stapling, peptide stitching, or peptide cyclization (e.g., the N-terminus and C-terminus are connected with an amide bond to form a continuous amide backbone, or a sidechain on the N-terminus crosslinks to a sidechain on the C-terminus). Resistance to proteolysis can be accomplished using various methods including but not limited to D-amino acid incorporation, end-capping, or cyclization of the individual peptide monomers. In certain embodiments, cyclization is by head-to-tail cyclization. This exploits the fact that the N- and C-termini are spatially close, as seen in our crystal structure. This could be accomplished by coupling the N- and C-termini to form an amide bond, or by coupling the sidechains of two residues that are the N- and C-termini or are close to them. Stapled or stitched peptides have been described in, for example, Walensky et al., Science (2004) 305:1466-1470; U.S. Pat. Nos. 8,592,377; 7,192,713; U.S. Patent Application Publication No. 2006/0008848; U.S. Patent Application Publication No. 2012/0270800; International Publication No. WO 2008/121767 and International Publication No. WO 2011/008260, each of which are incorporated herein by reference.

Further provided herein are methods of screening a library of peptide dimers using a display technology (e.g., yeast cell display, bacterial cell display, or phage display) for enhanced binding to a protein target such as Ras, Myc/Max, RalA, or another target. Also provided herein are pharmaceutical compositions, methods, uses, and kits comprising peptides useful as inhibitors of protein-protein interactions. In some cases, the pharmaceutical compositions, methods, uses, and kits comprising peptides are useful as inhibitors of protein-protein interactions that cannot currently be targeted by conventional therapy such as the Ras oncoprotein and its intereactions with effector molecules. Exemplary diseases that may be prevented and/or treated with peptides described herein include proliferative diseases (e.g., cancers) and other diseases, disorders, or conditions (e.g., rasopathies).

Peptides

The peptides are based on the aPP scaffold, GPSQPTYPGDDAPVEDLIRFYNDLQQYLNVVA (SEQ ID NO: 49), and bind a protein target. In certain embodiments, the peptides bind Ras, Myc/Max, and/or RalA. In certain embodiments, the peptides bind Ras. In certain embodiments, the peptides bind Myc/Max. In certain embodiments, the peptides bind RalA. In certain embodiments, the peptides bind both KRas and RalA.

In certain embodiments, provided herein are peptides comprising the sequence: $X_1PX_3X_4PX_6X_7PGX_{10}X_{11}AX_{13}X_{14}X_{15}DLX_{18}X_{19}YX_{21}X_{22}RLX_{25}X_{26}YLX_{29}X_{30}VA$ (SEQ ID NO: 1), wherein the peptides comprise one to two amino acids capable of cross-linking the peptide with another peptide. In certain embodiments, the amino acids capable of cross-linking the peptide with another peptide is capable of covalent cross-linking. Also provided are peptide dimers comprising a first peptide associated with a second peptide, wherein the first and second peptides each independently comprise a peptide of SEQ ID NO: 1, and wherein the first and second peptides each comprises one to two amino acids cross-linking the first peptide with the second peptide. In certain embodiments, the peptide dimer is covalently cross-linked. $X_1$ is Gly, Arg, or an amino acid capable of cross-linking the peptide with another peptide. In certain embodiments, $X_1$ is absent from SEQ ID NO: 1. $X_3$, $X_4$, and $X_6$ are each independently a charged amino acid. $X_{10}$ is a charged amino acid. $X_{11}$ is a charged amino acid or an amino acid capable of cross-linking the peptide with another peptide. $X_7$ is Tyr or an amino acid capable of cross-linking the peptide with another peptide. $X_{13}$ is Ser or an amino acid capable of cross-linking the peptide with another peptide. $X_{14}$ is Ile or Glu. $X_{15}$ is Glu, Asp, Gln, or Gly. $X_{18}$ is an aromatic or hydrophobic amino acid. $X_{19}$ is Glu, Asp, Gln, Ala, or Trp. $X_{21}$, $X_{25}$, and $X_{29}$ are each independently a Tyr, Phe, Trp, His, or an amino acid with a cyclohexyl side chain, wherein the Tyr, Phe, Trp, or cyclohexyl side chain can be substituted with one or more fluorines. $X_{22}$ is Ala, Gly, Ser, or Val. $X_{26}$ is Asn, Leu, Ile, or His. $X_{30}$ is Ala or Arg.

In certain embodiments, provided herein are peptides comprising the sequence: $X_1PX_3X_4PX_6X_7PGX_{10}X_{11}AX_{13}X_{14}X_{15}DLX_{18}X_{19}X_{20}X_{21}X_{22}X_{23}LX_{25}X_{26}YLX_{29}X_{30}VA$ (SEQ ID NO: 12), wherein the peptides comprise one to two amino acids capable of cross-linking the peptide with another peptide. In certain embodiments, the amino acids capable of cross-linking the peptide with another peptide is capable of covalent cross-linking. Also provided are peptide dimers comprising a first peptide associated with a second peptide, wherein the first and second peptides each independently comprise a peptide of SEQ ID NO: 12, wherein the first and second peptides each comprises one to two amino acids cross-linking the first peptide with the second peptide. In certain embodiments, the peptide dimer is covalently cross-linked. $X_1$ is Gly, Arg, or an amino acid capable of cross-linking the peptide with another peptide. In certain embodiments, $X_1$ is absent from SEQ ID NO: 12. $X_3$, $X_4$, and $X_6$ are each independently a charged amino acid. $X_{10}$ is a charged amino acid. $X_{11}$ is a charged amino acid or an amino acid capable of cross-linking the peptide with another peptide. $X_7$ is Tyr or an amino acid capable of cross-linking the peptide with another peptide. $X_{13}$ is Ser, Pro, or an amino acid capable of cross-linking the peptide with another peptide. $X_{14}$ is Ile, Glu, or Val. $X_{15}$ is Glu, Asp, Gln, or Gly. $X_{18}$ is an aromatic or hydrophobic amino acid. $X_{19}$ is Glu, Asp, Gln, Ala, Trp, or Arg. $X_{20}$ is Tyr or Phe. $X_{21}$ is a Tyr, Phe, Trp, His, or an amino acid with a cyclohexyl side chain, wherein Tyr, Phe, Trp, cyclohexyl side chain can be substituted with one or more fluorines. $X_{22}$ is Ala, Gly, Ser, Val, or Asn. $X_{23}$ is Arg or Asp. $X_{25}$ is a Tyr, Phe, Trp, His, Gln, or an amino acid with a cyclohexyl side chain, wherein Tyr, Phe, Trp, cyclohexyl side chain can be substituted with one or more fluorines. $X_{26}$ is Asn, Leu, Ile, His, or Gln. $X_{29}$ is a Tyr, Phe, Trp, His, Asn, or an amino acid with a cyclohexyl side chain, wherein Tyr, Phe, Trp, cyclohexyl side chain can be substituted with one or more fluorines. $X_{30}$ is Ala, Arg, or Val.

In certain embodiments, provided herein are peptides comprising the sequence: $X_{-6}X_{-5}X_{-4}X_{-3}X_{-2}X_{-1}X_1PX_3X_4PX_6X_7PGX_{10}X_{11}AX_{13}X_{14}X_{15}X_{16}LX_{18}X_{19}X_{20}X_{21}X_{22}X_{23}LX_{25}X_{26}YLX_{29}X_{30}X_{31}X_{32}$ (SEQ ID NO: 13), wherein the peptides comprise one to two amino acids capable of cross-linking the peptide with another peptide. In certain embodiments, the amino acids capable of cross-linking the peptide with another peptide is capable of covalent cross-linking. Also provided are peptide dimers comprising a first peptide associated with a second peptide, wherein the first and second peptides each independently comprise a peptide of SEQ ID NO: 13, wherein the first and second peptides each comprises one to two amino acids cross-linking the first peptide with the second peptide. In certain embodiments, the peptide dimer is covalently cross-linked. $X_3$ and $X_4$ are each independently a neutral or charged amino acid. $X_6$ is a charged amino acid or an amino acid capable of cross-linking the peptide with another peptide. $X_7$ is Tyr, His, or an amino acid capable of cross-linking the peptide with another peptide. $X_{10}$ is Pro, charged amino acid, or an amino acid capable of cross-linking the peptide with another peptide. $X_{11}$ is Ala, Ser, neutral or charged amino acid, or an amino acid capable of cross-linking the peptide with another peptide. $X_{13}$ is Ser, Pro, Thr, or an amino acid capable of cross-linking the peptide with another peptide. $X_{14}$ is Ile, Glu, Val, Leu, or an amino acid capable of cross-linking the peptide with another peptide. $X_{15}$ is Glu, Lys, Arg, Ala, Ser, Asp, Gln, or Gly. $X_{16}$ is Asp, Glu, Gln, Ala, or Ser. $X_{18}$ is an aromatic or hydrophobic amino acid. $X_{19}$ is Glu, Lys, Leu, Met, His, Asp, Gln, Ala, Ser, Trp, or Arg. $X_{20}$ is Tyr or Phe. $X_{21}$ is Gln, Tyr, Phe, Trp, His, or an amino acid with a cyclohexyl side chain, wherein Tyr, Phe, Trp cyclohexyl side chain can be substituted with one or more fluorines. $X_{22}$ is Ala, Gln, Trp, Leu, Tyr, Gly, Ser, Val, or Asn. $X_{23}$ is Arg, Asp, Leu, or Ala. $X_{25}$ is Gln, Tyr, Phe, Trp, His, Asp, or an amino acid with a cyclohexyl side chain, wherein Tyr, Phe, Trp, cyclohexyl side chain can be substituted with one or more fluorines. $X_{26}$ is Asn, Ala, Leu, Arg, Phe, Ile, His, or Gln. $X_{29}$ is Ala, Leu, Glu, Asn, Gln, Tyr, Phe, Trp, His, or an amino acid with a cyclohexyl side chain, wherein Tyr, Phe, Trp, cyclohexyl side chain can be substituted with one or more fluorines. $X_{30}$ is Ala, Arg or Val. $X_{31}$ is V or an amino acid capable of cross-linking the peptide with another peptide. $X_{32}$ is V, Ala, Arg, Ser, or an amino acid capable of cross-linking the peptide with another peptide.

Optional residues of SEQ ID NO: 13 are $X_{-6}$, $X_{-5}$, $X_{-4}$, $X_{-3}$, $X_{-2}$, $X_{-1}$, and $X_1$. If $X_{-6}$ is present, then $X_{-6}$ is Gly and $X_{-5}$ to $X_1$ are present. If $X_{-5}$ is present, then $X_{-5}$ is Cys or Sec and $X_{-4}$ to $X_1$ are present. If $X_{-4}$ is present, then $X_{-4}$ is Gly and $X_{-3}$ to $X_1$ are present. If $X_{-3}$ is present, then $X_{-3}$ is Gly and $X_{-2}$ to $X_1$ are present. If $X_{-2}$ is present, then $X_{-2}$ is Pro, Cys, Sec, or Gly and $X_{-1}$ and $X_1$ are present. If $X_1$ is present, then $X_{-1}$ is Arg or Gly and $X_1$ is present. When $X_1$ is present, $X_1$ is Gly, Arg, or an amino acid capable of cross-linking the peptide with another peptide. Additional embodiments for $X_1$ are described herein.

In certain embodiments of SEQ ID NO: 13, $X_{-6}$ to $X_1$ are not present, $X_{11}$, $X_{15}$, $X_{16}$, $X_{19}$ are each Ala or Ser, $X_{18}$ is His, $X_{20}$ is Tyr, and $X_{26}$ is Asn. In certain embodiments of SEQ ID NO: 13, $X_{-6}$ to $X_1$ are not present, $X_{11}$, $X_{15}$, $X_{16}$, $X_{19}$ are each Ala, $X_{18}$ is His, $X_{20}$ is Tyr, and $X_{26}$ is Asn.

In certain embodiments, provided herein are peptides comprising the sequence: $X_1PX_3X_4PX_6X_7PGX_{10}AAX_{13}X_{14}AALHAYX_{21}AX_{23}LX_{25}NYLX_{29}X_{30}VX_{32}$ (SEQ ID NO: 48), wherein the peptides comprise one to two amino acids capable of cross-linking the peptide with another peptide. In certain embodiments, the amino acids capable of cross-linking the peptide with another peptide is capable of covalent cross-linking. $X_1$ is optionally present. When present, $X_1$ is Gly, Arg, or an amino acid capable of cross-linking the peptide with another peptide. $X_3$, $X_4$, and $X_6$ are each independently a neutral or positively charged amino acid. $X_7$ is Tyr or an amino acid capable of cross-linking the peptide with another peptide. $X_{10}$ is Asp or a neutral amino acid. $X_{13}$ is Ser, Thr or an amino acid capable of cross-linking the peptide with another peptide. $X_{14}$ is Ile or Leu. $X_{21}$, $X_{25}$, $X_{29}$ are each independently a Tyr, Phe, Trp, His, or an amino acid with a cyclohexyl side chain, wherein Tyr, Phe, Trp, cyclohexyl side chain can be substituted with one or more fluorines. $X_{23}$ is Arg, Leu or Ala. $X_{30}$ is Ala or Arg. $X_{32}$ is Ala, Ser, or Arg.

In certain embodiments, provided are peptides comprising the sequence of SEQ ID NO: 48 except one or more Ala at positions 11, 15, 16, and 19 are replaced with Ser.

In certain embodiments, the peptide dimer is a homodimer. In certain embodiments, the peptide dimer is a heterodimer. In certain embodiments, the peptide dimer is a dimer though covalent cross-linking. For example, Cys, Sec, Dap modified with acrylic acid or Dab modified with acrylic acid are used as covalent cross-linkers. Other amino acids comprising an acrylamide, vinyl sulfonamide, iodoacetamide moieties, or other known Michael acceptors would be useful for cross-linking. In certain embodiments, the peptide dimer is a dimer though non-covalent cross-linking. For example, His, Tyr, Phe, or Trp are used as non-covalent cross-linkers.

In certain embodiments, the peptides do not comprise a sequence of SEQ ID NO: 7. In certain embodiments, the peptide monomer cannot homodimerize with the same peptide monomer but can heterodimerize with a different peptide monomer. This can be accomplished, for example, with the use of a "bump-hole" system whereby a residue in one peptide cannot be accommodated in a dimer with the same peptide (e.g., due to steric or otherwise unfavorable interaction), but can be accommodated in a dimer with a second peptide. The same would be true for the second peptide; in this way, neither peptide can form a homodimer but are able to heterodimerize.

Exemplary peptide monomers include, but are not limited to:

```
RDA1:
                                        (SEQ ID NO: 4)
GPRRPRCPGDDASIEDLHEYWARLWNYLYAVA,

RDA2:
                                        (SEQ ID NO: 5)
GPRRPRCPGDDASIEDLHEYWARLWNYLYRVA,

RDA3:
                                        (SEQ ID NO: 6)
GRRPRRPRCPGDDASIEDLHEYWARLWNYLYAVA, aPP-M:
                                        (SEQ ID NO: 7)
GPRRPRVPGDDAPVEDLIRFYNDLQQYLNVVA, 225-1:
                                        (SEQ ID NO: 8)
GCGGPRRPRYPGDDASIEDLHEYWARLWNYLYAVA, 225-1 S13C/I14E:
                                        (SEQ ID NO: 9)
GCGGPRRPRYPGDDACEEDLHEYWARLWNYLYAVA, 225-1 A30R:
                                        (SEQ ID NO: 10)
GCGGPRRPRYPGDDASIEDLHEYWARLWNYLYRVA, 225-3:
                                        (SEQ ID NO: 11)
GCGGPRRPRRPRYPGDDASIEDLHEYWARLWNYLYAVA, (SEQ ID NO: 14)
PRRPRCPGDDASIEDLHEYWARLWNYLYAVA, (SEQ ID NO: 15)
PRRPRCPGDDASIEDLHEYWARLWNYLYRVA, (SEQ ID NO: 16)
RRPRRPRCPGDDASIEDLHEYWARLWNYLYAVA, (SEQ ID NO: 17)
PRRPRYPGDDAPVEDLIRFYNDLQQYLNVVA, (SEQ ID NO: 18)
PRRPRYPGDDASIEDLHEYWARLWNYLYAVA (SEQ ID NO: 19)
CGGPRRPRYPGDDACEEDLHEYWARLWNYLYAVA (SEQ ID NO: 20)
PRRPRYPGDDASIEDLHEYWARLWNYLYRVA (SEQ ID NO: 21)
PRRPRRPRYPGDDASIEDLHEYWARLWNYLYAVA (SEQ ID NO: 22)
PRRPRCPGDDASLEDLHEYWARLWNYLYRVA, (SEQ ID NO: 23)
PRRPRCPGDQASLEELHEYWARLWNYLYRVA, (SEQ ID NO: 24)
PRRPRCPGDNASIKQLHAYWNRLYAYLAAVA, (SEQ ID NO: 25)
PRRPRCPGDDASIEDLHEYWQRLYAYLAAVA, (SEQ ID NO: 26)
PRRPRCPGDNASIKQLHAYWQRLYAYLAAVA, (SEQ ID NO: 27)
PRRPRCPGDNASIRQLHAYWQRLYAYLAAVA, (SEQ ID NO: 28)
GCGGPRRPRYPGDAASIAALHAYWARLWNYLYRVA,
```

-continued

225-H:
PRRPRYPGDAASIAALHAYWARLWNYLYRVA, (SEQ ID NO: 29)

225-I:
PRRPKYPGDAASCAALHAYWARLWNYLYRVA, (SEQ ID NO: 30)

225-J:
PRRPRYPGDAASIAALHAYWARLWNYLYRXA, (SEQ ID NO: 31)

225-K:
PRRPRYPGDAASIAALHAYWARLWNYLYRZA, (SEQ ID NO: 32)

225-L:
PRRPCYPGDAASIAALHAYWARLWNYLYRVA, (SEQ ID NO: 33)

225-M:
PRRPKCPGDAASIAALHAYWARLWNYLYRVA, (SEQ ID NO: 34)

225-N:
PRRPRYPGXAASIAALHAYWARLWNYLYRVA, (SEQ ID NO: 35)

225-4s1:
PRRPRYPGZAASIAALHAYWARLWNYLYRVA, (SEQ ID NO: 36)

291-A:
PRRPKYPGDAASIAALHAYWARLWNYLYRVR, (SEQ ID NO: 37)

291-1:
PRRPKHPGHAASIAALHAYWARLWNYLYRVR, (SEQ ID NO: 38)

291-H:
PRRPRHPGPNATISQLHHYWARLWNYLYRVR, (SEQ ID NO: 39)

291-I:
PRRPHHPGHAASIAALHAYWARLWNYLYRVR, (SEQ ID NO: 40)

291-Q3:
PRRPHYPGHAASIAALHAYWARLWNYLYRVR, (SEQ ID NO: 41)

MY01:
PRRPRCPGHAASIAALHAYWARLWNYLYRVR, (SEQ ID NO: 42)

RL01:
GPRRPRCPGDDASIRDLLKYWRLRLYLLAVA, (SEQ ID NO: 43)

RR01:
GPRRPRCPGDDASISDLLLYWLRLDRYLWAVA, (SEQ ID NO: 44)

225-1c:
GPRRPRCPGDDASIRDLVMYWYRLYFYLEAVA, (SEQ ID NO: 45)

225-4d:
PRRPKYPGDAASIAALHAYWARLWNYLYRVS, (SEQ ID NO: 46)

291-T:
RPRRPKYPGDAASIAALHAYWARLWNYLYRVS, (SEQ ID NO: 47)

Q:
PRRPRYPGDAASIAALHAYWARLWNYLYRVS, (SEQ ID NO: 49)

-continued

PRRPRCPGDNASIRQLHAYWQRLYAYLAAVA, (SEQ ID NO: 50)
and

R:
PRRPRCPGDAASIAALHAYWQRLYAYLAAVA. (SEQ ID NO: 51)

In certain embodiments, the peptides comprises an inter-monomer cross-linking amino acid for the purpose of stabilizing the dimer. The inter-monomer cross-linking amino acid can be at any position of SEQ ID NO: 1 or 96, 12, 13 or 48. In certain embodiments, the peptides comprises an inter-monomer cross-linking amino acid at position 1 of SEQ ID NO: 1 or 96, 12, 13 or 48. In certain embodiments, the peptides comprises an inter-monomer cross-linking amino acid at position 6 of SEQ ID NO: 1 or 96, 12, 13 or 48. In certain embodiments, the peptides comprises an inter-monomer cross-linking amino acid at position 7 of SEQ ID NO: 1 or 96, 12, 13 or 48. In certain embodiments, the peptides comprises an inter-monomer cross-linking amino acid at position 10 of SEQ ID NO: 1 or 96, 12, 13 or 48. In certain embodiments, the peptides comprises an inter-monomer cross-linking amino acid at position 11 of SEQ ID NO: 1 or 96, 12, 13 or 48. In certain embodiments, the peptides comprises an inter-monomer cross-linking amino acid at position 13 of SEQ ID NO: 1 or 96, 12, 13 or 48. In certain embodiments, the peptides comprises an inter-monomer cross-linking amino acid at position 31 of SEQ ID NO: 1 or 96, 12, 13 or 48. In certain embodiments, the peptides comprises an inter-monomer cross-linking amino acid at position 32 of SEQ ID NO: 1 or 96, 12, 13 or 48.

In certain embodiments, a cross-linking amino acid at a specific position of SEQ ID NO: 1 or 96, 12, 13 or 48 in a first peptide would crosslink to a cross-linking amino acid at the same position of a second peptide. In certain embodiments, a cross-linking amino acid at a specific position of SEQ ID NO: 1 or 96, 12, 13 or 48 in a first peptide would crosslink to a cross-linking amino acid at a different position of a second peptide. In certain embodiments, a cross-linking amino acid at position 7 of SEQ ID NO: 1 or 96, 12, 13 or 48 in a first peptide would crosslink to a cross-linking amino acid at position 7 of a second peptide. In certain embodiments, a cross-linking amino acid at position 1 of SEQ ID NO: 1 or 96, 12, 13 or 48 in a first peptide would crosslink to a cross-linking amino acid at positions 11 or 13 of a second peptide.

In certain embodiments, the peptides comprises an inter-monomer cross-linking amino acid at position ~2 of SEQ ID NO: 1 or 96, 12, 13, or 48. In certain embodiments, a cross-linking amino acid at position ~2 of SEQ ID NO: 1 or 96, 12, 13 or 48 in a first peptide would crosslink to a cross-linking amino acid at positions 11 or 13 of a second peptide.

In certain embodiments, inter-monomer cross-linking amino acid is a cysteine. In certain embodiments, inter-monomer cross-linking amino acid is a selenocysteine. In certain embodiments, inter-monomer cross-linking amino acid is an amino acid capable of forming a disulfide bond. In certain embodiments, inter-monomer cross-linking amino acid is an amino acid capable of forming a diselenide bond. In certain embodiments, inter-monomer cross-linking amino acid is an amino acid capable of forming a bond with a Cys or Sec. For example, electrophilic moieties such as those with acrylamide, vinyl sulfonamide, iodoacetamide moieties, or other known Michael acceptors.

Peptide properties to be improved include binding affinity, stability, and cell permeability and can be accomplished, for example, by mutating one or more amino acid residues in one or more peptide domains. The peptides can be made cell permeable by conjugation to a cell-penetrating peptide (such as TAT, antennapedia, transportan, and polyarginine) or to a stapled peptide. Other methods of improving peptide properties are known to those skilled in the art such as ligating the peptides to other drugs such as a drug-antibody conjugate, which are useful, for example, for tissue-specific targeting purposes or increasing potency or ligating the peptides to polyethylene glycol or similar molecules to improve half-life and slow renal clearance. In certain embodiments, the polyproline type-II helix domain has been engineered to have improved properties. In certain embodiments, the loop/linker domain has been engineered to have improved properties. In certain embodiments, the loop/linker domain is a type-I beta-turn. In certain embodiments, the C-terminal alpha-helix domain has been engineered to have improved properties. In certain embodiments, the charge on the peptide has been engineered to improve cell permeability. For example, the number of negatively charged (Asp, Glu) residues would be decreased, the number of positively charged (Arg, Lys, His) residues would be increased, and/or the number of hydrophobic (Tyr, Trp, Phe, Leu, Ile, Met) residues. As further disclosed herein, in certain embodiments, certain residues of the peptides are mutated to Ala and/or Ser. For example, at least one, two, three, or four residues selected from $X_{11}$, $X_{15}$, $X_{16}$, and $X_{19}$ can be mutated to Ala and/or Ser. In certain embodiments, negatively charged residues are mutated to Ala and/or Ser. In certain embodiments, at least one, two, three, or four negatively charged residues residues at positions $X_{11}$, $X_{15}$, $X_{16}$, and $X_{19}$ are mutated to Ala and/or Ser. In certain embodiments, the peptide's ability to bind serum proteins has been engineered to improve pharmacokinetics. In certain embodiments, the peptide is delivered using nanoparticles.

In certain embodiments, the peptide's ability to bind a second target has been engineered to recruit the second target to Ras. A peptide or peptide library would have residues mutated or randomized on the PPII helix, the loop, and/or the the part of the alpha helix not involved in binding to the first target. Mutated or randomized residues can be used for both the first or the second monomer of a heterodimer. In certain embodiments, the loop/linker domain is a type-I beta-turn. In certain embodiments, the peptides used herein are useful for selective tissue targeting. Examples of a second target include serum proteins such as serum albumin and serum retinoid binding protein, recycling receptors that are targets for ADC conjugation such as CD-20, transferrin receptor and insulin receptor for tissue targeting, the liver GalNAc receptor for liver delivery, and the Neonatal Fc receptor.

The first peptide and the second peptide can be associated covalently. The first peptide and the second peptide can also be associated non-covalently. Any covalent bond or non-covalent interaction may be used to form the dimer. In certain embodiments, the first peptide and the second peptide are associated through a disulfide bond, diselenide bond, carbon-carbon bond, amide bond, ester bond, hydrogen bond, salt bridge, pi stacking interaction, or non-polar hydrophobic interaction. In certain embodiments, the first peptide and the second peptide is associated through a disulfide bond. In certain embodiments, the first peptide and the second peptide is associated through a diselenide bond. In certain embodiments, the first peptide and the second peptide is associated through a carbon-carbon bond, amide bond, ester bond, hydrogen bond, salt bridge, pi stacking interaction, or non-polar hydrophobic interaction.

The peptides can each comprise one amino acid capable of cross-linking the peptide with another peptide. The peptides can each comprise two amino acids capable of cross-linking the peptide with another peptide. The peptide dimers can comprise a first and a second peptide, each comprising one amino acid cross-linking the first peptide with the second peptide. The peptide dimers can comprise a first and a second peptide, each comprising two amino acids cross-linking the first peptide with the second peptide. In certain embodiments the cross-links are covalent. In certain embodiments the cross-links are non-covalent.

In certain embodiments, $X_1$ is an amino acid capable of cross-linking the first peptide with the second peptide. In certain embodiments, $X_1$ is an amino acid cross-linking a first peptide with a second peptide. In certain embodiments, $X_1$ is a natural or non-natural amino acid capable of cross-linking the peptide with another peptide. In certain embodiments, $X_1$ is a natural or non-natural amino acid cross-linking the first peptide with the second peptide. In certain embodiments, $X_1$ is Cys, Sec, Phe, Trp, or Tyr. In certain embodiments, $X_1$ is Cys, Sec. In certain embodiments, $X_1$ is Cys. In certain embodiments, $X_1$ is Sec. In certain embodiments, $X_1$ is Phe, Trp, or Tyr.

In certain embodiments, each of $X_3$, $X_4$, and $X_6$ is independently a charged amino acid. In certain embodiments, each of $X_3$, $X_4$, and $X_6$ is independently a basic amino acid with a charged side chain. In certain embodiments, each of $X_3$, $X_4$, and $X_6$ is independently a positively charged amino acid. In certain embodiments, each of $X_3$, $X_4$, and $X_6$ is independently Arg, Lys, or His. In certain embodiments, each of $X_3$, $X_4$, and $X_6$ is independently Arg. In certain embodiments, each of $X_3$, $X_4$, and $X_6$ is independently Lys. In certain embodiments, each of $X_3$, $X_4$, and $X_6$ is independently His. In certain embodiments, each of $X_3$, $X_4$, and $X_6$ can be the same or different amino acids. In certain embodiments, each of $X_3$, $X_4$, and $X_6$ are the same amino acids. In certain embodiments, each of $X_3$, $X_4$, and $X_6$ are the different amino acids. In certain embodiments, each of $X_3$, $X_4$, and $X_6$ is an amino acid that provides stability such as through electrostatic effects with other amino acids within the peptide or with amino acids in another peptide. In certain embodiments, $X_3$, $X_4$, and $X_6$ are each independently a negatively charged amino acid. In certain embodiments, each of $X_3$, $X_4$, and $X_6$ is independently Asp or Glu.

In certain embodiments, $X_6$ is an amino acid capable of cross-linking the peptide with another peptide. In certain embodiments, $X_6$ is a natural or non-natural amino acid capable of cross-linking the peptide with another peptide. In certain embodiments, $X_6$ is a natural or non-natural amino acid cross-linking the first peptide with the second peptide. In certain embodiments, $X_6$ is Cys, Sec, Phe, Trp, or Tyr. In certain embodiments, $X_6$ is Cys or Sec. In certain embodiments, $X_6$ is Cys. In certain embodiments, $X_6$ is Sec. In certain embodiments, $X_6$ is Phe, Trp, or Tyr.

In certain embodiments, $X_6$ is Cys or Sec; and $X_7$ is Tyr.

In certain embodiments, $X_7$ is Tyr or an amino acid capable of cross-linking the first peptide with the second peptide. In certain embodiments, $X_7$ is Tyr, His, or an amino acid capable of cross-linking the first peptide with the second peptide. In certain embodiments, $X_7$ is Tyr. In certain embodiments, $X_7$ is His. In certain embodiments, $X_7$ is an amino acid cross-linking a first peptide with a second peptide. In certain embodiments, $X_7$ is a natural or non-natural amino acid capable of cross-linking the peptide with another peptide. In certain embodiments, $X_7$ is a natural or non-natural amino acid cross-linking the first peptide with the second peptide. In certain embodiments, $X_7$ is a positively or negatively charged amino acid. In certain embodiments, $X_7$ is Cys, Sec, Phe, Trp, or Tyr. In certain embodiments, $X_7$ is Cys, Sec, Tyr, or His. In certain embodiments, $X_7$ is Cys. In certain embodiments, $X_7$ is Sec. In certain embodiments, $X_7$ is Phe, Trp, or Tyr. In certain embodiments, $X_7$ is Y and $X_6$ is Cys or Sec.

In certain embodiments, $X_{10}$ is an amino acid with a charged side chain. In certain embodiments, $X_{10}$ is a negatively charged amino acid. In certain embodiments, $X_{10}$ is Glu or Asp. In certain embodiments, $X_{10}$ is Glu, Asp, or Ala. In certain embodiments, $X_{10}$ is Glu. In certain embodiments, $X_{10}$ is Asp. In certain embodiments, $X_{10}$ is Ala. In certain embodiments, $X_{10}$ is a positively charged amino acid. In certain embodiments, $X_{10}$ is Arg, His, or Lys. In certain embodiments, $X_{10}$ is Asp, His, or Pro. In certain embodiments, $X_{10}$ is Asp, His, Pro, or an amino acid comprising an acrylamide moiety. In certain embodiments, $X_{10}$ is Arg. In certain embodiments, $X_{10}$ is His. In certain embodiments, $X_{10}$ is Lys. In certain embodiments, $X_{10}$ is Pro. In certain embodiments, $X_{10}$ is an amino acid comprising an acrylamide moiety. In certain embodiments, the amino acid comprising an acrylamide moiety is Dab- and Dap-conjugated acrylamide residues In certain embodiments, $X_{10}$ is an amino acid capable of cross-linking the peptide with another peptide. In certain embodiments, $X_{10}$ is a natural or non-natural amino acid capable of cross-linking the peptide with another peptide. In certain embodiments, $X_{10}$ is a natural or non-natural amino acid cross-linking the first peptide with the second peptide. In certain embodiments, $X_{10}$ is Cys, Sec, Phe, Trp, or Tyr. In certain embodiments, $X_{10}$ is Cys. In certain embodiments, $X_{10}$ is Sec. In certain embodiments, $X_{10}$ is Phe, Trp, or Tyr. In certain embodiments, $X_{10}$ is L-2,4-diaminobutyric acid (Dab) conjugated to acrylamide or L-2,3-diaminopropionic acid (Dap) conjugated to acrylamide, as described further herein.

In certain embodiments, $X_{11}$ is an amino acids with a charged side chains. In certain embodiments, $X_{11}$ is a negatively charged amino acid. In certain embodiments, $X_{11}$ is Glu or Asp. In certain embodiments, $X_{11}$ is Glu. In certain embodiments, $X_{11}$ is Asp. In certain embodiments, $X_{11}$ is a positively charged amino acid. In certain embodiments, $X_{11}$ is Arg, His, or Lys. In certain embodiments, $X_{11}$ is Arg. In certain embodiments, $X_{11}$ is His. In certain embodiments, $X_{11}$ is Lys. In certain embodiments, $X_{11}$ is neutral amino acid. In certain embodiments, $X_{11}$ is an amino acid with hydrophobic side chain. In certain embodiments, $X_{11}$ is Asp, Gln, Asn, Ala, or Ser. In certain embodiments, $X_{11}$ is Ala, Ile, Leu, Val. In certain embodiments, $X_{11}$ is Ala. In certain embodiments, $X_{11}$ is Ser. In certain embodiments, $X_{11}$ is Asp or Ala. In certain embodiments, $X_{11}$ is Asp or an amino acid capable of cross-linking the first peptide with the second peptide. In certain embodiments, $X_{11}$ is Asp. In certain embodiments, $X_{11}$ is an amino acid cross-linking a first peptide with a second peptide. In certain embodiments, $X_{11}$ is a natural or non-natural amino acid capable of cross-linking the peptide with another peptide. In certain embodiments, $X_{11}$ is a natural or non-natural amino acid cross-linking the first peptide with the second peptide. In certain embodiments, $X_{11}$ is Cys, Sec, Phe, Trp, or Tyr. In certain embodiments, $X_{11}$ is Cys. In certain embodiments, $X_{11}$ is Sec. In certain embodiments, $X_{11}$ is Phe, Trp, or Tyr.

In certain embodiments, $X_{13}$ is Ser, Pro, or Thr. In certain embodiments, $X_{13}$ is Ser. In certain embodiments, $X_{13}$ is Pro. In certain embodiments, $X_{13}$ is Thr or Ala. In certain embodiments, $X_{13}$ is an amino acid capable of cross-linking the first peptide with the second peptide. In certain embodiments, $X_{13}$ is an amino acid cross-linking a first peptide with a second peptide. In certain embodiments, $X_{13}$ is a natural or non-natural amino acid capable of cross-linking the peptide with another peptide. In certain embodiments, $X_{13}$ is a natural or non-natural amino acid cross-linking the first peptide with the second peptide. In certain embodiments, $X_{13}$ is Cys, Sec, Phe, Trp, or Tyr. In certain embodiments, $X_{13}$ is Cys. In certain embodiments, $X_{13}$ is Sec. In certain embodiments, $X_{13}$ is Phe, Trp, or Tyr.

In certain embodiments, $X_{14}$ is Ile or Glu. In certain embodiments, $X_{14}$ is Ile. In certain embodiments, $X_{14}$ is Glu. In certain embodiments, $X_{14}$ is Leu or Asp. certain embodiments, $X_{14}$ is Ile, Val, Glu, Leu, or an amino acid cross-linking a first peptide with a second peptide. In certain embodiments, $X_{14}$ is Cys. In certain embodiments, $X_{14}$ is Sec.

In certain embodiments, $X_{15}$ is Glu, Asp, Gln, or Gly. In certain embodiments, $X_{15}$ is Glu, Lys, Arg, Ser, Asp, Gln, Gly, or Ala. In certain embodiments, $X_{15}$ is Glu. In certain embodiments, $X_{15}$ is Asp. In certain embodiments, $X_{15}$ is Gln. In certain embodiments, $X_{15}$ is Gly. In certain embodiments, $X_{15}$ is Ala.

In certain embodiments, $X_{16}$ is Asp, Glu, Gln, Ala, or Ser. In certain embodiments, $X_{16}$ is Asp. In certain embodiments, $X_{16}$ is Glu. In certain embodiments, $X_{16}$ is Gln. In certain embodiments, $X_{16}$ is Ala. In certain embodiments, $X_{16}$ is Ser.

In certain embodiments, $X_{18}$ is an aromatic amino acid. In certain embodiments, $X_{18}$ is a hydrophobic amino acid. In certain embodiments, $X_{18}$ is His, Phe, Tyr, Trp, Ala, Val, Leu, Ile, or Met. In certain embodiments, $X_{18}$ is His. In certain embodiments, $X_{18}$ is Phe, Tyr, or Trp. In certain embodiments, $X_{18}$ is Ala, Val, Leu, Ile, or Met. In certain embodiments, $X_{18}$ is Ala, Val, Leu, or Ile. In certain embodiments, $X_{18}$ is Met. In certain embodiments, $X_{18}$ is Ala. In certain embodiments, $X_{18}$ is Val. In certain embodiments, $X_{18}$ is Leu. In certain embodiments, $X_{18}$ is Ile.

In certain embodiments, $X_{19}$ is Glu, Asp, Gln, Ala, or Trp. In certain embodiments, $X_{19}$ is Glu, Asp, Gln, Ala, Ser, Trp, Arg, Lys, Leu, Met, or His. In certain embodiments, $X_{19}$ is Glu, Asp, Gln, Ala, Trp, Arg, or His. In certain embodiments, $X_{19}$ is Glu. In certain embodiments, $X_{19}$ is Asp. In certain embodiments, $X_{19}$ is Gln. In certain embodiments, $X_{19}$ is Ala. In certain embodiments, $X_{19}$ is Ser. In certain embodiments, $X_{19}$ is Trp. In certain embodiments, $X_{19}$ is Arg. In certain embodiments, $X_{19}$ is Lys. In certain embodiments, $X_{19}$ is Leu. In certain embodiments, $X_{19}$ is Met. In certain embodiments, $X_{19}$ is His.

In certain embodiments, $X_{20}$ is Tyr or Phe. In certain embodiments, $X_{20}$ is Tyr. In certain embodiments, $X_{20}$ is Phe.

In certain embodiments, $X_{21}$, $X_{25}$, and $X_{29}$ are each a hydrophobic and/or large amino acid. In certain embodiments, $X_{21}$ is Trp. In certain embodiments, $X_{21}$ is Tyr. In certain embodiments, $X_{21}$ is Phe. In certain embodiments, $X_{21}$ is His. In certain embodiments, $X_{21}$ is Gln. In certain embodiments, $X_{25}$ is Trp. In certain embodiments, $X_{25}$ is Tyr. In certain embodiments, $X_{25}$ is His. In certain embodiments, $X_{25}$ is Phe. In certain embodiments, $X_{25}$ is His. In certain embodiments, $X_{29}$ is Tyr. In certain embodiments, $X_{29}$ is Trp. In certain embodiments, $X_{29}$ is Phe. In certain embodiments, $X_{29}$ is His. In certain embodiments, each of $X_{21}$, $X_{25}$, $X_{29}$ can independently be Tyr, Trp, Phe, His, or an amino acid with a cyclohexyl side chain, wherein Tyr, Phe, Trp, or the cyclohexyl side chain is optionally fluorinated. In certain embodiments, $X_{25}$ is Tyr, Phe, Trp, His, Gln, Arg, or Asp. In certain embodiments, $X_{29}$ is Tyr, Phe, Trp, His, Gln, Arg, Asp, Asn, Ala, Leu, or Glu.

In certain embodiments, $X_{22}$ is a small amino acid. In certain embodiments, $X_{22}$ is Ala. In certain embodiments, $X_{22}$ is Gly, Ser, or Val. In certain embodiments, $X_{22}$ is Gly, Ser, Val, or Asn. In certain embodiments, $X_{22}$ is Gly. In certain embodiments, $X_{22}$ is Ser. In certain embodiments, $X_{22}$ is Val. In certain embodiments, $X_{22}$ is Ala, Gly, Ser, Val, Asn, Gln, Trp, Leu, or Tyr In certain embodiments, $X_{23}$ is Arg or Asp. In certain embodiments, $X_{26}$ is Asn, Leu, Ile, or His. In certain embodiments, $X_{26}$ is Asn, Leu, Ile, His, Gln, Arg, Phe, or Ala. In certain embodiments, $X_{26}$ is Asn. In certain embodiments, $X_{26}$ is Leu. In certain embodiments, $X_{26}$ is Ile. In certain embodiments, $X_{26}$ is His.

In certain embodiments, $X_{30}$ is Ala or Arg. In certain embodiments, $X_{30}$ is Ala, Arg, or Val. In certain embodiments, $X_{30}$ is Arg. In certain embodiments, $X_{30}$ is Ala. In certain embodiments, $X_{30}$ is Val.

In certain embodiments, $X_{31}$ is an amino acid capable of cross-linking the peptide with another peptide. In certain embodiments, $X_{31}$ is a natural or non-natural amino acid capable of cross-linking the peptide with another peptide. In certain embodiments, $X_{31}$ is a natural or non-natural amino acid cross-linking the first peptide with the second peptide. In certain embodiments, $X_{31}$ is Val or an amino acid capable of cross-linking the peptide with another peptide. In certain embodiments, $X_{31}$ is Cys, Sec, Phe, Trp, or Tyr. In certain embodiments, $X_{31}$ is Cys. In certain embodiments, $X_{31}$ is Sec. In certain embodiments, $X_{31}$ is Phe, Trp, or Tyr. In certain embodiments, $X_{31}$ is Dap-conjugated acrylamide. In certain embodiments, $X_{31}$ is Dab-conjugated acrylamide.

In certain embodiments, $X_{32}$ is Ala, Arg, Ser. In certain embodiments, $X_{32}$ is Ala. In certain embodiments, $X_{32}$ is Arg. In certain embodiments, $X_{32}$ is Ser. In In certain embodiments, $X_{32}$ is an amino acid capable of cross-linking the peptide with another peptide. In certain embodiments, $X_{32}$ is a natural or non-natural amino acid capable of cross-linking the peptide with another peptide. In certain embodiments, $X_{32}$ is a natural or non-natural amino acid cross-linking the first peptide with the second peptide. In certain embodiments, $X_{32}$ is Cys, Sec, Phe, Trp, or Tyr. In certain embodiments, $X_{32}$ is Cys. In certain embodiments, $X_{32}$ is Sec. In certain embodiments, $X_{32}$ is Phe, Trp, or Tyr. In certain embodiments, $X_{32}$ is Arg or Ala. In certain embodiments, $X_{32}$ is Dab- or Dap-conjugated acrylamide.

In certain embodiments, the peptide comprises a sequence that is about 80% to about 99% homologous to the amino acid sequences provided herein. In certain embodiments, the peptide comprises a sequence that is about 84% to about 99% homologous to the amino acid sequences provided herein. In certain embodiments, the peptide comprises a sequence that is about 87% to about 99% homologous to the amino acid sequences provided herein. In certain embodiments, the peptide comprises a sequence that is about 90% to about 99% homologous to the amino acid sequences provided herein. In certain embodiments, the peptide comprises a sequence that is about 93% to about 99% homologous to the amino acid sequences provided herein. In certain embodiments, the peptide comprises a sequence that is at least about 80%, 85%, 90%, 95%, 98%, or 99% homologous to the amino acid sequences provided herein.

In certain embodiments, the peptide comprises a sequence that is about 80% to about 99% identical to the amino acid sequences provided herein. In certain embodiments, the peptide comprises a sequence that is about 84% to about 99% identical to the amino acid sequences provided herein. In certain embodiments, the peptide comprises a sequence that is about 87% to about 99% identical to the amino acid sequences provided herein. In certain embodiments, the peptide comprises a sequence that is about 90% to about 99% identical to the amino acid sequences provided herein. In certain embodiments, the peptide comprises a sequence that is about 93% to about 99% identical to the amino acid sequences provided herein. In certain embodiments, the peptide comprises a sequence that is at least about 80%, 85%, 90%, 95%, 98%, or 99% identical to the amino acid sequences provided herein.

In certain embodiments, the peptide comprises a sequence that is about 80% to about 99% homologous to the amino acid sequence of SEQ ID NO: 1 or 96. In certain embodiments, the peptide comprises a sequence that is about 85% to about 99% homologous to the amino acid sequence of SEQ ID NO: 1 or 96. In certain embodiments, the peptide comprises a sequence that is about 90% to about 99% homologous to the amino acid sequence of SEQ ID NO: 1 or 96. In certain embodiments, the peptide comprises a sequence that is about 95% to about 99% homologous to the amino acid sequence of SEQ ID NO: 1 or 96. In certain embodiments, the peptide comprises a sequence that is about 97% to about 99% homologous to the amino acid sequence of SEQ ID NO: 1 or 96. In certain embodiments, the peptide comprises a sequence that is about 98% to about 99% homologous to the amino acid sequence of SEQ ID NO: 1 or 96. In certain embodiments, the peptide comprises a sequence that is at least about 80%, 85%, 90%, 95%, 98%, or 99% homologous to the amino sequence of SEQ ID NO: 1 or 96. The foregoing values are applicable to SEQ ID NO: 12, 13, and 48.

In certain embodiments, the peptide comprises a sequence that is about 80% to about 99% identical to the amino acid sequence of SEQ ID NO: 1 or 96. In certain embodiments, the peptide comprises a sequence that is about 84% to about 99% identical to the amino acid sequence of SEQ ID NO: 1 or 96. In certain embodiments, the peptide comprises a sequence that is about 87% to about 99% identical to the amino acid sequence of SEQ ID NO: 1 or 96. In certain embodiments, the peptide comprises a sequence that is about 90% to about 99% identical to the amino acid sequence of SEQ ID NO: 1 or 96. In certain embodiments, the peptide comprises a sequence that is about 93% to about 99% identical to the amino acid sequence of SEQ ID NO: 1 or 96. In certain embodiments, the peptide comprises a sequence that is about 96% to about 99% identical to the amino acid sequence of SEQ ID NO: 1 or 96. In certain embodiments, the peptide comprises a sequence that is at least about 80%, 84%, 87%, 90%, 93%, or 96% identical to the amino sequence of SEQ ID NO: 1 or 96. The foregoing values are applicable to SEQ ID NO: 12, 13, and 48.

In certain embodiments, the peptide comprises a sequence that differs from the amino acid sequence of SEQ ID NO: 1 or 96 by 1, 2, 3, 4, 5, 6, 7, 8, 9, or 10 amino acids. In certain embodiments, the peptide comprises a sequence that differs from the amino acid sequence of SEQ ID NO: 1 or 96 by 1 amino acid. In certain embodiments, the peptide comprises a sequence that differs from the amino acid sequence of SEQ ID NO: 1 or 96 by 2 amino acids. In certain embodiments, the peptide comprises a sequence that differs from the amino acid sequence of SEQ ID NO: 1 or 96 by 3 amino acids. In certain embodiments, the peptide comprises a sequence that differs from the amino acid sequence of SEQ ID NO: 1 or 96 by 4 amino acids. In certain embodiments, the peptide comprises a sequence that differs from the amino acid sequence of SEQ ID NO: 1 or 96 by 5 amino acids. In certain embodiments, the peptide comprises a sequence that differs from the amino acid sequence of SEQ ID NO: 1 or 96 by 6 amino acids. In certain embodiments, the peptide comprises a sequence that differs from the amino acid sequence of SEQ ID NO: 1 or 96 by 7 amino acids. In certain embodiments, the peptide comprises a sequence that differs from the amino acid sequence of SEQ ID NO: 1 or 96 by 8 amino acids. In certain embodiments, the peptide comprises a sequence that differs from the amino acid sequence of SEQ ID NO: 1 or 96 by 9 amino acids. In certain embodiments, the peptide comprises a sequence that differs from the amino acid sequence of SEQ ID NO: 1 or 96 by 10 amino acids. The foregoing differences are also applicable to SEQ ID NO: 12, 13, and 48.

In certain embodiments, the peptide comprises a sequence of GPRRPRCPGDDASIEDLHEYWARLWNYLYAVA (SEQ ID NO: 4). In certain embodiments, the peptide comprises a sequence of GPRRPRCPGDDASIEDLHEYWARLWNYLYRVA (SEQ ID NO: 5). In certain embodiments, the peptide comprises a sequence of GRRPRRPRCPGDDASIEDLHEYWARLWNYLYAVA (SEQ ID NO: 6). In certain embodiments, the peptide comprises a sequence of GPRRPRYPGDDAPVEDLIRFYNDLQQYLNVVA (SEQ ID NO: 7). In certain embodiments, the peptide comprises a sequence of GCGGPRRPRYPGDDASIEDLHEYWARLWNYLYAVA (SEQ ID NO: 8). In certain embodiments, the peptide comprises a sequence of GCGGPRRPRYPGDDACEEDLHEYWARLWNYLYAVA (SEQ ID NO: 9). In certain embodiments, the peptide comprises a sequence of GCGGPRRPRYPGDDASIEDLHEYWARLWNYLYRVA (SEQ ID NO: 10). In certain embodiments, the peptide comprises a sequence of GCGGPRRPRRPRYPGDDASIEDLHEYWARLWNYLYAVA (SEQ ID NO: 11). In certain embodiments, the peptide comprises a sequence of SEQ ID NO: 14-51.

In certain embodiments, the peptide comprises a sequence that is about 80% to about 99% homologous to the amino acid sequence of SEQ ID NO: 4. In certain embodiments, the peptide comprises a sequence that is about 85% to about 99% homologous to the amino acid sequence of SEQ ID NO: 4. In certain embodiments, the peptide comprises a sequence that is about 90% to about 99% homologous to the amino acid sequence of SEQ ID NO: 4. In certain embodiments, the peptide comprises a sequence that is about 95% to about 99% homologous to the amino acid sequence of SEQ ID NO: 4. In certain embodiments, the peptide comprises a sequence that is about 97% to about 99% homologous to the amino acid sequence of SEQ ID NO: 4. In certain embodiments, the peptide comprises a sequence that is about 98% to about 99% homologous to the amino acid sequence of SEQ ID NO: 4. In certain embodiments, the peptide comprises a sequence that is at least about 80%, 85%, 90%, 95%, 98%, or 99% homologous to the amino sequence of SEQ ID NO: 4. The foregoing values are applicable to SEQ ID NO: 14-51.

In certain embodiments, the peptide comprises a sequence that is about 80% to about 99% identical to the amino acid sequence of SEQ ID NO: 4. In certain embodiments, the peptide comprises a sequence that is about 84% to about 99% identical to the amino acid sequence of SEQ ID NO: 4. In certain embodiments, the peptide comprises a sequence that is about 87% to about 99% identical to the amino acid sequence of SEQ ID NO: 4. In certain embodiments, the peptide comprises a sequence that is about 90% to about 99% identical to the amino acid sequence of SEQ ID NO: 4. In certain embodiments, the peptide comprises a sequence that is about 93% to about 99% identical to the amino acid sequence of SEQ ID NO: 4. In certain embodiments, the peptide comprises a sequence that is about 96% to about 99% identical to the amino acid sequence of SEQ ID NO: 4. In certain embodiments, the peptide comprises a sequence that is at least about 80%, 84%, 87%, 90%, 93%, or 96% identical to the amino sequence of SEQ ID NO: 4. The foregoing values are applicable to SEQ ID NO: 14-51.

In certain embodiments, the peptide comprises a sequence that differs from the amino acid sequence of SEQ ID NO: 4 by 1, 2, 3, 4, 5, 6, 7, 8, 9, or 10 amino acids. In certain embodiments, the peptide comprises a sequence that differs from the amino acid sequence of SEQ ID NO: 4 by 1 amino acid. In certain embodiments, the peptide comprises a sequence that differs from the amino acid sequence of SEQ ID NO: 4 by 2 amino acids. In certain embodiments, the peptide comprises a sequence that differs from the amino acid sequence of SEQ ID NO: 4 by 3 amino acids. In certain embodiments, the peptide comprises a sequence that differs from the amino acid sequence of SEQ ID NO: 4 by 4 amino acids. In certain embodiments, the peptide comprises a sequence that differs from the amino acid sequence of SEQ ID NO: 4 by 5 amino acids. In certain embodiments, the peptide comprises a sequence that differs from the amino acid sequence of SEQ ID NO: 4 by 6 amino acids. In certain embodiments, the peptide comprises a sequence that differs from the amino acid sequence of SEQ ID NO: 4 by 7 amino acids. In certain embodiments, the peptide comprises a sequence that differs from the amino acid sequence of SEQ ID NO: 4 by 8 amino acids. In certain embodiments, the peptide comprises a sequence that differs from the amino acid sequence of SEQ ID NO: 4 by 9 amino acids. In certain embodiments, the peptide comprises a sequence that differs from the amino acid sequence of SEQ ID NO: 4 by 10 amino acids. The foregoing values are applicable to SEQ ID NO: 14-51.

In certain embodiments, the peptide comprises a sequence that is about 80% to about 99% homologous to the amino acid sequence of SEQ ID NO: 5. In certain embodiments, the peptide comprises a sequence that is about 85% to about 99% homologous to the amino acid sequence of SEQ ID NO: 5. In certain embodiments, the peptide comprises a sequence that is about 90% to about 99% homologous to the amino acid sequence of SEQ ID NO: 5. In certain embodiments, the peptide comprises a sequence that is about 95% to about 99% homologous to the amino acid sequence of SEQ ID NO: 5. In certain embodiments, the peptide comprises a sequence that is about 97% to about 99% homologous to the amino acid sequence of SEQ ID NO: 5. In certain embodiments, the peptide comprises a sequence that is about 98% to about 99% homologous to the amino acid sequence of SEQ ID NO: 5. In certain embodiments, the peptide comprises a sequence that is at least about 80%, 85%, 90%, 95%, 98%, or 99% homologous to the amino sequence of SEQ ID NO: 5.

In certain embodiments, the peptide comprises a sequence that is about 80% to about 99% identical to the amino acid sequence of SEQ ID NO: 5. In certain embodiments, the peptide comprises a sequence that is about 84% to about 99% identical to the amino acid sequence of SEQ ID NO: 5. In certain embodiments, the peptide comprises a sequence that is about 87% to about 99% identical to the amino acid sequence of SEQ ID NO: 5. In certain embodiments, the peptide comprises a sequence that is about 90% to about 99% identical to the amino acid sequence of SEQ ID NO: 5. In certain embodiments, the peptide comprises a sequence that is about 93% to about 99% identical to the amino acid sequence of SEQ ID NO: 5. In certain embodiments, the peptide comprises a sequence that is about 96% to about 99% identical to the amino acid sequence of SEQ ID NO: 5. In certain embodiments, the peptide comprises a sequence that is at least about 80%, 84%, 87%, 90%, 93%, or 96% identical to the amino sequence of SEQ ID NO: 5.

In certain embodiments, the peptide comprises a sequence that differs from the amino acid sequence of SEQ ID NO: 5 by 1, 2, 3, 4, 5, 6, 7, 8, 9, or 10 amino acids. In certain embodiments, the peptide comprises a sequence that differs from the amino acid sequence of SEQ ID NO: 5 by 1 amino acid. In certain embodiments, the peptide comprises a sequence that differs from the amino acid sequence of SEQ ID NO: 5 by 2 amino acids. In certain embodiments, the peptide comprises a sequence that differs from the amino acid sequence of SEQ ID NO: 5 by 3 amino acids. In certain embodiments, the peptide comprises a sequence that differs from the amino acid sequence of SEQ ID NO: 5 by 4 amino acids. In certain embodiments, the peptide comprises a sequence that differs from the amino acid sequence of SEQ ID NO: 5 by 5 amino acids. In certain embodiments, the peptide comprises a sequence that differs from the amino acid sequence of SEQ ID NO: 5 by 6 amino acids. In certain embodiments, the peptide comprises a sequence that differs from the amino acid sequence of SEQ ID NO: 5 by 7 amino acids. In certain embodiments, the peptide comprises a sequence that differs from the amino acid sequence of SEQ ID NO: 5 by 8 amino acids. In certain embodiments, the peptide comprises a sequence that differs from the amino acid sequence of SEQ ID NO: 5 by 9 amino acids. In certain embodiments, the peptide comprises a sequence that differs from the amino acid sequence of SEQ ID NO: 5 by 10 amino acids.

In certain embodiments, the peptide comprises a sequence that is about 80% to about 99% homologous to the amino acid sequence of SEQ ID NO: 6. In certain embodiments, the peptide comprises a sequence that is about 85% to about 99% homologous to the amino acid sequence of SEQ ID NO: 6. In certain embodiments, the peptide comprises a sequence that is about 90% to about 99% homologous to the amino acid sequence of SEQ ID NO: 6. In certain embodiments, the peptide comprises a sequence that is about 95% to about 99% homologous to the amino acid sequence of SEQ ID NO: 6. In certain embodiments, the peptide comprises a sequence that is about 97% to about 99% homologous to the amino acid sequence of SEQ ID NO: 6. In certain embodiments, the peptide comprises a sequence that is about 98% to about 99% homologous to the amino acid sequence of SEQ ID NO: 6. In certain embodiments, the peptide comprises a sequence that is at least about 80%, 85%, 90%, 95%, 98%, or 99% homologous to the amino sequence of SEQ ID NO: 6.

In certain embodiments, the peptide comprises a sequence that is about 80% to about 99% identical to the amino acid sequence of SEQ ID NO: 6. In certain embodiments, the peptide comprises a sequence that is about 84% to about 99% identical to the amino acid sequence of SEQ ID NO: 6. In certain embodiments, the peptide comprises a sequence that is about 87% to about 99% identical to the amino acid sequence of SEQ ID NO: 6. In certain embodiments, the peptide comprises a sequence that is about 90% to about 99% identical to the amino acid sequence of SEQ ID NO: 6. In certain embodiments, the peptide comprises a sequence that is about 93% to about 99% identical to the amino acid sequence of SEQ ID NO: 6. In certain embodiments, the peptide comprises a sequence that is about 96% to about 99% identical to the amino acid sequence of SEQ ID NO: 6. In certain embodiments, the peptide comprises a sequence that is at least about 80%, 84%, 87%, 90%, 93%, or 96% identical to the amino sequence of SEQ ID NO: 6.

In certain embodiments, the peptide comprises a sequence that differs from the amino acid sequence of SEQ ID NO: 6 by 1, 2, 3, 4, 5, 6, 7, 8, 9, or 10 amino acids. In certain embodiments, the peptide comprises a sequence that differs from the amino acid sequence of SEQ ID NO: 6 by 1 amino acid. In certain embodiments, the peptide comprises a sequence that differs from the amino acid sequence of SEQ ID NO: 6 by 2 amino acids. In certain embodiments, the peptide comprises a sequence that differs from the amino acid sequence of SEQ ID NO: 6 by 3 amino acids. In certain embodiments, the peptide comprises a sequence that differs from the amino acid sequence of SEQ ID NO: 6 by 4 amino acids. In certain embodiments, the peptide comprises a sequence that differs from the amino acid sequence of SEQ ID NO: 6 by 5 amino acids. In certain embodiments, the peptide comprises a sequence that differs from the amino acid sequence of SEQ ID NO: 6 by 6 amino acids. In certain embodiments, the peptide comprises a sequence that differs from the amino acid sequence of SEQ ID NO: 6 by 7 amino acids. In certain embodiments, the peptide comprises a sequence that differs from the amino acid sequence of SEQ ID NO: 6 by 8 amino acids. In certain embodiments, the peptide comprises a sequence that differs from the amino acid sequence of SEQ ID NO: 6 by 9 amino acids. In certain embodiments, the peptide comprises a sequence that differs from the amino acid sequence of SEQ ID NO: 6 by 10 amino acids.

In certain embodiments, the peptide comprises a sequence that is at least about 80% to 99% homologous to SEQ ID NO: 7. In certain embodiments, the peptide comprises a sequence that is about 85% to about 99% homologous to the amino acid sequence of SEQ ID NO: 7. In certain embodiments, the peptide comprises a sequence that is about 90% to about 99% homologous to the amino acid sequence of SEQ ID NO: 7. In certain embodiments, the peptide comprises a sequence that is about 95% to about 99% homologous to the amino acid sequence of SEQ ID NO: 7. In certain embodiments, the peptide comprises a sequence that is about 97% to about 99% homologous to the amino acid sequence of SEQ ID NO: 7. In certain embodiments, the peptide comprises a sequence that is about 98% to about 99% homologous to the amino acid sequence of SEQ ID NO: 7. In certain embodiments, the peptide comprises a sequence that is at least about 80%, 85%, 90%, 95%, 98%, or 99% homologous to the amino sequence of SEQ ID NO: 7.

In certain embodiments, the peptide comprises a sequence that is at least about 80% to 99% homologous to SEQ ID NO: 7. In certain embodiments, the peptide comprises a sequence that is about 85% to about 99% identical to the amino acid sequence of SEQ ID NO: 7. In certain embodiments, the peptide comprises a sequence that is about 90% to about 99% identical to the amino acid sequence of SEQ ID NO: 7. In certain embodiments, the peptide comprises a sequence that is about 95% to about 99% identical to the amino acid sequence of SEQ ID NO: 7. In certain embodiments, the peptide comprises a sequence that is about 97% to about 99% identical to the amino acid sequence of SEQ ID NO: 7. In certain embodiments, the peptide comprises a sequence that is about 98% to about 99% identical to the amino acid sequence of SEQ ID NO: 7. In certain embodiments, the peptide comprises a sequence that is at least about 80%, 85%, 90%, 95%, 98%, or 99% identical to the amino sequence of SEQ ID NO: 7.

In certain embodiments, the peptide comprises a sequence that differs from the amino acid sequence of SEQ ID NO: 7 by 1, 2, 3, 4, 5, 6, 7, 8, 9, or 10 amino acids. In certain embodiments, the peptide comprises a sequence that differs from the amino acid sequence of SEQ ID NO: 7 by 1 amino acid. In certain embodiments, the peptide comprises a sequence that differs from the amino acid sequence of SEQ ID NO: 7 by 2 amino acids. In certain embodiments, the peptide comprises a sequence that differs from the amino acid sequence of SEQ ID NO: 7 by 3 amino acids. In certain embodiments, the peptide comprises a sequence that differs from the amino acid sequence of SEQ ID NO: 7 by 4 amino acids. In certain embodiments, the peptide comprises a sequence that differs from the amino acid sequence of SEQ ID NO: 7 by 5 amino acids. In certain embodiments, the peptide comprises a sequence that differs from the amino acid sequence of SEQ ID NO: 7 by 6 amino acids. In certain embodiments, the peptide comprises a sequence that differs from the amino acid sequence of SEQ ID NO: 7 by 7 amino acids. In certain embodiments, the peptide comprises a sequence that differs from the amino acid sequence of SEQ ID NO: 7 by 8 amino acids. In certain embodiments, the peptide comprises a sequence that differs from the amino acid sequence of SEQ ID NO: 7 by 9 amino acids. In certain embodiments, the peptide comprises a sequence that differs from the amino acid sequence of SEQ ID NO: 7 by 10 amino acids.

In certain embodiments, the peptide comprises a sequence that is at least about 80% to 99% homologous to SEQ ID NO: 8. In certain embodiments, the peptide comprises a sequence that is at least about 90% to 99% homologous to SEQ ID NO: 8. In certain embodiments, the peptide comprises a sequence that is at least about 94% to 99% homologous to SEQ ID NO: 8.

In certain embodiments, the peptide comprises a sequence that is at least about 80% to 99% identical to SEQ ID NO: 8. In certain embodiments, the peptide comprises a sequence that is at least about 90% to 99% identical to SEQ ID NO: 8. In certain embodiments, the peptide comprises a sequence that is at least about 94% to 99% identical to SEQ ID NO: 8.

In certain embodiments, the peptide comprises a sequence that differs from the amino acid sequence of SEQ ID NO: 8 by 1, 2, 3, 4, 5, 6, 7, 8, 9, or 10 amino acids. In certain embodiments, the peptide comprises a sequence that differs from the amino acid sequence of SEQ ID NO: 8 by 1 amino acid. In certain embodiments, the peptide comprises a sequence that differs from the amino acid sequence of SEQ ID NO: 8 by 2 amino acids. In certain embodiments, the peptide comprises a sequence that differs from the amino acid sequence of SEQ ID NO: 8 by 3 amino acids. In certain embodiments, the peptide comprises a sequence that differs from the amino acid sequence of SEQ ID NO: 8 by 4 amino acids. In certain embodiments, the peptide comprises a sequence that differs from the amino acid sequence of SEQ ID NO: 8 by 5 amino acids. In certain embodiments, the peptide comprises a sequence that differs from the amino acid sequence of SEQ ID NO: 8 by 6 amino acids. In certain embodiments, the peptide comprises a sequence that differs from the amino acid sequence of SEQ ID NO: 8 by 7 amino acids. In certain embodiments, the peptide comprises a sequence that differs from the amino acid sequence of SEQ ID NO: 8 by 8 amino acids. In certain embodiments, the peptide comprises a sequence that differs from the amino acid sequence of SEQ ID NO: 8 by 9 amino acids. In certain embodiments, the peptide comprises a sequence that differs from the amino acid sequence of SEQ ID NO: 8 by 10 amino acids.

In certain embodiments, the peptide comprises a sequence that is at least about 80% to 99% homologous to SEQ ID NO: 9. In certain embodiments, the peptide comprises a sequence that is at least about 90% to 99% homologous to SEQ ID NO: 9. In certain embodiments, the peptide comprises a sequence that is at least about 94% to 99% homologous to SEQ ID NO: 9.

In certain embodiments, the peptide comprises a sequence that is at least about 80% to 99% identical to SEQ ID NO: 9. In certain embodiments, the peptide comprises a sequence that is at least about 90% to 99% identical to SEQ ID NO: 9. In certain embodiments, the peptide comprises a sequence that is at least about 94% to 99% identical to SEQ ID NO: 9.

In certain embodiments, the peptide comprises a sequence that differs from the amino acid sequence of SEQ ID NO: 9 by 1, 2, 3, 4, 5, 6, 7, 8, 9, or 10 amino acids. In certain embodiments, the peptide comprises a sequence that differs from the amino acid sequence of SEQ ID NO: 9 by 1 amino acid. In certain embodiments, the peptide comprises a sequence that differs from the amino acid sequence of SEQ ID NO: 9 by 2 amino acids. In certain embodiments, the peptide comprises a sequence that differs from the amino acid sequence of SEQ ID NO: 9 by 3 amino acids. In certain embodiments, the peptide comprises a sequence that differs from the amino acid sequence of SEQ ID NO: 9 by 4 amino acids. In certain embodiments, the peptide comprises a sequence that differs from the amino acid sequence of SEQ ID NO: 9 by 5 amino acids. In certain embodiments, the peptide comprises a sequence that differs from the amino acid sequence of SEQ ID NO: 9 by 6 amino acids. In certain embodiments, the peptide comprises a sequence that differs from the amino acid sequence of SEQ ID NO: 9 by 7 amino acids. In certain embodiments, the peptide comprises a sequence that differs from the amino acid sequence of SEQ ID NO: 9 by 8 amino acids. In certain embodiments, the peptide comprises a sequence that differs from the amino acid sequence of SEQ ID NO: 9 by 9 amino acids. In certain embodiments, the peptide comprises a sequence that differs from the amino acid sequence of SEQ ID NO: 9 by 10 amino acids.

In certain embodiments, the peptide comprises a sequence that is at least about 80% to 99% homologous to SEQ ID NO: 10. In certain embodiments, the peptide comprises a sequence that is at least about 90% to 99% homologous to SEQ ID NO: 10. In certain embodiments, the peptide comprises a sequence that is at least about 94% to 99% homologous to SEQ ID NO: 10.

In certain embodiments, the peptide comprises a sequence that is at least about 80% to 99% identical to SEQ ID NO: 10. In certain embodiments, the peptide comprises a sequence that is at least about 90% to 99% identical to SEQ ID NO: 10. In certain embodiments, the peptide comprises a sequence that is at least about 94% to 99% identical to SEQ ID NO: 10.

In certain embodiments, the peptide comprises a sequence that differs from the amino acid sequence of SEQ ID NO: 9 by 1, 2, 3, 4, 5, 6, 7, 8, 9, or 10 amino acids. In certain embodiments, the peptide comprises a sequence that differs from the amino acid sequence of SEQ ID NO: 10 by 1 amino acid. In certain embodiments, the peptide comprises a sequence that differs from the amino acid sequence of SEQ ID NO: 10 by 2 amino acids. In certain embodiments, the peptide comprises a sequence that differs from the amino acid sequence of SEQ ID NO: 10 by 3 amino acids. In certain embodiments, the peptide comprises a sequence that differs from the amino acid sequence of SEQ ID NO: 10 by 4 amino acids. In certain embodiments, the peptide comprises a sequence that differs from the amino acid sequence of SEQ ID NO: 10 by 5 amino acids. In certain embodiments, the peptide comprises a sequence that differs from the amino acid sequence of SEQ ID NO: 10 by 6 amino acids. In certain embodiments, the peptide comprises a sequence that differs from the amino acid sequence of SEQ ID NO: 10 by 7 amino acids. In certain embodiments, the peptide comprises a sequence that differs from the amino acid sequence of SEQ ID NO: 10 by 8 amino acids. In certain embodiments, the peptide comprises a sequence that differs from the amino acid sequence of SEQ ID NO: 10 by 9 amino acids. In certain embodiments, the peptide comprises a sequence that differs from the amino acid sequence of SEQ ID NO: 10 by 10 amino acids.

In certain embodiments, the peptide comprises a sequence that is at least about 80% to 99% homologous to SEQ ID NO: 11. In certain embodiments, the peptide comprises a sequence that is at least about 90% to 99% homologous to SEQ ID NO: 11. In certain embodiments, the peptide comprises a sequence that is at least about 94% to 99% homologous to SEQ ID NO: 11.

In certain embodiments, the peptide comprises a sequence that is at least about 80% to 99% identical to SEQ ID NO: 11. In certain embodiments, the peptide comprises a sequence that is at least about 90% to 99% identical to SEQ ID NO: 11. In certain embodiments, the peptide comprises a sequence that is at least about 94% to 99% identical to SEQ ID NO: 11.

In certain embodiments, the peptide comprises a sequence that differs from the amino acid sequence of SEQ ID NO: 11 by 1, 2, 3, 4, 5, 6, 7, 8, 9, or 10 amino acids. In certain embodiments, the peptide comprises a sequence that differs from the amino acid sequence of SEQ ID NO: 11 by 1 amino acid. In certain embodiments, the peptide comprises a sequence that differs from the amino acid sequence of SEQ ID NO: 11 by 2 amino acids. In certain embodiments, the peptide comprises a sequence that differs from the amino acid sequence of SEQ ID NO: 11 by 3 amino acids. In certain embodiments, the peptide comprises a sequence that differs from the amino acid sequence of SEQ ID NO: 11 by 4 amino acids. In certain embodiments, the peptide comprises a sequence that differs from the amino acid sequence of SEQ ID NO: 11 by 5 amino acids. In certain embodiments, the peptide comprises a sequence that differs from the amino acid sequence of SEQ ID NO: 11 by 6 amino acids. In certain embodiments, the peptide comprises a sequence that differs from the amino acid sequence of SEQ ID NO: 11 by 7 amino acids. In certain embodiments, the peptide comprises a sequence that differs from the amino acid sequence of SEQ ID NO: 11 by 8 amino acids. In certain embodiments, the peptide comprises a sequence that differs from the amino acid sequence of SEQ ID NO: 11 by 9 amino acids. In certain embodiments, the peptide comprises a sequence that differs from the amino acid sequence of SEQ ID NO: 11 by 10 amino acids.

In certain embodiments, the peptide comprises a sequence wherein any one of the amino acids at positions 9, 10, 12, 16, 17, 20, 23, 24, 27, 28, 31, or 32 of SEQ ID NO: 1 or 96 is any natural or non-natural amino acid. In certain embodiments, the peptide comprises a sequence of SEQ ID NO: 1 or 96, wherein 1, 2, 3, 4, 5, 6, 7, 8, 9, 10, 11, or 12 amino acids at positions 9, 10, 12, 16, 17, 20, 23, 24, 27, 28, 31, or 32 can be changed.

In certain embodiments, the peptide is a first peptide that associates with a second peptide to form a peptide dimer that binds to a target protein. In certain embodiments, the peptide dimer binds to a target protein. In certain embodiments, the target protein is Ras. Examples of Ras include NRas, HRas, and KRas including KRas4A and KRas4B. In certain embodiments, the target protein is Ras mutant. In certain embodiments, a Ras mutant is NRas, HRas, or KRas with one or more of the following mutations: G12D, G12S, G12V, G12C, G12R, G12A, G12D, G13R, G13V, G13S, G13C, G13A, Q61L, Q61R, Q61K, or Q61H. In certain embodiments, the target protein is Max/Myc. In certain embodiments, the target protein is RalA. In certain embodiments, the target proteins are Ras and RalA.

In certain embodiments, the second peptide comprises the same sequence as the sequence of the first peptide. In certain embodiments, the second peptide comprises a different sequence from the sequence of the first peptide. In certain embodiments, the second peptide comprises a sequence of SEQ ID NO: 1 or 96. In certain embodiments, the second peptide comprises a sequence of SEQ ID NO: 1 or 96, 12, 13, or 48. In certain embodiments, $X_{21}$ or $X_{25}$ of the second peptide is Tyr, Phe, Trp, His, or an amino acid with a cyclohexyl side chain, wherein Tyr, Phe, Trp, or cyclohexyl side chain are optionally fluorinated. In certain embodiments, $X_{21}$ of the second peptide is Trp. In certain embodiments, $X_{25}$ of the second peptide is Tyr. In certain embodiments, $X_{25}$ of the first peptide is Trp. In certain embodiments, $X_{25}$ of the second peptide is Tyr and $X_{25}$ of the first peptide is Trp. In certain embodiments, $X_{18}$ of the second peptide is His, and each of $X_{21}$ and $X_{25}$ are Trp. In certain embodiments, the first peptide and the second peptide are associated through a disulfide bond, diselenide bond, carbon-carbon bond, amide bond, ester bond, hydrogen bond, salt bridge, pi stacking interaction, or non-polar hydrophobic interaction. In certain embodiments, the first peptide and the second peptide are associated through a disulfide bond or diselenium bond. In certain embodiments, two peptides are associated through pi stacking interaction. For example, a tyrosine on one peptide interacts with another tyrosine on another peptide through pi stacking.

In certain embodiments, the peptides bind their target (e.g., Ras proteins) with mid-to-low nanomolar binding affinity. Without wishing to be bound by theory, the peptides directly engage the Ras effector domain, and block Ras from binding effector proteins necessary for its oncogenic activity. In certain embodiments, the peptides bind Ras as a head-to-tail dimer. In certain embodiments, the peptides bind Ras as as a head-to-tail homodimer. In certain embodiments, the peptides bind Ras as a head-to-tail heterodimer.

The binding affinity of the peptides described herein to a target (e.g., Ras proteins) may be measured by the dissociation constant ($K_d$) of a peptide described herein and the target using methods known in the art (e.g., fluorescence polarization measurements). In certain embodiments, the peptide dimer binds Ras with a dissociation constant ($K_d$) of less than approximately 500 nM, 200 nM, 150 nM, 140 nM, 130 nM, 120 nM, 110 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 2 nM, 1 nM, or 0.5 nM. In certain embodiments, the peptide dimer binds Ras with a dissociation constant ($K_d$) of less than approximately 400 pM, 200 pM, 150 pM, 140 pM, 130 pM, 120 pM, 110 pM, 100 pM, 90 pM, 80 pM, 70 pM, 60 pM, 50 pM, 40 pM, 30 pM, 20 pM, 10 pM, 9 pM, 8 pM, 7 nM, 6 nM, or 5 nM. The foregoing $K_d$ values are applicable to both peptide homodimers and heterodimers.

In certain embodiments, the peptide dimer binds Ras with a dissociation constant ($K_d$) of less than approximately 500 nM. In certain embodiments, the peptide dimer binds Ras with a dissociation constant ($K_d$) of less than approximately 150 nM. In certain embodiments, the peptide dimer binds Ras with a dissociation constant ($K_d$) of less than approximately 150 nM. In certain embodiments, the peptide dimer binds Ras with a dissociation constant ($K_d$) of less than approximately 60 nM. In certain embodiments, the peptide dimer binds Ras with a dissociation constant ($K_d$) of less than approximately 40 nM. In certain embodiments, the peptide dimer binds Ras with a dissociation constant ($K_d$) of less than approximately 20 nM. In certain embodiments, the peptide dimer binds Ras with a dissociation constant ($K_d$) of less than approximately 10 nM. In certain embodiments, the peptide dimer binds Ras with a dissociation constant ($K_d$) of less than approximately 5 nM. In certain embodiments, the peptide dimer binds Ras with a dissociation constant ($K_d$) of less than approximately 10 nM. In certain embodiments, the peptide dimer binds Ras with a dissociation constant ($K_d$) of less than approximately 5 nM. In certain embodiments, the peptide dimer binds Ras with a dissociation constant ($K_d$) of less than approximately 1 nM. In certain embodiments, the peptide dimer binds Ras with a dissociation constant ($K_d$) of less than approximately 1 nM.

In certain embodiments, the peptide dimer binds Ras with a dissociation constant ($K_d$) of less than approximately 400 pM. In certain embodiments, the peptide dimer binds Ras with a dissociation constant ($K_d$) of less than approximately 200 pM. In certain embodiments, the peptide dimer binds Ras with a dissociation constant ($K_d$) of less than approximately 150 pM. In certain embodiments, the peptide dimer binds Ras with a dissociation constant ($K_d$) of less than approximately 100 pM. In certain embodiments, the peptide dimer binds Ras with a dissociation constant ($K_d$) of less than approximately 80 pM. In certain embodiments, the peptide dimer binds Ras with a dissociation constant ($K_d$) of less than approximately 60 pM. In certain embodiments, the peptide dimer binds Ras with a dissociation constant ($K_d$) of less than approximately 40 pM. In certain embodiments, the peptide dimer binds Ras with a dissociation constant ($K_d$) of less than approximately 20 pM. In certain embodiments, the peptide dimer binds Ras with a dissociation constant ($K_d$) of less than approximately 10 pM. In certain embodiments, the peptide dimer binds Ras with a dissociation constant ($K_d$) of less than approximately 5 pM. In certain embodiments, the peptide dimer binds Ras with a dissociation constant ($K_d$) of less than approximately 1 pM. In certain embodiments, the peptide dimer binds Ras with a dissociation constant ($K_d$) of less than approximately 1 pM.

In certain embodiments, the peptide dimer has a higher binding affinity for an oncogenic form of the target protein than a non-oncogenic form. In certain embodiments, the peptide dimer has a higher binding affinity for Ras.GTP than Ras.GDP. In certain embodiments, the peptide dimer has a binding affinity for Ras.GTP that is greater than the binding affinity for Ras.GDP by approximately 1.5×, 2×, 3×, 4×, 5×, 6×, 7×, 8×, 9×, or 10×.

Ras inhibition can be measured using methods such as cell viability assays (e.g. MTT or CellTiterGlo), caspase cleavage assays (e.g. by quantitative western blotting or Caspase 3/7 Glo), quantitative western blotting of Ras pathway activation (e.g. activation of the MAPK pathway, PI3K/Akt pathway, Ral pathway) by measuring, for example, phosphorylated protein relative to total protein.

In certain embodiments, peptide monomers are a minimum of 3,000 Da and a maximum of 9,000 Da. In certain embodiments, peptide monomers are a minimum of 3,000 Da and a maximum of 6,000 Da. In certain embodiments, peptide monomers are a minimum of 6,000 Da and a maximum of 9,000 Da. In certain embodiments, peptide dimers are a minimum of 6,000 Da and a maximum of 18,000 Da. In certain embodiments, peptide dimers are a minimum of 6,000 Da and a maximum of 12,000 Da. In certain embodiments, peptide dimerse are a minimum of 12,000 Da and a maximum of 18,000 Da.

In certain embodiments, the peptide comprises additional amino acids at the N-terminus of SEQ ID NOs: 1-11, 96 and 99. In certain embodiments, the peptide comprises additional amino acids at the C-terminus of SEQ ID NOs: 1-11, 96 and 99. In certain embodiments, the additional amino acids comprise $X_{-2}G$ or GR at the N-terminus of SEQ ID NOs: 1-5, 7, 96 and 99. In certain embodiments, the additional amino acids comprise GCG at the N-terminus of SEQ ID NOs: 1-5, 7, 96 and 99. As used herein, X with a negative number as a subscript represents the position of an amino acid residue that is located at the N-terminal side relative to $X_1$ of SEQ ID NO: 1 or 96.

In certain embodiments, $X_2$ is an amino acid capable of cross-linking the first peptide with the second peptide. In certain embodiments, $X_{-2}$ is an amino acid cross-linking a first peptide with a second peptide. In certain embodiments, $X_{-2}$ is a natural or non-natural amino acid capable of cross-linking the peptide with another peptide. In certain embodiments, $X_{-2}$ is a natural or non-natural amino acid cross-linking the first peptide with the second peptide. In certain embodiments, $X_{-2}$ is Cys, Sec, Phe, Trp, or Tyr. In certain embodiments, $X_{-2}$ is Cys. In certain embodiments, $X_{-2}$ is Sec. In certain embodiments, $X_{-2}$ is Phe, Trp, or Tyr.

In certain embodiments, $X_{13}$ is Cys or Sec, and $X_{14}$ is Glu. In certain embodiments, $X_{18}$ is His, and each of $X_{25}$ and $X_{21}$ is Trp.

In certain embodiments, $X_1$ is Gly; each of $X_3$, $X_4$, and $X_6$ is Arg; and $X_7$ is Cys. In certain embodiments, $X_1$ is Gly; each of $X_3$, $X_4$, and $X_6$ is Arg; $X_7$ is Cy; and $X_{30}$ is Ala. In certain embodiments, $X_1$ is Gly; each of $X_3$, $X_4$, and $X_6$ is Arg; $X_7$ is Cys; and $X_{30}$ is Arg. In certain embodiments, $X_{-2}$ is Gly; $X_{-1}$ is Arg; $X_1$ is Arg; each of $X_3$, $X_4$, and $X_6$ is Arg; $X_7$ is Cys; and $X_{30}$ is Ala. In each of the foregoing embodiments, it is also comtemplated that Sec is used in place of Cys.

In certain embodiments, a heterodimerized peptide comprises a primary peptide and a secondary peptide. The primary peptide forms a majority of contacts to Ras.

In certain embodiments, a heterodimerized peptide comprises a primary peptide selected from SEQ ID NO: 22, 23, and 49. In certain embodiments, a heterodimerized peptide comprises a secondary peptide selected from SEQ ID NO: 24-27, 50, and 51. In certain embodiments, a heterodimerized peptide comprises a primary peptide of SEQ ID NO: 22 and and a secondary peptide of SEQ ID NO: 24. In certain embodiments, a heterodimerized peptide comprises a primary peptide selected from SEQ ID NO: 22 and a secondary peptide of SEQ ID NO: 25. In certain embodiments, a heterodimerized peptide comprises a primary peptide of SEQ ID NO: 22 and and a secondary peptide of SEQ ID NO: 26. In certain embodiments, a heterodimerized peptide comprises a primary peptide of SEQ ID NO: 22 and and a secondary peptide of SEQ ID NO: 27. In certain embodiments, a heterodimerized peptide comprises a primary peptide of SEQ ID NO: 22 and and a secondary peptide of SEQ ID NO: 50. In certain embodiments, a heterodimerized peptide comprises a primary peptide of SEQ ID NO: 22 and and a secondary peptide of SEQ ID NO: 51.

In certain embodiments, a heterodimerized peptide comprises a primary peptide of SEQ ID NO: 23 and a secondary peptide of SEQ ID NO: 24. In certain embodiments, a heterodimerized peptide comprises a primary peptide of SEQ ID NO: 23 and a secondary peptide of SEQ ID NO: 25. In certain embodiments, a heterodimerized peptide comprises a primary peptide of SEQ ID NO: 23 and a secondary peptide of SEQ ID NO: 26. In certain embodiments, a heterodimerized peptide comprises a primary peptide of SEQ ID NO: 23 and a secondary peptide of SEQ ID NO: 27. In certain embodiments, a heterodimerized peptide comprises a primary peptide of SEQ ID NO: 23 and a secondary peptide of SEQ ID NO: 50. In certain embodiments, a heterodimerized peptide comprises a primary peptide of SEQ ID NO: 23 and and a secondary peptide of SEQ ID NO: 51.

In certain embodiments, a heterodimerized peptide comprises a primary peptide of SEQ ID NO: 49 and a secondary peptide of SEQ ID NO: 24. In certain embodiments, a heterodimerized peptide comprises a primary peptide of SEQ ID NO: 49 and a secondary peptide of SEQ ID NO: 25. In certain embodiments, a heterodimerized peptide comprises a primary peptide of SEQ ID NO: 49 and a secondary peptide of SEQ ID NO: 26. In certain embodiments, a heterodimerized peptide comprises a primary peptide of SEQ ID NO: 49 and a secondary peptide of SEQ ID NO: 27. In certain embodiments, a heterodimerized peptide comprises a primary peptide of SEQ ID NO: 49 and and a secondary peptide of SEQ ID NO: 50. In certain embodiments, a heterodimerized peptide comprises a primary peptide of SEQ ID NO: 49 and and a secondary peptide of SEQ ID NO: 51.

In one aspect, provided herein are peptides designed to prevent or minimize dimerization prior to cell penetration. The peptides disclosed herein can comprise masked Cys or Sec. Prior to cell penetration, cysteine or selenocysteine residues in a peptide monomer can be disulfide bonded or selenium-sulfide bonded to a small organic thiol moieties to prevent crosslinking because sulfur in disulfide form or in selenium-sulfide form are not nucleophilic. In certain embodiments, a peptide monomer comprises a cysteine that is disulfide bonded to a small organic thiol moiety. In certain embodiments, a peptide monomer comprises a selenocysteine that is selenium-sulfide bonded to a small organic thiol moiety. In certain embodiments, the small organic thiol moiety is an aliphatic thiol moiety. In certain embodiments, the aliphatic thiol is an alkyl thiol moiety. In certain embodiments, the alkyl thiol is a $C_{1-5}$ alkyl thiol. In certain embodiments, the small organic thiol moiety is $SR^S$, wherein $R^S$ is a substituted or unsubstituted $C_{1-5}$ alkyl. In certain embodiments, $R^S$ is a substituted $C_{1-5}$ alkyl. In certain embodiments, $R^S$ is an unsubstituted $C_{1-5}$ alkyl. In certain embodiments, the small organic thiol moiety is t-butyl thiol. In certain embodiments, the small organic thiol moiety is ethanethiol. The inventive peptides described herein which are monomeric can comprise Cys that are either not disulfide bonded or Cys that are disulfide bonded. In certain embodiments, the inventive peptides are monomers comprising a Cys that is not disulfide bonded. In certain embodiments, the inventive peptides are monomers comprising a Cys that is disulfide bonded. In certain embodiments, the peptide comprises a sequence selected from the group consisting of SEQ ID NO: 30, 33, and 34, wherein the Cys is not disulfide bonded. In certain embodiments, the peptide comprises a sequence selected from the group consisting of SEQ ID NO: 30, 33, and 34, wherein the Cys is disulfide bonded to small organic thiol moieties. In any of the foregoing embodiments, Sec is also contemplated in place of Cys.

Following cell penetration, the disulfide bonded cysteines of the peptide monomers are reduced in the cytoplasm environment, allowing the free thiol of the cysteine residues to crosslink to a second peptide monomer comprising an electrophilic side chain that can react with the thiol nucleophile. This strategy is also applicable to peptides comprising selenocysteines, which can serve as the nucleophile for crosslinking. For example, electrophilic side chains include those with acrylamide, vinyl sulfonamide, iodoacetamide moieties. Other Michael acceptors capable of reacting with Cys or Sec are also applicable for crosslinking the peptides and are known in the art. For example, the peptides can contain residues modified with moieties capable of crosslinking to Cys or Sec. For example, amino acid side chains comprising an acrylamide moiety. In certain embodiments, the peptides comprise an amino acid sidechain containing an acrylamide moiety. In certain embodiments, the peptides comprise L-2,4-diaminobutyric acid (Dab) residues or L-2,3-diaminopropionic acid (Dap) residues. As used herein, residue X is a L-2,4-diaminobutyric acid (Dab) residue and residue Z is a L-2,3-diaminopropionic acid (Dap) residue.

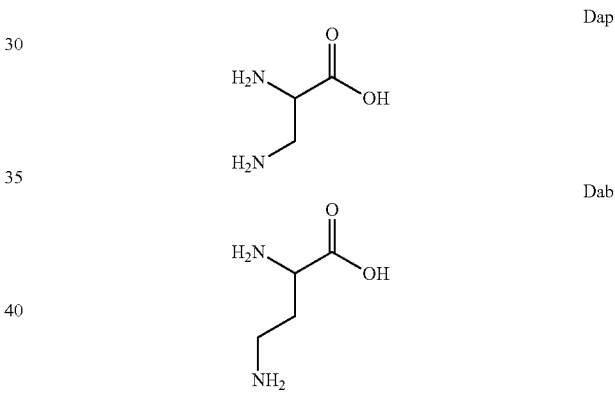

In certain embodiments, the Dab or Dap residues have acrylic acid coupled to the side chain nitrogen to form an acrylamide side chain with either 1 or 2 carbons separating the acrylamide from the peptide backbone alpha carbon. Side chains for Dap and Dab residues coupled to acrylic acid to form a side chain with an acrylamide are shown below. Such Dap or Dab-modified residues are referred to as Dab- and Dap-conjugated acrylamide residues.

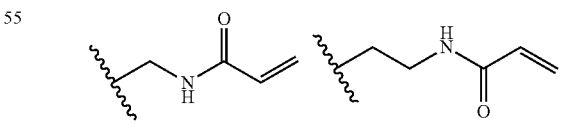

In certain embodiments, the peptide comprises a sequence selected from the group consisting of SEQ ID NO: 31, 32, 35, and 36, wherein X is L-2,4-diaminobutyric acid (Dab) residue or wherein Z is a L-2,3-diaminopropionic acid (Dap) residue conjugated to acrylamide.

In certain embodiments, peptides comprising a L-2,4-diaminobutyric acid (Dab) residue or L-2,3-diaminopropionic acid (Dap) residue are coupled with acrylic acid to the side chain nitrogen of Dap or Dab to form a side chain comprising an acrylamide.

Peptide dimers can be formed from any combination of SEQ ID NO: 30, 33, and 34 with SEQ ID NO: 31, 32, 35, and 36.

Provided herein are also selective dimer destabilization strategies. Destabilizing the dimer in endosomes can improve endosomal escape and therefore cytosolic access of the dimer. Monomers are thought to be more efficient at escaping endosomes compared to dimers. Dimer destabilization can be pH-induced or induced with bulky residues. pH-induced dimer destabilization involves placing histidines residues into one peptide monomer such that they are spatially close to cationic residues or other histidines on the opposing monomer. At regular cytosolic pH (~7.4) these histidines are less positively charged than in endosomes (pH-5-6), and thus the dimer is selectively destabilized in endosomes, thus leading to more efficient escape. Histidine's pKa of 6.0-6.5 causes it to be largely neutral at cytosolic pH values (pH 7.2-7.4), but results in protonation in the endosomes, which typically begin around pH 6.0 and progress to pH 5.0 or lower as the endosome transitions to a lysosome. The placement of histidine residues near positive charges on the opposing monomer leads to electrostatic repulsion between the two peptide monomers upon entry into the endosome, which destabilizes the dimer, favoring the monomer state.

SEQ ID NO: 38-41 illustrate this histidine pH-induced destabilization strategy. In certain embodiments, the peptide comprises a sequence wherein the His are placed at positions $X_6$, $X_7$, and/or $X_{10}$. His placed at one, two, or three of these positions is applicable to any of the peptides described herein. In certain embodiments, the peptide comprises a sequence selected from the group consisting of SEQ ID NO: 38 to 41. FIGS. 36A-B compare cells containing the same concentration of SEQ ID NO: 37, which does not contain histidines, and SEQ ID NO: 38, which contains histidines, using live-cell microscopy.

Dimer destabilization can also be achieved using residues comprising bulky moieties near the dimer interface to prevent dimerization. Upon entry into the cell, the bulky moieties of the residues are removed, permitting dimerization and binding to a protein target such as Ras, Myc/Max, or RalA. This strategy is applicable to any peptides described herein comprising Cys or Sec. In certain embodiments, the peptide comprises Cys or Sec protected by a thiol molecule. For example, an inventive peptide described herein comprises a Cys or Sec at a certain position (e.g., $X_7$) and is protected by disulfide bonding to an organic thiol, e.g., by reacting the reduced thiol with 2,2'-dipyridyldisulfide, 4,4'-dipyridyldisulfide, 2,2'-dithiobis(5-nitropyridine), or similar reagents. In certain embodiments, the peptide comprises Cys or Sec protected by bonding to an organic thiol molecule. In certain embodiments, the organic thiol molecule is an aryl thiol, heteroaryl thiol, or an aliphatic thiol. In certain embodiments, the organic thiol molecule is a heteroaryl thiol. In certain embodiments, the organic thiol molecule is selected from 2,2'-dipyridyldisulfide, 4,4'-dipyridyldisulfide, and 2,2'-dithiobis(5-nitropyridine). In certain embodiments, the peptide comprises Sec protected with the reagent 2,2'-dithiobis(5-nitropyridine). Upon escape from endosomes into the cytosol, this disulfide bond would be reduced by cell's environment and dimerization would be permitted. In certain embodiments, the peptide comprises Cys protected by disulfide bonding to 2,2'-Dipyridyldisulfide. In certain embodiments, the peptide comprises Cys protected by disulfide bonding to 4,4'-dipyridyldisulfide. In certain embodiments, the peptide comprises Cys protected by disulfide bonding to 2,2'-dithiobis (5-nitropyridine). Sequences demonstrating this strategy include SEQ ID NO: 30, 33, 34, and 42. It is understood that Cys can be replaced with Sec in any of the embodiments described herein.

As previously discussed, other targets besides Ras are contemplated. SEQ ID NO: 43 binds the Myc/Max heterodimer. SEQ ID NO: 44 binds the RalA protein. SEQ ID NO: 45 binds both RalA and KRas. SEQ ID NO: 43-45 are peptides comprising Cys at position 7, which dimerizes using disulfide bonds.

Further provided herein are peptides comprising a oligomerization domain that allows the peptide to associate with another peptide to form a dimer, wherein the oligomerization domain comprises a sequence: $PX_aX_bPX_cX_dP$ (SEQ ID NO: 2), wherein each of $X_a$, $X_b$, and X, is any non-proline amino acid, and $X_d$ is an amino acid capable of cross-linking the peptide with another peptide. In certain embodiments, each of $X_a$ and $X_b$ is independently any non-proline amino acid, and each of $X_c$ and $X_d$ is independently any non-proline amino acid or an amino acid capable of cross-linking the peptide with another peptide (e.g., cysteine, selenocysteine). In certain embodiments, each of $X_c$ and $X_d$ is independently any non-proline amino acid but each is not an amino acid capable of cross-linking the peptide with another peptide. The peptides comprising a oligomerization domain are useful as inhibitors of protein-protein interactions. The peptides comprising a oligomerization domain are useful for binding and inhibiting a target protein such as Ras or a Ras mutant.

In certain embodiments, the cross-linking amino acid in the first peptide of the dimer forms a cross-link to the accompanying cross-linking amino acid in the second peptide's $PX_aX_bPX_cX_dP$ motif. In certain embodiments, the $PX_aX_bPX_cX_dP$ motifs in the first and second peptides are in an antiparallel configuration. In certain embodiments, the $PX_aX_bPX_cX_dP$ motif adopts a PPII helical configuration. In certain embodiments, the $PX_aX_bPX_cX_dP$ motifs would each be connected to an alpha helix at either their N- or C-termini and would stabilize the alpha helices in an antiparallel configuration.

In certain embodiments, $X_c$ is Cys, Sec, Phe, Trp, or Tyr. In certain embodiments, $X_c$ is an amino acid capable of cross-linking the peptide with another peptide. In certain embodiments, $X_c$ is Cys or Sec. In certain embodiments, $X_c$ is Cys. In certain embodiments, $X_c$ is Sec.

In certain embodiments, $X_d$ is Cys, Sec, Phe, Trp, or Tyr. In certain embodiments, $X_d$ is an amino acid capable of cross-linking the peptide with another peptide. In certain embodiments, $X_d$ is Cys or Sec. In certain embodiments, $X_d$ is Cys. In certain embodiments, $X_d$ is Sec.

In certain embodiments, when $X_c$ is an amino acid capable of cross-linking the peptide with another peptide, $X_d$ is not an amino acid capable of cross-linking the peptide with another peptide. In certain embodiments, when $X_d$ is an amino acid capable of cross-linking the peptide with another peptide, $X_c$ is not an amino acid capable of cross-linking the peptide with another peptide.

In certain embodiments, the peptides comprise SEQ ID NO: 2 or 99, wherein $X_a$ and $X_b$ are each Arg. In certain embodiments, the peptides comprise SEQ ID NO: 2 or 99, wherein $X_c$ is Arg, and $X_d$ is Cys. In certain embodiments, the peptides comprise SEQ ID NO: 2 or 99, wherein $X_c$ is Arg, and $X_d$ is Tyr. In certain embodiments, the peptides comprise SEQ ID NO: 2 or 99, wherein $X_c$ is Lys, and $X_d$ is Tyr. In certain embodiments, the peptides comprise SEQ ID NO: 2 or 99, wherein $X_c$ is Cys, and $X_d$ is Tyr. In certain embodiments, the peptides comprise SEQ ID NO: 2 or 99, wherein $X_c$ is Lys, and $X_d$ is Cys. In certain embodiments, the peptides comprise SEQ ID NO: 2 or 99, wherein $X_c$ is Lys, and $X_d$ is His. In certain embodiments, the peptides comprise SEQ ID NO: 2 or 99, wherein $X_c$ is Arg, and $X_d$ is His. In certain embodiments, the peptides comprise SEQ ID NO: 2 or 99, wherein $X_c$ is His, and $X_d$ is His. In certain embodiments, the peptides comprise SEQ ID NO: 2 or 99, wherein $X_c$ is His, and $X_d$ is Tyr. In certain embodiments, the peptides comprise SEQ ID NO: 2 or 99, wherein $X_a$ and $X_b$ are each Arg and each of $X_c$ and $X_d$ have any of the foregoing general and specific embodiments.

In any of the embodiments of SEQ ID NO: 2 or 99, $X_a$, $X_b$, $X_c$, and $X_d$ corresponds to $X_3$, $X_4$, $X_6$, and $X_7$, respectively, as described herein.

The peptide further comprises an alpha-helical domain comprising a sequence: $X_{13}X_{14}X_{15}DLX_{18}X_{19}YX_{21}X_{22}RLX_{25}X_{26}YLX_{29}X_{30}VA$ (SEQ ID NO: 3), wherein $X_{13}$, $X_{14}$, $X_{15}$, $X_{18}$, $X_{19}$, $X_{21}$, $X_{22}$, $X_{25}$, $X_{26}$, $X_{29}$, and $X_{30}$ are as defined herein.

Further provided herein are peptides comprising an alpha-helical domain comprising a sequence: $X_{13}X_{14}X_{15}DLX_{18}X_{19}YX_{21}X_{22}RLX_{25}X_{26}YLX_{29}X_{30}VA$ (SEQ ID NO: 3), wherein $X_{13}$, $X_{14}$, $X_{15}$, $X_{18}$, $X_{19}$, $X_{21}$, $X_{22}$, $X_{25}$, $X_{26}$, $X_{29}$, and $X_{30}$ are as defined herein.

In certain embodiments, the inventive peptides are soluble in aqueous media. In certain embodiments, the inventive peptides can penetrate cells. In certain embodiments, the peptides comprise a reduced number of negative charges. In certain embodiments, the number of negative charges of a peptide is reduced by 1, 2, 3, 4, 5, or 6 negative charges compared to the starting peptide. For example, introducing Ala or Ser in place of anionic residues can help to increase cell penetration. In certain embodiments, the disclosed peptides comprise at least one, two, or three non-negatively charged amino acids at positions $X_{11}$, $X_{15}$, and/or $X_{16}$. In certain embodiments, the disclosed peptides comprise at least one, two, three, or four non-negatively charged amino acids at positions $X_{11}$, $X_{15}$, $X_{16}$, and/or $X_{19}$. In certain embodiments, the disclosed peptides comprise four non-negatively charged amino acids at positions $X_{11}$, $X_{15}$, $X_{16}$, and $X_{19}$. In certain embodiments, the non-negatively charged amino acids are neutral amino acids. In certain embodiments, the non-negatively charged amino acids are selected from the group consisting of Ala, Val, Leu, Ile, Pro, Phe, Trp, Met, Gly, Ser, Thr, Cys, Tyr, Asn, and Gln. In certain embodiments, the non-negatively charged amino acids are positively charged amino acids. In certain embodiments, the positively charged amino acids are selected from the group consisting of Lys, Arg, and His. In certain embodiments, the peptides comprise Ala at amino acid positions $X_{11}$, $X_{15}$, $X_{16}$, and $X_{19}$.

In certain embodiments, the disclosed peptides comprise at least one, two, three, or four Ala and/or Ser at positions $X_{11}$, $X_{15}$, $X_{16}$, and/or $X_{19}$. In certain embodiments, the disclosed peptides comprise at least one, two, or three Ala at positions $X_{11}$, $X_{15}$, and/or $X_{16}$. In certain embodiments, the disclosed peptides comprise at least one, two, three, or four Ala at positions $X_{11}$, $X_{15}$, $X_{16}$, and/or $X_{19}$. In certain embodiments, the disclosed peptides comprise Ala at positions $X_{11}$, $X_{15}$, $X_{16}$, and $X_{19}$. The foregoing embodiments for Ala at positions $X_{11}$, $X_{15}$, and/or $X_{16}$ are also applicable to Ser at positions $X_{11}$, $X_{15}$, and/or $X_{16}$.

Methods of Preparing the Inventive Peptides

The synthesis of the inventive peptides first involves the selection of a desired sequence and number of amino acids including unnatural amino acids. Once the amino acids are selected, synthesis of the inventive peptides can be achieved using standard deprotection and coupling reactions. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis*, 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, Hecht, *Bioorganic chemistry: Peptides and Proteins*, Oxford University Press, New York: 1998, the entire contents of which are incorporated herein by reference.

In certain embodiments, the methods comprises associating the inventive stapled peptides by ligating it to another polypeptide or a protein following the strategies as described in US Publication No. US 2012/0270800 and International Application No. PCT/US2010/001952, which are also incorporated herein by reference. In certain embodiments, the other polypeptide to be ligated is stapled or stitched.

In certain embodiments, the method comprises a solution phase synthesis of the inventive peptides. Solution phase synthesis, as mentioned above, is a well-known technique for the construction of polypeptides. An exemplary solution phase synthesis comprises the steps of: (1) providing an amino acid protected at the N-terminus with an amino protecting group; (2) providing an amino acid protected at the C-terminus with an oxygen protecting group; (3) coupling the N-protected amino acid to the C-protected amino acid; (4) deprotecting the product of the coupling reaction either at the N-terminus or C-terminus; and (5) repeating steps (3) to (4) until a desired polypeptide is obtained, wherein at least two of the amino acids coupled at any of the above steps each comprise at least one terminally unsaturated amino acid sidechain, and, optionally, an amino acid comprising two terminally unsaturated amino acid side chains. During the course of the above synthesis, various parameters can be varied, including, but not limited to, stereochemistry of amino acids, and amino acid residues utilized.

In certain embodiments, the method comprises a solid phase synthesis of the inventive peptides. Solid phase synthesis, as mentioned above, is a well-known technique for the construction of polypeptides. An exemplary solid phase synthesis includes the steps of: (1) providing a resin-bound amino acid; (2) deprotecting the resin bound amino acid; (3) coupling an amino acid to the deprotected resin-bound amino acid; (4) repeating steps (3) until a desired peptide is obtained.

During the course of the above synthesis, various parameters can be varied, including, but not limited to placement of amino acids with side chains, stereochemistry of amino acids, side chain length and functionality, and amino acid residues utilized.

In certain embodiments, the synthesized peptide contains amino acid capable of cross-linking the peptide with another peptide. For example, the amino acid can enable the peptide to be stapled when contacted with a specific catalyst to promote the stapling, or multiple stapling, to provide a stapled version of the peptide to provide a conformationally stabilized peptide. Such amino acids include those with terminally unsaturated amino acid side chains.

Other modifications may include conjugation of the peptides with a cell permeating agent, therapeutically active agent, label, or diagnostic agent anywhere on the peptide scaffold, e.g., such as at the N-terminus of the peptide, the C-terminus of the peptide, on an amino acid side chain of the peptide. Such modification may be useful in delivery of the peptide or therapeutically active agent to a cell, tissue, or organ. Such modifications may, in certain embodiments, allow for targeting to a particular type of cell or tissue.

In certain embodiments, one or more of the amino acids in a peptide may be modified, for example, by the addition of a chemical entity such as a carbohydrate group, a hydroxyl group, a phosphate group, a farnesyl group, an isofarnesyl group, palmitoyl, geranylgeranyl, lauryl, a fatty acid group, a linker for conjugation, functionalization, or other modification. Use of lipids can help the peptides localize to the plasma membrane, where Ras is localized.

In certain embodiments, the inventive peptides comprises D-amino acids. In certain embodiments, the inventive peptides comprise up to 10% D-amino acids. In certain embodiments, the inventive peptides comprise up to 20% D-amino acids. In certain embodiments, the inventive peptides comprise up to 30% D-amino acids. In certain embodiments, the inventive peptides comprise up to 40% D-amino acids. In certain embodiments, the inventive peptides comprise up to 50% D-amino acids. In certain embodiments, the inventive peptides comprise up to 60% D-amino acids. In certain embodiments, the inventive peptides comprise up to 70% D-amino acids. In certain embodiments, the inventive peptides comprise up to 80% D-amino acids. In certain embodiments, the inventive peptides comprise up to 90% D-amino acids.

In certain embodiments, the inventive peptides are entirely D-amino acids. Such "mirror image" proteins can fold into the corresponding mirror image conformation and is expected to have the same PPII-loop-alpha helix conformation, as well as the ability to dimerize (and crosslink via a disulfide or diselinide at the aforementioned positions) as an inventive peptide comprising L-amino acids. In certain embodiments, computational methods are used to discover binders to targets. In certain embodiments, "mirror image display" technologies where yeast, phage, etc. display is used with D-amino acid target proteins. In certain embodiments, Ras-binding peptides disclosed herein do not comprise D-amino acids.

Peptide Conjugation to Other Peptides or to Stapled or Stitched Peptides

The peptides described herein can be conjugated to another peptide which are stapled to stitched or to another peptide that are cell-penetrating peptides (e.g., TAT). Stapled or stitched peptide or cell-penetrating peptides allow the peptides provided herein to permeate cells. Stapled or stitched peptides have been described in, for example, Walensky et al., Science (2004) 305:1466-1470; U.S. Pat. Nos. 8,592,377; 7,192,713; U.S. Patent Application Publication No. 2006/0008848; U.S. Patent Application Publication No. 2012/0270800; International Publication No. WO 2008/121767 and International Publication No. WO 2011/008260, each of which are incorporated herein by reference. Cell-penetrating peptides are described in, for example, Margus, et al., Cell-penetrating peptides as versatile vehicles for oligonucleotide delivery. *Mol Ther.* (2012); 20(3):525-33

Dimer Display Technology

The methods of screening provided herein can be used with various in vitro display methods. A method of high-throughput screening is useful for identifying peptides that bind a target protein. A number of methods exist for preparing and evaluating large numbers of proteins (or peptides) for binding activity, which are collectively referred to as "display" technologies. Most of these technologies rely on biosynthesis machinery (i.e., ribosomes, either in a cell or in vitro) to synthesize the proteins based on a DNA template encoding their sequence, and some means of physically linking the expressed protein to the DNA encoding it. This latter feature provides a ready means of determining the identity of the proteins that are selected for their activity using PCR and well-established DNA sequencing technology, which enables the amplification and analysis of even single molecules of DNA. Once proteins are expressed and linked to their encoding DNA, those with the desired properties can be isolated from the rest using a variety of techniques, which are generally either a "screen" (in which each individual species is evaluated one-by-one) or a "selection" (in which the molecules are evaluated in bulk). Display technologies can be used both to identify binding agents from naïve libraries, and to improve the properties of proteins that already possess the desired activity. This latter method, which typically involves preparing mutant libraries of the original protein, isolating the best variants, and repeating these steps, is referred to as "directed evolution." Directed evolution has been reviewed, for example, in Dougherty and Arnold, Directed evolution: new parts and optimized function. *Curr Opin Biotechnol.* (2009); 20(4): 486-91.

One exemplary display technique is phage display, which involves expressing proteins of interest as a fusion to a coat protein from the M13 phage. Large libraries of phage can be prepared by transforming the appropriate library DNA into *E. coli*, and once produced, the active members of the library can be isolated, typically through a "panning" selection in which a target binding protein is immobilized and the phage are washed over the surface to bind the active variants. Phage display is the most commonly used display technology and has been used to identify proteins and peptides that bind a wide variety of biological and nonbiological targets (Levin, A. M. and Weiss, G. A. Optimizing the affinity and specificity of proteins with molecular display. *Mol Biosyst* 2, 49-57 (2006)).

Figure 2:
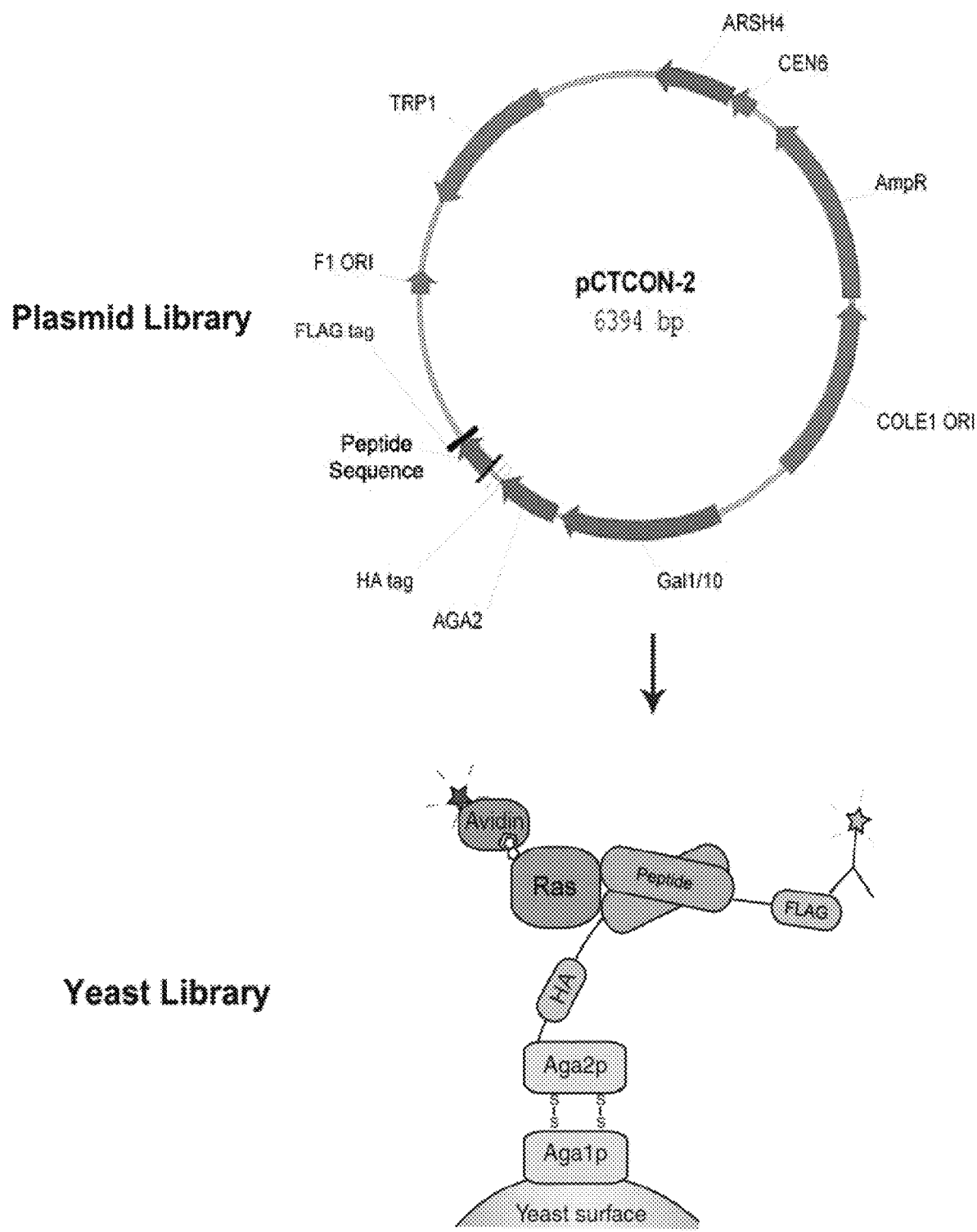
FIG. 2 shows a yeast display system. A DNA library encoding the peptide library is transformed into yeast strain EBY100, which expresses the Aga2p-peptide fusion and secretes it to the cell surface. Yeast cells are then incubated with fluorescently labeled target protein (in this case, Ras) and fluorescently labeled antibody to one of the epitope tags (to measure the abundance of displayed fusion protein), then screened using fluorescent activated cell sorting (FACS).
Figure 2:
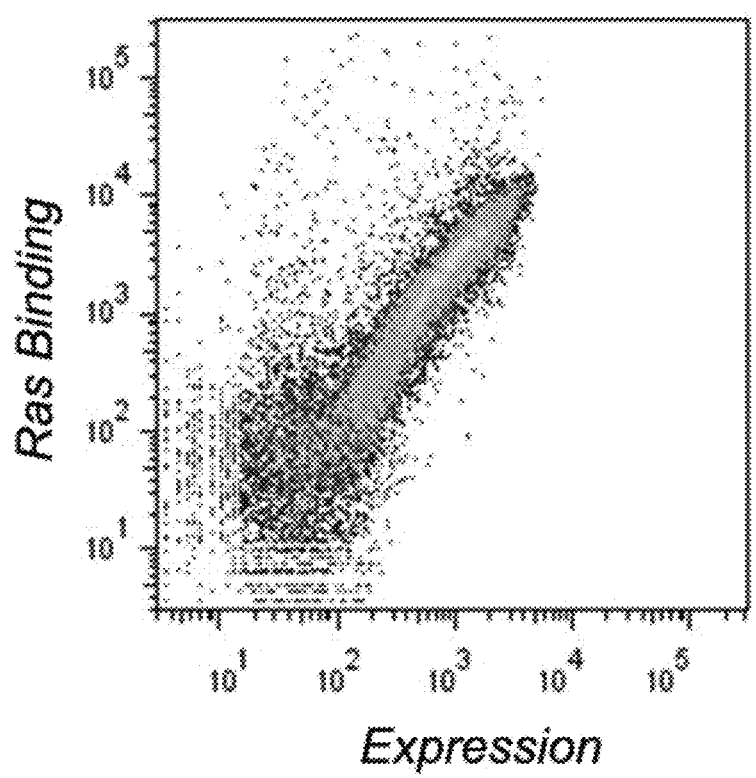

Yeast surface display is further described in Boder and Wittrup, *Yeast surface display for screening combinatorial polypeptide libraries*, Nat Biotechnol 15, 553-7 (1997) and in U.S. Pat. No. 6,300,065. Generally, the yeast surface display method involves transforming a DNA library into cells (such as *S. cerevisiae*), in which the displayed proteins are fused to a yeast surface protein, Aga2p (FIG. 2). Yeast cells are large enough to enable screening by fluorescence-activated cell sorting (FACS), which can evaluate >$10^7$ cells per hour and is capable of sorting cells based on multiple fluorescent signals. This permits multiparameter sorting, allowing cells to be selected not based solely on their absolute binding (e.g., to a fluorescently labeled target protein) but based on ratios of different fluorophores. This enables cell selections that may not possible with some other display cells such as phages; for example, the target binding signal can be normalized to expression level if a labeled antibody to an epitope on the fusion protein is used, or cells can be selected based on their preference for one labeled target protein over a differently labeled target. Normalization to expression is particularly useful as it is not possible with phage, which often possess strong expression biases for displayed proteins.

An additional feature of yeast display is that the displayed proteins pass through the yeast secretory system, which facilitates the formation of disulfide bonds (and folding in general, relative to E. coli). This feature is advantageous for proteins that require properly-formed disulfide bonds for activity; although some disulfide-containing proteins and peptides have been successfully displayed on phage, many are unable to be properly formed.

In addition to yeast surface display, an analogous bacterial system has been developed that displays proteins as fusions to a cell surface protein. Although this method possesses some of the advantages of yeast surface display, and in principle can achieve higher library sizes than yeast (although smaller than phage), it does not possess the folding and disulfide formation capabilities of the yeast system. Finally, there are a number of in vitro display methods, which involve generating DNA templates and producing proteins in cell-free translation extracts. These methods can accommodate the highest theoretical library sizes, as transformation is not required, and can often detect the activity of single sequences, as PCR is typically used to amplify isolated hits. In certain embodiments, mRNA display or ribosome display can be used to display the peptide libraries.

Provided herein are methods of screening a library of peptide dimers. The methods comprises transforming display cells with a vector encoding a first peptide and a second peptide, wherein the first and second peptides associate to form a peptide dimer fused to a cell wall protein; contacting the display cells with a first label, wherein the first label comprises a target protein and associates with a cell expressing the peptide dimer having enhanced binding to the target and does not associate with a cell which does not express the peptide dimer having enhanced binding to the target; isolating the display cells with which the first label is associated; and identifying the first and second peptides which exhibit enhanced binding to the target. Alternatively, the method can comprise transforming display cells with a first vector encoding a first peptide and second vector encoding a second peptide.

Figure 5:
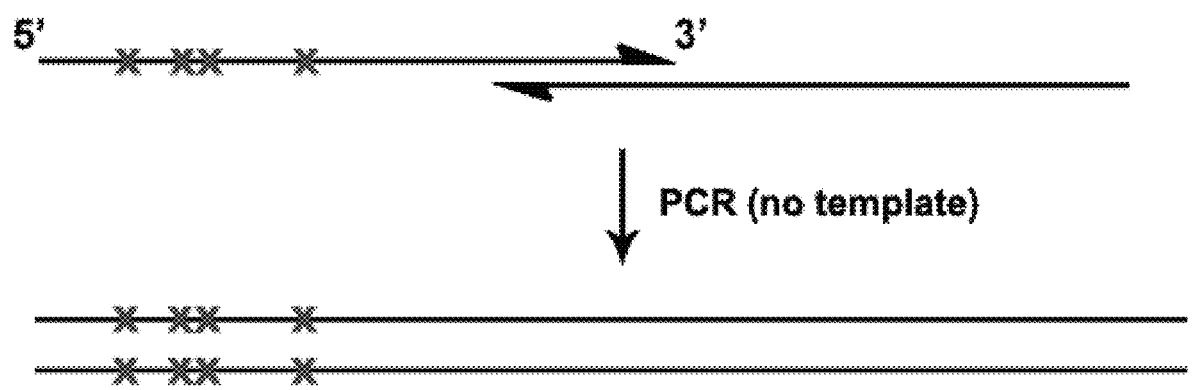
FIG. 5 shows the PCR strategy for preparing library fragments. A set of primers with sufficient overlap are annealed and extended, serving as templates for one another. Mutations are introduced through the use of multiple degenerate codons within each primer (site saturation mutagenesis), providing high combinatorial diversity in the resulting library.

Peptide libraries can be generated using methods such as PCR (see FIG. 5). For example, random mutagenesis (error-prone PCR) of a template sequence can be used. A set of primers with sufficient overlap are annealed to a template and extended, thereby serving as templates for one another. Mutations are introduced through the use of multiple degenerate codons within each primer (site saturation mutagenesis), providing high combinatorial diversity in the resulting library. Another way to generate libraries is to start with a defined mixture of a number of codons (one for each amino acid) that are incorporated into the primer with a mixture of trimer phosphoroamidites during the primer synthesis.

The peptide libraries can be designed from any peptide based on the pancreatic polypeptide family. In certain embodiments, the peptides used to design the libraries are based on avian, human, bovine, ovine, porcine, canine pancreatic polypeptides or mutants thereof. In certain embodiments, the peptides used to design the libraries are based on avian pancreatic polypeptide (aPP) or mutants thereof. The peptide libraries can be designed from any peptide comprising a scaffold of the pancreatic polypeptide family. The peptide libraries can be designed from any peptide comprising PPII helix domain and an alpha-helical domain. The peptide libraries can be designed from any peptide comprising PPII helix domain, a loop domain, and an alpha-helical domain. In certain embodiments, the loop domain is a type-I beta-turn. In certain embodiments, the peptides used to design the libraries are based on SEQ ID NO: 1 or 96 or 4-11. In certain embodiments, the peptides used to design the libraries are based on SEQ ID NO: 1 or 96. In certain embodiments, the peptide libraries can be designed from any peptide with 80% to 99% homology to SED ID NO: 1 or 96 or 4-11. In certain embodiments, the peptide libraries can be designed from any peptide with 80% to 99% identify to SED ID NO: 1 or 96 or 4-11. In certain embodiments, the peptide libraries can be designed from any peptide comprising SEQ ID NO: 2 or 99. In certain embodiments, the peptide libraries can be designed from any peptide comprising SEQ ID NO: 3.

In certain embodiments, the inventive peptides/dimers as described herein is a peptide homodimer of two peptides each comprising an alpha-helical structure. In certain embodiments, the inventive peptides/dimers as described herein is a peptide homodimer of two peptides each comprising a polyproline type-II conformation. In certain embodiments, the inventive peptides/dimers as described herein is a peptide homodimer of two peptides each comprising an alpha-helical structure connected to polyproline type-II conformation by a loop domain. In certain embodiments, the loop/linker domain is a type-I beta-turn. In certain embodiments, the inventive peptides/dimers as described herein is a peptide heterodimer of two peptides each comprising an alpha-helical structure. In certain embodiments, the inventive peptides/dimers as described herein is a peptide heterodimer of two peptides each comprising a polyproline type-II conformation. In certain embodiments, the inventive peptides/dimers as described herein is a peptide heterodimer of two peptides each comprising an alpha-helical structure connected to polyproline type-II conformation by a loop.

In certain embodiments, the two peptides are bound covalently. In certain embodiments, the two peptides are bound non-covalently. In certain embodiments, two peptides are associated through a disulfide bond, diselenium bond, carbon-carbon bond, amide bond, ester bond, hydrogen bond, salt bridge, pi stacking interaction, or non-polar hydrophobic interaction. In certain embodiments, two peptides are associated through a disulfide bond. In certain embodiments, two peptides are associated through a diselenium bond. In certain embodiments, two peptides are associated through a hydrogen bond, salt bridge, or non-polar hydrophobic interaction. In certain embodiments, two peptides are associated through pi stacking interaction. For example, a tyrosine on one peptide interacts with another tyrosine on another peptide through pi stacking.

In certain embodiments, each of the two peptides independently comprises the sequence of SEQ ID NO: 1 to SEQ ID NO: 11 or sequences thereof which are at least approximately 80%, 85%, 90%, 95%, 98%, or 99% homologous or identical. In certain embodiments, each of the two peptides comprise a moiety that is an amino acid capable of cross-linking the peptide with another peptide. In certain embodiments, each of the two peptides comprise a moiety cross-linking the two peptides to one another. In certain embodiments, the amino acid capable of cross-linking is Cys or Sec.

In certain embodiments, the moiety capable of cross-linking is a non-natural amino acid capable of cross-linking the first peptide with the second peptide. In certain embodiments, the display cells are mammalian cells, bacterial cells, or phages. In certain embodiments, the display cells are yeast cells. In certain embodiments, the display cells are *S. cerevisiae*. In certain embodiments, the peptide dimers are fused to a yeast surface protein. In certain embodiments, the yeast surface protein is Aga2p.

In certain embodiments, the target protein is asymmetric. In certain embodiments, the target protein is Ras or a Ras mutant. In certain embodiments, the peptides possess a higher selectivity for Ras.GTP than Ras.GDP. In certain embodiments, the peptides are at least approximately 1.5×, 2×, 3×, 4×, 5×, 6×, 7×, 8×, 9×, or 10× more selective for Ras.GTP than Ras.GDP.

The first label is used to label the target protein and is then incubated with the display cells. In certain embodiments, the first label is a fluorescent label bound to a target protein. In certain embodiments, the first label is biotin bound to Ras. Other fluorophores can be used to label the target protein such as phycoerythrin, allophycocyanin, Alexa647, Alexa488, and FITC.

An optional second label can be used to measure the abundance of the displayed fusion protein on the display cell. The second label can be an antibody that is fluorescently labeled or microbeads capable of binding the first label. Exemplary methods useful for sorting the display cells containing the bound target protein include fluorescent activated cell sorting (FACS) and magnetic-activated cell sorting (MACS).

Methods of Use and Treatment

Provided herein are methods of treating a disease or condition associated with Ras in a subject in need thereof comprising administering an effective amount of a peptide as described herein to the subject. Provided herein are methods of treating a disease or condition associated with Ras in a subject in need thereof comprising instructing the subject to take an effective amount of a peptide as described herein to the subject. Also provided herein are peptides for use in treating a disease or condition associated with Ras in a subject in need thereof.

In certain embodiments, the disease associated with Ras is a proliferative disease. As used herein a proliferative disease, condition, or disorder includes, but is not limited to, cancer, hematopoietic neoplastic disorders, benign neoplasms (i.e., tumors), diabetic retinopathy, rheumatoid arthritis, macular degeneration, obesity, and atherosclerosis. In certain embodiments, the proliferative disease is cancer. Exemplary cancers include, but are not limited to, carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, stomach cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, and Kaposi's sarcoma.

Exemplary hematopoietic neoplastic disorders include, but are not limited to, disorders involving hyperplastic/neoplastic cells of hematopoietic origin, e.g., arising from myeloid, lymphoid or erythroid lineages, or precursor cells thereof. In certain embodiments, the disorders arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T-cell lymphomas, adult T cell leukemia/lymphoma (ATL), cutaneous T-cell lymphoma (CTCL), large granular lymphocytic leukemia (LGF), Hodgkin's disease, and Reed-Stemberg disease.

In certain embodiments, the disease associated with Ras is a non-proliferative disease. In certain embodiments, the disease associated with Ras is a RASopathy. In certain embodiments, the disease associated with Ras is CFC syndrome, capillary malformation-arteriovenous malformation syndrome, Costello syndrome, Legius syndrome, Neurofibromatosis type 1, Noonan syndrome, or Noonan syndrome with multiple lentigines (formerly LEOPARD syndrome).

Pharmaceutical Compositions

Provided herein are pharmaceutical compositions comprising a peptide as described herein and a pharmaceutically acceptable excipient. Pharmaceutical compositions comprise compositions for therapeutic use. Such compositions may optionally comprise one or more additional therapeutically active agents. In accordance with some embodiments, a method of administering a pharmaceutical composition comprising an inventive composition to a subject in need thereof is provided. In some embodiments, the inventive composition is administered to humans. For the purposes of the present invention, the "active ingredient" generally refers to a peptide as described herein.

Although the descriptions of pharmaceutical compositions provided herein are principally directed to pharmaceutical compositions for administration to humans, it will be understood by the skilled artisan that such compositions are generally suitable for administration to animals of all sorts. Modification of pharmaceutical compositions for administration to various animals is well understood, and the ordinarily skilled veterinary pharmacologist can design and/or perform such modification with merely ordinary, if any, experimentation.

Pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or disorder of the subject treated and further depending upon the route by which the composition is to be administered. By way of example, the composition may comprise between 0.1% and 100% (w/w) active ingredient.

As used herein, a pharmaceutically acceptable excipient includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by the United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the Formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

General considerations in the formulation and/or manufacture of pharmaceutical agents may be found, for example, in Remington: The Science and Practice of Pharmacy $21^{st}$ ed., Lippincott Williams & Wilkins, 2005.

Inventive peptides provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the disease, disorder, or disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The peptides provided herein or pharmaceutical composition thereof, may be administered by any route. In some embodiments, the peptide or pharmaceutical composition thereof, are administered by a variety of routes, including oral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), and the disorder of the subject (e.g., whether the subject is able to tolerate oral administration). At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the peptides or pharmaceutical composition thereof, may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. The exact amount of an inventive peptide required to achieve an effective amount will vary from subject to subject, depending, for example, on species, age, and general disorder of a subject, severity of the side effects or disorder, identity of the particular compound(s), mode of administration, and the like.

In some embodiments, the present invention encompasses "therapeutic cocktails" comprising inventive peptides. In some embodiments, the inventive peptide comprises a single species which can bind to multiple targets. In some embodiments, different inventive peptides comprise different targeting moiety species, and all of the different targeting moiety species can bind to the same target. In some embodiments, different inventive peptides comprise different targeting moiety species, and all of the different targeting moiety species can bind to different targets. In some embodiments, such different targets may be associated with the same cell type. In some embodiments, such different targets may be associated with different cell types.

It will be appreciated that inventive peptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more therapeutically active agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body. It will further be appreciated that therapeutically active agent and the inventive peptides utilized in this combination may be administered together in a single composition or administered separately in different compositions.

The particular combination employed in a combination regimen will take into account compatibility of the therapeutically active agent and/or procedures with the inventive peptide and/or the desired therapeutic effect to be achieved. It will be appreciated that the combination employed may achieve a desired effect for the same disorder (for example, an inventive peptide may be administered concurrently with another therapeutically active agent used to treat the same disorder), and/or they may achieve different effects (e.g., control of any adverse effects).

As used herein, a "therapeutically active agent" refers to any substance used as a medicine for treatment, prevention, delay, reduction or amelioration of a disorder, and refers to a substance that is useful for therapy, including prophylactic and therapeutic treatment. A therapeutically active agent also includes a compound that increases the effect or effectiveness of another compound, for example, by enhancing potency or reducing adverse effects of the inventive peptides.

In certain embodiments, a therapeutically active agent is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, $\beta$-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), or inhibitors/intercalators of DNA, RNA, protein-protein interactions, protein-receptor interactions.

In some embodiments, inventive pharmaceutical compositions may be administered in combination with any therapeutically active agent or procedure (e.g., surgery, radiation therapy) that is useful to treat, alleviate, ameliorate, relieve, delay onset of, inhibit progression of, reduce severity of, and/or reduce incidence of one or more symptoms or features of cancer.

Kits

Provided herein are a variety of kits comprising one or more of the peptides of the invention. For example, the invention provides a kit comprising an inventive peptide and instructions for use. A kit may comprise multiple different peptides. A kit may comprise any of a number of additional components or reagents in any combination. All of the various combinations are not set forth explicitly but each combination is included in the scope of the invention.

According to certain embodiments of the invention, a kit may include, for example, (i) one or more inventive peptides and, optionally, one or more particular therapeutically active agents to be delivered; (ii) instructions for administration to a subject in need thereof.

Kits typically include instructions which may, for example, comprise protocols and/or describe disorders for production of inventive peptides, administration of inventive peptides to a subject in need thereof, design of novel inventive peptide. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, may be enclosed. An identifier, e.g., a bar code, radio frequency identification (ID) tag, may be present in or on the kit or in or one or more of the vessels or containers included in the kit. An identifier can be used, e.g., to uniquely identify the kit for purposes of quality control, inventory control, tracking, movement between workstations.

In order that the invention described herein may be more fully understood, the following examples are set forth. It should be understood that these examples are for illustrative purposes only and are not to be construed as limiting this invention in any manner.

EXAMPLES

In order that the invention described herein may be more fully understood, the following examples are set forth. It should be understood that these examples are for illustrative purposes only and are not to be construed as limiting this invention in any manner.

Experimental Methods

General Methods.

Oligonucleotide primers were ordered from Eurofins MWG Operon or Integrated DNA Technologies. Trimer phosphoroamidite-containing primers were ordered from the Yale Keck Oligo facility, synthesized with trimer phosphoroamitide building blocks (Glen Research). PCR was performed with LongAmp Taq polymerase (New England Biolabs) and purified with a PCR cleanup kit (Qiagen). Plasmids were propagated in *E. coli* with standard methods and purified using a miniprep kit (Qiagen). Absorbance measurements were performed with a NanoDrop 2000C spectrophotometer (Thermo Scientific). HPLC was performed with an Agilent 1200 series instrument equipped with a Supelco 250×10 mm C18 column. LC/MS was performed with an Agilent 1260 series instrument equipped with an Agilent 150×2.1 mm C18 column, connected to an Agilent 1100 series quadrupole MSD. Gel filtration and desalting were performed on an Akta FPLC (Amersham/GE Healthcare).

Peptide Synthesis.

Peptides were synthesized on the solid phase by standard Fluorenylmethyloxycarbonyl chloride (Fmoc) methods, typically on a 30 μmol scale using Rink amide resin. The N-terminal Fmoc protecting group of the resin-bound peptide was removed by two 10 minutes treatments of 25% piperidine in N-Methyl-2-pyrrolidone (NMP), followed by four washes of NMP. Fmoc-protected amino acid (6 equivalents, at 0.19 M final concentration) were pre-mixed with PyClock (5.7 equivalents) and N,N-Diisopropylethylamine (DIEA, 12 equivalents), then bubbled with the resin under nitrogen for 1 hour. For couplings expected to be difficult (e.g. following α,α-disubstituted amino acids, 3-branched amino acids, and proline) two sequential 1-hour coupling reactions were done. After coupling, the resin was washed four times in NMP and de-protected as before. Olefin methathesis was carried out with two 2-hour treatments of 10 mM Grubbs I catalyst in 1,2-dichloroethane (DCE). FITC was added to the peptide N-terminus by bubbling resin overnight in 30 mg/ml FITC with 10% v/v DIEA in NMP. Following the synthesis, peptides were deprotected and cleaved in 95% trifluoroacetic acid (TFA), 2.5% triisopropylsilane (TIS), and 2.5% $H_2O$, then purified by high-performance liquid chromatography (HPLC) using a 10-100% gradient of acetonitrile in $H_2O$ with 0.1% TFA. Collected fractions were dried by speedvac and lyophilization.

Circular Dichroism Spectroscopy.

CD measurements were carried out on a Jasco J-710 spectrophotometer equipped with a PTC-348W temperature controller. Samples (~190 μl) were placed in a 1 mm quartz cuvette (sealed with parafilm) at 20-80 μM in 50 mM sodium phosphate pH 8 unless otherwise noted. For spectra, the CD was scanned from 260 nm to 190 nm at a scanning speed of 20 nm/min in 0.1 nm increments at 25° C. For melting curves, the temperature was increased from 10 to 90° C. at a rate 2° C./min while recording the CD at 222 nm. Raw curves were smoothened using a Savitzky-Golay filter.

Matrix-Assisted Laser Desorption/Ionization.

MALDI was performed on a Waters MALDI Micro MX. 200 pmol of protein was raised to 20 ul in water containing 0.1% TFA, then bound to a ZipTip tC18 tip, washed with water+0.1% TFA, then eluted with 50% MeCN+0.1% TFA. Samples were added to a metal MALDI plate that had been pre-spotted with a saturated solution of sinapinic acid in 40% MeCN+0.1% TFA, then air-dried before analysis.

Library Transformation into Yeast.

Yeast display protocols were generally carried out as described by Wittrup and colleagues.[1,2] Yeast density was quantified by absorbance (1 $AU_{600}$=$10^7$ cells/ml), and cells were pelleted at 15,000×g for ~45 seconds (in 1.5 ml eppendorf tube) or at 2,500×g for 3 minutes (for larger volumes). Linearized pCTCON2 (1 μg) was mixed with PCR insert (4 μg) and precipitated by raising to 100 μl in water, adding 2 μl of PelletPaint (Novagen) followed by 10 ul of 4 M $NH_4Ac$, mixing, then adding 200 μl of ethanol and incubating for 5 minutes. The DNA was pelleted, washed with 200 μl of 70% ethanol, then washed with 100% ethanol and air-dried. The DNA was resuspended in 2 μl of water and stored at 4° C. until transformation. *S. cerevisiae* strain EBY100 (obtained from K. Dane Wittrup, Massachusetts Institute of Technology) was grown in YPD media at 30° C., shaking at 225 rpm. Cells were passaged twice prior to transformation to ensure a healthy culture. The day of the transformation, cells were diluted to an $OD_{600}$ of 0.1 in 110 ml of YPD media and grown until $OD_{600}$=1.4, at which point 1 ml of Tris-DTT buffer (2.5 M DTT in 1 M Tris pH 8) was added. After 15 additional minutes of shaking, the cells were pelleted, resuspended in 50 ml of 10 mM Tris, 270 mM sucrose, 1 mM $MgCl_2$, pH 7.5, pelleted again, and washed with a further 25 ml of the same buffer. The cells were resuspended to a final volume of ~600 ul with buffer, then mixed with precipitated library DNA (1 μg vector/4 μg insert per 50 ul cells) and incubated for 10 minutes before electroporating at 0.54 kV, 25 μF in a GenePulser II electroporator (Bio-Rad). Cells were immediately rescued into 30 ml of pre-warmed 30° C. YPD, transferred to a 30° C. shaker for 60 minutes, then pelleted and resuspended in SDCAA media supplemented with ampicillin and kanamycin. Serial dilutions were plated onto SDCAA plates to determine the library transformation efficiency. For generation of library templates using error-prone PCR, the method of Zaccolo et al.[3] utilizing dPTP and 8-oxo-dGTP was used as described in Chao et al.[1]

Screening Yeast Libraries by MACS.

Yeast libraries were grown in SDCAA media, then passaged into SGCAA media 20-24 hours prior to sorting. Yeast (up to 5*$10^9$ cells) were pelleted, washed with MACS buffer (15 mM sodium phosphate pH 7.4, 150 mM NaCl, 5 mM KCl, 0.5% w/v BSA), then incubated with biotinylated Ras for 45-60 minutes at a density of $10^9$ cells/ml at room temperature before pelleting, washing with buffer, and resuspending in 1 ml of buffer. Anti-biotin microbeads (50 ul, Miltenyi) were added and the cells were rotated at 4° C. for 30 minutes, then separated on an AutoMACS instrument (Miltenyi) using the Possel_s program. Eluted cells were resuspended in SDCAA and a 1/100 dilution was plated on SDCAA to estimate the number of retained cells.

Screening Yeast Libraries by FACS.

Yeast libraries were grown in SDCAA media, then passaged into SGCAA media 20-24 hours prior to sorting. Yeast cells were pelleted, washed with FACS buffer (15 mM sodium phosphate pH 7.4, 150 mM NaC, 5 mM KCl, 0.1% w/v BSA), then incubated with biotinylated Ras for 45-60 minutes at room temperature before pelleting, washing with buffer, and resuspending in 100 ul of buffer per $10^7$ cells. Ras incubation was done at a density of $10^7$ cells/ml unless the concentration of [Ras] fell below 100 nM; in this case, the binding volume was chosen such that there were at least 500,000 molecules of Ras per yeast cell (per the guidelines of Chao et al[1]). Secondary reagents were then added (Anti-HA Alexa488 at a 1:200 dilution, and either SA-PE, SA-APC, or NA-PE at a 1:100 dilution) and incubated for 10 minutes at 4° C. in the dark before pelleting, washing, and re-pelleting. Immediately prior to sorting, the cells were resuspended in FACS buffer to an approximate density of $2*10^7$ cells/ml.

Expression and Purification of Ras Proteins.

Ras proteins were recombinantly expressed in E. coli BL21 Rosetta I pLysS cells with C-terminal $His_6$ (SEQ ID NO:55) and yBBr tags. The identity of the plasmid backbone is not known (parent KRas vector was originally obtained from Johannes Yeh) but is likely pET-derived, with ampicillin resistance. The cells were grown to $OD_{600}$=0.7, induced with 0.3 mM IPTG for 5 hours at 30° C., then harvested and resuspended in 50 mM Tris pH 7.5 at 4° C., 300 mM NaCl, 10 mM imidazole, 5 mM $MgCl_2$ prior to snap-freezing in liquid nitrogen. For purification, the pellet was thawed, raised to 40 ml in the same buffer, and mixed with a Roche Complete EDTA-free protease inhibitor tablet. The cells were lysed with a tip sonicator (VirSonic, 6 cycles of 10 s on, 15 s off at 6.5 power level), then pelleted at 30,000×g for 30 minutes and filtered through a 1.2 uM Supor membrane (Pall Corporation). The clarified lysate was added to 2 ml of HisPur Cobalt resin (Thermo Pierce) that had been equilibrated with the lysis buffer, and drained by gravity. The column was washed with 20 ml of buffer, then protein was eluted with ~5 ml of buffer containing 150 mM imidazole. Immediately following elution from the column, DTT was added for a final concentration of ~1 mM and a small portion of protease inhibitor (reserved from the lysis step) was added. The protein was concentrated in a Centriprep YM-10 (Millipore) to 2 ml and purified by gel filtration on a Superdex 75 10/300 column (GE Healthcare) into 50 mM Tris pH 7.4, 100 mM NaCl, 5 mM $MgCl_2$, 1 mM DTT. For long-term storage, proteins were concentrated to >100 μM, mixed with glycerol to 10%, and snap-frozen in liquid nitrogen and stored at −80° C.

Rap1a, RalA, and Rab25 were expressed and purified following the same protocol. Rap1a and RalA were cloned into identical ($His_6$ (SEQ ID NO:55)/yBBr tagged) vectors as for the Ras proteins; $His_6$-tagged (SEQ ID NO:55) Rab25 was expressed from a pET vector.

Nucleotide Exchange with Calf Intestinal Alkaline Phosphatase.

For enzymatic nucleotide exchange, the Ras protein was buffer exchanged by gel filtration on a Superdex 75 10/300 column into 32 mM Tris pH 8, 200 mM $(NH_4)_2SO_4$, 1 mM DTT, 0.5 mM $NaN_3$, 1 μM $ZnCl_2$. The protein was concentrated to >100 μM, then mixed with GppNHp or GppCp to 0.5-1.0 mM, followed by 10-20 units of calf intestinal alkaline phosphatase (New England Biolabs). The protein was incubated at room temperature for 30 minutes, then $MgCl_2$ was added to 5 mM and the protein was gel filtered as before into 50 mM Tris pH 7.4, 100 mM NaCl, 5 mM $MgCl_2$, 1 mM DTT. For subsequent exchange to GTP or GDP, Ras protein loaded with GppCp was incubated with a 50-100 fold excess of desired nucleotide in the presence of 10 mM EDTA for 30 minutes at room temperature before adding $MgCl_2$ to 20 mM and removing excess nucleotide by gel filtration as usual.

Quantification of Nucleotide Loading by HPLC.

Ras proteins (~2 nmol) were raised to 150 ul with ultrapure water, then mixed with 150 ul of 100 mM potassium phosphate pH 6.5, 10 mM tetrabutylammonium bromide. Samples were analyzed by reverse-phase HPLC (Supelco semi-prep C18 column) using a 20 minute isocratic run in 100 mM potassium phosphate pH 6.5, 10 mM tetrabutylammonium bromide, 7.5% acetonitrile. Elution times for GDP, GTP, and GppNHp were determined with the pure nucleotide (Sigma Alrich).

Purification of B-Raf RBD.

The Raf RBD was recombinantly expressed in E. coli BL21 Rosetta I pLysS cells with an N-terminal glutathione S-transferase (GST) tag. The gene for the RBD was subcloned into a pGEX-5X plasmid (GE Healthcare) by Johannes Yeh. The cells were grown to $OD_{600}$=0.7, induced with 0.3 mM IPTG for 5 hours at 30° C., then harvested and resuspended in lysis buffer (PBS+1 mM DTT and 0.5 mM EDTA) prior to snap-freezing in liquid nitrogen. For purification, the pellet was thawed, raised to 40 ml in the same buffer, and mixed with a Roche Complete EDTA-free protease inhibitor tablet. The cells were lysed with a tip sonicator (VirSonic, 6 cycles of 10 s on, 15 s off at 6.5 power level), then pelleted at 30,000×g for 30 minutes and filtered through a 1.2 uM Supor membrane (Pall Corporation). The clarified lysate was added to 2 ml of immobilized glutathione resin (Thermo Pierce) that had been equilibrated with the lysis buffer, and drained by gravity. The column was washed with 20 ml of buffer, then protein was eluted with 50 mM Tris pH 8.0, 10 mM reduced glutathione, 1 mM DTT, 0.5 mM EDTA. The sample was concentrated in a Centriprep YM-10 (Millipore) to 2 ml and purified by gel filtration on a Superdex 200 10/300 column (GE Healthcare) into 50 mM Tris pH 7.4, 100 mM NaCl, 5 mM $MgCl_2$, 1 mM DTT. For long-term storage, proteins were concentrated to >100 μM, mixed with glycerol to 10%, and snap-frozen in liquid nitrogen and stored at −80° C.

Purification of Sfp phosphopantetheinyl transferase.

Sfp was recombinantly expressed in E. coli BL21 cells from a pET29-Sfp vector obtained from Christopher Walsh (Harvard Medical School). The cells were grown to $OD_{600}$=0.7, induced with 1 mM IPTG for 6 hours at 25° C., harvested and resuspended in 50 mM sodium phosphate pH 7.5, 300 mM NaCl, 10 mM imidazole prior to snap-freezing in liquid nitrogen. The protein was purified by Cobalt affinity chromatography as described above for the Ras proteins. The purified protein was gel filtered on a Superdex 75 10/300 column (GE Healthcare) into 10 mM Tris pH 7.5, 1 mM EDTA, 10% glycerol. Fractions eluting with the peak at ~15 ml were pooled, split into aliquots, snap-frozen in liquid nitrogen, and stored at −80° C.

Synthesis of Biotin-CoA (LK04).

Coenzyme A (Sigma-Aldrich, 10 mM in Dulbecco's phosphate-buffered saline) was mixed with one equivalent of Biotin-$Peg_2$-Maleimide (Thermo Pierce, 20 mM in 50 mM Tris, pH 7) followed by 0.2 equivalents of TCEP (Sigma-Aldrich, 0.5 M in water). The reaction was incubated at room temperature for 2 hours, then purified by HPLC using a 20 minute 0-40% MeCN gradient in water with 0.1% TFA.

Synthesis of Alexa647-CoA (LK06).

Coenzyme A (Sigma-Aldrich, 10 mM in Dulbecco's phosphate-buffered saline) was diluted to 5 mM in 50 mM Tris pH 7, then TCEP was added to 7.5 mM (3 ul of a 500 mM stock). After 5 minutes, 1 mg of Alexa647-C2-maleimide (Life Technologies) was dissolved in 34 ul of DMSO and added to the reaction, and incubated in the dark at room temperature for 45 minutes before diluting the reaction with 500 ul of milliQ and purifying by HPLC using a 20 minute 0-60% MeCN gradient in water with 0.1% TFA.

Protein Labeling by Sfp Phosphopantetheinyl Transferase.

Purified Ras was gel filtered on a Superdex 75 10/300 column into 64 mM Tris pH 7.5, 5 mM $MgCl_2$, 1 mM DTT. Ras (50-150 μM) was mixed with 1.0-1.3 equivalents of CoA linker (LK04 or LK06), followed by Sfp to 3-5 μM. The reaction was incubated at room temperature for 1 hour, then gel filtered as before into 50 mM Tris pH 7.4, 100 mM NaCl, 5 mM $MgCl_2$, 1 mM DTT.

Recombinant Production of 225 Peptides.

pET30a (Novagen) was digested with NcoI-HF and XhoI (New England Biolabs) and ligated with a PCR fragment containing the peptide sequence with 5' NcoI and 3' XhoI sites. To shuttle the ORF into an ampicillin-resistant plasmid (for expression strain compatibility reasons), this plasmid was digested with XbaI and XhoI (New England Biolabs) and the insert subcloned into a pET19b vector (Novagen). The resulting plasmids were transformed into BL21 cells containing the pG-KJE8 plasmid (Clontech), which carries the dnaK, dnaJ, grpE, GroEL, and GroES chaperones under control of an arabinose-inducible promoter. Cells were grown in LB media at 37° C. to an $OD_{600}$ of ~0.7, then induced with 500 μM of IPTG and 200 mg of arabinose for 5 hours at 30° C. The cells were pelleted at 5,000×g for 15 minutes, resuspended in 50 mM sodium phosphate pH 7.5, 1000 mM NaCl, 10 mM imidazole, and snap-frozen. All subsequent steps were performed at 4° C. The pellet was thawed and mixed with EDTA-free protease inhibitor (Roche), lysed with a tip sonicator (VirSonic, 6 cycles of 10 s on, 15 s off at 6.5 power level), then pelleted at 30,000×g for 30 minutes and filtered through a 1.2 μM filter. The clarified lysate was rocked with 2 ml of cobalt resin (Thermo Pierce) for 30 minutes, then transferred to a column and drained by gravity. The resin was washed with ~20 ml of lysis buffer, then the fusion protein was eluted with lysis buffer containing 350 mM imidazole. DTT and EDTA were added to concentrations of 1 mM and 0.5 mM, respectively, along with protease inhibitor (Roche). The eluted protein was concentrated to 2 ml, buffer exchanged into 50 mM Tris pH 8, 250 mM NaCl, 1 mM DTT, 0.5 mM EDTA using two tandem 5 ml HiTrap Desalting columns (GE Healthcare), then cleaved with TEV protease overnight at room temperature. The cleavage reaction was passed over two tandem SepPak Classic C18 cartridges (Waters) to bind the peptide, the cartridges were washed with water+0.1% TFA, and then the peptide was eluted with 75% MeCN+0.1% TFA. After concentrating by speedvac, the peptide was purified by HPLC using a 10-100% gradient of acetonitrile in $H_2O$ with 0.1% TFA. Collected fractions were dried by speedvac and lyophilization.

Labeling of Peptides with FITC.

HPLC-purified peptides were diluted to 250-500 μM in DMSO, then 2 equivalents of TCEP were added from a 5 mM TCEP stock in 50 mM Tris pH 7. After 5 minutes of incubation at rt, 2 equivalents of N-(5-Fluoresceinyl)maleimide was added from a 2.5 mM stock in DMSO, and the reaction was incubated at rt for 30 minutes in the dark. The sample was quenched by adding 50% MeCN+0.1% TFA, then purified by HPLC as for the unlabeled peptides.

Labeling of Peptides with Biotin.

HPLC-purified peptides were diluted to 250-500 μM in DMSO, then 2 equivalents of TCEP were added from a 50 mM TCEP stock in 50 mM Tris pH 7. After 5 minutes of incubation at rt, 2 equivalents of Biotin-$PEG_2$-maleimide (Thermo Pierce) was added from a 20 mM stock in 50 mM Tris pH 7, and the reaction was incubated at rt for 30 minutes in the dark. The sample was quenched by adding 50% MeCN+0.1% TFA, then purified by HPLC as for the unlabeled peptides.

Fluorescence Polarization.

FITC-labeled peptides were diluted to 30 nM in 50 mM Tris pH 7.4, 100 mM NaCl, 5 mM $MgCl_2$, 1 mM DTT, then added to 40 ul of 2X protein stock (in the same buffer) dispensed into a 384-well black microplate (Corning). The plate was rested for 45 minutes at room temperature, then fluorescence anisotropy was recorded on a SpectraMax M5 (Molecular Devices) with excitation at 485 nm, emission at 525 nm, cutoff at 515 nm, PMT high, 100 reads, slow carriage speed, and a 500 ms settling time. Each concentration point was prepared in triplicate, and each well was read twice (and averaged). Data were plotted using Prism (Graphpad) and fit to a one-site specific binding model with hill coefficient.

Synthesis of mant nucleotides. Syntheses of mGppNHp and mGDP were performed as described by Hiratsuka.[4] 20 umol of Guanosine 5'-[β,γ-imido]triphosphate trisodium salt hydrate (GppNHp) or Guanodine diphosphate (GDP) (Sigma) was dissolved in 1000 ul of ultrapure water in a round-bottomed flask, and the pH was adjusted to ~9.5 with 1 M NaOH. The solution was heated to 38° C. in a water bath, and N-Methylisatoic anhydride (65 umol, 3.25 equiv, Aldrich, crushed to a fine powder) was added in four portions over 1 hour while stirring and maintaining the pH at 9-10 with 1 M NaOH. After 3 hours, 1 M HCl was added to lower the pH to ~7 and terminate the reaction, and the tube was incubated on ice to precipitate excess N-Methylisatoic anhydride, then centrifuged at max speed for 5 minutes. The supernatant was removed, then the crude products were purified by HPLC using a 0-60% gradient of acetonitrile in $H_2O$ with 0.1% TFA. Collected fractions were dried by speedvac and lyophilization, and quantified by absorbance ($\epsilon_{252}$=21500 at pH 7). These nucleotides were loaded onto Ras proteins using alkaline phosphatase as described above for their unlabeled counterparts.

A general scheme for the synthesis of mantGppNHp is provided below. GppNHp was dissolved in ultrapure water at 38° C. and the pH was adjusted to ~9.5 with NaOH, then N-Methylisatoic anhydride (3 equiv) was added portionwise while maintaining the pH between 9 and 10 with periodic addition of NaOH. After 3 hours, the reaction was terminated with HCl and the product was precipitated on ice before purifying by HPLC.

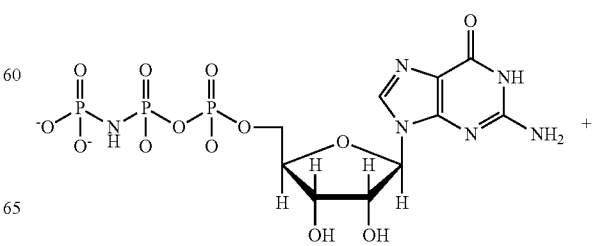

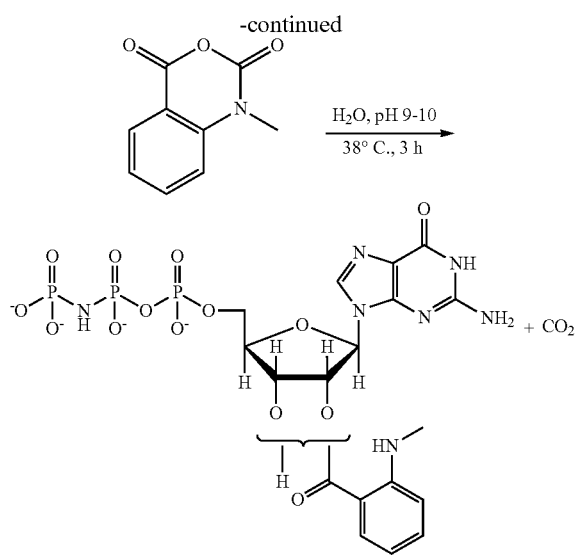

Mant Nucleotide Dissociation Experiments.

To the wells of a black 96-well plate (Corning) was added 100 ul of buffer (50 mM Tris pH 7.4, 100 mM NaCl, 5 mM MgCl$_2$, 1 mM DTT) containing 2 µM Raf or peptide, followed by 50 ul of 2 µM mant-nucleotide loaded Ras protein. After incubating for 10 minutes in the dark at rt, 50 ul of a 2.6 mM stock of unlabeled nucleotide was added for final concentrations of 500 nM Ras, 1 µM Raf or peptide, and 0.65 mM unlabeled nucleotide. The wells were mixed using a multichannel pipette, then the mant fluorescence was tracked over the course of 2 hours with a SpectraMax M5 (Molecular Devices), recording six reads every 30 seconds (excitation 370 nm, emission 450 nm, cutoff 435 nm).

Surface Plasmon Resonance.

Biotinylated KRas (GppNHp or GDP) was diluted to 50 nM in Biacore running buffer (50 mM Tris pH 7.4, 100 mM NaCl, 5 mM MgCl$_2$, 2 mM DTT+0.02% Triton X-100, filtered and degassed, with 1 uM GppNHp for the GppNHp-containing protein samples) and immobilized on a Streptavidin CAPture chip with a Biacore X100 SPR system (GE Healthcare) that had been primed three times with buffer and conditioned with 3×60 s treatments of CAPture regeneration solution. I recorded single-cycle runs with 180 second binding and 900 second stabilization, with a buffer wash after each regeneration step that preceded an analysis step. The custom parameters were as follows: Capture 1: 300 s @ 2 ul/min, 120 s stabilization; Capture 2: 45 s @ 5 ul/min, 180 s stabilization, Sample: 30 ul/min, Regeneration: 120 s @ 10 ul/min, 60 s stabilization. I began with one startup cycle and two blank cycles for background subtraction, then did sample injections at 1.23 nM, 3.7 nM, 11 nM, 33 nM, and 100 nM of 225-3 peptide that was prepared from a freshly dissolved and quantified sample of 225-3 in 5 mM NaOH. All samples were prepared in cap-free Biacore tubes (GE Healthcare). Data were processed and analyzed by the instrument software, using a two-step binding model.

Pulldown Assays in Capan-1 Cell Lysate.

Capan-1 adenocarcinoma cells were obtained from the American Type Culture Collection and cultured at 37° C. (humidified atmosphere at 5% CO$_2$) in Iscove's Modified Dulbecco's Medium (IMDM) with 20% fetal bovine serum and 1X antibiotic/antimycotic (anti-anti, Gibco) using 75 cm$^2$ culture flasks (Falcon). Cells from two flasks were grown to ~90% confluency, trypsinized for 15 minutes at 37° C., pelleted, washed with cold PBS, then lysed by incubating for 10 minutes in 50 mM HEPES pH 7.5, 100 mM NaCl, 10 mM MgCl$_2$, 1 mM EDTA, 5 mM DTT, 1% v/v Triton X-100, and 5X HALT Protease Inhibitor (Thermo). The cells were pelleted at 16,000×g for 10 minutes in a tabletop centrifuge, then the supernatant was snap-frozen and stored at −80° C. The day of the pulldowns, the lysate was thawed and diluted 10-fold in lysis buffer containing only 0.01% v/v Triton X-100 (high detergent concentrations interfere with the Ras-peptide interaction). All subsequent steps were performed at 4° C. For peptide pulldowns, the lysate was pre-incubated with mock or with Raf RBD (3 µM) for 10 minutes before adding biotinylated 225-3 (5 µM) and incubating for 45 minutes, followed by the addition of 50 ul of Streptavidin MyOne T1 Dynabeads (Life Technologies) that had been blocked with Dulbecco's PBS containing 0.1 mg/ml of BSA for 10 minutes at rt. The samples were rotated for 30 minutes, then the beads were collected with a magnet and washed with 3×400 µl of lysis buffer containing 0.1% v/v Triton X-100. The samples were eluted from the beads by boiling in SDS loading buffer for 5 minutes, then pelleting at 16,000×g in a tabletop centrifuge. For Raf RBD pulldowns, the lysate was pre-incubated with mock or with peptide (10 µM) for 10 minutes before adding GST-tagged Raf RBD (5 µM) and 50 ul of glutathione agarose beads (Thermo) and rotating for 60 minutes. The supernatant was removed by spinning through a filter column (Thermo) and the beads were washed with 3×400 µl of lysis buffer containing 0.1% v/v Triton X-100. The samples were eluted from the beads by soaking in SDS loading buffer for 5 minutes, then pelleting at 16,000×g in a tabletop centrifuge and boiling for 5 minutes. Samples were run out on a 10% SDS-PAGE gel at 150 V for 45 minutes, then transferred to an 0.45 µm nitrocellulose membrane (Whatman) in 15 mM Tris, 192 mM glycine, 20% methanol using a western blotting chamber (Invitrogen) at 50 V for 45 minutes. The membrane was blocked for 1 hour with 5% dry nonfat milk in tris-buffered saline with 0.1% v/v Tween-20 (TBS/T), washed with TBS/T, then incubated overnight at 4° C. in 5% BSA in TBS/T with a 1:1000 dilution of Anti-Ras rabbit mAb (Cell Signaling, #3339). The next day, the membrane was washed with TBS/T, incubated for 1 hour at rt with Anti-rabbit HRP conjugate (Cell Signaling), washed once more, then visualized with SuperSignal West Pico chemiluminescent imaging reagents (Thermo) and BioMax Light film (Kodak/Carestream Health).

Nuclear Magnetic Resonance.

To prepare $^{15}$N-labeled KRas or peptide, cells were grown in minimal media containing 1 g/l of [15]NH$_4$Cl and expressed as for unlabeled protein. KRas and 225-1 were purified as described above, then buffer exchanged into NMR buffer (50 mM HEPES pH 7.4, 50 mM NaCl, 2 mM MgCl$_2$, 2 mM TCEP, 0.1 mM EDTA, 0.02% NaN$_3$). Ras and peptide were mixed at <50 µM to avoid aggregation, then concentrated to 100-200 µM, mixed with 1/19 volumes of D$_2$O (final concentration of 5%), filtered through an 0.45 µm membrane, then added to a Shigemi BMS-3 NMR sample tube. NMR experiments were performed at 298K, using TROSY, on a 700 MHz Bruker (equipped with cryoprobe). Data were processed with NMRpipe and visualized using NMRview.

Reduction Tests.

Peptides were dissolved in buffer and incubated with 0 mM, 5 mM, or 50 mM DTT before analyzing by reverse-phase HPLC. Reduced peptides elute earlier than oxidized peptides, as determined by LC/MS analysis of the samples.

Complex Formation, Crystallization and Data Collection.

K-Ras/RDA complexes were formed by mixing K-Ras with 1.2 fold molar excess of RDA peptide at 25 pM K-Ras concentration in 20 mM Tris pH 8.0, 50 mM NaCl, 5 mM $MgCl_2$. After incubation at for 1 hour, the complex was purified by size exclusion chromatography. Crystals of K-Ras in complex with RDA1 and GMP-PNP were grown after mixing 0.5 µl of complex (9 mg/ml in 20 mM Tris pH 8.0, 50 mM NaCl, 5 mM $MgCl_2$) and 0.5 µl of reservoir solution containing 0.3 M calcium chloride and 23% (w/v) PEG 3350. K-Ras/RDA2/GMP-PNP complex was crystallized using 0.5 µl of complex (11.5 mg/ml) mixed with 1 µl of the reservoir solution containing 0.1-0.2 M ammonium sulfate, 20-22% PEG 3350. All crystals were grown at 20° C. by sitting drop vapor diffusion. For cryo-protection, all harvested crystals were briefly incubated in the reservoir solutions supplemented with 20% glycerol prior to be flash-frozen in liquid nitrogen. All diffraction data were collected at 24-ID beamline at the Advanced Photon Source, and were processed with XPD and HKL2000 suite.

Structure Determination and Refinement.

K-Ras/RDA1/GMP-PNP complex crystallized in the space group of P21 with four molecules in the asymmetric unit. K-Ras/RDA2/GMP-PNP complex also crystallized in the space group of P21 but with a single molecule in the asymmetric unit. Both structures were determined by molecular replacement with PHASER using the previously determined K-Ras structure (PDB access 3GFT) as a search model. RDA peptide models were built through iterative cycles of manual model building in COOT and structure refinement using REFMAC. The final models were refined using PHENIX at 2.15 Å and 1.7 Å, respectively, and validated by MolProbity.

Live-Cell Confocal Microscopy.

Human tumor cell lines (e.g., H358 or HPAF-II) were seeded into LabTek II culture chambers in DMEM media supplemented with 10% fetal calf serum and grown overnight at 37° C. under standard cell culture conditions. The following day, media was replaced with media containing 5 uM of fluorescein-labeled peptide and incubated for 4 hours at 37° C. The cells were washed, stained with NucBlue Hoechst 33342 and Dextran 10k Alexa647, then imaged on a confocal microscope. The fluorescent peptides were visualized with a 488 nm laser and is shown in green in FIGS. 34A-B.

Example 1: Ras Binding Peptides Characterization and Ras-Peptide Crystal Structure Binding Affinity.

Binding affinity of the peptides to K-Ras was determined by fluorescence polarization experiments. Below is the sequence of the peptides used along with their dissociation constants measured.

| Peptide | Peptide Sequence | $K_d$ |
|---|---|---|
| RDA1 | GPRRPRCPGDDASIEDLHEYWARLWNYLYAVA (SEQ ID NO: 4) | 17 nM |
| RDA2 | GPRRPRCPGDDASIEDLHEYWARLWNYLYRVA (SEQ ID NO: 5) | 8 nM |
| RDA3 | GRRPRRPRCPGDDASIEDLHEYWARLWNYLYAVA (SEQ ID NO: 6) | 6 nM |

Reduction Tests.

Figure 31A:
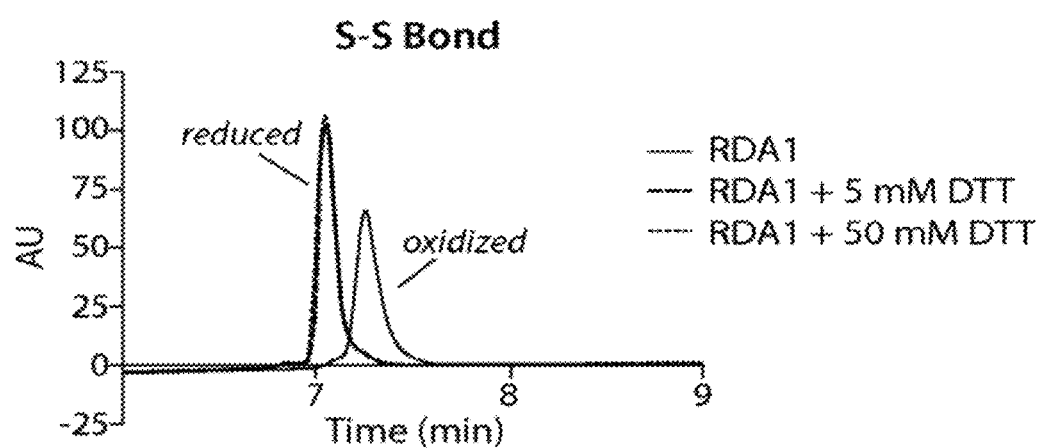
FIGS. 31A-B shows a HPLC assay that can distinguish between oxidized (disulfide-crosslinked) peptide dimers from reduced (non-crosslinked) peptide monomers. By adding 5 mM or 50 mM DTT, a reducing agent much stronger than the cellular environment, we can show that the selenocysteine-containing peptide dimers (FIG. 31B) cannot be reduced, unlike their cysteine-containing analogs (FIG. 31A). Method: peptides were dissolved in buffer and incubated with 0 mM, 5 mM, or 50 mM DTT before analyzing by reverse-phase HPLC. Reduced peptides elute earlier than oxidized peptides, as determined by LC/MS analysis of the samples.
Figure 31B:
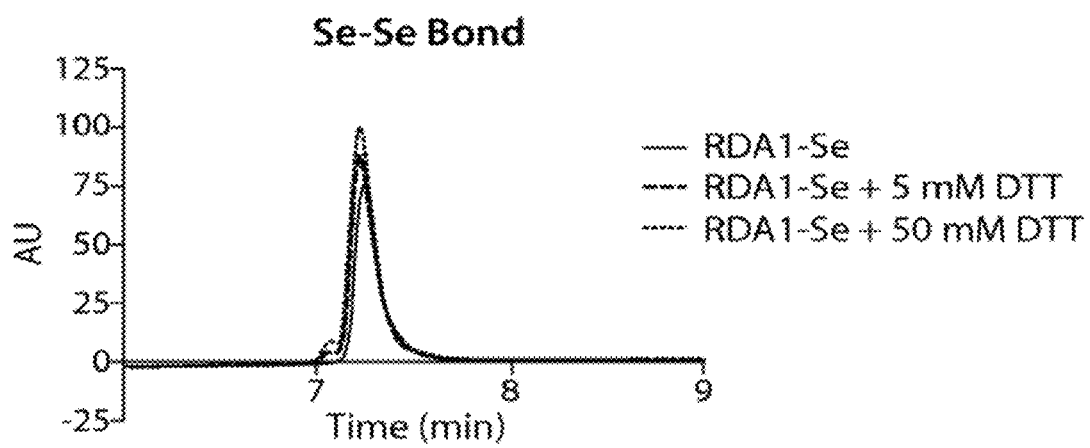

This is an HPLC assay that can distinguish between oxidized (disulfide-crosslinked) peptide dimers from reduced (non-crosslinked) peptide monomers. By adding 5 mM or 50 mM DTT, a reducing agent much stronger than the cellular environment, it was observed that the selenocysteine-containing peptide dimers cannot be reduced, unlike their cysteine-containing analogs (see FIGS. 31A-B).

Ras-RDA Structures.

Figure 32:
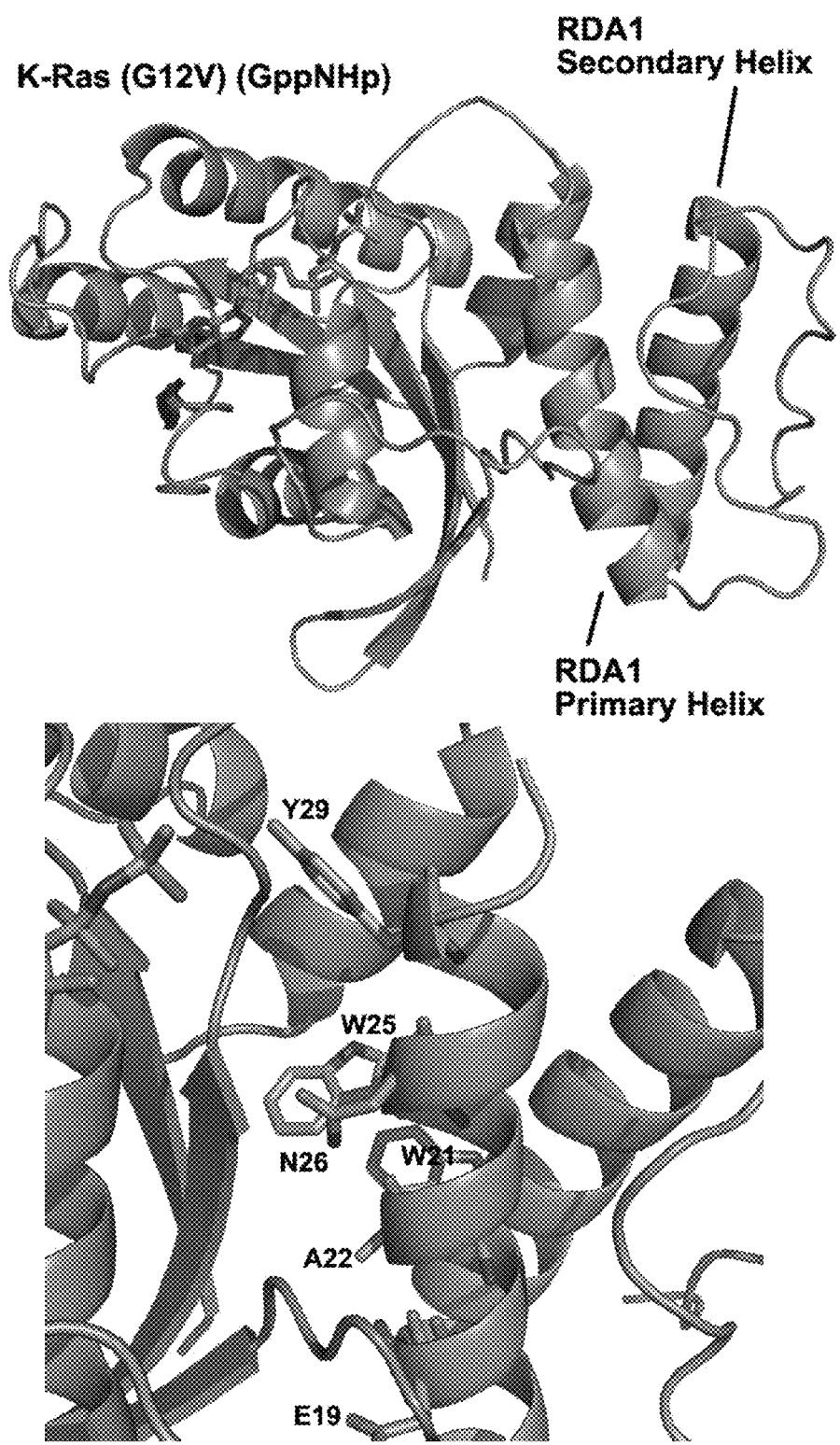
FIG. 32 shows structures of Ras RDA1 (SEQ ID NO: 4). The first shows the overall structure, at 2.2 Angstrom resolution. The second two show close-ups of the primary helix with the key binding residues identified.
Figure 32:
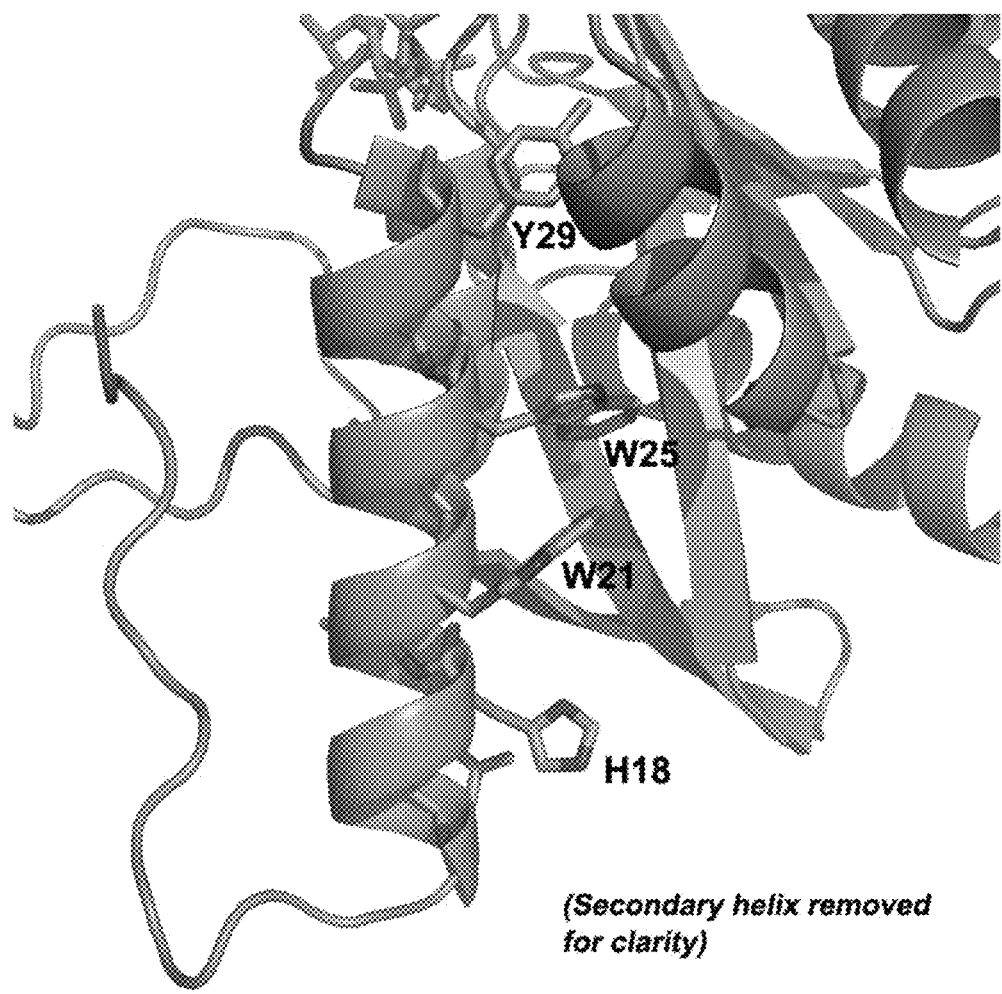
Figure 33A:
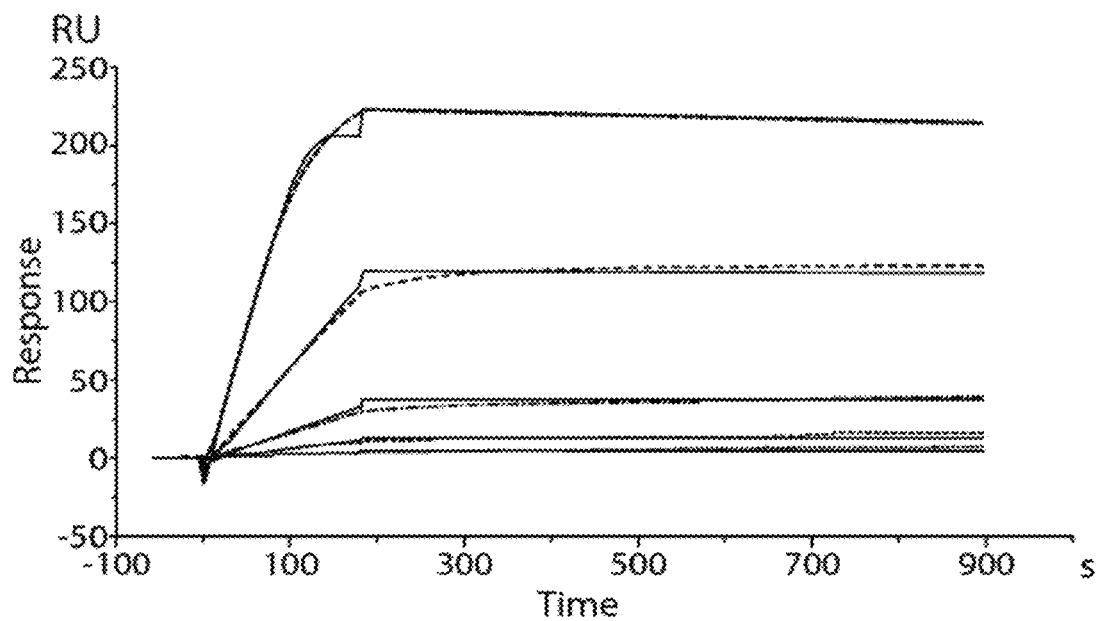
FIGS. 33A-B show surface plasmon resonance measurements of Ras-peptide interactions. Biotinylated KRas (bound to either GppNHp or GDP) was immobilized on a streptavidin capture chip, then free dimeric peptides were injected at increasing concentrations. The high affinity of the interactions permitted "single cycle" runs that lack a regeneration step between injections and produce step-like binding curves. Data were fit using a two-step binding model.
Figure 33B:
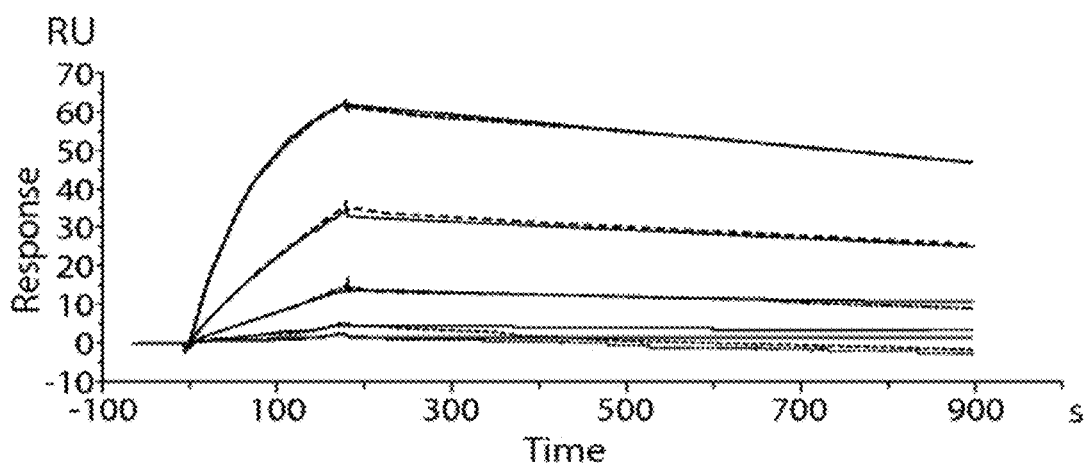

FIG. 32 shows the overall structure, at 2.2 Angstrom resolution. FIG. 32 also shows the primary helix and the key binding residues identified.

Example 2: Yeast Display Screen for Ras-Binding Peptides

We pursued two strategies to identify peptides that bind the Ras effector domain, both of which involved screening large peptide libraries by yeast surface display. Our first approach was to screen naïve libraries that were based on a small peptide scaffold with no known ability to bind Ras. These libraries were designed to contain as much structural diversity as possible, while remaining in a stable conformation. Our second approach was to screen a library based on the domain of a protein known to bind the Ras effector domain. In this case, the goal of the screen was to identify a stabilized mutant of the domain that was capable of binding Ras in the absence of the scaffolding provided by its parent protein.

Library Scaffold Selection.

To identify candidate scaffolds for the naïve libraries, we searched the Protein Data Bank for polypeptides with a mass between 1000 and 5000 Da for which either an X-Ray or nuclear magnetic resonance (NMR) structure was available. We manually curated the results to select peptides on the basis of structural stability, whether provided by noncovalent interactions or covalent ones (e.g. disulfide bonds). The helical avian pancreatic polypeptide (aPP, PDB: 1PPT) was chosen for preliminary studies.

Avian pancreatic polypeptide (aPP) is a 32-amino acid miniprotein originally isolated from chicken pancreas. Its structure consists of an N-terminal polyproline type II (PPII) helix, a type-I β-turn, and a C-terminal a-helix. aPP forms head-to-tail homodimers in solution, stabilized by intermolecular contacts between residues from both the helices and loops. Intramolecular hydrophobic interactions between the PPII and a-helices stabilize aPP monomers into a well-defined fold with relatively high stability (melting transition ($T_m$) 62° C.), an attractive property for a scaffold since high thermal stability has been shown to enhance the evolvability of some proteins. Schepartz and co-workers demonstrated that residues from the a-helices of various proteins could be grafted onto the exposed face of the aPP a-helix to afford chimeric proteins that retained the ability to bind the original protein's targets. For example, Zondlo et al. grafted residues from the DNA-binding domain of the yeast transcription factor GCN4 onto the aPP scaffold to generate a miniprotein capable of binding the GCN4 half-site with low-nanomolar affinity. In another instance, Kritzer et al. grafted residues from the hDM2-binding domain of p53 onto aPP, then applied mutagenesis and screening to improve the affinity of the resulting peptide.

Schepartz and co-workers also demonstrated that aPP could be endowed with cell-penetrating properties by replacing multiple residues with arginines, which are known to enhance cell uptake in some contexts. In one case, Daniels et al. substituted residues from the PPII helix and β-turn with arginine to afford peptides that penetrated HeLa cells at a concentration of 1 µM and were not sequestered in endosomes. In a separate study, Smith et al. replaced residues from the a-helix with arginines to produce peptides that also penetrated HeLa cells at 1 µM, albeit with a significant fraction of peptides remaining localized to endosomes. This potential for cell penetration, along with the stable secondary structure and established examples of engineering, made aPP an attractive scaffold for the screening and evolution of Ras-targeted libraries.

Figure 3A:
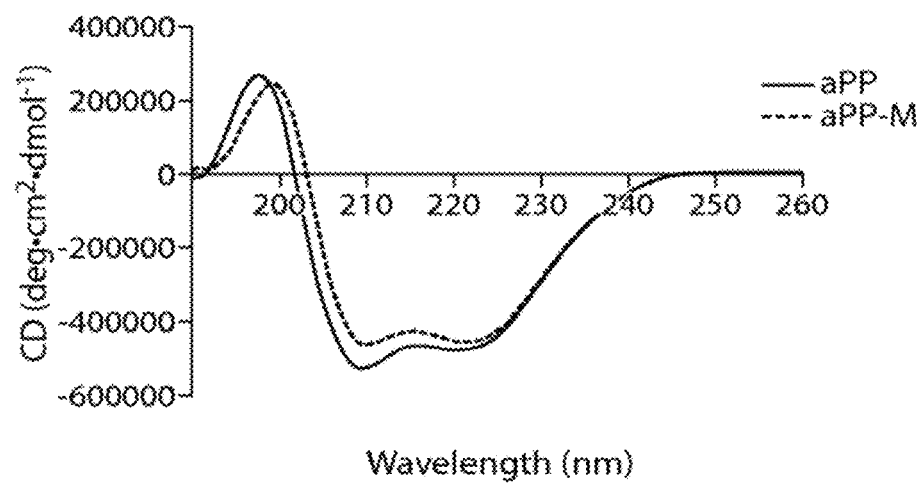
FIGS. 3A-B show that aPP-M has higher thermal stability than wild-type aPP.
Figure 3B:
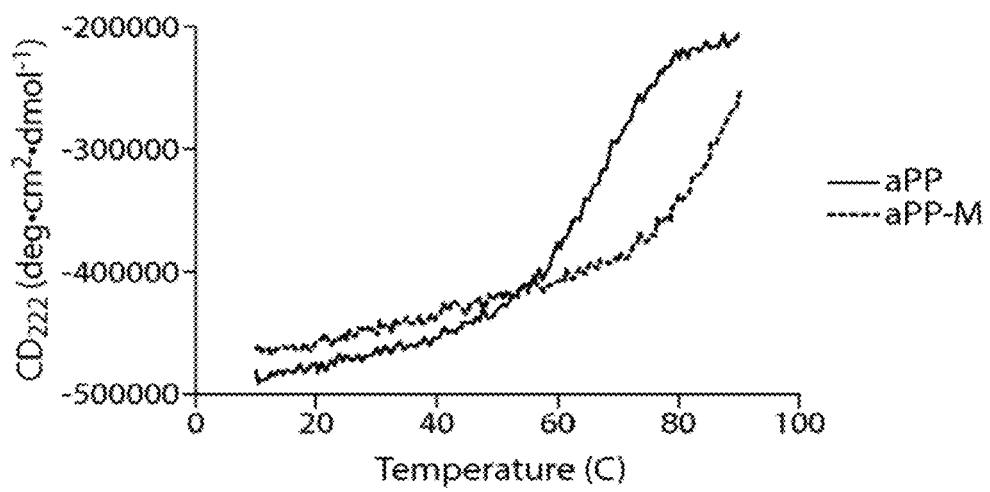
Figures 4A, 4B:
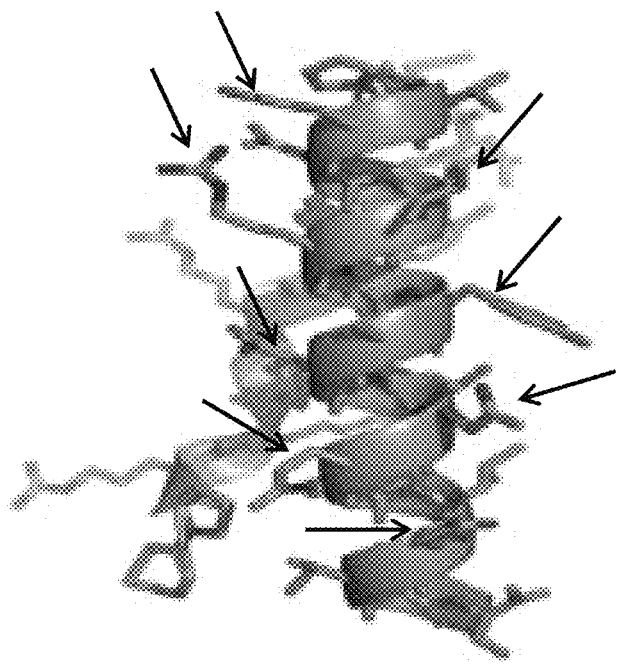
FIGS. 4A-B show library scaffolds and residues selected for randomization. A structure of aPP are found in FIG. 4A, with randomized residues indicated with an arrow.

An important caveat of these cell-penetration studies is that while the aPP mutants retained their aPP fold as determined by circular dichroism (CD) spectroscopy, they were destabilized by the introduction of arginines. Because a less stable scaffold is predicted to tolerate fewer mutations before losing its fold, a smaller fraction of the resulting library would have a defined conformation. We therefore sought to identify an aPP mutant that incorporated some of the arginine substitutions that were shown to confer cell permeability, but that did not compromise the stability in the scaffold. As our aim was to use the a-helical surface for randomization, we focused on the most cell-penetrating peptide from the PPII-displayed arginine series, which contained six arginine mutations. Inspection of the aPP crystal structure suggested that three of the mutated residues form potentially stabilizing contacts with other amino acids within the peptide. To test the hypothesis that these residues contributed to the majority of the destabilization, we synthesized an aPP mutant, aPP-M, that left these positions unchanged (wild-type), while mutating the remaining three to arginine (see FIGS. 4A-B for sequences). To assess the stability of this peptide, we recorded its CD spectrum and melting profile alongside that of aPP (FIGS. 3A-B). We truncated both peptides after the $32^{nd}$ amino acid, which is the end of the a-helix. The CD spectrum at 25° C. was nearly identical for the two peptides and consistent with those published in the literature, indicating that the overall conformation remained unchanged. Unexpectedly, the Tm of aPP-M was increased relative to aPP, from 64.5° C. to >77° C. The origin of this additional stability is not entirely clear, although it is known that arginine can be stabilizing in the context of PPII helices. Due to its improved stability and arginine content, we used the aPP-M mutant as the scaffold for yeast display libraries.

The most practical way to cope with the instability of disulfide bonds in cells is to replace the disulfide with a more stable linker. One possibility would be to incorporate a diselenide bond, which is isosteric with a disulfide but has a redox potential that renders it stable to the reducing environment of human cells. Craik and co-workers have shown that such substitutions are able to improve the stability of conotoxins without perturbing their structure. A second options would be to replace the disulfide with an unnatural linker, such as the all-hydrocarbon bridges used for "stapled peptides." This could potentially be more stable than a disulfide or diselenide (as it cannot be reduced) and may contribute to cell penetration, but would not be as isosteric. Additionally, there is no published precedent for stabilizing P3 structures with such linkers, so there would likely be the need for method development to optimize the synthesis, reaction conditions, linker length and composition, and so on.

Target Protein Preparation.

Target proteins must be labeled for yeast display studies so that they can be detected on the cell surface. This is typically accomplished by biotinylating the target protein and using streptavidin beads for magnetic activated cell sorting (MACS) or streptavidin-fluorophore conjugates for FACS. One drawback of this approach is that peptides capable of binding streptavidin can produce false positives, which can out-compete true target binders if their affinity is sufficiently high. Selection for these secondary-binding sequences can be partially suppressed by utilizing different biotin binding agents, for example, performing MACS with beads conjugated to anti-biotin antibodies, followed by alternating between neutravidin-phycoerythrin (NA-PE) and streptavidin-allophycocyanin (SA-PE) for FACS. For our initial library screens and directed evolution efforts, we adopted this approach, although we did encounter contamination from secondary binders on several occasions. For our more recent yeast display studies, we have attempted to avoid this issue by performing FACS with Ras proteins that have been directly conjugated to a small-molecule fluorophore, with no accompanying secondary step.

Figure 6:
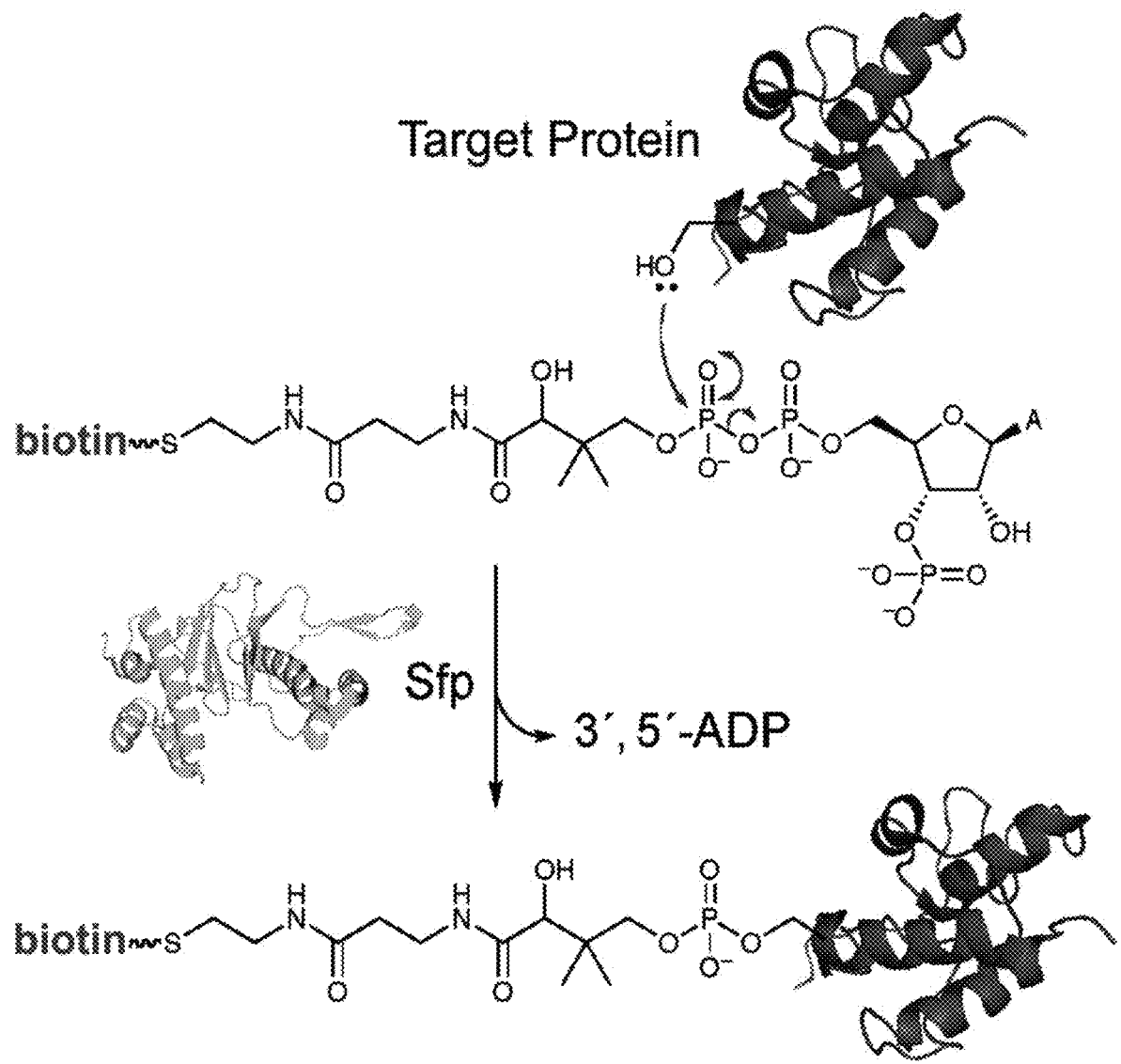
FIG. 6 shows site-specific labeling of proteins with Sfp phosphopantetheinyl transferase. The sulfhydryl moiety of CoA is reacted with a maleimide-functionalized label of choice (e.g., biotin), then the resulting conjugate is transferred to the yBBr tag on the target protein by Sfp.

To prepare the target protein, the gene for residues 1-177 of human KRas (G12V) was subcloned into a pET expression vector, with a native N-terminus and C-terminal His$_6$ (SEQ ID NO: 55) and yBBr tags. The His$_6$ tag (SEQ ID NO: 55) enables the fusion protein to be purified from cell lysate using standard immobilized metal affinity chromatography (IMAC) methods with Nickel-NTA or Cobalt resins. The yBBr peptide is an optimized 11-amino acid substrate sequence (DSLEFIASKLA (SEQ ID NO: 94)) for Sfp phosphopantetheinyl transferase, which can catalyze the covalent addition of the phosphopantetheinyl group from Coenzyme A (CoA) onto the sidechain hydroxyl of the serine residue at position 2 in the peptide. This reaction generally tolerates substitutions at the sulfhydryl end of CoA, and thus can be used to attach fusion proteins to conjugates of CoA with biotin, fluorophores, etc with high selectivity (FIG. 6). We viewed this strategy as preferable to nonspecific labeling, e.g. using amine or thiol-reactive probes, which could potentially perturb the native structure of Ras by modifying the lysine and cysteine residues that lie within or proximal to the effector domain. We chose the G12V mutant of KRas for these studies since it is one of the most common oncogenic mutations found in human cancers, and has a lower background rate of GTP hydrolysis than wild-type.

Figure 7A:
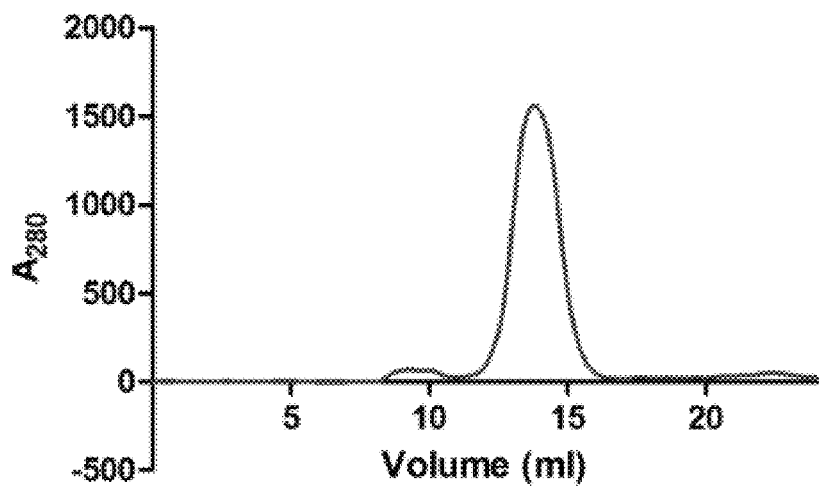
FIGS. 7A-C show the purification of Ras proteins.
Figure 7B:
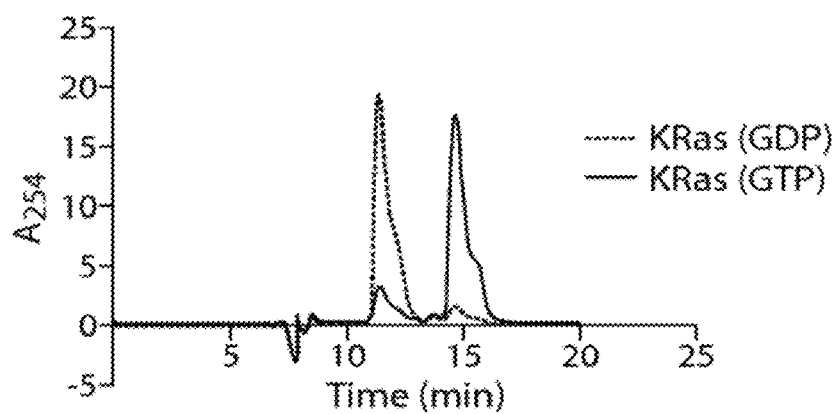
Figure 7C:
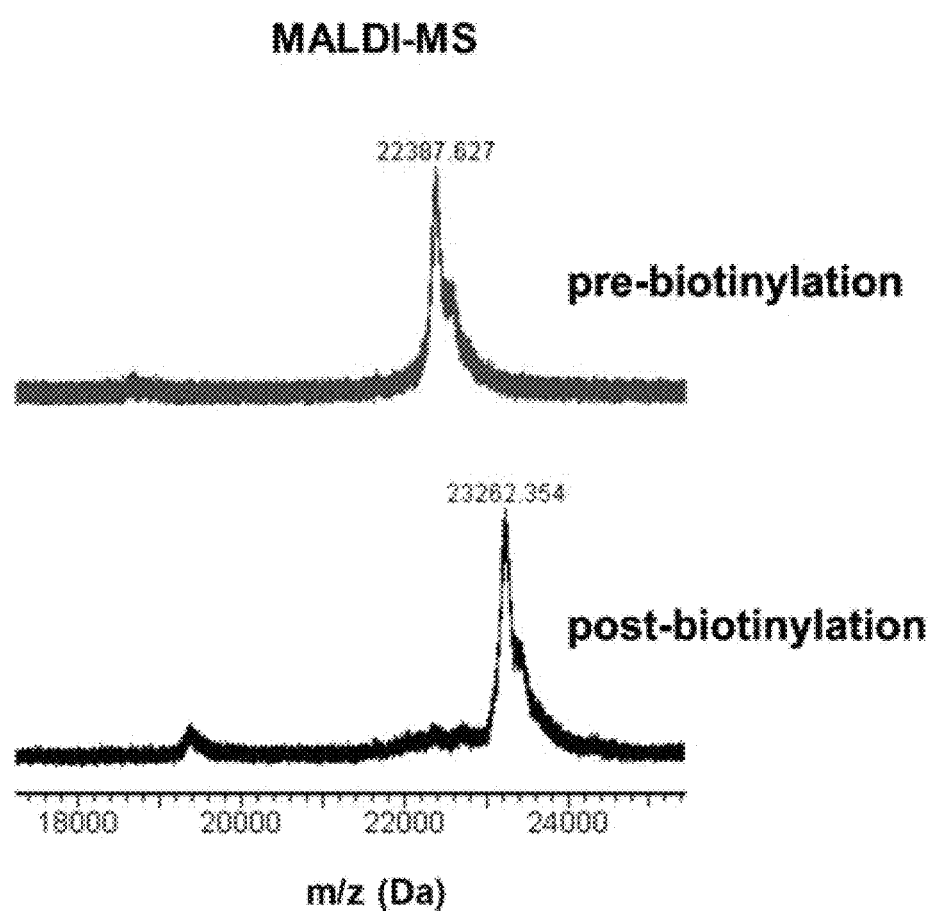
Figure 8:
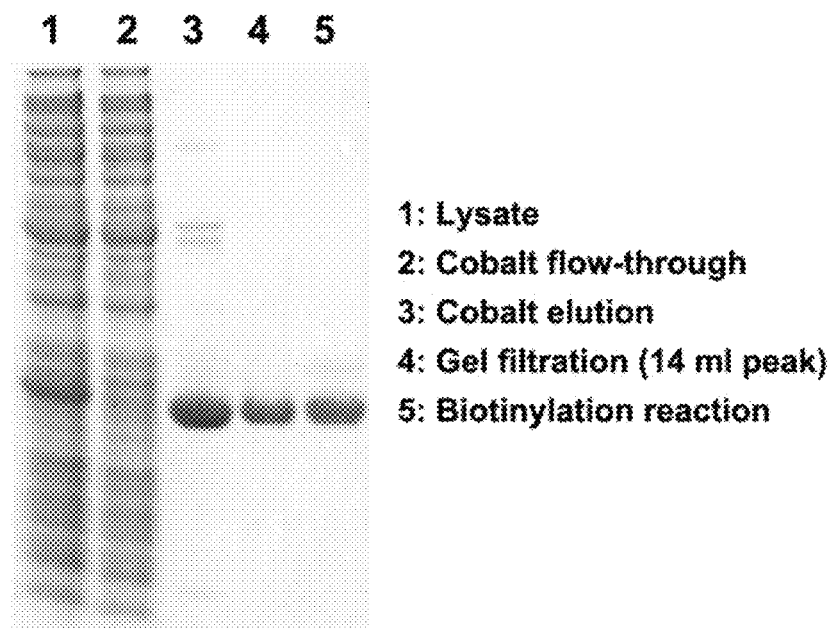
FIG. 8 shows a SDS-PAGE gel of Ras protein samples from the purification steps (Coomassie stain).

We expressed the KRas construct in *E. coli* (DE3) cells containing the T7 lysozyme and the Rosetta I plasmid, which carries six tRNAs whose codons are commonly found in human genes but are not present in *E. coli*. The pET expression system works by placing both the recombinant protein (which has a T7 promoter) and T7 RNA polymerase under control of the lac operator, which is constitutively suppressed by the lac repressor. Addition of isopropyl β-D-1-thiogalactopyranoside (IPTG, an allolactose analog) relieves the repression of these two proteins, permitting expression of T7 RNA polymerase and thus the expression of the recombinant protein. We grew the cells in Lysogeny Broth (LB) media at 37° C. until they reached an optical density (OD) of approximately 0.7, then induced expression of the fusion protein with IPTG at 30° C. The cells were lysed by sonication, clarified by centrifugation, and Ras was purified using Cobalt resin. The crude protein was further purified by gel filtration (FIG. 7A), enzymatically loaded with the desired guanine nucleotide (FIG. 7B), and then labeled with biotin or fluorophore using Sfp as detailed by Yin, J., et al. Site-specific protein labeling by Sfp phosphopantetheinyl transferase. Nat Protoc 1, 280-5 (2006). (FIG. 6). Labeling was verified by Matrix-assisted laser desorption/ionization mass spectrometry (MALDI-MS) analysis of the protein before and after the Sfp reaction (FIG. 7C).

GTPases typically bind guanine nucleotides with high affinity; in the case of HRas, the dissociation constant ($K_d$) is in the low-picomolar range. Such high affinities mean that recombinantly expressed Ras proteins retain their nucleotides throughout the purification process, typically in a mixture of GDP- and GTP-bound states. Wild-type forms of Ras will slowly hydrolyze GTP to GDP even in the absence of GAP proteins, but mutants such as the G12V used in our studies tend to hydrolyze very slowly. This heterogeneous mixture is not ideal for yeast display or biochemical assays, as the conformation and binding properties of Ras are markedly different between the two nucleotide states. The high nucleotide binding affinity poses a challenge from the standpoint of manipulation: proteins cannot be loaded simply by providing a large excess of the desired nucleotide, and enzymes such as alkaline phosphatase are unable to efficiently degrade the nucleotides because they are free in solution at concentrations far below the enzyme $K_m$.

Two strategies have been developed to prepare homogenously loaded Ras proteins. The first involves the addition of EDTA to the purified protein, which chelates $Mg^{2+}$ ions and removes them from the nucleotide binding pocket. This lowers the affinity of the Ras-nucleotide interaction and allows nucleotides to be exchanged by adding a large excess (typically 100-fold) of the desired nucleotide and incubating at room temperature.[34] In our experience, this method can load proteins up to a level of 85-90%, and was used to prepare proteins for our early yeast display and biochemical experiments. A second approach is to add alkaline phosphatase and non-hydrolyzable GTP analogs, such as Guanosine 5'-[β,γ-imido]triphosphate (GppNHp) or β,γ-methyleneguanosine 5'-triphosphate (GppCp) to Ras proteins that have been exchanged into buffer that is $Mg^{2+}$-free. Under these conditions, the Ras-nucleotide affinity is sufficiently low to permit exchange of the initial nucleotide with the nonhydrolyzable analog, and if Ras is sufficiently concentrated (>100 µM) the concentration of hydrolysable nucleotides becomes high enough to be efficiently degraded by the alkaline phosphatase.[33] If GppCp is used, GDP or GTP can be efficiently loaded back on the protein following phosphatase removal, as GppCp has 100-fold lower affinity and is easily competed by an excess of natural nucleotide.[35] This method can be used to achieve nearly quantitative conversion to Ras proteins loaded with the desired nucleotide, and was used for our more recent studies. We determined the Ras nucleotide state by injecting purified proteins onto a reverse-phase (C18) high-performance liquid chromatography (HPLC) column equilibrated with phosphate buffer containing 7.5% acetonitrile and 100 mM tetrabutylammonium bromide. The tetrabutylammonium ions bind guanine nucleotides at a stoichiometry proportional to the number of phosphate groups, such that GTP is complexed with more lipophilic cations than GDP and thus behaves as a more hydrophobic molecule. Developing the column under isocratic conditions affords clear separation of GDP and GTP (FIG. 7B), whose retention times can be determined using purified nucleotide standards.

Yeast Display Screening.

Figure 9:
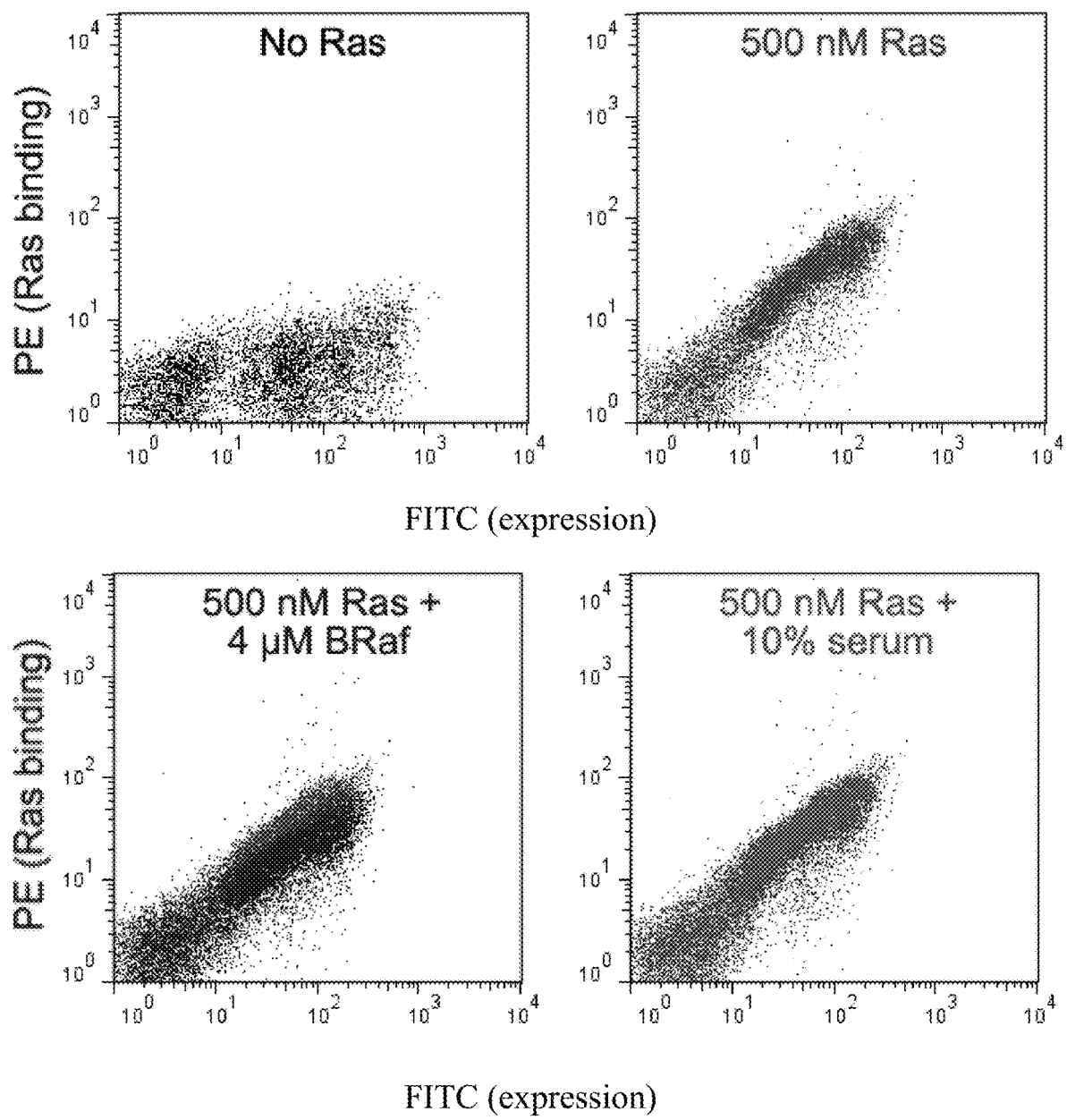
FIG. 9 shows flow cytometric analysis of initial hit from aPP-scaffolded library. Yeast cells were incubated in the presence of no Ras, 500 nM KRas, 500 nM KRas and 4 µM B-Raf RBD, or 500 nM KRas with 10% v/v human serum. The 500 nM KRas sample is overlaid in the Raf and serum plots for comparison.

We carried out yeast display protocols as described by Chao, G., et al. *Isolating and engineering human antibodies using yeast surface display. Nat Protoc* 1, 755-68 (2006). We first performed an initial pilot screen with the aPP library, using biotinylated KRas(G12V)-GTP as the target. As the size of the library was larger than the number of cells that can be conveniently evaluated by FACS, we began the screen with a MACS step. We screened $2*10^9$ cells at a Ras concentration of 1 µM, and isolated approximately 190,000 cells. We sorted the resulting library by FACS for one round at 1.8 µM, then three rounds at 550 nM. These five sorts afforded a cell population that showed strong binding to Ras at 550 nM (FIG. 9). To test whether the displayed peptides bound the Ras effector domain, we incubated yeast with KRas that had been pre-mixed with a large excess of the RBD of BRaf. The apparent Ras binding was decreased, although some still appeared to be bound. We sequenced the isolated population and found three closely related peptide sequences (see FIG. 10 and discussion below).

Directed Evolution of aPP-Scaffolded Peptides.

FIG. 10 provides a list of peptides identified through the course of the evolution. Preliminary studies were focused on three hits derived from the aPP-mutant library, which were named 221-1, 221-2, and 221-3. All three shared several of the randomized residues in common: H18, W21, W25, N26, and Y29 (FIG. 10). At the remaining positions, there was no strong consensus (E/G at residue 15, A/E/W at residue 19, and A/Q at residue 23). We also observed a spontaneous mutation at R6 to lysine in 221-3. We noted that there was a relatively high prevalence of hydrophobic residues in these sequences, suggesting that the observed binding could be due to weakly specific hydrophobic interactions. To assess this possibility, we performed yeast surface binding assays on the aPP hit population in the presence and absence of human serum, which contains a heterogenous mixture of proteins and would be predicted to lower Ras-peptide binding if the interaction was primarily driven by hydrophobic interactions. The FACS plots showed essentially no change in binding even when serum was added to 10% v/v (FIG. 9), indicating that the Ras-peptide interaction is resilient to nonspecific competitors.

Directed evolution was used to improve the affinity of the aPP hits. Yeast display was done as before, using an initial MACS round followed by FACS, at a lower concentration of KRas. Additionally, we decided to conduct the evolution in the presence of 5% v/v human serum and 100 µg/ml non-specific DNA (single stranded, from salmon sperm) to maintain a selective pressure against nonspecific binding. The summary of conditions and their resulting sequences is shown in FIG. 10, with color-coding to indicate the round in which mutations first appeared.

For the second round (which afforded the 223 peptides), we diversified the three 221 hits from the first round by error-prone PCR, then performed MACS at a KRas concentration of 100 nM. We enriched the resulting population over five rounds of screening by FACS at 50 nM KRas, affording two unique sequences that shared two mutations in common (P13S and V30A) along with an additional mutation each (X23R for 223-1 and VI41 for 223-2). By inspection of the nucleotide sequences, we found that 223-1 was derived from 221-2, and that 223-2 was derived from 221-1. It is important to note that one cannot assume that all of these mutations are beneficial; it is possible that there are neutral or deleterious mutations that were selected by virtue of their genetic linkage to favorable ones. It seems reasonable in the case of these two sequences to conclude that S13 and A30 are favorable, as they arose independently from different parent sequences and remained fixed (with one exception) in the subsequent rounds of evolution.

For the third round (which afforded the 224 peptides), we diversified the two 223 hits from the second round by error-prone PCR, then performed MACS at a KRas concentration of 25 nM. We screened the resulting library twice by FACS at 25 nM KRas, and obtained three unique sequences. Nucleotide analysis indicated that 224-1, 224-2, and 224-3 were derived from 223-1, and that 224-4 was derived from 223-2. The 224-1, 224-2, and 224-3 peptides share a common Y7C mutation (see below), with 224-1 carrying an additional F20Y mutation and 224-2 carrying the V14I mutation observed earlier in 223-2. The sequence of 224-4 is identical to 223-2, with the exception of an additional PRR inserted at the beginning of the PPII helix. This apparently favorable mutation was most likely introduced into the library by primer sliding during the PCR, perhaps because the sequence immediately prior to the aPP peptide is repetitive ($G_4SG_4SG_4$ (SEQ ID NO: 95)).

We initially characterized the Y7C mutation found in 224-1, 224-2 and 224-3 as an artifact, assuming that this cysteine (in the PPII helix) was improving the apparent affinity of the peptide by forming a disulfide bond with one of the surface-exposed cysteine residues in KRas. This assumption later proved to be incorrect (see Chapter 2), but for the subsequent (fourth) round that afforded the 225 peptides, we decided to remove both this mutation and the PRR extension from the parent library templates. We prepared the library by error-prone PCR of a synthetic template prepared by the overlap extension method described above (FIG. 5). The template contained all of the mutations found in the third round, with the exception of Y7C and the PRR extension, in a shuffled (combinatorial) format. We also increased the concentration of KRas to 100 nM, to avoid overly-stringent conditions that might enrich rare clones that contained the Y7C mutation. After one rounds of MACS and two rounds of FACS at 100 nM, 9 of 11 clones corresponded to the 225-1 sequence, with a single clone containing an E19A mutation (225-5) and a single clone containing the A30P mutation (225-6). Note that the numbering for this round is non-chronological, due to a record-keeping error. None of the clones contained the Y7C mutation.

For the fifth and final round (which afforded the 226 peptides), we prepared the library as before by error-prone PCR of the hit templates. Following one round of MACS at 100 nM KRas, we performed three rounds of FACS with decreasing the KRas concentration, starting at 100 nM, then proceeding to 50 nM and finally to 20 nM. This population contained seven unique sequences, five of which contained the Y7C mutation, including one identical to 224-1 (226-4). Of the remaining two, one was identical to 225-1 (226-1) and the other was identical except for an I14V reversion. Based on these sequences, we concluded that we had reached the point where improvements in affinity appeared to require the acquisition of a cysteine, at least given the library diversity that was accessible to our error-prone mutagenesis approach. We decided to stop the evolution at this point and more thoroughly characterize our peptides in vitro. Because the 225-1 sequence was the most common clone in the 225 round, and appeared again without a cysteine in the 226 round, we chose it as the representative peptide for these studies. We also decided to test a version of 225-1 that contained the PRR extension found in 224-4, reasoning that it may provide improved affinity and potentially cell penetration. We named this peptide 225-3.

Example 3: In Vitro Characterization of Ras-Binding Peptides

From the directed evolution efforts, we selected two aPP-derived peptides, 225-1 and 225-3, for further study. These peptides bound KRas at nanomolar concentrations in the yeast display system, competed with Ras for Raf binding, and were remarkably tolerant to the presence of blocking agents (DNA and serum). This example describes the recombinant production of these peptides in E. coli, characterization of their binding properties in vitro, and initial efforts towards defining their binding site on the Ras surface.

Expression and Purification of 225 Peptides.

During the course of the directed evolution experiments, we prepared a small number of aPP peptides (mostly from the 223 and 224 series) using solid-phase peptide synthesis, as was done by Schepartz and co-workers for their studies (see Daniels, D. S. and Schepartz, A. Intrinsically cell-permeable miniature proteins based on a minimal cationic PPII motif. J Am Chem Soc 129, 14578-9 (2007); Kritzer, J. A., et al. Miniature protein inhibitors of the p53-hDM2 interaction. Chembiochem 7, 29-31 (2006); Smith, B. A., et al. Minimally cationic cell-permeable miniature proteins via alpha-helical arginine display. J Am Chem Soc 130, 2948-9 (2008)). However, due to the length of these sequences, and the prevalence of residue pairs that are challenging from a coupling standpoint (e.g. RP and RR), these syntheses were laborious and costly, and it was sometimes difficult to obtain clean samples even after multiple rounds of HPLC purification. Given that these peptides are composed entirely of naturally occurring amino acids, we sought to develop a recombinant expression system to overproduce our aPP peptides in E. coli. This approach has a number of advantages for sequences of this length, provided the yield is sufficient: protein expression in bacteria is generally less expensive and time-consuming than solid-phase synthesis, and the relatively low rate of translation errors[4] is such that closely related side products are less prevalent, although there are many unrelated cellular proteins that must be purified away. We subcloned an E. coli codon-optimized fragment encoding the 225-1 and 225-3 peptides (see FIG. 11 for sequences) into a pET30a expression vector, which contains an N-terminal $His_6$ tag (SEQ ID NO: 55) and S-tag, and placed a tobacco etch protease (TEV) cleavage site immediately prior to the start of the peptide sequence. At the N-termini of the peptides, we added a GCG tripeptide to act as a flexible linker between the TEV site and the start of the PPII helix (to promote efficient proteolysis) and to provide a handle (cysteine —SH group) to allow labeling of the peptides with fluorophores and biotin for subsequent experiments.

We transformed these constructs into BL21 Rosetta pLysS cells, which were grown in LB with antibiotics to maintain the plasmid, and induced expression at 30° C. using IPTG, as described for the purification of the Ras proteins. Following induction, we harvested the cells by centrifugation, lysed them by sonication, and purified the His-tagged peptide fusion using cobalt affinity chromatography. We cleaved the eluted protein by addition of TEV, then purified the resulting reaction by HPLC.

Figure 12A:
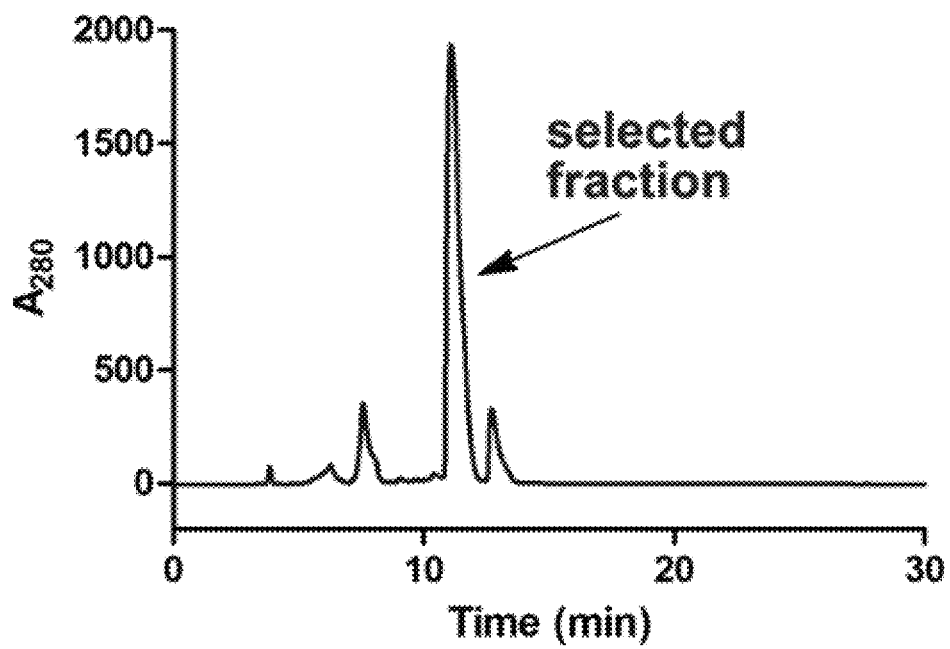
FIGS. 12A-C show the purification of 225 peptides. Following cobalt affinity chromatography and overnight TEV cleavage of the expressed fusion construct, the reaction was purified by reverse-phase HPLC (FIG. 12A). The indicated peak, containing the 225 peptide, was collected and analyzed by LC/MS (FIG. 12B and FIG. 12C). The different column size for the HPLC and LC/MS instruments accounts for the discrepancy in retention times between A and B. Data is shown for the 225-1 peptide (GCGGPRRPRYPGDDASIEDLHEYWARLWNYLYAVA (SEQ ID NO: 8)).
Figure 12B:
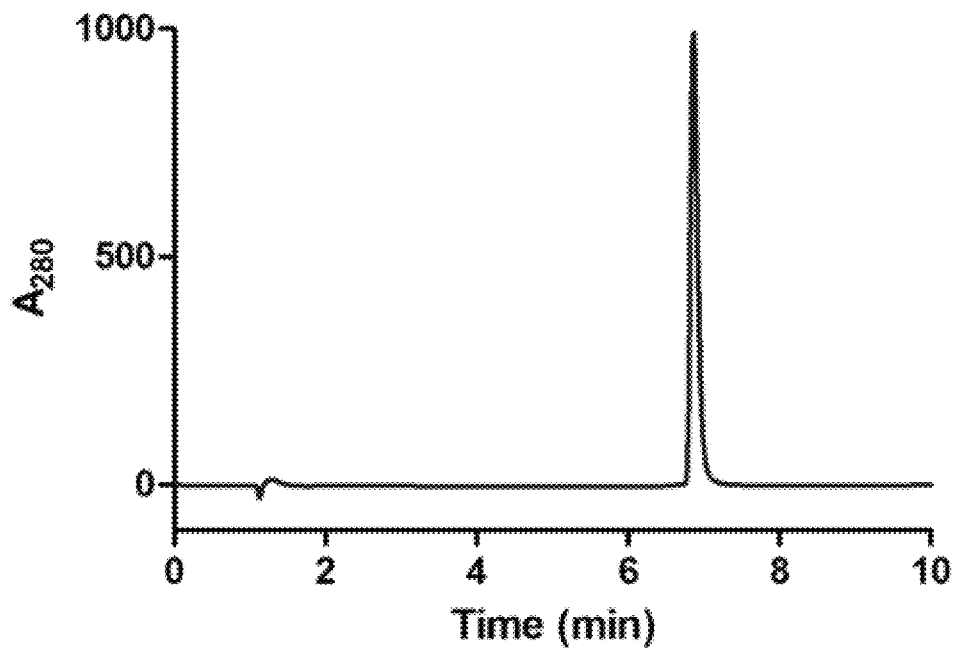
Figure 12C:
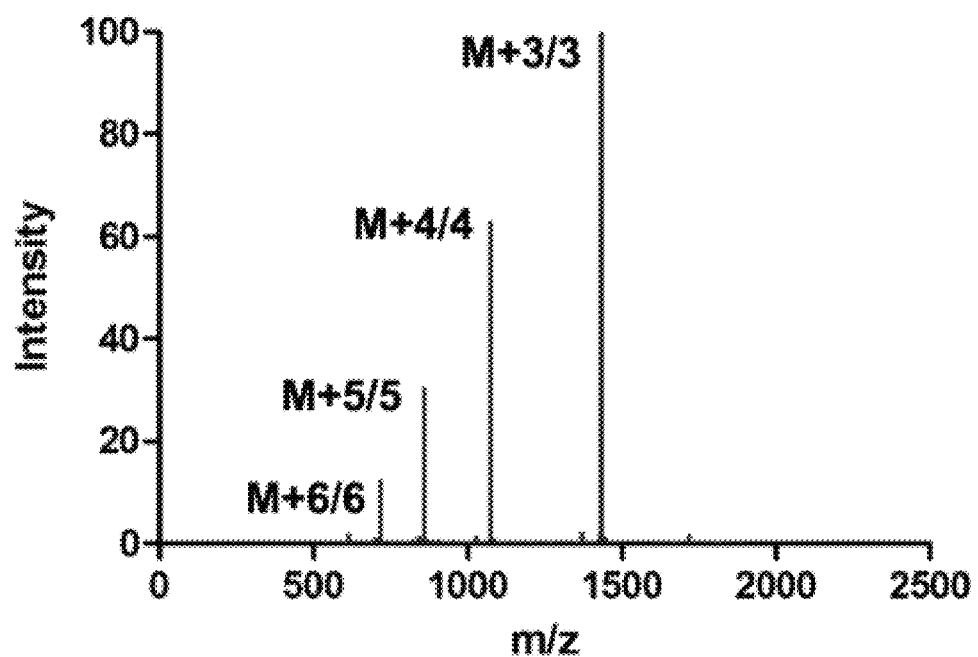

Representative data for the purification of the 225-1 peptide are shown in FIGS. 12A-C. The 225 peptides absorb strongly at 280 nm due to the two tryptophan and four tyrosine residues, and the HPLC trace of the TEV reaction shows a strong peak at 11 minutes (FIG. 12A) that contains the cleaved peptide with no apparent contamination when analyzed by liquid chromatography-mass spectrometry (LC/MS) (FIGS. 12B-C). Following purification, the peptides were dissolved in dimethyl sulfoxide (DMSO) and their concentration was determined by measuring the $A_{280}$ in a mixture of 50% DMSO and 50% phosphate buffer (pH 7.5), using an extinction coefficient predicted by the amino acid sequence and an experimentally determined correction factor (0.91) for this particular solvent combination.

The yields of 225-1 and 225-3 obtained with this expression system were modest, typically on the order of ~50 nmol (~220 µg) for a two-liter prep, which was sufficient material for preliminary studies. However, our subsequent efforts to express point mutants for alanine scanning (see section III.E) were much more poorly expressed, sometimes requiring 6+ liters of culture and, in the case of some mutants, affording no expression at all. Due to the relatively hydrophobic nature of the sequences, we hypothesized that co-expression with molecular chaperones might improve the peptide yield. We therefore expressed our constructs in BL21 cells carrying a modified form of the pG-KJE8 plasmid (Clontech) which carries the dnaK, dnaJ, grpE, GroEL, and GroES chaperones under control of an arabinose-inducible promoter. Inducing with IPTG accompanied by 200 mg/l of arabinose dramatically improved the yield for most of the mutant peptides tested, allowing us to prepare sufficient quantities of all the alanine point mutants for biochemical studies. Co-expression with chaperones also improved the yield of the 225-1 peptide (albeit more modestly), and this approach was adopted for the production of all subsequent peptides.

For experiments that required functionalized peptides, we labeled the cysteine near the N-terminus with maleimide conjugates (e.g. FITC-maleimide or Biotin-PEG$_2$-maleimide). We first treated the purified 225 peptides with tris(2-carboxyethyl)phosphine (TCEP), a reducing agent that lacks thiols and is less likely to react with sulfhydryl-reactive molecules such as maleimides. The peptides were then labeled with the appropriate maleimide conjugate at room temperature, followed by purification by HPLC and characterization by LC/MS as for the unlabeled peptides. We typically performed these reactions in a mixture of DMSO and pH 7 buffer, to aid the solubility of the reactants and to ensure that the pH was conducive to selective labeling of the maleimide groups by the cysteine.

Upon attempting to dissolve the 225-1 and 225-3 peptides in buffer, we found that 225-1 had relatively good solubility (up to ~100-200 µM at neutral pH), whereas the 225-3 peptide was not soluble at neutral pH and could only be solubilized at micromolar concentrations at low (<5) or high (>11) pH. However, preliminary testing indicated that the 225-3 peptide possessed a stronger binding affinity than 225-1, and was also somewhat cell permeable. We therefore conducted the majority of the following experiments using 225-3, and used 225-1 only in instances where high concentrations at neutral pH were required (e.g. NMR). Because the difference between these two peptide sequences is relatively minor, and because they exhibit similar binding affinities, CD spectra, and inhibition of nucleotide dissociation from Ras, we will generally refer to them as the 225 peptides.

Characterization of Peptide Secondary Structure by Circular Dichroism.

Figure 13A:
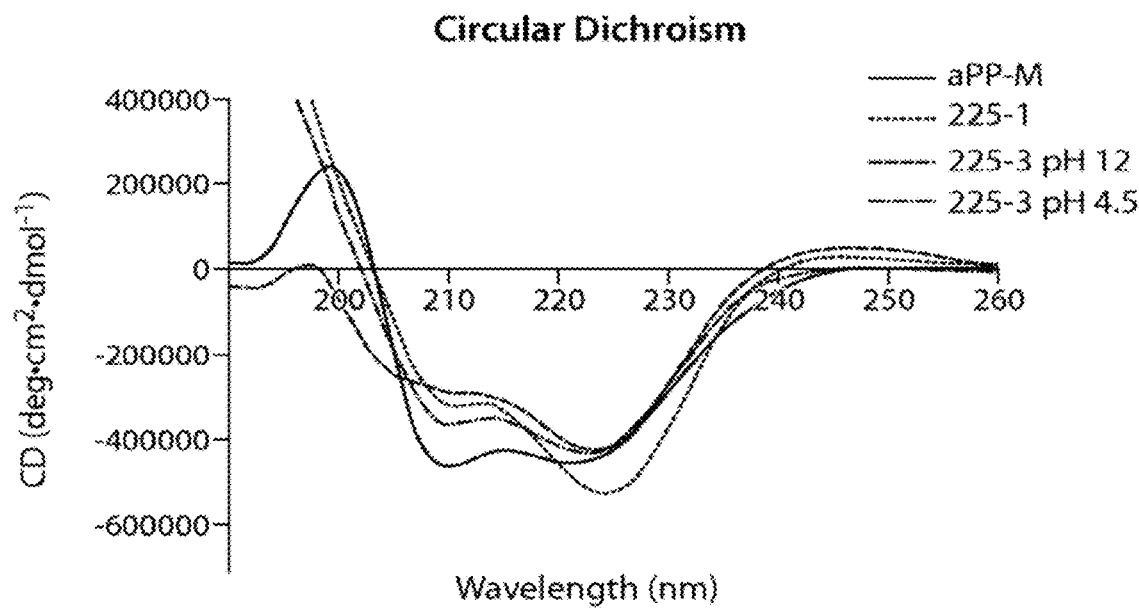
FIGS. 13A-B show the circular dichroism spectra of aPP-M and 225 peptides.
Figure 13B:
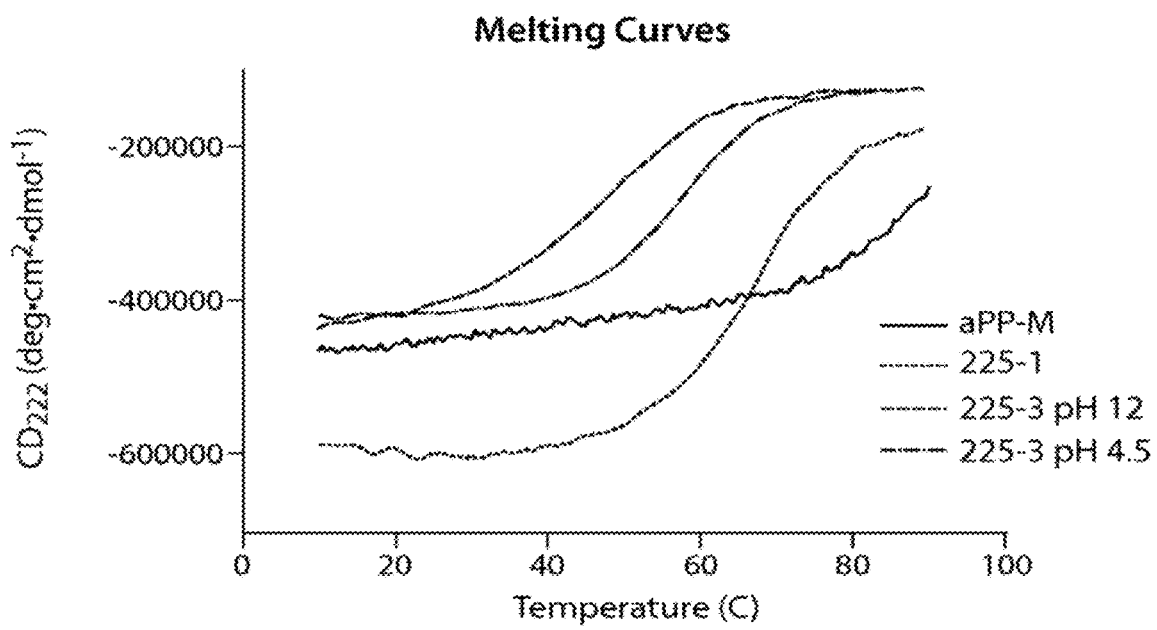

The 225 peptides contain 12 amino acid substitutions relative to aPP-M, and 15 compared to aPP. Most of these changes occur in residues not predicted to contribute to the aPP fold (based on inspection of the crystal structure); however, with nearly half of the amino acids mutated from aPP to the 225 peptides it was not obvious that their conformations would be the same. To gain an initial insight into the secondary structure of the 225 peptides, we recorded CD spectra of 225-1 and 225-3. The 225-1 peptide was readily soluble in buffered phosphate at pH 8, but the 225-3 peptides could only be prepared at sufficiently high concentration for CD studies at pH<5 and pH>11 (see above). We therefore recoded the CD for 225-3 at pH 4.5 and pH 12. The data are shown in FIGS. 13A-B. The 225 peptides have CD spectra similar to that of aPP-M, although the two minima (typically at 208 nm and 222 nm for a-helices) appear to be slightly red-shifted for the 225 peptides compared to aPP-M. In addition, the relative intensities of the minima are different: whereas aPP-M has nearly identical CD at 208 nm and 222 nm, the 225 peptides have stronger CD at 225 compared to 210. In the context of a-helices, increased $[\theta_{222}]/[\theta_{208}]$ ratios are often associated with the transition from noncoiled helices to coiled coil structures.[5] These data suggest that the 225 peptides may form a similar type of structure in solution; one possibility is that they are more prone to form head-to-tail homodimers (as has been reported for aPP) than their aPP-M parent.

To gain insight into the stability of the 225 peptides, we recorded the CD at 222 nm from 10° C. to 90° C. The melting curves show sigmoidal transitions for the three 225 peptide samples tested; for 225-3, pH 12 ($T_m$ of 46.2° C.) appears to destabilize the fold compared to pH 4.5 ($T_m$ of 57° C.), and at neutral pH, 225-1 has a $T_m$ of 66.6° C. This $T_m$ for 225-1 is lower than for the aPP-M parent ($T_m$>77° C.), but still higher than that of wild-type aPP ($T_m$ of 64.5° C.). This relatively high melting transition suggests that the 225 peptides are thermally stable. Although a detailed understanding of the peptide conformation requires more direct structural information (e.g. from NMR or X-ray crystallography), these CD data, along with the fact that nearly all of the residues known to contribute to the aPP fold were conserved during the course of our evolution, suggests that the 225 peptides likely share a similar structure as their aPP parent.

Quantification of the Ras-Peptide Binding Affinity by Fluorescence Polarization.

The yeast display system suggested that the 225 peptides were capable of binding the Ras proteins at mid-to-low nanomolar concentrations. To gain a more quantitative measure of the Ras-peptide binding affinity, we conducted fluorescence polarization (FP) assays with 225 peptides that had been labeled with fluorescein isothiocyanate (FITC). This assay relies on measuring the fluorescence in both the plane that is parallel to the excitation light and the plane perpendicular to it, such that FITC-labeled peptides with relatively slow tumbling in solution will exhibit higher anisotropy than those that tumble quickly. As the 225 peptides are significantly smaller than the Ras proteins (4.5 kDa compared to 21 kDa), the transition from a free peptide in solution to a Ras-bound peptide is predicted to exhibit an increase in the fluorescence polarization. We measured the FP of the 225-3 peptide at varying concentrations of KRas (G12V).GppNHp and determined a dissociation constant ($K_d$) of 20 nM (FIG. 14). This affinity is comparable to that of HRas for the B-Raf RBD, and is twice as strong as that of KRas for the B-Raf RBD.[7] The hill coefficient for this binding curves was 1.0, suggesting that the binding is non-cooperative. We noted that these FP experiments routinely produced messy data, and many replicates were required to obtain clean curves, although the affinity was reproducibly in the range we report here. This was particularly true of peptides from the 225-1 series (i.e. those that lacked the N-terminal PRR extension, see Chapter I). We therefore proceeded to perform the remainder of the FP experiments with 225-3 and its derivatives.

We next measured binding curves for the 225-3 peptide and the GDP form of KRas (G12V), as well as the GppNHp and GDP forms of KRas (WT). The mutation state of Ras did not appear to have a strong effect on the peptide binding affinity, whereas the GppNHp nucleotide state was slightly preferred over the GDP state for both proteins. The nucleotide selectivity observed for these peptides is significantly less than that of naturally occurring Ras-binding proteins, which typically exhibit >100-fold selectivity for the GTP state. However, these proteins have evolved to possess this property, whereas we included no explicit selectivity requirement during our initial directed evolution effort. In more recent yeast display experiments, we have attempted to improve the nucleotide selectivity by screening for peptides with higher ratios of binding to KRas.GTP vs. KRas.GDP (see Chapter 3).

The three Ras proteins are all capable of binding most Ras effectors, with only slight differences in affinity for the Raf RBD.[7] To determine the isoform selectivity of the 225-3 peptide, we performed FP with the GppNHp-bound forms of KRas, HRas, and NRas (FIG. 14). The $K_d$ of 225-3 for KRas (20 nM) is only slightly higher than that for HRas and NRas (45 nM), indicating that all three Ras isoforms bind the 225-3 peptide with similar affinity.

The Ras proteins belong to a large family of GTPases, some of which share significant structural and sequence similarity to Ras. As a number of these proteins are involved in housekeeping functions across many cell types, an important property of a Ras inhibitor is the ability to discriminate between the Ras proteins and their close family members. To determine the selectivity of the 225 peptides, we performed FP assays with GppNHp-bound Rap1a, RalA, and Rab25, which all share the same GTPase fold as the Ras proteins. Rap1a and RalA were selected because they are the two proteins closest in primary sequence to the Ras proteins, whereas Rab25 belongs to the distantly related Rab protein family with less than 30% sequence identity to Ras.[8] Rap1a was of particular interest to us because it is capable of binding some Ras effectors, including the Raf RBD, and some Rap effector proteins are in turn capable of binding Ras.[9] RalA and Rap25 did not bind 225-3 to an appreciable extent, with a $K_d$ of ~10 µM for Rab25 and >10 µM for RalA (FIG. 14). Rap1a appeared to bind 225-3 with slightly higher affinity (3.5 µM), but was still more than 100-fold weaker than Ras. These data suggest that the 225-3 peptide has remarkable specificity for the Ras proteins over closely related family members, despite the lack of an explicit selection for specificity during the evolution experiments.

Quantification of the Ras-Peptide Binding Affinity by SPR.

To obtain an independent measure of the Ras-peptide binding affinity, we performed binding assays using surface plasmon resonance (SPR, often referred to as Biacore). This assay involves immobilizing a molecule of interest on the surface of a gold wafer, and directing polarized light through a prism to the wafer. This is done under conditions of total internal reflection, in which the intensity of the light reflected from the surface is dependent on the refractive indices of the materials on either side of the gold surface. Relatively small changes at the surface, such as binding of a biomolecule to the immobilized ligand, alter the refractive index and result in a change in the intensity of the reflected light. SPR systems work by immobilizing a molecule of interest on the gold wafer, then flowing a second molecule over the chip while continuously recording the reflected light. A binding event between the immobilized and "free" molecule is detected as an increase in resonance units (RU) and can be used to measure both the kinetic and thermodynamic parameters of binding events. One advantage of this method is that the "free" molecule is detected purely by its mass, and thus does not require any labeling. The immobilized molecule may be captured on the chip covalently (e.g. by nonspecific coupling of amino or thiol groups) or non-covalently (e.g. with a biotin-streptavidin pair).

Our initial approach was to immobilize the 225 peptides on the chip surface and flow free, unlabeled Ras proteins over it. The advantage of this setup is that the Ras proteins are ~5 times larger in mass than the peptides, and are thus expected to produce a stronger signal upon binding since the RU signal detected by the SPR system is roughly proportional to mass. We selected a streptavidin-functionalized gold chip and immobilized 225-3 peptide that had been biotinylated at the cysteine handle (see above). The peptides were captured successfully on the chip as determined by an increase in the baseline RU signal, but upon adding unlabeled Ras protein, no appreciable increase in binding signal was observed. The cause of this was not immediately apparent; our initial assumption was that the biotinylation somehow rendered the peptide incapable of binding Ras, or that the Ras-peptide binding was not compatible with the biotin-streptavidin binding (e.g., for steric reasons). However, this explanation was not consistent with pulldown assays in which the same biotinylated 225-3 peptides were successfully used to bind both purified KRas and Ras from cell lysates using streptavidin beads (see FIGS. 18A-B).

Given our knowledge at the present, we can account for these observations with the peptide-dimer model: upon introducing the biotinylated peptides to the streptavidin chip, the extremely high affinity of the biotin-streptavidin interaction (~50 fM)[10] led all of the biotin moieties to become immobilized. Streptavidin is a homotetrameric protein with four biotin-binding sites, and by inspection of the crystal structure, it was apparent that the two peptides could not plausibly engage adjacent biotin-binding sites while remaining in a head-to-tail aPP-like homodimer structure. Because the biotin-streptavidin interaction is essentially irreversible on the timescale of these experiments, it is likely that the homodimers were effectively torn apart upon introduction to the streptavidin chip, and thus were immobilized in a state that was incapable of binding the Ras proteins. We note that this explanation makes the following prediction: immobilization of biotinylated peptide, followed by incubation with unlabeled peptide, should result in the formation of dimers on the chip surface that are capable of binding Ras.

Figure 15A:
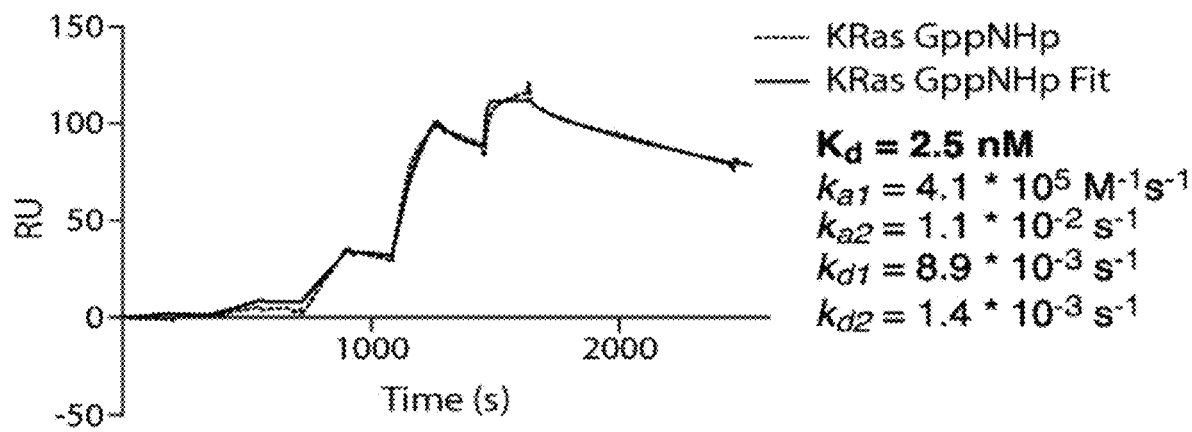
FIGS. 15A-B show surface plasmon resonance measurements of the Ras-peptide interaction. Biotinylated KRas (bound to either GppNHp, FIG. 15A, or GDP, FIG. 15B) was immobilized on a streptavidin capture chip, then free 225-1 peptide was injected at increasing concentrations. The high affinity of the interactions permitted "single cycle" runs that lack a regeneration step between injections and produce step-like binding curves. Data were fit using a two-step binding model.
Figure 15B:
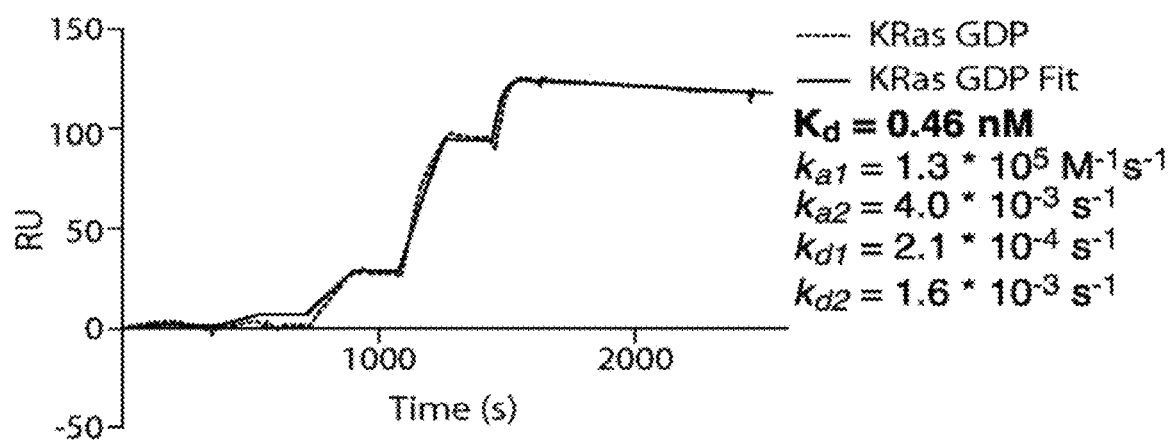

At the time of these experiments, the cause of this phenomenon remained unresolved, and we proceeded with the alternate SPR strategy of immobilizing the Ras proteins and flowing free peptides over the surface. We used Sfp-biotinylated Ras proteins as described in Chapter I for yeast display, testing both the GppNHp- and GDP-bound states. The Ras proteins could be stably captured on the chip, and exhibited stable binding to the unlabeled 225-3 peptide (FIGS. 15A-B). SPR affinity experiments are typically performed in one of two ways: "multi-cycle" runs, where protein is immobilized, a single injection of ligand is flowed over the surface, and the chip is subsequently regenerated so that a new batch of protein and ligand can be introduced, and "single-cycle" runs, where the protein is immobilized and multiple injections are performed in series. Single-cycle runs are faster and more cost-effective than multi-cycle runs, and afford accurate data provided the off-rate of the binding event is slow relative to the on-rate (i.e. when the binding affinity is high), and was the method we used for our studies.

Both the GppNHp and GDP states bound 225-3 with high affinity, affording dissociation constants of 2.5 nM and 0.46 nM, respectively. It is apparent both by visual inspection of the curves and by the calculated kinetic parameters that the dissociation is slower for the GDP state of Ras than GTP, an observation that is consistent with off-rate selection experiments we have performed using yeast display. We found that both curves were best fit by a two-step binding model, which did not match our expectations, and the results of these experiments also disagreed somewhat with those from fluorescence polarization: the calculated affinities were an order of magnitude higher than those found by FP, and the nucleotide selectivity was reversed.

The precise cause of these discrepancies are not entirely clear to us, although the peptide-dimer model may offer some insight, as it predicts that there should be multiple interdependent equilibria present within the system. Since the peptide is prepared at varying concentrations (from 1-100 nM) and injected over the immobilized chip, higher concentrations of peptide would experience a stronger effective $K_d$ for Ras since a greater proportion of peptides would be present in the dimeric (Ras-binding) state. This may result in a distortion of the binding curves and data fitting since the concentration of peptide added may not accurately reflect the effective concentration of peptide dimer available to bind Ras. In FP experiments, the peptide is held at a constant concentration and thus may be less susceptible to this effect; however, as the FP is expected to be different for the monomeric peptide, the dimeric peptide, and the Ras-peptide dimer complex, it is also likely that multiple states are contributing to the bulk FP signal. Both of these binding assays thus possess caveats that restrict the conclusions that can be drawn from them, and it is probably safest to assert simply that the peptide-Ras interaction is in the mid-to-low nanomolar range.

Alanine Scanning Mutagenesis of the 225-3 Peptide. We next sought to gain a more detailed understanding of the Ras-peptide interaction. As discussed above, our CD and evolution results suggested that the 225 peptides retained the general fold of aPP, but the peptide residues involved in Ras binding were not readily apparent. Because the aPP library was diversified on the outward face of the a-helix, and because essentially all of the mutations that appeared during the evolution were located in this region, it is tempting to speculate that the 225 peptides engage Ras primarily through residues on its a-helix. To test this hypothesis, we performed alanine scanning mutagenesis by testing variants of 225-3 that each contained a single alanine point mutation. Alanine is the most common amino acid used in this type of experiment because it is small, yet mimics the conformational preferences of most amino acids. Alanine is particularly suitable for this peptide in particular because it is generally stabilizing in both PPII and a-helices, which likely constitute the majority of the 225 peptide secondary structure.

Figure 16:
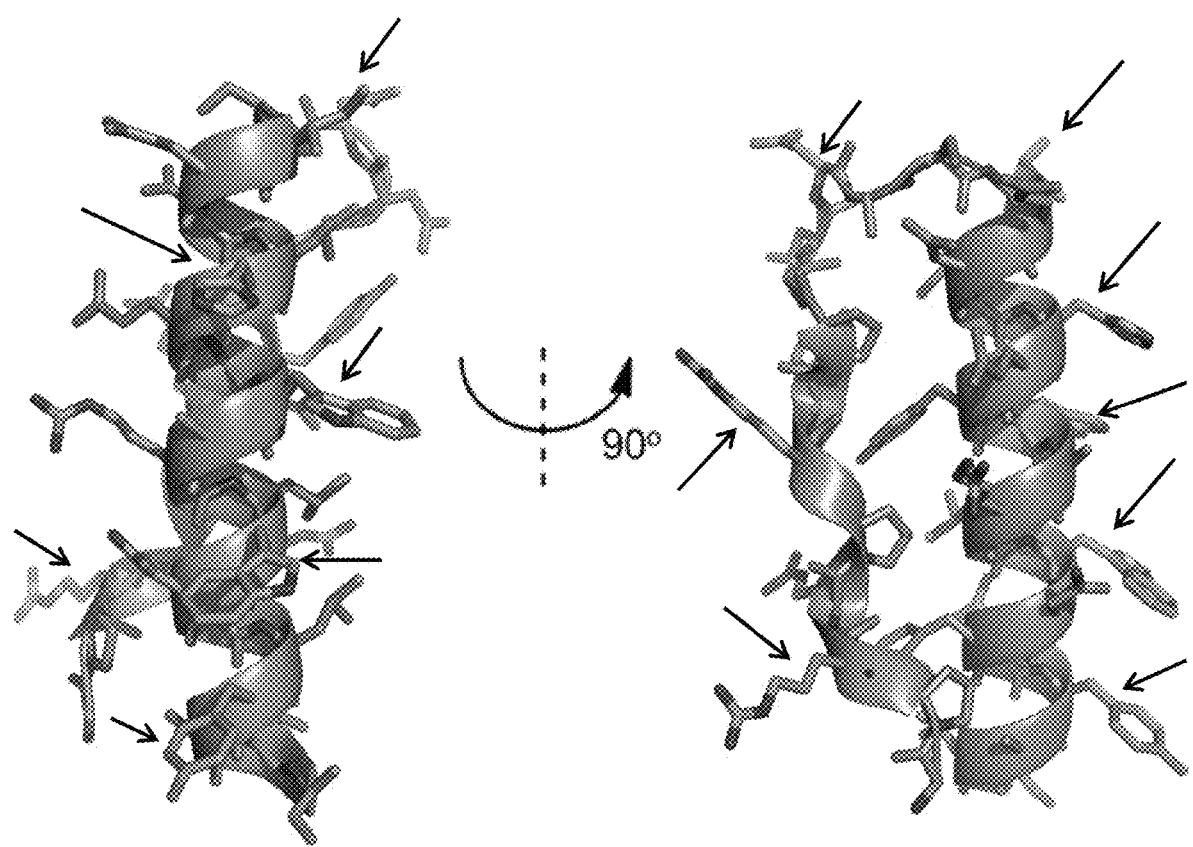
FIG. 16 shows positions selected for alanine mutagenesis. Residues for the 225 peptides were modeled onto the crystal structure of aPP (PDB: 1PPT). Positions chosen for mutation to alanine are indicated with arrows. Crystal structure is from Blundell, T. L., et al. *X-ray analysis (1.4-A resolution) of avian pancreatic polypeptide: Small globular protein hormone. Proc Natl Acad Sci USA* 78, 4175-9 (1981).

We selected 10 residues for mutagenesis: two in the PPII helix, two in the loop, and six in the a-helix (see FIG. 16). The plasmids for these mutants were constructed using site-directed mutagenesis PCR and expressed and purified as described above. Of these, nine could be expressed and purified, although some of these were absolutely dependent on co-expression with chaperones. Only one mutant, E15A, could not be expressed, even in the presence of chaperones. This residue is on the a-helix and is predicted to be outward-facing, and the peptide-dimer model does not predict any interactions between this residue and residues on the neighboring peptide, so the reason for this poor expression is not presently clear.

Figure 17A:
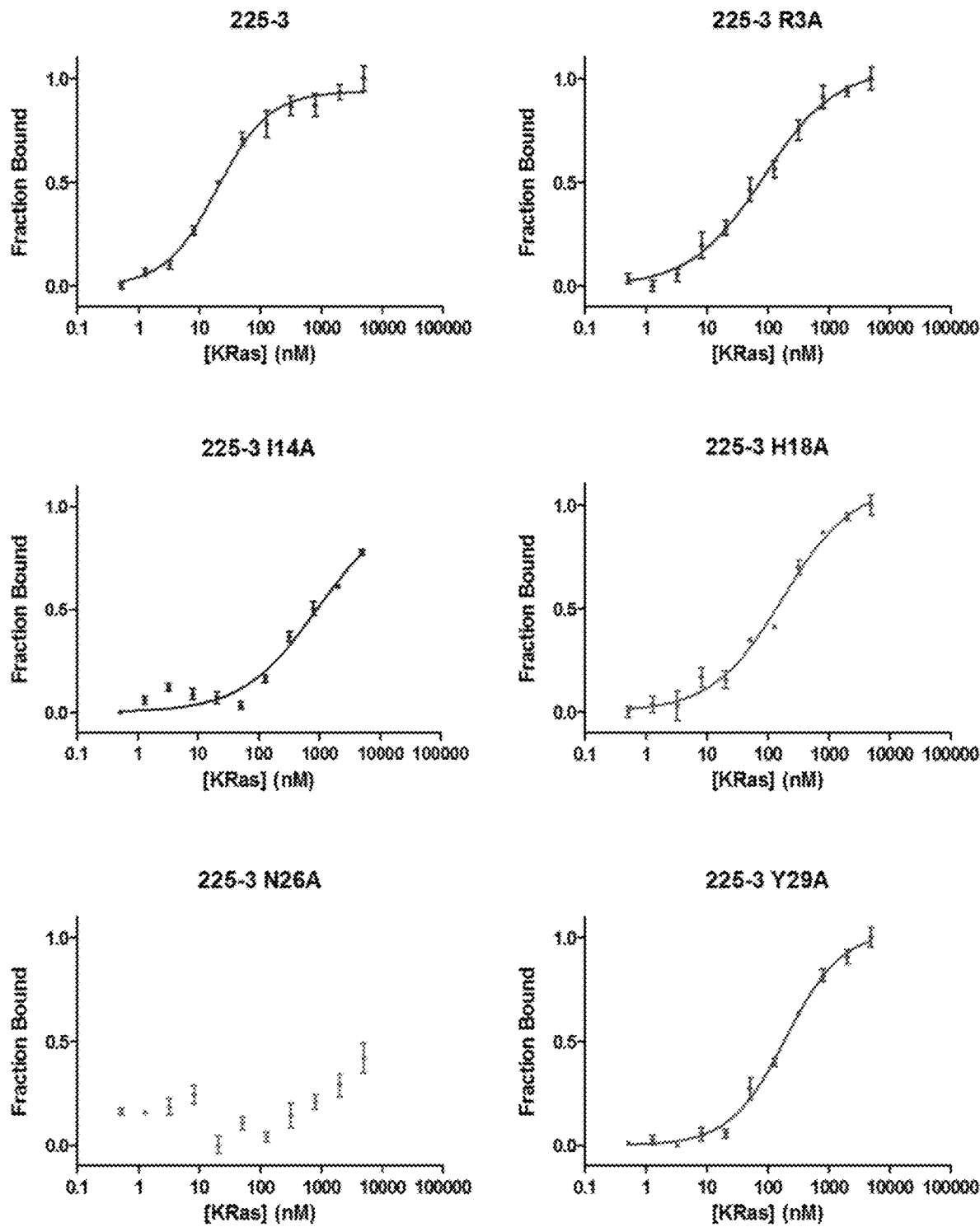
FIGS. 17A-C show properties of single alanine mutants of the 225-3 peptide.
Figure 17A:
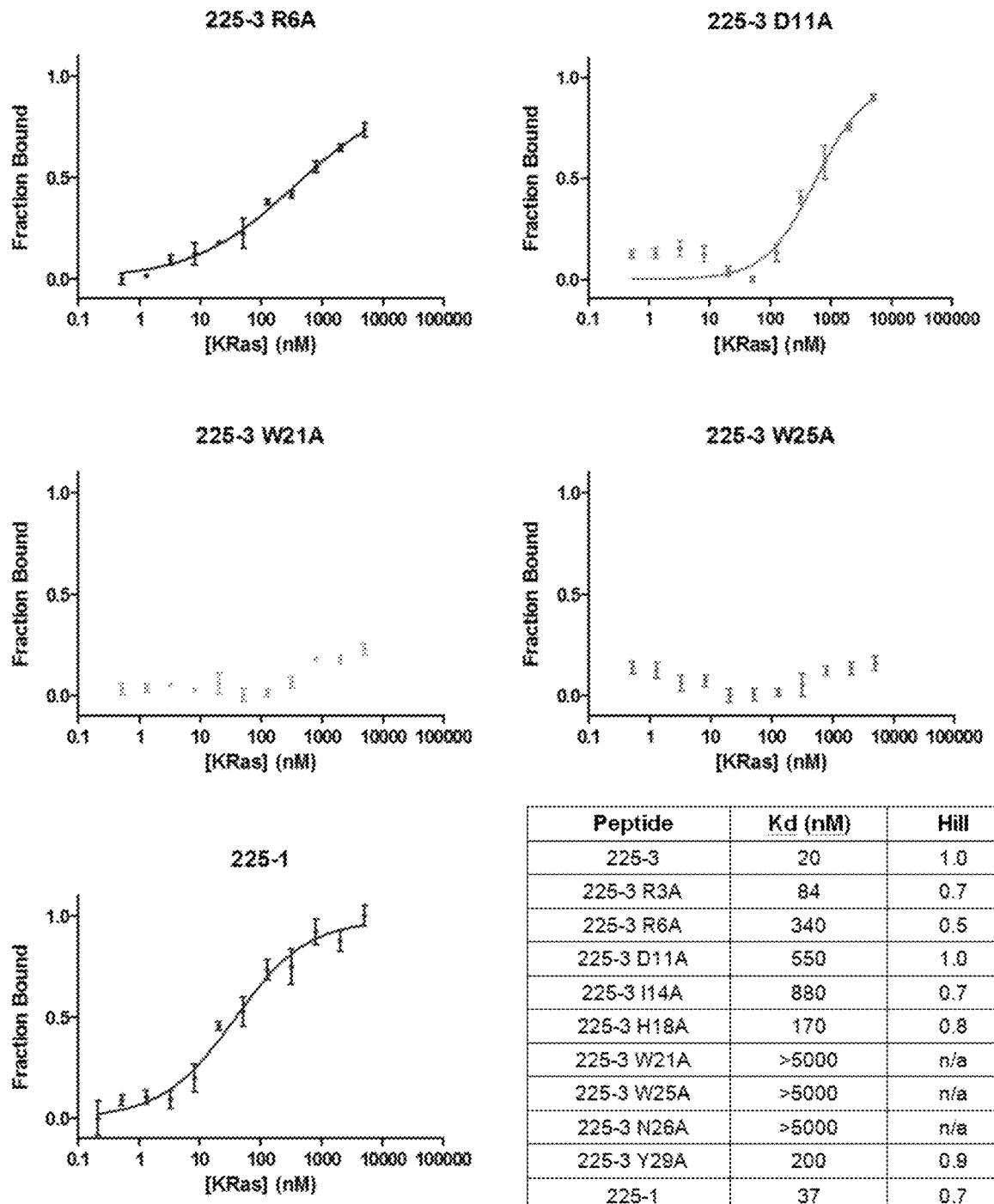
Figure 17B:
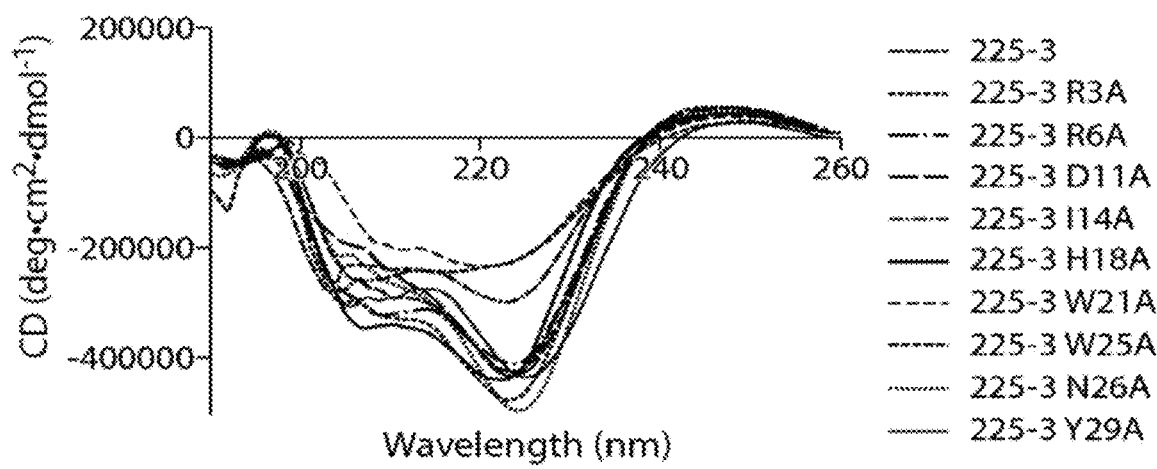
Figure 17C:
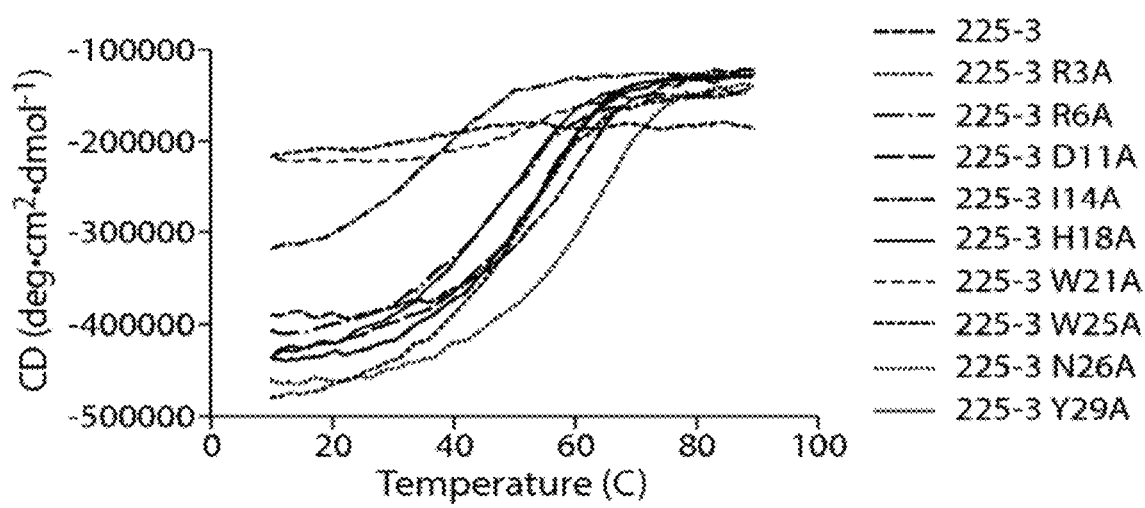

Once purified, the alanine mutants were labeled with FITC and tested by FP (FIGS. 17A-C). The typical expectation for an alanine scan is to find some mutants that affect the property being studied, and others that have little or no effect. Unexpectedly, every mutant tested disrupted binding by at least four-fold, and most caused at least a 10-fold reduction in measured affinity. Three of these mutations (I14A, W21A, and W25A, all on the a-helix) appeared to have a significant destabilizing effect on the peptide secondary structure as assessed by CD. Our initial interpretation of these data was that the other seven residues were all involved in binding to Ras, suggesting that the peptide engaged Ras not just though the a-helix but by presenting one "side" of the peptide with contacts from both the PPII and a-helices. In light of the peptide-dimer model, these data suggest an alternative explanation: that some of the residues tested contact Ras, whereas others are involved in stabilizing the dimer. Indeed, inspection of the aPP dimer structure (FIGS. 23A-C) shows that several of the residues tested are likely involved in forming contacts between monomers: the PPII helix (which contains two arginines that appeared to stabilize binding) is in close proximity to a patch of acidic residues on the opposing peptide, and the pair of W21 residues (which are Tyr in aPP) appear to be in an appropriate distance for r-stacking with each other. Thus, the interpretation of the alanine scan is somewhat complicated by our inability, given these data, to distinguish between residues that directly engage Ras and residues that stabilize the peptide-peptide dimerization. Additionally, it should be noted that since the peptides are in a homodimer, the alanine scan mutants did not interrogate the role of a single residue but rather a pair of residues.

When performing assays with biologically active molecules, it is valuable to have a negative control molecule that is as similar as possible to the active compound while lacking some or all of the target activity. In the context of our studies, this would ideally be a 225 peptide with a single mutation that abrogates binding to Ras, without disrupting the peptide structure. From the alanine scan series, three peptides had $K_d$ values exceeding 5 μM: W21A, W25A, and N26A. As discussed above, both of the tryptophan mutants appeared to be destabilized compared to the 225-3 parent as judged by CD. However, the N26A mutant had a CD profile that was unchanged compared to 225-3, and we therefore selected this peptide for use as a negative control in our subsequent studies.

Pulldown Assays in Cancer Cell Lysates.

The data thus far indicate that the 225 peptides bind the Ras proteins with nanomolar affinity and good specificity. All of these experiments were performed with recombinantly expressed Ras proteins, however, and it remained possible that these proteins did not accurately reflect the nature of Ras in living cells (due to posttranslational modifications, differences in fold, participation of partner proteins, etc). To test whether the 225 peptides were capable of binding the endogenous Ras proteins in cancer cells, and whether they could disrupt the binding of these endogenous proteins with effectors, we performed pulldown assays in lysates of the Capan-1 pancreatic adenocarcinoma cell line, which harbors a mutant form of Ras (G12V) and has been shown to be dependent on Ras activity for survival.

We grew the cells with standard methods and lysed them in nondenaturing conditions (buffer containing 1% v/v of the nonionic detergent Triton X-100, see Methods for additional details). We incubated the lysate with biotinylated 225-3 peptide, biotinylated 225-3 N26A peptide, or DMSO control, then captured the peptides with magnetic streptavidin-coated beads and ran the samples on a sodium dodecyl sulfate-polyacrylamide gel electrophoresis (SDS-PAGE) gel, followed by transfer to a nitrocellulose membrane and western blotting for Ras. To test whether these peptides were capable of competing with Ras effectors, we performed in parallel the same set of experiments with lysates that had been pre-incubated with an excess of the Raf RBD. This treatment is expected to result in nearly all Ras molecules being bound to Raf (due to the high Ras-Raf affinity), and if Raf and the 225 peptides share a binding site, the prediction is that the amount of Ras pulled down by the peptides will be diminished.

Figure 18A:
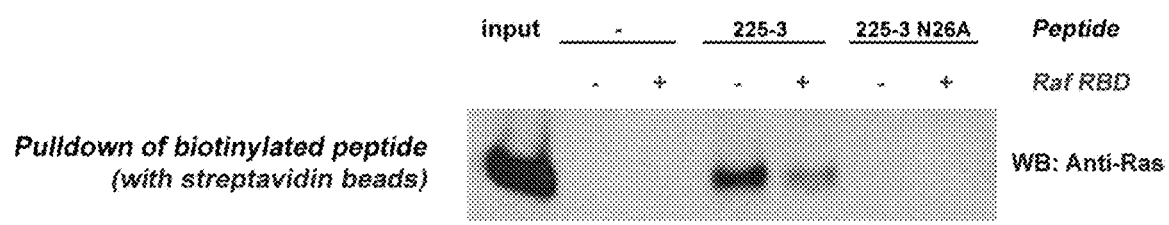
FIGS. 18A-B show the 225-3 peptide binds endogenous Ras in cancer cell lysates and blocks its interaction with Raf Capan-1 adenocarcinoma cells were lysed and incubated with 225-3 peptides and/or GST-tagged Raf RBD, then either the peptide (FIG. 18A) or Raf (FIG. 18B) was pulled down with the indicated beads. The bound samples were boiled with SDS, run on an SDS-PAGE gel, transferred to a nitrocellulose membrane, and western blotted with a pan-Ras antibody.

The results of this experiment are shown in FIG. 18A. The lysate contained a significant amount of Ras as judged by the input lane, but Ras was not pulled down by beads alone, nor by beads in the presence of the N26A mutant of 225-3. The active form of 225-3 pulled down Ras, but not when the lysate was pre-incubated with the Raf RBD. These data demonstrate that the 225 peptides are capable of binding endogenous Ras in human cancer cell lines, and that the peptides appear to share a binding site with Raf, suggesting that the 225 peptides may be capable of inhibiting Ras effector binding in vivo.

Figure 18B:
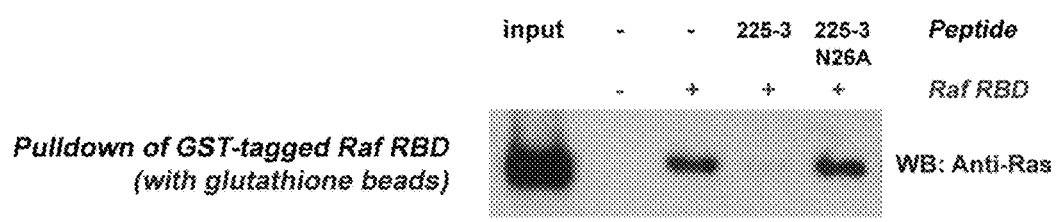

It is possible that this apparent competition was not the result of Raf and 225-3 sharing overlapping binding sites, but was instead due to the ability of Raf to sequester Ras in aggregates, or block the biotin binding sites on the beads, and so forth. As a control experiment, we reversed the pulldown strategy and instead captured the Raf RBD, which is tagged with glutathione-S-transferase (GST), using glutathione beads. This assay is often used to determine the Ras activity status in cancer cells,[14] as only the GTP-bound form of Ras can bind Raf with appreciable affinity. Ras was not pulled down by glutathione beads alone, but was in the presence of GST-tagged Raf, and pre-incubation with the N26A mutant of 225-3 did not disrupt this pulldown, whereas 225-3 abrogated it completely (FIG. 18B). This confirms the results of II-9A, indicating that the 225 peptides are capable of competing with a canonical Ras effector for binding to endogenous Ras.

Identification of the 225 Binding Site on Ras.

The pulldown data shown above suggest that the 225 peptides bind at or near the Ras effector domain, as they are capable of competing with Raf proteins for Ras binding. However, it is also possible that this competition is the result of an allosteric mechanism, where Raf and the 225 peptides bind nonoverlapping sites but engage distinct conformations of Ras that are sufficiently different as to prevent the other ligand from binding simultaneously. We therefore sought to define the precise 225 peptide binding site on the Ras surface. One characteristic of Ras effector proteins is their ability to interfere with dissociation of guanine nucleotides from the nucleotide binding pocket on Ras. To assess whether the 225 peptides share this property, we performed a Ras nucleotide dissociation assay originally reported by John and coworkers[15] which relies on fluorescent analogs of guanine nucleotides. We synthesized the N-methylanthraniloyl ester of GppNHp (mantGppNHp), whose fluorescence is known to increase upon binding Ras.

Figure 19:
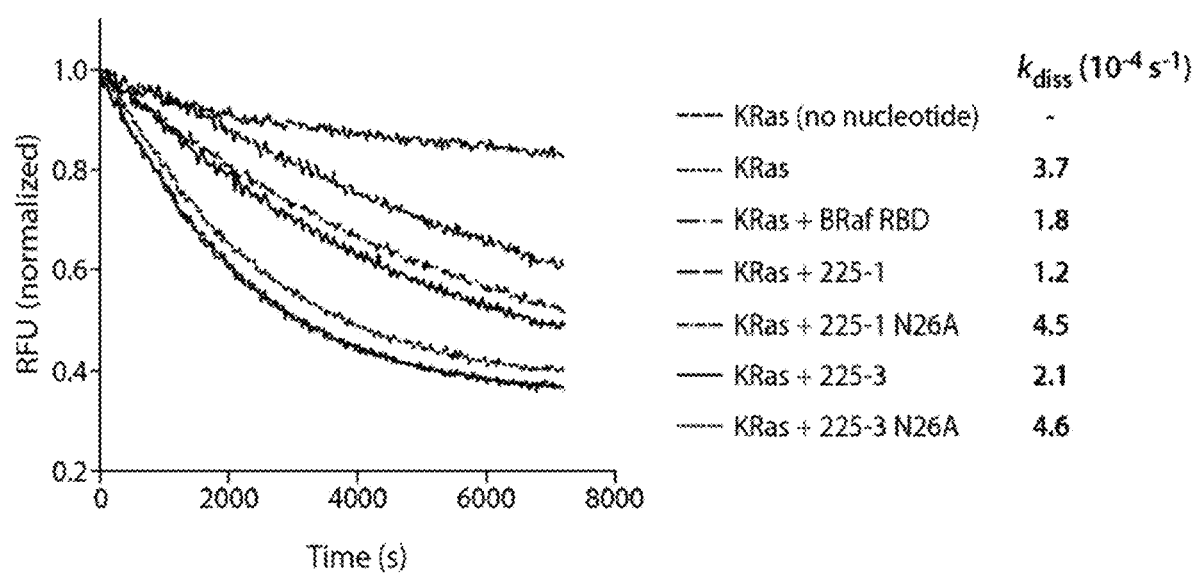
FIG. 19 shows the 225 peptides interfere with nucleotide dissociation from Ras. Peptides were mixed with KRas (G12V) loaded with mant-GppNHp, then GppNHp was added to 625 µM and the dissociation of mant-labeled nucleotide was tracked as a decrease in fluorescence (excitation: 370 nm, emission: 450 nm). Dissociation constants were calculated by fitting the data to a one phase exponential decay with $RFU_\infty=0.37$.

We performed nucleotide dissociation inhibition assays in a manner similar to the classic $^{32}$P-labeled nucleotide experiments that involve adding "cold" nucleotide to proteins bound with "hot" nucleotide. KRas was loaded with mantGppNHp using alkaline phosphatase as described for Ras GppNHp, then incubated with peptide, Raf RBD, or nothing before adding a large excess of GppNHp. This excess of unlabeled nucleotide effectively renders the dissociation of mantGppNHp irreversible, and thus the dissociation rate constant can be measured by fitting the curves to an exponential decay (FIG. 19).

In the absence of additional "cold" nucleotide the fluorescence level was relatively stable, indicating that photobleaching, protein unfolding, etc. did not lead to a significant reduction in signal over the timecourse of the experiment. Upon adding an excess of GppNHp, the fluorescence decreased in an exponential fashion, and this was abrogated by the introduction of the Raf RBD, as had been previously reported.[15] The addition of either 225-1 or 225-3 had a similar effect, slowing the apparent rate of nucleotide dissociation to a level comparable with that of the Raf RBD, but addition of 225-1 N26A or 225-3 N26A did not decrease the rate of dissociation, indicating that this effect was dependent on binding to Ras. Thus, the 225 peptides appear to inhibit the dissociation of nucleotides from Ras, suggesting that either their binding site overlaps with the nucleotide binding pocket or that peptide binding restricts the protein from accessing conformations with lower nucleotide affinity.

To develop a more granular understanding of the Ras-peptide interaction, we performed solution NMR experiments to identify the residues on each molecule that were involved in binding. The method we used was $^1$H-$^{15}$N heteronuclear quantum spin correlation (HSQC) spectroscopy, an NMR technique that detects chemically distinct N—H bonds (in the case of proteins, primarily the amide N—H bond) in a molecule and produces a 2D plot of crosspeaks, located according to the individual shifts of the proton and nitrogen atoms in the N—H pair (see e.g. FIGS. 20A-C). Due to the variability in chemical environment throughout the protein, most N—H bonds can be distinguished from one another under the proper conditions, and with the aid of several additional measurements (such as $^1$H-$^{13}$C HSQC, HCCH TOCSY, and so on) the $^1$H-$^{15}$N HSQC crosspeaks can be assigned to specific residues within the protein. If these assignments are known, changes in the protein conformation upon binding a ligand can be mapped to specific sites within the protein by comparing the HSQC spectra in the presence and absence of the ligand and identifying the crosspeaks that shift.

The assignments for KRas(WT) GDP were published in 2012, enabling us to perform HSQC studies without assigning the Ras protein de novo. We expressed the KRas protein in E. coli as before, but using minimal synthetic media with $^{15}$NH$_4$Cl as the sole nitrogen source. This protein was purified, exchanged into the buffer reported for the NMR assignment, then $^1$H-$^{15}$N HSQC measurements were performed on a Bruker 700 MHz NMR spectrometer equipped with a cryoprobe. For these studies, we used transverse relaxation optimized spectroscopy (TROSY), a variant of the standard $^1$H-$^{15}$N HSQC experiment that improves the quality of HSQC signals from relatively large proteins.

The $^1$H-$^{15}$N HSQC spectrum of $^{15}$N-labeled KRas is shown in FIG. 20A. This measurement afforded clear, distinct crosspeaks that corresponded well with the spectrum reported previously. To identify residues on KRas that experienced a change in chemical environment upon peptide binding, we recorded the same measurement in the presence of unlabeled 225-1 peptide, which lacks $^{15}$N and thus is not visible in the HSQC spectrum. As discussed above, we used 225-1 for these experiments because 225-3 is not soluble at the concentrations required for preparing these NMR samples (>100 μM). We found that between two and three equivalents of peptide (according to our absorbance-based quantification) were required to achieve saturation, an observation that did not make sense at the time but can now be explained by the peptide-dimer model, which predicts a binding stoichiometry of 1:2 Ras:peptide. The HSQC spectrum of the Ras-peptide complex is shown in FIG. 20B, and the free Ras and Ras-peptide spectra are overlaid in FIG. 20C.

The overlay shows that a significant number of residues experience a change in chemical environment upon binding to Ras, as evidenced by the large number of crosspeaks that shift between the "free" and bound spectra. It is not possible to know the identity of the peaks in the Ras-peptide spectrum without further measurements (necessitating $^{13}$C and possibly $^{2}$H labeling), but by identifying the (assigned) peaks in the free spectrum that shift, one can develop an initial picture of which residues are affected upon peptide binding. We manually tabulated the crosspeaks in the free spectrum that shifted upon binding to peptide, then used the published assignments to map them to the crystal structure of Ras (FIG. 21). We found that these residues were located in a well-defined cluster on one face of Ras that shared considerable overlap with the Ras effector domain, as defined by co-crystal structures of Ras in complex with effector proteins. Residues elsewhere on the Ras protein appeared to be unaffected, as their corresponding crosspeaks in the HSQC spectrum did not shift to an appreciable extent. These data thus suggest that the 225 peptide engage a specific binding site on the Ras surface, and that this site overlaps with the effector domain, consistent with the ability of the 225 peptides to block effector binding.

We next sought to perform the analogous NMR experiment on the 225 peptides, by comparing the HSQC spectra of $^{15}$N-labeled 225 in the presence or absence of unlabeled Ras. The crosspeak assignments for this protein have obviously not been established, but given the relatively small size of the peptide (35 amino acids for 225-1) we anticipated that performing these assignments would be straightforward. First, we expressed the 225-1 peptide in $^{15}$N-containing minimal media as for KRas, and recorded HSQC spectra for the free peptide in the same buffer used for the Ras experiments. This afforded a relatively clean spectrum, albeit with several crosspeaks that appeared to overlap one another (FIG. 22A). We then recorded HSQC spectra for the $^{15}$N-labeled 225-1 peptide in the presence of KRas. Unexpectedly, this spectrum contained double the number of peaks as the peptide-only sample (FIG. 22B).

This observation cannot be explained by contaminating signal from the protein, as KRas was unlabeled (the natural abundance of $^{15}$N is less than 0.5% of total nitrogen) and most of the new crosspeaks did not overlay with either the free or peptide-bound Ras spectrum. These data are also not consistent with partial saturation, as many of the peaks present in the peptide-only spectrum are absent from the Ras-peptide spectrum. Another explanation is that the peptide is capable of binding Ras in two conformations. This is formally possible, but unlikely, given that the intensities appear fairly uniform for all of the crosspeaks in the Ras-peptide spectrum. This would only be observed if the two conformations were populated in roughly equal proportions, requiring them to be of similar energies, which is improbable for two states that are sufficiently different to cause distinct HSQC spectra.

An alternative explanation is that the Ras proteins contain two distinct binding sites for the 225 peptides that can be occupied simultaneously. This is consistent with the presence of two crosspeaks for each amino acid, and is also compatible with the observation that at least two equivalents of peptide are required to saturate Ras. We initially deemed this model unlikely, as the Ras HSQC experiments suggested a single binding site and the FP assays showed typical sigmoidal binding curves with a hill coefficient of 1.0. However, upon recalling that aPP and some of its relatives are capable of forming head-to-tail dimers in solution (FIGS. 23A-C), we considered the possibility that the 225 peptides engaged Ras as a dimer. This is consistent with the $^{15}$N-labeled peptide HQSC spectra: a head-to-tail homodimer is symmetric and thus the two monomers are predicted to experience identical chemical environments, and thus possess identical $^{1}$H-$^{15}$N crosspeaks. Ras is not symmetric, however, so upon binding Ras the peptide-dimer symmetry is broken and the two monomers experience different environments, leading to a splitting in the spectrum.

The crystal structure of aPP, which crystallizes as a dimer, is shown in FIGS. 23A-C. In light of this model, a number of previously confusing observations make sense, as discussed in the previous sections of this chapter. Particularly interesting was the recurrence of the Y7C mutation during the directed evolution efforts: by inspection of the corresponding tyrosine in the aPP structure (FIG. 23C), it is apparent that the Y7 residues on opposing monomers come within close contact (7-stacking in the case of aPP), and it is plausible that the presence of cysteines at this position lead to the formation of a disulfide bond that stabilizes the peptide dimer and thereby increases its affinity for Ras.

The gold standard for the structural characterization of protein complexes is X-ray crystallography, which can provide a detailed and complete structure at atomic resolution. In collaboration with crystallographers in the Verdine laboratory (Seung-joo Lee and Rou-Jia Sung) we have attempted to crystallize the KRas-225 and HRas-225 complexes, which were prepared as described for the KRas-225-1 complexes studied by NMR. So far, we have had no success, but our efforts in this area are ongoing.

One implication of the peptide-dimer model is that the 225 peptides are not fully optimized for binding to Ras. This is a consequence of the constraints imposed by the peptide homodimer: each residue (and therefore each mutation that was tested during the evolution) must appear in two positions within the Ras-binding dimer, whereas the Ras protein is asymmetric. Thus, it is likely that there are multiple positions within the Ras-peptide binding interface where a favorable amino acid mutation is prohibited because it is not compatible with the context of the corresponding site across the peptide dimer. This predicts that peptide heterodimers may be capable of gaining affinity relative to the 225 homodimer.

Example 4: Improving the Affinity and Specificity of the 225 Peptides

The peptide-dimer hypothesis proposed in Chapter II suggests that the 225 peptides may not be fully optimized for binding to Ras, as Ras is asymmetric and thus likely has distinct preferences for contact residues that are constrained to be the same amino acid in the peptide homodimer. This chapter discusses our preliminary efforts to test the dimer hypothesis using yeast surface display, and to identify peptide mutants that can heterodimerize with 225-1 and bind Ras with improved affinity relative to the 225-1 homodimer. We also discuss our efforts to identify peptide mutants that possess improved selectivity for Ras.GTP vs. Ras.GDP relative to the 225 peptides.

Complementation of the N26A Mutant on the Yeast Surface.

If the peptide-dimer hypothesis is correct, one prediction is that there should exist peptide heterodimers with improved binding for Ras, due to optimized contacts that are not possible in a homodimer. For example, there are likely a number of residues in the 225 peptides that form a critical contact in the context of one peptide-binding half-site on the Ras surface. If this contact is sufficiently stabilizing that any mutation at this site abrogates binding, then the corresponding residue on the partner peptide will be constrained to be that same amino acid, even if a different amino acid would be preferable. The consequence of this fact is that the strongest peptide homodimer is likely to be the sequence that represents the best compromise between the amino acid preferences at each half-site. If this is the case, then the 225 peptides may be sacrificing potentially favorable interactions due to the constraints of binding as a homodimer.

An alternative way to express this concept is that deleterious mutations in the peptide are likely to have a stronger effect in the context of one half-site than in the other. For instance, we had shown that the N26A mutation abrogates binding to Ras by at least 100-fold, but it is unlikely that the two N26 residues in the homodimer contribute equally to this effect, given that they must experience different environments and engage distinct residues (since Ras is asymmetric). Provided that this mutation does not disrupt the actual dimerization of the 225 peptides, it is more plausible that the N26A mutation has a significant destabilizing effect at one half-site and a weak, neutral, or even positive effect at the other. If this were the case, it predicts that a heterodimer of 225-1 and 225-1 N26A should have significantly improved binding to Ras relative to a N26A homodimer.

Figure 24:
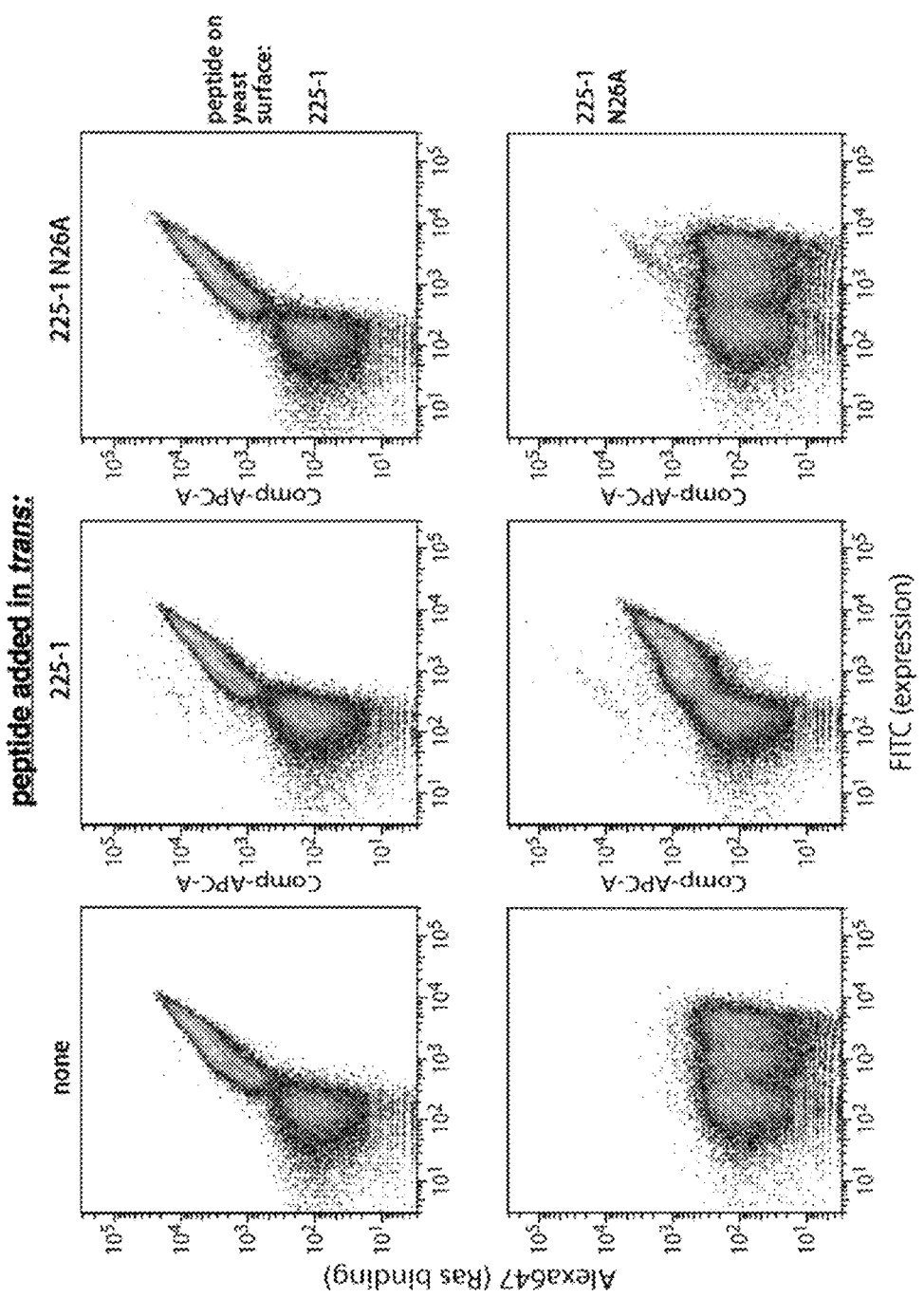
FIG. 24 shows the N26A mutant can bind Ras as a heterodimer with 225-1. Yeast displaying either 225-1 or 225-1 N26A were pre-incubated with 25 µM of (free) 225-1 or 225-1 N26A peptide, then pelleted and incubated with 500 nM KRas.

A method for screening libraries of peptide heterodimers would greatly improve our ability to identify stronger Ras binders. Although the kinetics and thermodynamics of the 225 homodimerization are not presently known, it occurred to us that if monomer exchange were rapid enough, it might be possible to conduct yeast surface display with heterodimers between 225 mutants (displayed on the yeast surface) and 225-1 peptide (supplied in trans and allowed to exchange into a heterodimer with the displayed mutant). In light of the prediction that a 225-1 and 225-1 N26A should be capable of binding Ras better than a 225-1 N26 homodimer, we sought to test this idea using yeast cells expressing either 225-1 or 225-1 N26A and providing free 225-1 or 225-1 N26A peptide in trans. After some optimization, we found that heterodimer formation appeared to be possible by pre-incubating the yeast cells with mid-micromolar concentrations of free peptide, followed by pelleting (to remove excess peptide) and subsequent incubation with Ras (FIG. 24).

KRas, and this binding appeared relatively unaffected by pre-incubation with free 225-1 or 225-1 N26A. Yeast cells expressing 225-1 N26A did not bind Ras at a detectable level, consistent with the in vitro data (Chapter II), nor did they bind when pre-incubated with free 225-1 N26A. However, when pre-incubated with free 225-1, these cells exhibited strong binding to Ras, consistent with the hypothesis that the 225 peptides bind Ras as dimers. It is important to note that these data only show partial rescue of the 225-1 N26A mutant's ability to bind Ras, and thus cannot formally reject the possibility that the N26A mutant is equally deleterious to both half-sites. However, it is likely that our dimer-exchange technique occurs incompletely: the peptides displayed by the yeast are constrained to the cell surface, and thus the local concentration of these peptides is high, meaning that homodimerization of displayed peptides should be strongly favored over heterodimerization with free peptides in solution. Because we cannot determine what fraction of surface-displayed peptides are present in homodimeric vs. heterodimeric form, it is difficult to quantitatively interpret the increase in binding observed upon incubation of surface-displayed 225-1 N26A peptide with free 225-1. However, there is no significant decrease in binding when the surface-displayed 225-1 peptide is pre-incubated with 225-1 N26A, which would not be expected if the heterodimer were significantly weaker than the 225-1 homodimer. It remains possible that heterodimer formation was particularly inefficient in this specific case, but given that the peptides are identical to those used in the converse experiment, this seems unlikely. Thus, these experiments argue that the 225 peptides can at least partly complement the loss of function of the N26A mutations when bound in a heterodimer.

Identification of Heterodimers that Bind Ras with Increased Affinity.

Figure 26A:
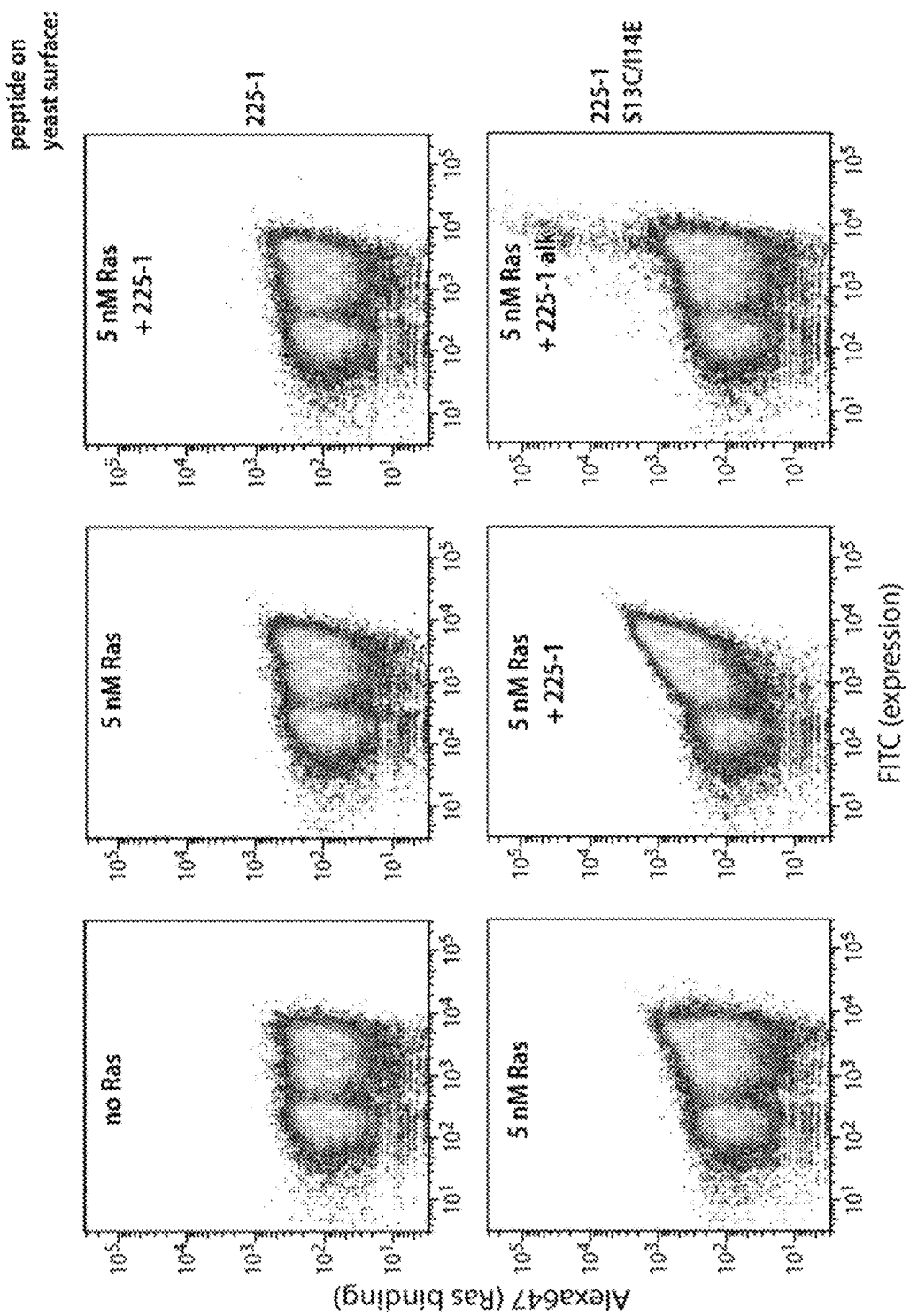
FIGS. 26A-B show the 225-1 S13C/I14E mutant forms a heterodimer with 225-1 that binds Ras with increased affinity.
Figure 26B:
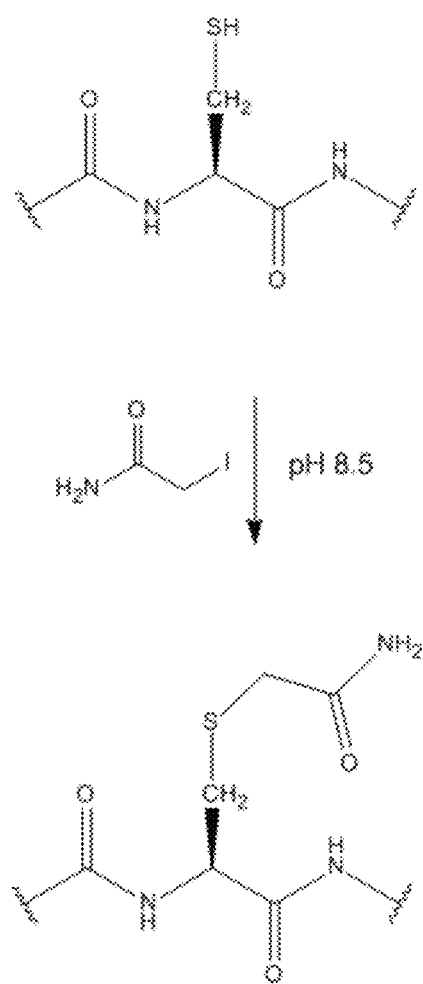

Encouraged by the observation that yeast surface display could be used to present heterodimers, we performed a complementation screen to identify mutant/225-1 heterodimers that bound Ras with higher affinity than the 225-1 homodimer. The experimental approach was as described for the N26A complementation studies, where we pre-incubated yeast cells with 225-1 and pelleted before adding Ras. We selected a Ras concentration of 5 nM, which affords very weak binding for 225-1 (FIGS. 26A-B). For this experiment, we used a scanning mutagenesis library based on the 225-1 peptide that systematically varied adjacent pairs of residues throughout the sequence (FIG. 25). The theoretical library size of this library is approximately 12,400 members (in terms of amino acid diversity), which is small relative to the library sizes that can be transformed into yeast. However, this approach allows for the systematic evaluation of mutations throughout the sequence, whereas libraries designed by error-prone PCR tend to be biased towards certain substitutions and are unlikely to cover every amino acid mutation at every site,[1] much less every possible amino acid pair at adjacent sites. We therefore considered this strategy to be a superior way of testing sequence space for this experiment.

Using the scanning mutagenesis library, we performed the complementation screen at 5 nM KRas.GTP, and after three rounds of sorting, isolated a population that appeared to bind Ras more strongly than 225-1, in a manner dependent on pre-incubation with free 225-1 (FIG. 26A). Sequencing this population revealed it to be primarily composed of a single clone with a S13C/I14E double mutation. Provided below are peptide mutants with improved properties relative to 225-1. For consistency, residue numbers are reported using the positions in the aPP peptide. Mutations are underlined.

| Peptide | Peptide Sequence |
|---|---|
| 225-1 | GCGGPRRPRYPGDDASIEDLHEYWARLWNYLYAVA (SEQ ID NO: 8) |
| 225-1 S13C/I14E | GCGGPRRPRYPGDDA<u>CE</u>EDLHEYWARLWNYLYAVA (SEQ ID NO: 9) |
| 225-1 A30R | GCGGPRRPRYPGDDASIEDLHEYWARLWNYLY<u>R</u>VA (SEQ ID NO: 10) |

Figure 27:
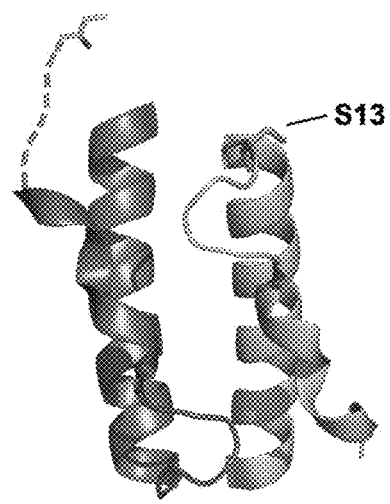
FIG. 27 shows the model illustrating the location of S13 and the N-terminal cysteine. The left peptide represents 225-1 with an unreacted cysteine handle on the N-terminus, and the right peptide represents the partner with S13 (which is cysteine in the S13C/I14E double mutant) indicated.

This mutation is interesting because we once again see the emergence of a cysteine residue. In light of our prior hypothesis regarding the Y7C mutation that was found in our initial evolution studies (that we hypothesize is involved in forming a disulfide bond between monomers), we wondered whether this mutation may also be improving the Ras binding affinity by stabilizing the dimer. This mutant can only bind Ras at 5 nM when pre-incubated with the 225-1 peptide; therefore, it is unlikely that this cysteine is involved in forming a disulfide with the corresponding cysteine across the dimer. Indeed, inspection of the structure of the aPP dimer demonstrates that these residues are far apart and not expected to interact in the context of a formed dimer. However, we recalled that the free 225-1 peptide used in these complementation studies contained a free cysteine at its N-terminus (for labeling purposes), and the aPP dimer model predicts that this residue may be capable of interacting with the C13 residue in the displayed mutant (FIG. 27). Thus, one explanation for the improved binding is that the S13C/I14E double mutant forms a disulfide-stabilized heterodimer.

If this hypothesis is correct, then blocking the cysteine on the free 225-1 peptide should eliminate the improvement in binding. To test this, we alkylated the cysteine on the 225-1 peptide with iodoacetamide (a small organic molecule with good selectivity for thiols, see FIG. 26B), then repeated the complementation experiment. Consistent with our prediction, the improvement in binding to Ras was almost completely eliminated with this peptide when compared to unlabeled 225-1. This suggests that the S13C/I114E double mutant may indeed show improved binding to Ras by forming a disulfide-stabilized heterodimer with 225-1. It remains possible that this effect is not due to disulfide formation, but is rather a consequence of perturbing the 225-1 structure by the alkylation. However, iodoacetamide is a relatively small molecule and the N-terminal cysteine on 225-1 was previously modified with biotin and fluorophores without abolishing activity, so we consider this explanation unlikely.

Figure 28:
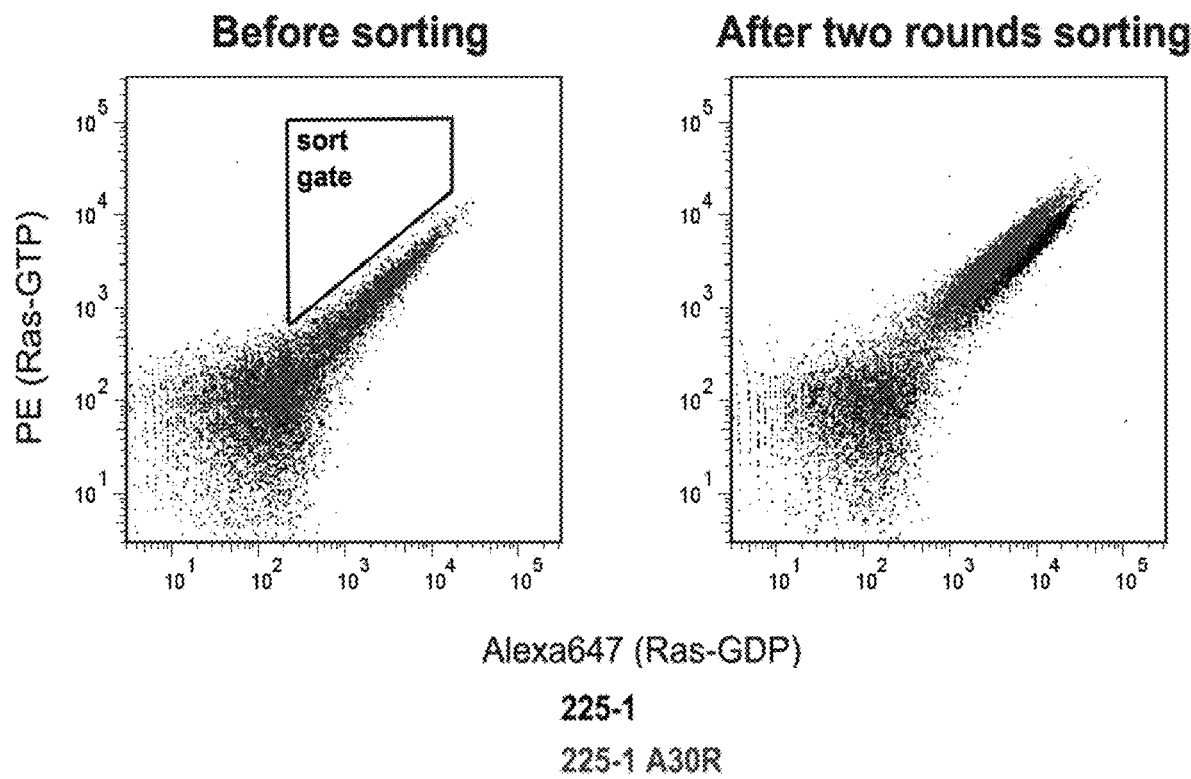
FIG. 28 shows the 225-1 A30R mutant is more selective for KRas (GTP) than 225-1. Yeast displaying either 225-1 or 225-1 A30R were incubated with 500 nM of biotinylated KRas(GTP) and 500 nM of Alexa647-labeled KRas(GDP), then washed and incubated with streptavidin-phycoerythrin (SA-PE) before sorting.

Improving the Nucleotide Specificity of the 225 Peptides. As previously discussed, we found that the selectivity of the 225 peptides for Ras.GTP vs. Ras.GDP was relatively poor (and was different depending on the binding assay used). Because Ras.GTP is the target of biological relevance, we wondered whether there were 225-1 mutants that exhibit improved selectivity for Ras.GTP. One advantage of yeast surface display is the ability to use multiple fluorescent channels, and thus multiple binding agents, which enables multiparameter sorting. We therefore performed a yeast display screen in which we added Ras. GTP and Ras-GDP, labeled with different fluorophores (Ras GTP was biotinylated and detected with SA-PE, Ras-GDP was directly labeled with Alexa647). When cells displaying 225-1 were labeled with 500 nM each of Ras.GTP and Ras.GDP, we observed a linear relationship between the two fluorescence channels, consistent with the observation that the 225-1 can bind both nucleotide states with comparable affinity (FIG. 28). A similar profile was observed for the scanning mutagenesis library. We then performed a screen, selecting cells that lay above the limits of the 225-1 population in the GTP-selective region (see indicated gate). After two rounds of sorting, we isolated a population that appeared to bind Ras-GTP more selectively than the 225-1 parent (FIG. 28). Sequencing this population revealed a single conserved mutation of A30R, near the C-terminus of the peptide. The rationale for this substitution is not evident and will require more detailed structural data of the Ras-peptide complex to understand, but as one obvious difference between Ras.GTP and Ras-GDP is the presence of an additional phosphate in Ras GTP, it is tempting to speculate that the arginine may be forming an electrostatic interaction with this anionic group.

Means of Improving the 225 Peptides.

The ultimate goal of this project is to identify new ways of engaging the Ras effector domain with small peptides, and ideally to develop a molecule that is capable of suppressing Ras activity in cancer cells. We have used yeast display and directed evolution to identify peptides which bind with mid-to-low nanomolar affinity to the Ras surface and likely target the effector domain directly. At present, the 225 (homodimer) peptides do not appear to possess Ras-inhibitory activity when used to treat cancer cells, and there are a number of possibilities for why this may be the case. Although the peptides do appear to be weakly cell permeable, the intracellular concentration they can achieve may be too low given their affinity and/or the cellular abundance of Ras proteins, so it is possible that improvements in either the permeability of affinity of the peptides may be required for activity. It is also possible that, once inside the cell, the 225 peptides are sequestered by non-Ras proteins or away from the inner leaflet of the plasma membrane, where active Ras is located. Indeed, preliminary results with FITC-labeled 225 peptides suggest that they may be predominantly localized to the nucleus, perhaps because a portion of the peptides are recognized as nuclear localization signals (NLS). The PPII helix of the 225 peptides does bear some similarity to an NLS identified in *S. pombe* that is rich in proline and basic amino acids, although to our knowledge an equivalent signal in human cells has not yet been characterized.[2] Should this prove to be the case, it may be possible to weaken such localization by testing mutants of the PPII helix that remove the arginine residues, e.g. by reverting them to the amino acids found in aPP. Finally, it is possible that the 225 peptides are rapidly degraded upon entry to human cells, causing them to be cleared before they can exert an effect on Ras signaling.

At present, we are evaluating the activity of the putative disulfide-stabilized dimers (i.e. Y7C homodimers and S13C/114E-225-1 heterodimers). In principle, these molecules may possess both stronger affinity and improved stability relative to the 225-1 homodimers, and if we obtain encouraging results in vitro, we may test their activity in living cells. Disulfide bonds are generally not stable in human cells, but nevertheless may contribute towards the stability of the peptide-Ras complex since it is apparent that they are not strictly required for dimerization and Ras binding. One could also imagine preparing the corresponding selenocysteine peptides in hopes of obtained non-reducible variants, as discussed in Chapter I.

One additional strategy to improve the biological activity of the 225 peptides is to target them to the cellular compartment where active Ras proteins are localized; namely, the inner leaflet of the plasma membrane. One obvious way to achieve this is simply to mimic the Ras proteins and conjugate the peptides to a lipophilic group, such as a famesyl or hexadecyl moiety. In principle, this should result in the Ras proteins experiencing a relatively high local concentration of the 225 peptides, which could improve the ability of the 225 peptides to compete with effectors, which generally are not tethered to the membrane. We conducted initial tests of this strategy with the 225 peptides prior to discovering that they act as a dimer, and the negative results we obtained are likely a consequence of dimer disruption upon membrane anchoring (analogous to the inability of biotinylated peptides to bind Ras when immobilized to a streptavidin SPR chip). If the disulfide-stabilized dimers prove stable, we will attempt to prepare mono-lipidated dimers (using substoichiometric equivalents of label during the lipidation reaction) to test whether such peptides are able to inhibit Ras activity in cells.

Figure 29:
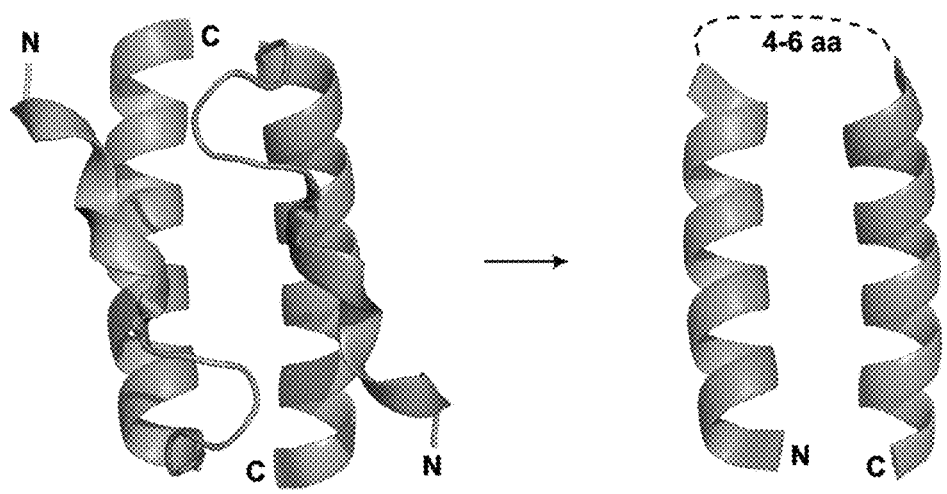
FIG. 29 shows the design of a library to identify monomeric 225 derivatives. The a-helices from the 225 peptides are shown above the corresponding helices in the new library; $X_{4-6}$ is the randomized loop, with X being NNK. Underlined A's replace hydrophobic amino acids that previously packed with the PPII helix.
Figure 30:
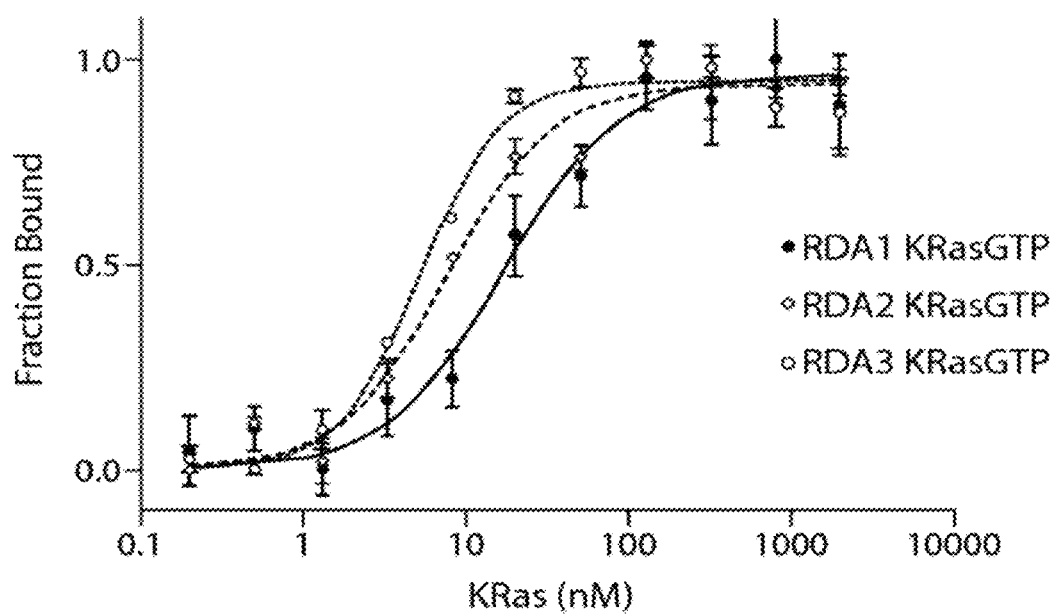
FIG. 30 shows binding affinity by fluorescence polarization, a standard assay for measuring dissociation constants. RDA1: $K_d=17$ nM; RDA2: $K_d=8$ nM; RDA3: $K_d=6$ nM.

Future Directions for the Ras Project. If the peptide-dimer hypothesis is correct, then the size of the Ras-binding 225 species is approximately 9 kDa. This is rather large compared to the cell-penetrating active peptides discussed in the Introduction, and it would be preferable for the molecular weight to be significantly lower. We do not currently know which residues on the peptide dimer are involved in binding the Ras surface, but it seems likely that they are predominantly localized on the a-helix, given that this was the peptide face that was randomized for the library (if the 225 peptides engaged Ras through the PPII helices, which were the same for all library members, one would not expect a rare and specific a-helical consensus to be required for binding). Furthermore, the a-helix was the site of nearly all the mutations that arose during the directed evolution, with the exception of the cysteine mutants that we hypothesize are involved in dimer stabilization. If the a-helices do indeed comprise the Ras-interacting region of the 225 peptide dimer, then the PPII helices may be dispensable, provided that we can identify an alternative means of stabilizing the dimer. The head-to-tail orientation of the dimer model suggests a possible solution to this: because the N- and C-termini of each a-helix are in close proximity, it may be possible to condense the molecule into a monomer, in which one a-helix is followed by a loop (of yet unknown composition) and then the second a-helix (FIG. 29).

In principle, this approach could afford a peptide whose molecular weight is nearly half that of the 225 dimer. One key issue, however, is the length and composition of the loop between helices. Inspection of the aPP dimer suggests that a loop length of 4-6 amino acids may be ideal, but the optimal length is difficult to predict, particularly given that we do not possess an actual structure of the 225 dimer. The loop composition is similarly difficult to predict. Fortunately, this problem is well suited to yeast surface display: by constructing a library with randomized loops of 4-6 amino acids between the two 225 a-helices, it should be possible to identify loops that stabilize the two helices into a Ras-binding conformation, provided that our model of the Ras-peptide interaction is largely correct. We have designed such a library (FIG. 29), with the added feature of cysteine residues at the N- and C-termini of the construct, to allow for the possibility of disulfide bridging across the helices. Because the optimal distance between these two residues is also challenging to predict, the library was synthesized to allow two different positions for each cysteine (by inserting a glycine residue), with four possible combinations total. Furthermore, because several hydrophobic a-helical residues on the "interior" of the 225 peptide are involved in packing with the PPII helix, we either replaced them with alanine or randomized them.

We have prepared this library and plan to begin screening it soon. Should it afford hits, we will perform the same battery of in vitro assays used to characterize the 225 peptides, to determine whether the new sequences bind the Ras effector domain with reasonable affinity and specificity. We may then use directed evolution to improve the properties of the peptides, and will ultimately aim to test their activity in cells. As disulfide bonds are not generally stable in human cells, we will need to develop an alternative means of stabilizing the peptide should our new peptides prove dependent on the disulfide bonds for activity. One possibility would be to replace the cysteine residues with selenocysteine. It could also be possible to prepare a head-to-tail backbone cyclized peptide, either through chemical synthesis or an intein strategy.[3] Finally, if the new peptides largely retain an a-helical binding conformation, they may be suitable candidates for all-hydrocarbon stapling. We intend to pursue these avenues if hits from the yeast display screens emerge.

Example 5: Covalent Peptide Dimer Formation

A peptide monomer comprising a cysteine (SEQ ID NO: 30) protected with t-butyl and a peptide monomer comprising an acrylamide (SEQ ID NO: 31) were mixed together in 50 mM Tris-Cl pH 8 at a final concentration of 5 µM for each peptide. To these samples were added either 1 mM or 10 mM reduced glutathione, and the samples were incubated at room temperature for 45 minutes before adding 80 µl of reaction to 10 µl of 1% trifluoroacetic acid and analyzing by LC-MS using a C18 column and a 10-100% acetonitrile gradient in water with 0.1% trifluoroacetic acid.

Figure 35A:
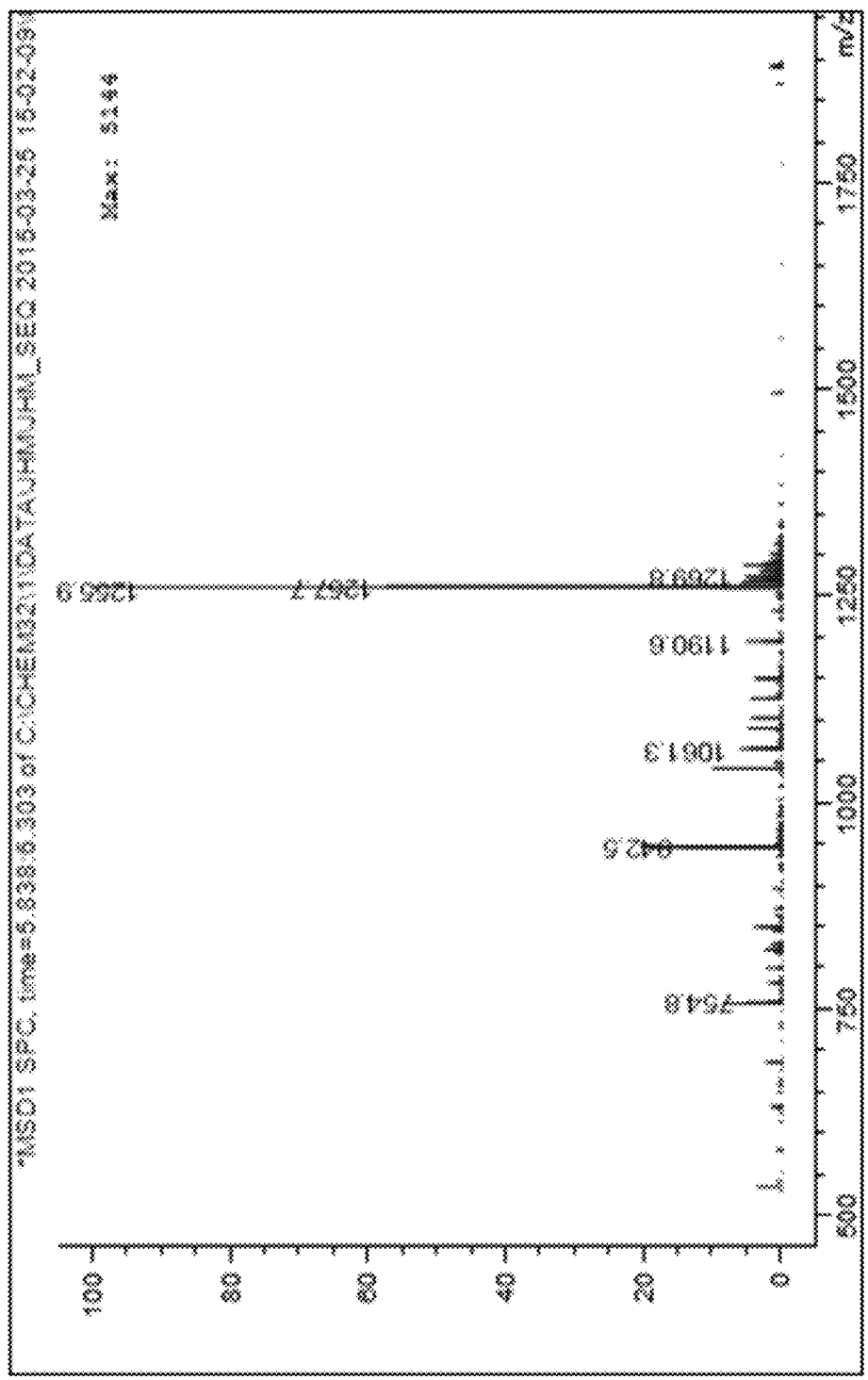
FIGS. 35A-B shows a mass chromatogram from an LC-MS analysis of peptide of SEQ ID NO: 30 mixed with a peptide of SEQ ID NO: 31, either with 1 mM (FIG. 35A) or 10 mM (FIG. 35B) glutathione.
Figure 35B:
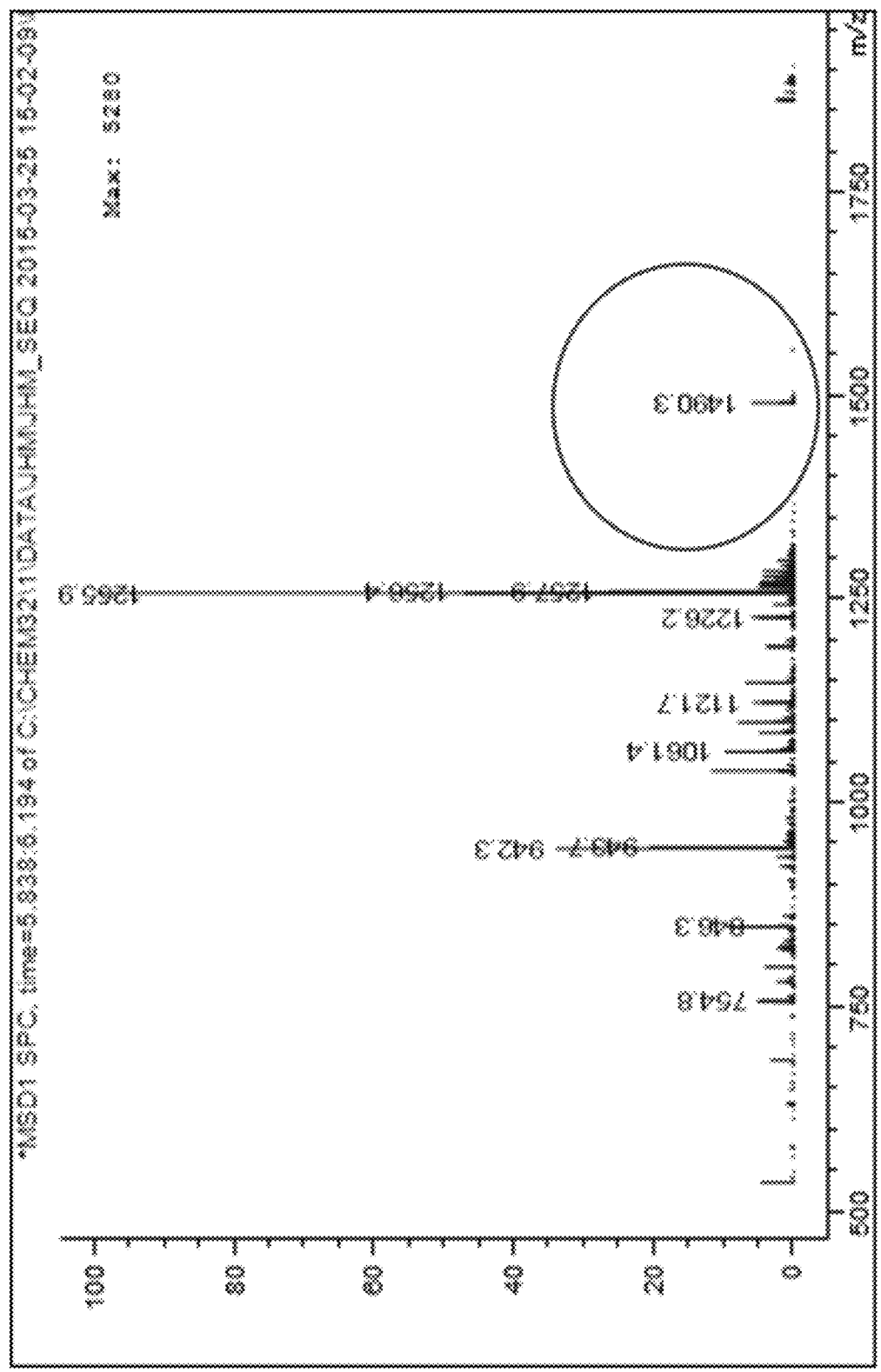

FIGS. 35A-B show a mass chromatogram from an LC-MS analysis of SEQ ID NO: 30 peptide monomer mixed with a SEQ ID NO: 31 peptide monomer, either with a low level of glutathione (1 mM) (FIG. 35A), which cannot reduce the t-butyl thiol protected cysteine effectively), or a higher level of glutathione (10 mM) (FIG. 35B), which results in covalent crosslinking between the peptide of SEQ ID NO: 30 and the peptide of SEQ ID NO: 31, as seen by the appearance of the indicated ion.

Example 6: Selective Dimer Destabilization

Figure 36A:
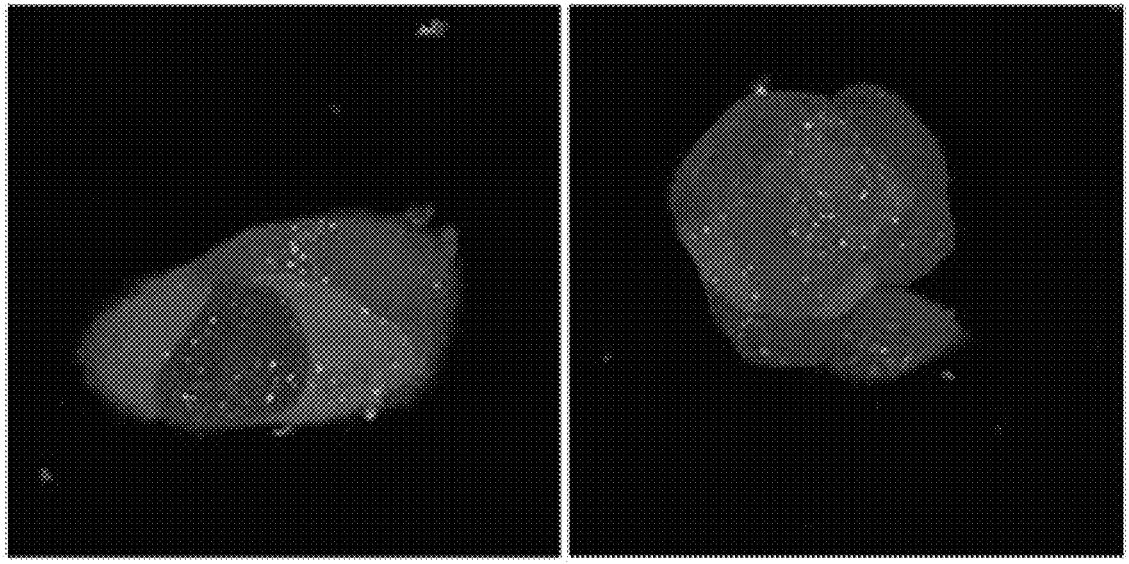
FIGS. 36A-B shows live-cell confocal microscopy using labeled peptide dimers, performed in H358 lung adenocarcinoma cells, at 5 µM concentration of fluorescein-labeled peptide, in DMEM media supplemented with 10% fetal calf serum.
Figure 36B:
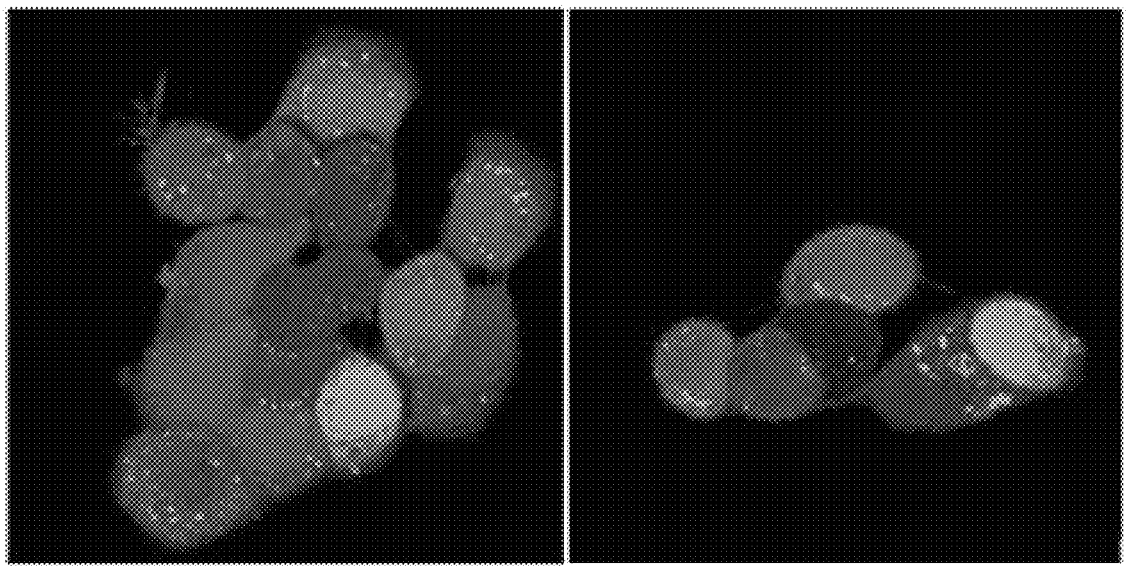

Live-cell confocal microscopy was performed with labeled peptides, performed in H358 lung adenocarcinoma cells, at 5 µM concentration of fluorescein-labeled peptide, in DMEM media supplemented with 10% fetal calf serum. FIG. 36A shows peptides of SEQ ID NO: 37, which lacks histidines. FIG. 36B shows peptides of SEQ ID NO: 38, which contains two histidines per monomer (four histidines per dimer; "His tetrad").

Example 7: Dimer Destabilization Using Bulky Moieties

Figure 37:
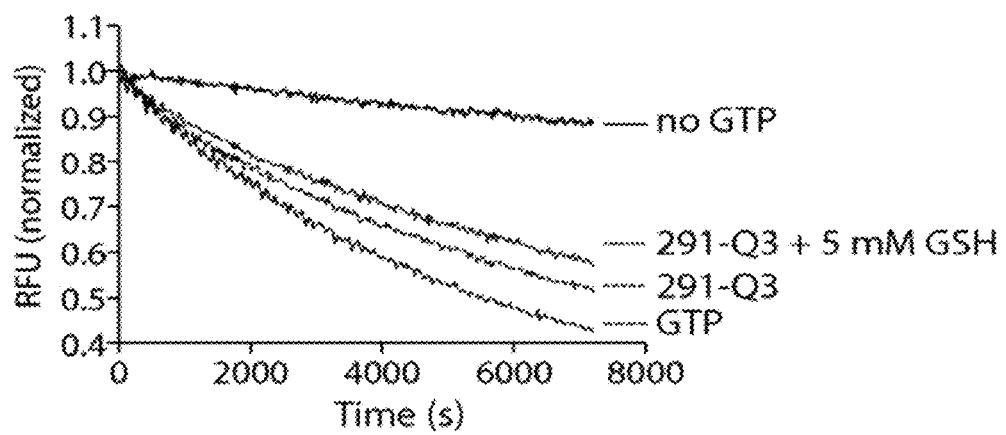
FIG. 37 shows a 291-Q3 peptide of SEQ ID NO: 42 in which the Cys was reacted with 2,2'-Dipyridyldisulfide to create a disulfide-protected cysteine. This cysteine is uncaged in the presence of low glutathione levels to form the disulfide-bonded species, which is a better Ras binder. The data demonstrate an increase in Ras binding upon addition of 5 mM reduced glutathione, which results in the formation of the covalent disulfide-bonded dimer, as verified by mass spectrometry.

FIG. 37 shows a peptide of SEQ ID NO: 42 in which the Cys was reacted with 2,2'-Dipyridyldisulfide to create a disulfide-protected cysteine. This cysteine is uncaged in the presence of low glutathione levels to form the disulfide-bonded species, which is a better Ras binder. The following data demonstrate an increase in Ras binding upon addition of 5 mM reduced glutathione, which results in the formation of the covalent disulfide-bonded dimer, as verified by mass spectrometry. The experimentals are the similar to those described for FIG. 19.

Example 8: Peptides Binding to Additional Targets

Figure 38A:
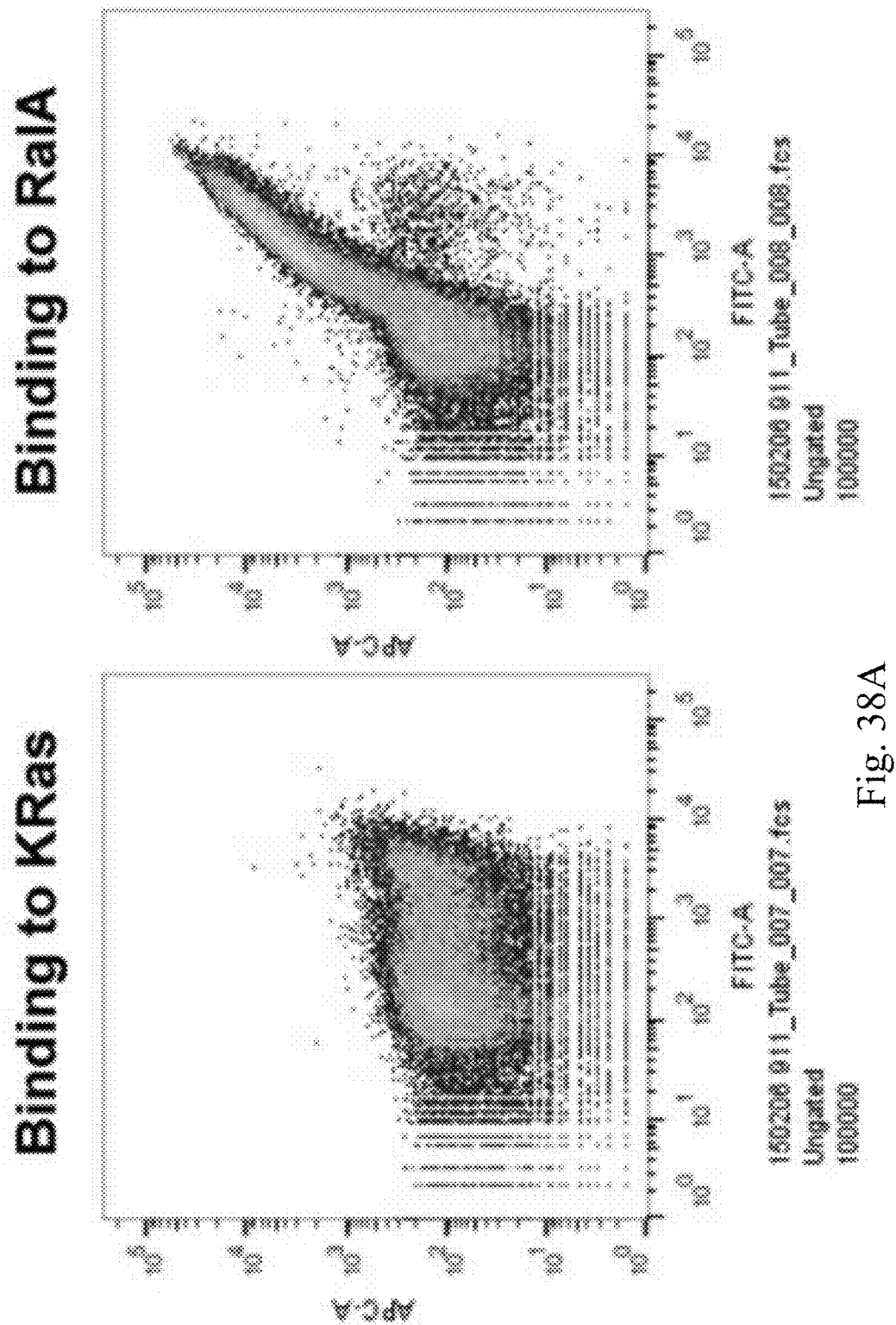
FIGS. 38A-C show yeast surface display binding data for peptides of SEQ ID NO: 43 to 45 with the corresponding protein target.
Figure 38B:
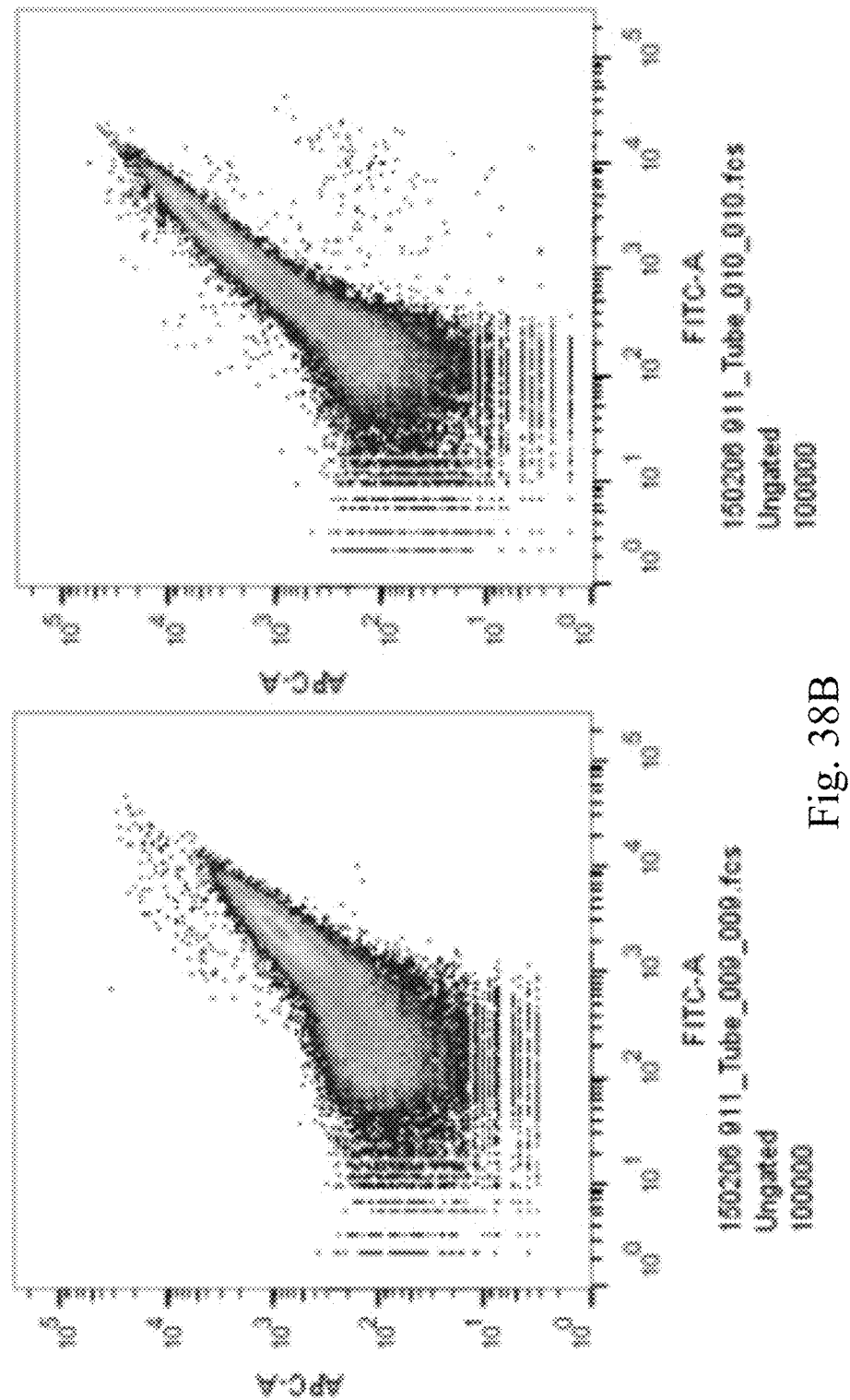
Figure 38C:
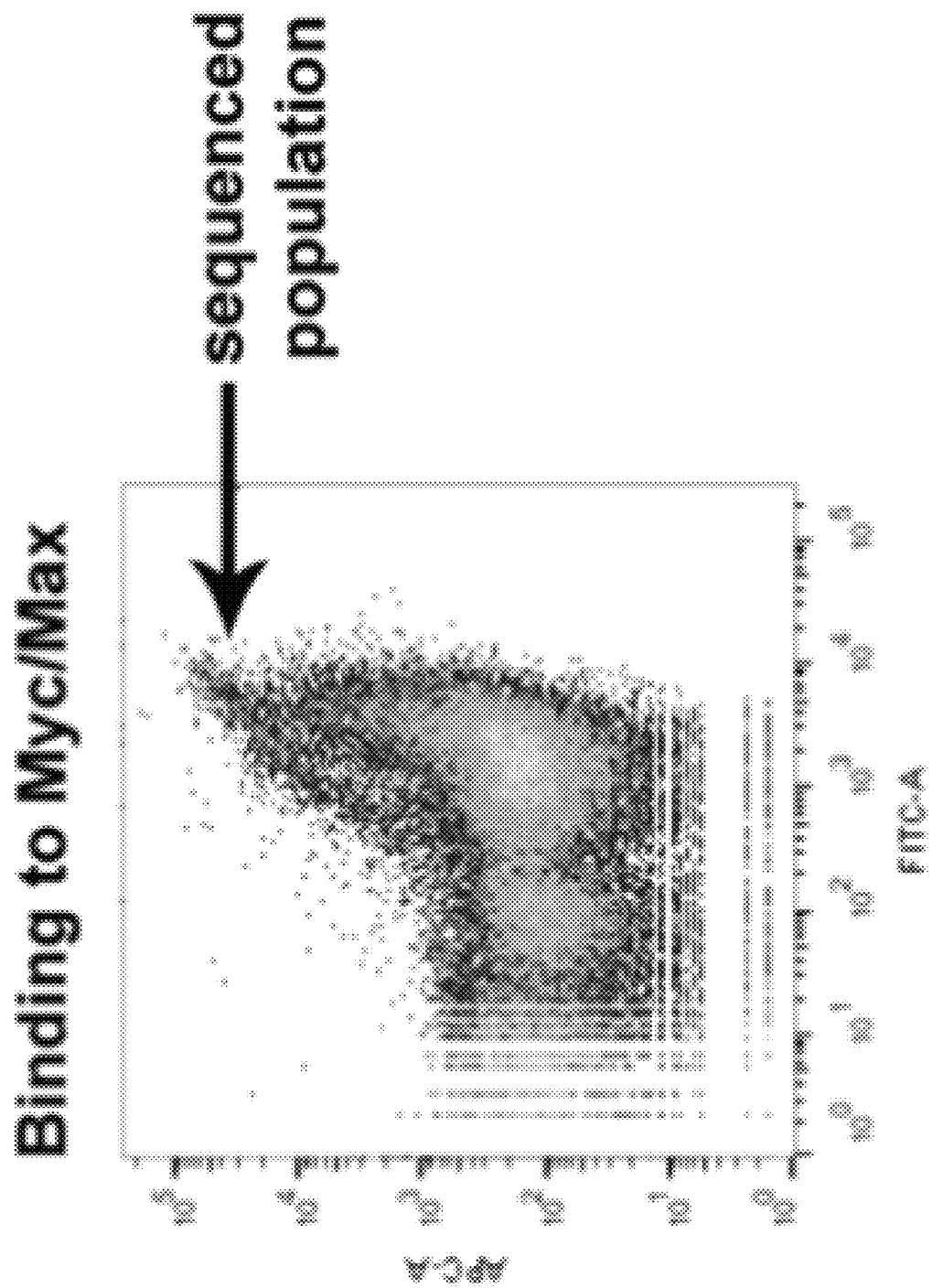

FIGS. 38A-C shows yeast surface display binding data for peptides of SEQ ID NO: 43 to 45 with their corresponding protein targets. Experimental for yeast display assays were similar to those used for FIG. 9. MY01 peptide of SEQ ID NO: 43 corresponds to the indicated high-binding population in FIG. 38C. Purification of the RalA protein was similar to the methods used for KRas constructs as discussed previously.

Purification of the Myc/Max proteins was done as follows. A bicistronic pET vector containing $His_6$-yBBr-TEV-Myc (residues 353-434) and untagged Max (residues 22-102) was transformed into chemically competent BL21 cells. The cells were grown to $OD_{600}$=0.7, induced with 0.25 mM IPTG for 5 hours at 30° C., then harvested and resuspended in lysis buffer (20 mM HEPES pH 7.5, 500 mM KCl, 5% glycerol) prior to snap-freezing in liquid nitrogen. For purification, the pellet was thawed, raised to 40 ml in the same buffer, and mixed with a Roche Complete EDTA-free protease inhibitor tablet. The cells were lysed with a tip sonicator (VirSonic, 6 cycles of 10 s on, 15 s off at 6.5 power level), then pelleted at 30,000×g for 30 minutes and filtered through a 0.45 uM Tuffryn membrane (Pall Corporation). The clarified lysate was added to 2 ml of HisPur Ni-NTA resin (Thermo Pierce) that had been equilibrated with the same buffer, and drained by gravity. The column was washed with 20 ml of buffer, then protein was eluted with buffer containing 150 mM imidazole and some protease inhibitor. Immediately following elution from the column, EDTA was added to 0.5 mM. The protein was concentrated in a Centriprep YM-10 (Millipore) to 2 ml and gel filtered into 20 mM HEPES pH 7.5, 150 mM KCl, 1 mM EDTA, 5% glycerol using a Superdex 75 column. The protein was labeled with Alexa647 as described for the Ras proteins above.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A peptide comprising an oligomerization domain comprising a sequence of:

$$PX_aX_bPX_cX_dP, \quad (SEQ\ ID\ NO:\ 2)$$

wherein each of $X_a$ and $X_b$ is independently any non-proline amino acid, and each of $X_c$ and $X_d$ is independently an amino acid capable of cross-linking the peptide with a second peptide, wherein $X_a$ is covalently cross-linked to the second peptide.

2. A peptide comprising an oligomerization domain comprising a sequence of:

$$PX_aX_bPX_cX_dP, \quad (SEQ\ ID\ NO:\ 2)$$

wherein each of $X_a$, $X_b$, and $X_c$ is independently any non-proline amino acid, and $X_d$ is an amino acid covalently cross-linked to a second peptide, wherein the second peptide comprises a sequence of:
$PX_aX_bPX_cX_dP$ (SEQ ID NO: 2).

3. A peptide comprising an oligomerization domain comprising a sequence of:
$PX_aX_bPX_cX_dP$ (SEQ ID NO: 2),
wherein each of $X_a$, $X_b$, and $X_c$ is independently any non-proline amino acid, and $X_d$ is an amino acid covalently cross-linked to a second peptide, further comprising an alpha-helical domain comprising a sequence of:

$$X_{13}X_{14}X_{15}DLX_{18}X_{19}YX_{21}X_{22}RLX_{25}X_{26}YLX_{29}X_{30}VA, \quad (SEQ\ ID\ NO:\ 100)$$

wherein $X_{13}$ is Ser, Pro, Thr, or an amino acid capable of cross-linking the peptide with another peptide;

$X_{14}$ is Ile, Glu, Val, Leu, or an amino acid capable of cross-linking the peptide with another peptide;

$X_{15}$ is Glu, Lys, Arg, Ala, Ser, Asp, Gln, or Gly;

$X_{18}$ is an aromatic or hydrophobic amino acid;

$X_{19}$ is Glu, Lys, Leu, Met, His, Asp, Gln, Ala, Ser, Trp, or Arg;

$X_{21}$ is Gln, Tyr, Phe, Trp, His, or an amino acid with a cyclohexyl side chain, wherein Tyr, Phe, Trp, or the cyclohexyl side chain can be substituted with one or more fluorines;

$X_{22}$ is Ala, Gln, Trp, Leu, Tyr, Gly, Ser, Val, or Asn;

$X_{25}$ is Gln, Tyr, Phe, Trp, His, Asp, or an amino acid with a cyclohexyl side chain, wherein Tyr, Phe, Trp, or the cyclohexyl side chain can be substituted with one or more fluorines;

$X_{26}$ is Asn, Ala, Leu, Arg, Phe, Ile, His, or Gln;

$X_{29}$ is Ala, Leu, Glu, Asn, Gln, Tyr, Phe, Trp, His, or an amino acid with a cyclohexyl side chain, wherein Tyr, Phe, Trp, or the cyclohexyl side chain can be substituted with one or more fluorines and $X_{30}$ is Ala, Arg or Val.

4. The peptide of claim 3, wherein the alpha-helical domain associates with a target protein.

5. A peptide comprising an oligomerization domain comprising a sequence of:

$$PX_aX_bPX_cX_dP, \quad (SEQ\ ID\ NO:\ 2)$$

wherein each of $X_a$, $X_b$, and $X_c$ is independently any non-proline amino acid, and $X_d$ is an amino acid covalently cross-linked to a second peptide, wherein $X_d$ is Cys, Sec, Phe, Trp, or Tyr.

6. The peptide of claim 1, wherein the second peptide comprises a sequence of:

$$PX_aX_bPX_cX_dP. \quad (SEQ\ ID\ NO:\ 2)$$

7. The peptide of claim 1, further comprising an alpha-helical domain comprising a sequence of:

$$X_{13}X_{14}X_{15}DLX_{18}X_{19}YX_{21}X_{22}RLX_{25}X_{26}YLX_{29}X_{30}VA, \quad (SEQ\ ID\ NO:\ 100)$$

wherein $X_{13}$ is Ser, Pro, Thr, or an amino acid capable of cross-linking the peptide with another peptide;

$X_{14}$ is Ile, Glu, Val, Leu, or an amino acid capable of cross-linking the peptide with another peptide;

$X_{15}$ is Glu, Lys, Arg, Ala, Ser, Asp, Gln, or Gly;

$X_{18}$ is an aromatic or hydrophobic amino acid;

$X_{19}$ is Glu, Lys, Leu, Met, His, Asp, Gln, Ala, Ser, Trp, or Arg;

$X_{21}$ is Gln, Tyr, Phe, Trp, His, or an amino acid with a cyclohexyl side chain, wherein Tyr, Phe, Trp, or the cyclohexyl side chain can be substituted with one or more fluorines;

$X_{22}$ is Ala, Gln, Trp, Leu, Tyr, Gly, Ser, Val, or Asn;

$X_{25}$ is Gln, Tyr, Phe, Trp, His, Asp, or an amino acid with a cyclohexyl side chain, wherein Tyr, Phe, Trp, or the cyclohexyl side chain can be substituted with one or more fluorines;

$X_{26}$ is Asn, Ala, Leu, Arg, Phe, Ile, His, or Gln;

$X_{29}$ is Ala, Leu, Glu, Asn, Gln, Tyr, Phe, Trp, His, or an amino acid with a cyclohexyl side chain, wherein Tyr, Phe, Trp, or the cyclohexyl side chain can be substituted with one or more fluorines and $X_{30}$ is Ala, Arg or Val.

8. The peptide of claim 7, wherein the alpha-helical domain associates with a target protein.

9. A peptide comprising an oligomerization domain comprising a sequence of:

$$PX_aX_bPX_cX_dP, \quad \text{(SEQ ID NO: 2)}$$

wherein each of $X_a$, $X_b$, and $X_c$ is independently any non-proline amino acid, and $X_d$ is an amino acid covalently cross-linked to a second peptide, wherein the peptide comprising an oligomerization domain has a sequence of:

PRRPRCPGHAASIAALHAYWARLWNYLYRVR (SEQ ID NO: 42).

10. The peptide of claim 9, further comprising an alpha-helical domain comprising a sequence of:

$$X_{13}X_{14}X_{15}DLX_{18}X_{19}YX_{21}X_{22}RLX_{25}X_{26}YLX_{29}X_{30}VA, \quad \text{(SEQ ID NO: 100)}$$

wherein $X_{13}$ is Ser, Pro, Thr, or an amino acid capable of cross-linking the peptide with another peptide;

$X_{14}$ is Ile, Glu, Val, Leu, or an amino acid capable of cross-linking the peptide with another peptide;

$X_{15}$ is Glu, Lys, Arg, Ala, Ser, Asp, Gln, or Gly;

$X_{18}$ is an aromatic or hydrophobic amino acid;

$X_{19}$ is Glu, Lys, Leu, Met, His, Asp, Gln, Ala, Ser, Trp, or Arg;

$X_{21}$ is Gln, Tyr, Phe, Trp, His, or an amino acid with a cyclohexyl side chain, wherein Tyr, Phe, Trp, or the cyclohexyl side chain can be substituted with one or more fluorines;

$X_{22}$ is Ala, Gln, Trp, Leu, Tyr, Gly, Ser, Val, or Asn;

$X_{25}$ is Gln, Tyr, Phe, Trp, His, Asp, or an amino acid with a cyclohexyl side chain, wherein Tyr, Phe, Trp, or the cyclohexyl side chain can be substituted with one or more fluorines;

$X_{26}$ is Asn, Ala, Leu, Arg, Phe, Ile, His, or Gln;

$X_{29}$ is Ala, Leu, Glu, Asn, Gln, Tyr, Phe, Trp, His, or an amino acid with a cyclohexyl side chain, wherein Tyr, Phe, Trp, or the cyclohexyl side chain can be substituted with one or more fluorines and $X_{30}$ is Ala, Arg or Val.

11. A peptide comprising an oligomerization domain comprising a sequence of:

$$PX_aX_bPX_cX_dP, \quad \text{(SEQ ID NO: 2)}$$

wherein each of $X_a$, $X_b$, and $X_c$ is independently any non-proline amino acid, and $X_d$ is an amino acid covalently cross-linked to a second peptide, wherein $X_d$ is not Cys.

12. The peptide of claim 1, wherein $X_d$ is not Cys.

* * * * *

SEQUENCE LISTING

```
<160> NUMBER OF SEQ ID NOS: 100

<210> SEQ ID NO 1
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Arg, any amino acid capable of cross-
      linking the peptide with another peptide or absent
<220> FEATURE:
<221> NAME/KEY: MOD_RES
<222> LOCATION: (3)..(4)
<223> OTHER INFORMATION: Any charged amino acid
<220> FEATURE:
<221> NAME/KEY: MOD_RES
<222> LOCATION: (6)..(6)
<223> OTHER INFORMATION: Any charged amino acid
<220> FEATURE:
<221> NAME/KEY: MOD_RES
<222> LOCATION: (7)..(7)
<223> OTHER INFORMATION: Tyr or any amino acid capable of cross-linking
      the peptide with another peptide
<220> FEATURE:
```

```
<221> NAME/KEY: MOD_RES
<222> LOCATION: (10)..(10)
<223> OTHER INFORMATION: Any charged amino acid
<220> FEATURE:
<221> NAME/KEY: MOD_RES
<222> LOCATION: (11)..(11)
<223> OTHER INFORMATION: Any charged amino acid or any amino acid
      capable of cross-linking the peptide with another peptide
<220> FEATURE:
<221> NAME/KEY: MOD_RES
<222> LOCATION: (13)..(13)
<223> OTHER INFORMATION: Ser or any amino acid capable of cross-linking
      the peptide with another peptide
<220> FEATURE:
<221> NAME/KEY: MOD_RES
<222> LOCATION: (14)..(14)
<223> OTHER INFORMATION: Ile or Glu
<220> FEATURE:
<221> NAME/KEY: MOD_RES
<222> LOCATION: (15)..(15)
<223> OTHER INFORMATION: Glu, Asp, Gln or Gly
<220> FEATURE:
<221> NAME/KEY: MOD_RES
<222> LOCATION: (18)..(18)
<223> OTHER INFORMATION: Any aromatic or hydrophobic amino acid
<220> FEATURE:
<221> NAME/KEY: MOD_RES
<222> LOCATION: (19)..(19)
<223> OTHER INFORMATION: Glu, Asp, Gln, Ala or Trp
<220> FEATURE:
<221> NAME/KEY: MOD_RES
<222> LOCATION: (21)..(21)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (22)..(22)
<223> OTHER INFORMATION: Ala, Gly, Ser or Val
<220> FEATURE:
<221> NAME/KEY: MOD_RES
<222> LOCATION: (25)..(25)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (26)..(26)
<223> OTHER INFORMATION: Asn, Leu, Ile or His
<220> FEATURE:
<221> NAME/KEY: MOD_RES
<222> LOCATION: (29)..(29)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (30)..(30)
<223> OTHER INFORMATION: Ala or Arg
<220> FEATURE:
<221> NAME/KEY: MISC_FEATURE
<222> LOCATION: (1)..(32)
<223> OTHER INFORMATION: Wherein the peptide comprises one to two amino
      acids capable of cross-linking the peptide with another peptide
<220> FEATURE:
<223> OTHER INFORMATION: See specification as filed for detailed
      description of substitutions and preferred embodiments

<400> SEQUENCE: 1

Xaa Pro Xaa Xaa Pro Xaa Xaa Pro Gly Xaa Xaa Ala Xaa Xaa Xaa Asp
1               5                   10                  15

Leu Xaa Xaa Tyr Xaa Xaa Arg Leu Xaa Xaa Tyr Leu Xaa Xaa Val Ala
            20                  25                  30

<210> SEQ ID NO 2
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid except Pro
<220> FEATURE:
<221> NAME/KEY: MOD_RES
<222> LOCATION: (5)..(5)
<223> OTHER INFORMATION: Any amino acid except Pro
<220> FEATURE:
<221> NAME/KEY: MOD_RES
<222> LOCATION: (6)..(6)
<223> OTHER INFORMATION: Any amino acid capable of cross-linking the
      peptide with a second peptide
<220> FEATURE:
<223> OTHER INFORMATION: See specification as filed for detailed
      description of substitutions and preferred embodiments

<400> SEQUENCE: 2

Pro Xaa Xaa Pro Xaa Xaa Pro
1               5

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or any amino acid capable of cross-linking
      the peptide with another peptide
<220> FEATURE:
<221> NAME/KEY: MOD_RES
<222> LOCATION: (2)..(2)
<223> OTHER INFORMATION: Ile or Glu
<220> FEATURE:
<221> NAME/KEY: MOD_RES
<222> LOCATION: (3)..(3)
<223> OTHER INFORMATION: Glu, Asp, Gln or Gly
<220> FEATURE:
<221> NAME/KEY: MOD_RES
<222> LOCATION: (6)..(6)
<223> OTHER INFORMATION: Any aromatic or hydrophobic amino acid
<220> FEATURE:
<221> NAME/KEY: MOD_RES
<222> LOCATION: (7)..(7)
<223> OTHER INFORMATION: Glu, Asp, Gln, Ala or Trp
<220> FEATURE:
<221> NAME/KEY: MOD_RES
<222> LOCATION: (9)..(9)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (10)..(10)
<223> OTHER INFORMATION: Ala, Gly, Ser or Val
<220> FEATURE:
<221> NAME/KEY: MOD_RES
<222> LOCATION: (13)..(13)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (14)..(14)
<223> OTHER INFORMATION: Asn, Leu, Ile or His
<220> FEATURE:
<221> NAME/KEY: MOD_RES
<222> LOCATION: (17)..(17)
```

```
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (18)..(18)
<223> OTHER INFORMATION: Ala or Arg
<220> FEATURE:
<221> NAME/KEY: MISC_FEATURE
<222> LOCATION: (1)..(20)
<223> OTHER INFORMATION: Wherein the peptide comprises one to two amino
      acids capable of cross-linking the peptide with another peptide
<220> FEATURE:
<223> OTHER INFORMATION: See specification as filed for detailed
      description of substitutions and preferred embodiments

<400> SEQUENCE: 3

Xaa Xaa Xaa Asp Leu Xaa Xaa Tyr Xaa Xaa Arg Leu Xaa Xaa Tyr Leu
1               5                   10                  15

Xaa Xaa Val Ala
            20

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Pro Arg Arg Pro Arg Cys Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Pro Arg Arg Pro Arg Cys Pro Gly Asp Asp Ala Ser Ile Glu Asp
1               5                   10                  15

Leu His Glu Tyr Trp Ala Arg Leu Trp Asn Tyr Leu Tyr Arg Val Ala
            20                  25                  30

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Arg Arg Pro Arg Arg Pro Arg Cys Pro Gly Asp Asp Ala Ser Ile
1               5                   10                  15

Glu Asp Leu His Glu Tyr Trp Ala Arg Leu Trp Asn Tyr Leu Tyr Ala
            20                  25                  30

Val Ala

<210> SEQ ID NO 7
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Pro Arg Arg Pro Arg Tyr Pro Gly Asp Asp Ala Pro Val Glu Asp
1               5                   10                  15

Leu Ile Arg Phe Tyr Asn Asp Leu Gln Gln Tyr Leu Asn Val Val Ala
            20                  25                  30

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Cys Gly Gly Pro Arg Arg Pro Arg Tyr Pro Gly Asp Asp Ala Ser
1               5                   10                  15

Ile Glu Asp Leu His Glu Tyr Trp Ala Arg Leu Trp Asn Tyr Leu Tyr
            20                  25                  30

Ala Val Ala
        35

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Cys Gly Gly Pro Arg Arg Pro Arg Tyr Pro Gly Asp Asp Ala Cys
1               5                   10                  15

Glu Glu Asp Leu His Glu Tyr Trp Ala Arg Leu Trp Asn Tyr Leu Tyr
            20                  25                  30

Ala Val Ala
        35

<210> SEQ ID NO 10
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Cys Gly Gly Pro Arg Arg Pro Arg Tyr Pro Gly Asp Asp Ala Ser
1               5                   10                  15

Ile Glu Asp Leu His Glu Tyr Trp Ala Arg Leu Trp Asn Tyr Leu Tyr
            20                  25                  30

Arg Val Ala
        35

<210> SEQ ID NO 11
<211> LENGTH: 38
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 11

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Trp Ala Arg Leu Trp Asn
            20                  25                  30

Tyr Leu Tyr Ala Val Ala
        35

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Arg, any amino acid capable of cross-
      linking the peptide with another peptide or absent
<220> FEATURE:
<221> NAME/KEY: MOD_RES
<222> LOCATION: (3)..(4)
<223> OTHER INFORMATION: Any charged amino acid
<220> FEATURE:
<221> NAME/KEY: MOD_RES
<222> LOCATION: (6)..(6)
<223> OTHER INFORMATION: Any charged amino acid
<220> FEATURE:
<221> NAME/KEY: MOD_RES
<222> LOCATION: (7)..(7)
<223> OTHER INFORMATION: Tyr or any amino acid capable of cross-linking
      the peptide with another peptide
<220> FEATURE:
<221> NAME/KEY: MOD_RES
<222> LOCATION: (10)..(10)
<223> OTHER INFORMATION: Any charged amino acid
<220> FEATURE:
<221> NAME/KEY: MOD_RES
<222> LOCATION: (11)..(11)
<223> OTHER INFORMATION: Any charged amino acid or any amino acid
      capable of cross-linking the peptide with another peptide
<220> FEATURE:
<221> NAME/KEY: MOD_RES
<222> LOCATION: (13)..(13)
<223> OTHER INFORMATION: Ser, Pro or any amino acid capable of cross-
      linking the peptide with another peptide
<220> FEATURE:
<221> NAME/KEY: MOD_RES
<222> LOCATION: (14)..(14)
<223> OTHER INFORMATION: Ile, Glu or Val
<220> FEATURE:
<221> NAME/KEY: MOD_RES
<222> LOCATION: (15)..(15)
<223> OTHER INFORMATION: Glu, Asp, Gln or Gly
<220> FEATURE:
<221> NAME/KEY: MOD_RES
<222> LOCATION: (18)..(18)
<223> OTHER INFORMATION: Any aromatic or hydrophobic amino acid
<220> FEATURE:
<221> NAME/KEY: MOD_RES
<222> LOCATION: (19)..(19)
<223> OTHER INFORMATION: Glu, Asp, Gln, Ala, Trp or Arg
<220> FEATURE:
<221> NAME/KEY: MOD_RES
<222> LOCATION: (20)..(20)
<223> OTHER INFORMATION: Tyr or Phe
<220> FEATURE:
<221> NAME/KEY: MOD_RES
<222> LOCATION: (21)..(21)

```
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (22)..(22)
<223> OTHER INFORMATION: Ala, Gly, Ser, Val or Asn
<220> FEATURE:
<221> NAME/KEY: MOD_RES
<222> LOCATION: (23)..(23)
<223> OTHER INFORMATION: Arg or Asp
<220> FEATURE:
<221> NAME/KEY: MOD_RES
<222> LOCATION: (25)..(25)
<223> OTHER INFORMATION: Tyr, Phe, Trp, His, Gln or any amino acid with
      a cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (26)..(26)
<223> OTHER INFORMATION: Asn, Leu, Ile, His or Gln
<220> FEATURE:
<221> NAME/KEY: MOD_RES
<222> LOCATION: (29)..(29)
<223> OTHER INFORMATION: Tyr, Phe, Trp, His, Asn or any amino acid with
      a cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (30)..(30)
<223> OTHER INFORMATION: Ala, Arg or Val
<220> FEATURE:
<223> OTHER INFORMATION: See specification as filed for detailed
      description of substitutions and preferred embodiments

<400> SEQUENCE: 12

Xaa Pro Xaa Xaa Pro Xaa Xaa Pro Gly Xaa Xaa Ala Xaa Xaa Xaa Asp
1               5                   10                  15

Leu Xaa Xaa Xaa Xaa Xaa Xaa Leu Xaa Xaa Tyr Leu Xaa Xaa Val Ala
            20                  25                  30

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(7)
<223> OTHER INFORMATION: Any naturally occurring amino acid or absent
<220> FEATURE:
<221> NAME/KEY: MOD_RES
<222> LOCATION: (9)..(10)
<223> OTHER INFORMATION: Any neutral or charged amino acid
<220> FEATURE:
<221> NAME/KEY: MOD_RES
<222> LOCATION: (12)..(12)
<223> OTHER INFORMATION: Any charged amino acid or any amino acid
      capable of cross-linking the peptide with another peptide
<220> FEATURE:
<221> NAME/KEY: MOD_RES
<222> LOCATION: (13)..(13)
<223> OTHER INFORMATION: Tyr, His or any amino acid capable of cross-
      linking the peptide with another peptide
<220> FEATURE:
<221> NAME/KEY: MOD_RES
<222> LOCATION: (16)..(16)
<223> OTHER INFORMATION: Pro, any charged amino acid or any amino acid
      capable of cross-linking the peptide with another peptide
<220> FEATURE:
<221> NAME/KEY: MOD_RES
<222> LOCATION: (17)..(17)
<223> OTHER INFORMATION: Ala, Ser, any neutral or charged amino acid or
      any amino acid capable of cross-linking the peptide with another
```

```
            peptide
<220> FEATURE:
<221> NAME/KEY: MOD_RES
<222> LOCATION: (19)..(19)
<223> OTHER INFORMATION: Ser, Pro, Thr or any amino acid capable of
      cross-linking the peptide with another peptide
<220> FEATURE:
<221> NAME/KEY: MOD_RES
<222> LOCATION: (20)..(20)
<223> OTHER INFORMATION: Ile, Glu, Val, Leu or any amino acid capable of
      cross-linking the peptide with another peptide
<220> FEATURE:
<221> NAME/KEY: MOD_RES
<222> LOCATION: (21)..(21)
<223> OTHER INFORMATION: Glu, Lys, Arg, Ala, Ser, Asp, Gln or Gly
<220> FEATURE:
<221> NAME/KEY: MOD_RES
<222> LOCATION: (22)..(22)
<223> OTHER INFORMATION: Asp, Glu, Gln, Ala or Ser
<220> FEATURE:
<221> NAME/KEY: MOD_RES
<222> LOCATION: (24)..(24)
<223> OTHER INFORMATION: Any aromatic or hydrophobic amino acid
<220> FEATURE:
<221> NAME/KEY: MOD_RES
<222> LOCATION: (25)..(25)
<223> OTHER INFORMATION: Glu, Lys, Leu, Met, His, Asp, Gln, Ala, Ser,
      Trp or Arg
<220> FEATURE:
<221> NAME/KEY: MOD_RES
<222> LOCATION: (26)..(26)
<223> OTHER INFORMATION: Tyr or Phe
<220> FEATURE:
<221> NAME/KEY: MOD_RES
<222> LOCATION: (27)..(27)
<223> OTHER INFORMATION: Gln, Tyr, Phe, Trp, His or any amino acid with
      a cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (28)..(28)
<223> OTHER INFORMATION: Ala, Gln, Trp, Leu, Tyr, Gly, Ser, Val or Asn
<220> FEATURE:
<221> NAME/KEY: MOD_RES
<222> LOCATION: (29)..(29)
<223> OTHER INFORMATION: Arg, Asp, Leu or Ala
<220> FEATURE:
<221> NAME/KEY: MOD_RES
<222> LOCATION: (31)..(31)
<223> OTHER INFORMATION: Gln, Tyr, Phe, Trp, His, Asp or any amino acid
      with a cyclohexyl side chain, wherein Tyr, Phe, Trp,
      cyclohexyl side chain can be substituted with
      one or more fluorines
<220> FEATURE:
<221> NAME/KEY: MOD_RES
<222> LOCATION: (32)..(32)
<223> OTHER INFORMATION: Asn, Ala, Leu, Arg, Phe, Ile, His or Gln
<220> FEATURE:
<221> NAME/KEY: MOD_RES
<222> LOCATION: (35)..(35)
<223> OTHER INFORMATION: Ala, Leu, Glu, Asn, Gln, Tyr, Phe, Trp, His or
      any amino acid with a cyclohexyl side chain, wherein Tyr, Phe,
      Trp, cyclohexyl side chain can be substituted with one or
      more fluorines
<220> FEATURE:
<221> NAME/KEY: MOD_RES
<222> LOCATION: (36)..(36)
<223> OTHER INFORMATION: Ala, Arg or Val
<220> FEATURE:
<221> NAME/KEY: MOD_RES
<222> LOCATION: (37)..(37)
<223> OTHER INFORMATION: Val or any amino acid capable of cross-linking
      the peptide with another peptide
<220> FEATURE:
<221> NAME/KEY: MOD_RES
<222> LOCATION: (38)..(38)
<223> OTHER INFORMATION: Val, Ala, Arg, Ser or any amino acid capable of
      cross-linking the peptide with another peptide
<220> FEATURE:
```

```
<221> NAME/KEY: MISC_FEATURE
<222> LOCATION: (1)..(38)
<223> OTHER INFORMATION: Wherein the peptide comprises one to two amino
      acids capable of cross-linking the peptide with another peptide
<220> FEATURE:
<223> OTHER INFORMATION: See specification as filed for detailed
      description of substitutions and preferred embodiments

<400> SEQUENCE: 13

Xaa Xaa Xaa Xaa Xaa Xaa Xaa Pro Xaa Xaa Pro Xaa Xaa Pro Gly Xaa
1               5                   10                  15

Xaa Ala Xaa Xaa Xaa Xaa Leu Xaa Xaa Xaa Xaa Xaa Leu Xaa Xaa
            20                  25                  30

Tyr Leu Xaa Xaa Xaa Xaa
        35

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Arg Arg Pro Arg Cys Pro Gly Asp Asp Ala Ser Ile Glu Asp Leu
1               5                   10                  15

His Glu Tyr Trp Ala Arg Leu Trp Asn Tyr Leu Tyr Ala Val Ala
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Arg Arg Pro Arg Cys Pro Gly Asp Asp Ala Ser Ile Glu Asp Leu
1               5                   10                  15

His Glu Tyr Trp Ala Arg Leu Trp Asn Tyr Leu Tyr Arg Val Ala
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Arg Arg Pro Arg Arg Pro Arg Cys Pro Gly Asp Asp Ala Ser Ile Glu
1               5                   10                  15

Asp Leu His Glu Tyr Trp Ala Arg Leu Trp Asn Tyr Leu Tyr Ala Val
            20                  25                  30

Ala

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 17

Pro Arg Arg Pro Arg Tyr Pro Gly Asp Asp Ala Pro Val Glu Asp Leu
1               5                   10                  15

Ile Arg Phe Tyr Asn Asp Leu Gln Gln Tyr Leu Asn Val Val Ala
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Pro Arg Arg Pro Arg Tyr Pro Gly Asp Asp Ala Ser Ile Glu Asp Leu
1               5                   10                  15

His Glu Tyr Trp Ala Arg Leu Trp Asn Tyr Leu Tyr Ala Val Ala
            20                  25                  30

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Cys Gly Gly Pro Arg Arg Pro Arg Tyr Pro Gly Asp Asp Ala Cys Glu
1               5                   10                  15

Glu Asp Leu His Glu Tyr Trp Ala Arg Leu Trp Asn Tyr Leu Tyr Ala
            20                  25                  30

Val Ala

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Arg Arg Pro Arg Tyr Pro Gly Asp Asp Ala Ser Ile Glu Asp Leu
1               5                   10                  15

His Glu Tyr Trp Ala Arg Leu Trp Asn Tyr Leu Tyr Arg Val Ala
            20                  25                  30

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Pro Arg Arg Pro Arg Arg Pro Arg Tyr Pro Gly Asp Asp Ala Ser Ile
1               5                   10                  15

Glu Asp Leu His Glu Tyr Trp Ala Arg Leu Trp Asn Tyr Leu Tyr Ala
            20                  25                  30

Val Ala

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Arg Arg Pro Arg Cys Pro Gly Asp Asp Ala Ser Leu Glu Asp Leu
1               5                   10                  15

His Glu Tyr Trp Ala Arg Leu Trp Asn Tyr Leu Tyr Arg Val Ala
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Arg Arg Pro Arg Cys Pro Gly Asp Gln Ala Ser Leu Glu Glu Leu
1               5                   10                  15

His Glu Tyr Trp Ala Arg Leu Trp Asn Tyr Leu Tyr Arg Val Ala
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Arg Arg Pro Arg Cys Pro Gly Asp Asn Ala Ser Ile Lys Gln Leu
1               5                   10                  15

His Ala Tyr Trp Asn Arg Leu Tyr Ala Tyr Leu Ala Ala Val Ala
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Arg Arg Pro Arg Cys Pro Gly Asp Asp Ala Ser Ile Glu Asp Leu
1               5                   10                  15

His Glu Tyr Trp Gln Arg Leu Tyr Ala Tyr Leu Ala Ala Val Ala
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Pro Arg Arg Pro Arg Cys Pro Gly Asp Asn Ala Ser Ile Lys Gln Leu
1               5                   10                  15

His Ala Tyr Trp Gln Arg Leu Tyr Ala Tyr Leu Ala Ala Val Ala
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Arg Arg Pro Arg Cys Pro Gly Asp Asn Ala Ser Ile Arg Gln Leu
1               5                   10                  15

His Ala Tyr Trp Gln Arg Leu Tyr Ala Tyr Leu Ala Ala Val Ala
            20                  25                  30

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Cys Gly Gly Pro Arg Arg Pro Arg Tyr Pro Gly Asp Ala Ala Ser
1               5                   10                  15

Ile Ala Ala Leu His Ala Tyr Trp Ala Arg Leu Trp Asn Tyr Leu Tyr
            20                  25                  30

Arg Val Ala
        35

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Pro Arg Arg Pro Arg Tyr Pro Gly Asp Ala Ser Ile Ala Ala Leu
1               5                   10                  15

His Ala Tyr Trp Ala Arg Leu Trp Asn Tyr Leu Tyr Arg Val Ala
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Pro Arg Arg Pro Lys Tyr Pro Gly Asp Ala Ala Ser Cys Ala Ala Leu
1               5                   10                  15

His Ala Tyr Trp Ala Arg Leu Trp Asn Tyr Leu Tyr Arg Val Ala
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any naturally occurring amino acid

<400> SEQUENCE: 31

Pro Arg Arg Pro Arg Tyr Pro Gly Asp Ala Ala Ser Ile Ala Ala Leu
1               5                   10                  15

His Ala Tyr Trp Ala Arg Leu Trp Asn Tyr Leu Tyr Arg Xaa Ala
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Arg Arg Pro Arg Tyr Pro Gly Asp Ala Ala Ser Ile Ala Ala Leu
1               5                   10                  15

His Ala Tyr Trp Ala Arg Leu Trp Asn Tyr Leu Tyr Arg Glx Ala
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Pro Arg Arg Pro Cys Tyr Pro Gly Asp Ala Ala Ser Ile Ala Ala Leu
1               5                   10                  15

His Ala Tyr Trp Ala Arg Leu Trp Asn Tyr Leu Tyr Arg Val Ala
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Arg Arg Pro Lys Cys Pro Gly Asp Ala Ala Ser Ile Ala Ala Leu
1               5                   10                  15

His Ala Tyr Trp Ala Arg Leu Trp Asn Tyr Leu Tyr Arg Val Ala
            20                  25                  30

<210> SEQ ID NO 35
<211> LENGTH: 31
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any naturally occurring amino acid

<400> SEQUENCE: 35

Pro Arg Arg Pro Arg Tyr Pro Gly Xaa Ala Ala Ser Ile Ala Ala Leu
1               5                   10                  15

His Ala Tyr Trp Ala Arg Leu Trp Asn Tyr Leu Tyr Arg Val Ala
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Arg Arg Pro Arg Tyr Pro Gly Glx Ala Ala Ser Ile Ala Ala Leu
1               5                   10                  15

His Ala Tyr Trp Ala Arg Leu Trp Asn Tyr Leu Tyr Arg Val Ala
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Arg Arg Pro Lys Tyr Pro Gly Asp Ala Ala Ser Ile Ala Ala Leu
1               5                   10                  15

His Ala Tyr Trp Ala Arg Leu Trp Asn Tyr Leu Tyr Arg Val Arg
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Pro Arg Arg Pro Lys His Pro Gly His Ala Ala Ser Ile Ala Ala Leu
1               5                   10                  15

His Ala Tyr Trp Ala Arg Leu Trp Asn Tyr Leu Tyr Arg Val Arg
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Pro Arg Arg Pro Arg His Pro Gly Pro Asn Ala Thr Ile Ser Gln Leu
1               5                   10                  15
```

His His Tyr Trp Ala Arg Leu Trp Asn Tyr Leu Tyr Arg Val Arg
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Pro Arg Arg Pro His His Pro Gly His Ala Ala Ser Ile Ala Ala Leu
1               5                   10                  15

His Ala Tyr Trp Ala Arg Leu Trp Asn Tyr Leu Tyr Arg Val Arg
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Arg Arg Pro His Tyr Pro Gly His Ala Ala Ser Ile Ala Ala Leu
1               5                   10                  15

His Ala Tyr Trp Ala Arg Leu Trp Asn Tyr Leu Tyr Arg Val Arg
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Pro Arg Arg Pro Arg Cys Pro Gly His Ala Ala Ser Ile Ala Ala Leu
1               5                   10                  15

His Ala Tyr Trp Ala Arg Leu Trp Asn Tyr Leu Tyr Arg Val Arg
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Pro Arg Arg Pro Arg Cys Pro Gly Asp Asp Ala Ser Ile Arg Asp
1               5                   10                  15

Leu Leu Lys Tyr Trp Trp Arg Leu Arg Leu Tyr Leu Leu Ala Val Ala
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic

```
                      polypeptide

<400> SEQUENCE: 44

Gly Pro Arg Arg Pro Arg Cys Pro Gly Asp Asp Ala Ser Ile Ser Asp
1               5                   10                  15

Leu Leu Leu Tyr Trp Leu Arg Leu Asp Arg Tyr Leu Trp Ala Val Ala
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Pro Arg Arg Pro Arg Cys Pro Gly Asp Asp Ala Ser Ile Arg Asp
1               5                   10                  15

Leu Val Met Tyr Trp Tyr Arg Leu Tyr Phe Tyr Leu Glu Ala Val Ala
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Pro Arg Arg Pro Lys Tyr Pro Gly Asp Ala Ala Ser Ile Ala Ala Leu
1               5                   10                  15

His Ala Tyr Trp Ala Arg Leu Trp Asn Tyr Leu Tyr Arg Val Ser
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Pro Arg Arg Pro Lys Tyr Pro Gly Asp Ala Ala Ser Ile Ala Ala
1               5                   10                  15

Leu His Ala Tyr Trp Ala Arg Leu Trp Asn Tyr Leu Tyr Arg Val Ser
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Arg, any amino acid capable of cross-
      linking the peptide with another peptide or absent
<220> FEATURE:
<221> NAME/KEY: MOD_RES
<222> LOCATION: (3)..(4)
<223> OTHER INFORMATION: Any neutral or positively charged amino acid
<220> FEATURE:
```

```
<221> NAME/KEY: MOD_RES
<222> LOCATION: (6)..(6)
<223> OTHER INFORMATION: Any neutral or positively charged amino acid
<220> FEATURE:
<221> NAME/KEY: MOD_RES
<222> LOCATION: (7)..(7)
<223> OTHER INFORMATION: Tyr or any amino acid capable of cross-linking
     the peptide with another peptide
<220> FEATURE:
<221> NAME/KEY: MOD_RES
<222> LOCATION: (10)..(10)
<223> OTHER INFORMATION: Asp or any neutral amino acid
<220> FEATURE:
<221> NAME/KEY: MOD_RES
<222> LOCATION: (13)..(13)
<223> OTHER INFORMATION: Ser, Thr or any amino acid capable of cross-
     linking the peptide with another peptide
<220> FEATURE:
<221> NAME/KEY: MOD_RES
<222> LOCATION: (14)..(14)
<223> OTHER INFORMATION: Ile or Leu
<220> FEATURE:
<221> NAME/KEY: MOD_RES
<222> LOCATION: (21)..(21)
<223> OTHER INFORMATION: Tyr, Phe, Trp, His or any amino acid with a
     cyclohexyl side chain, wherein Tyr, Phe, Trp, cyclohexyl side
     chain can be substituted with one or more fluorines
<220> FEATURE:
<221> NAME/KEY: MOD_RES
<222> LOCATION: (23)..(23)
<223> OTHER INFORMATION: Arg, Leu or Ala
<220> FEATURE:
<221> NAME/KEY: MOD_RES
<222> LOCATION: (25)..(25)
<223> OTHER INFORMATION: Tyr, Phe, Trp, His or any amino acid with a
     cyclohexyl side chain, wherein Tyr, Phe, Trp, cyclohexyl side
     chain can be substituted with one or more fluorines
<220> FEATURE:
<221> NAME/KEY: MOD_RES
<222> LOCATION: (29)..(29)
<223> OTHER INFORMATION: Tyr, Phe, Trp, His or any amino acid with a
     cyclohexyl side chain, wherein Tyr, Phe, Trp, cyclohexyl side
     chain can be substituted with one or more fluorines
<220> FEATURE:
<221> NAME/KEY: MOD_RES
<222> LOCATION: (30)..(30)
<223> OTHER INFORMATION: Ala or Arg
<220> FEATURE:
<221> NAME/KEY: MOD_RES
<222> LOCATION: (32)..(32)
<223> OTHER INFORMATION: Ala, Ser or Arg
<220> FEATURE:
<221> NAME/KEY: MISC_FEATURE
<222> LOCATION: (1)..(32)
<223> OTHER INFORMATION: Wherein the peptide comprises one to two amino
     acids capable of cross-linking the peptide with another peptide
<220> FEATURE:
<223> OTHER INFORMATION: See specification as filed for detailed
     description of substitutions and preferred embodiments

<400> SEQUENCE: 48

Xaa Pro Xaa Xaa Pro Xaa Xaa Pro Gly Xaa Ala Ala Xaa Xaa Ala Ala
1               5                   10                  15

Leu His Ala Tyr Xaa Ala Xaa Leu Xaa Asn Tyr Leu Xaa Xaa Val Xaa
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 49
```

Pro Arg Arg Pro Arg Tyr Pro Gly Asp Ala Ala Ser Ile Ala Ala Leu
1               5                   10                  15

His Ala Tyr Trp Ala Arg Leu Trp Asn Tyr Leu Tyr Arg Val Ser
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Arg Arg Pro Arg Cys Pro Gly Asp Asn Ala Ser Ile Arg Gln Leu
1               5                   10                  15

His Ala Tyr Trp Gln Arg Leu Tyr Ala Tyr Leu Ala Ala Val Ala
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Pro Arg Arg Pro Arg Cys Pro Gly Asp Ala Ala Ser Ile Ala Ala Leu
1               5                   10                  15

His Ala Tyr Trp Gln Arg Leu Tyr Ala Tyr Leu Ala Ala Val Ala
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Pro Ser Gln Pro Thr Tyr Pro Gly Asp Asp Ala Pro Val Glu Asp
1               5                   10                  15

Leu Ile Arg Phe Tyr Asn Asp Leu Gln Gln Tyr Leu Asn Val Val Ala
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Pro Arg Arg Pro Arg Tyr Pro Gly Asp Asp Ala Pro Val Glu Asp
1               5                   10                  15

Leu Ile Arg Phe Tyr Asn Asp Leu Gln Gln Tyr Leu Asn Val Val Ala
            20                  25                  30

<210> SEQ ID NO 54
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Any naturally occurring amino acid
<220> FEATURE:
<221> NAME/KEY: MOD_RES
<222> LOCATION: (18)..(19)
<223> OTHER INFORMATION: Any naturally occurring amino acid
<220> FEATURE:
<221> NAME/KEY: MOD_RES
<222> LOCATION: (21)..(21)
<223> OTHER INFORMATION: Any naturally occurring amino acid
<220> FEATURE:
<221> NAME/KEY: MOD_RES
<222> LOCATION: (23)..(23)
<223> OTHER INFORMATION: Any naturally occurring amino acid
<220> FEATURE:
<221> NAME/KEY: MOD_RES
<222> LOCATION: (25)..(26)
<223> OTHER INFORMATION: Any naturally occurring amino acid
<220> FEATURE:
<221> NAME/KEY: MOD_RES
<222> LOCATION: (29)..(29)
<223> OTHER INFORMATION: Any naturally occurring amino acid

<400> SEQUENCE: 54

Gly Pro Arg Arg Pro Arg Tyr Pro Gly Asp Asp Ala Pro Val Xaa Asp
1               5                   10                  15

Leu Xaa Xaa Phe Xaa Ala Xaa Leu Xaa Xaa Tyr Leu Xaa Val Val Ala
            20                  25                  30

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Pro Arg Arg Pro Arg Tyr Pro Gly Asp Asp Ala Pro Val Glu Asp
1               5                   10                  15

Leu His Ala Phe Trp Ala Ala Leu Trp Asn Tyr Leu Tyr Val Val Ala
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Pro Arg Arg Pro Arg Tyr Pro Gly Asp Asp Ala Pro Val Gly Asp
```

```
                1               5                   10                  15
Leu His Glu Phe Trp Ala Gln Leu Trp Asn Tyr Leu Tyr Val Val Ala
                20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Pro Arg Arg Pro Lys Tyr Pro Gly Asp Asp Ala Pro Val Glu Asp
1               5                   10                  15

Leu His Trp Phe Trp Ala Ala Leu Trp Asn Tyr Leu Tyr Val Val Ala
                20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Pro Arg Arg Pro Arg Tyr Pro Gly Asp Asp Ala Ser Val Glu Asp
1               5                   10                  15

Leu His Glu Phe Trp Ala Arg Leu Trp Asn Tyr Leu Tyr Ala Val Ala
                20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Pro Arg Arg Pro Arg Tyr Pro Gly Asp Asp Ala Ser Ile Glu Asp
1               5                   10                  15

Leu His Ala Phe Trp Ala Ala Leu Trp Asn Tyr Leu Tyr Ala Val Ala
                20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Pro Arg Arg Pro Arg Cys Pro Gly Asp Asp Ala Ser Val Glu Asp
1               5                   10                  15

Leu His Glu Tyr Trp Ala Arg Leu Trp Asn Tyr Leu Tyr Ala Val Ala
                20                  25                  30

<210> SEQ ID NO 62
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 62

Gly Pro Arg Arg Pro Arg Cys Pro Gly Asp Asp Ala Ser Ile Glu Asp
1               5                   10                  15

Leu His Glu Phe Trp Ala Arg Leu Trp Asn Tyr Leu Tyr Ala Val Ala
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Pro Arg Arg Pro Arg Cys Pro Gly Asp Asp Ala Ser Val Glu Asp
1               5                   10                  15

Leu His Glu Phe Trp Ala Arg Leu Trp Asn Tyr Leu Tyr Ala Val Ala
            20                  25                  30

<210> SEQ ID NO 64
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Pro Arg Arg Pro Arg Arg Pro Arg Tyr Pro Gly Asp Asp Ala Ser
1               5                   10                  15

Ile Glu Asp Leu His Ala Phe Trp Ala Ala Leu Trp Asn Tyr Leu Tyr
            20                  25                  30

Ala Val Ala
        35

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Pro Arg Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Pro Arg Arg Pro Arg Tyr Pro Gly Asp Asp Ala Ser Ile Glu Asp
1               5                   10                  15
```

Leu His Ala Tyr Trp Ala Arg Leu Trp Asn Tyr Leu Tyr Ala Val Ala
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Pro Arg Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Pro Val Ala
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Pro Arg Arg Pro Arg Tyr Pro Gly Asp Asp Ala Ser Val Glu Asp
1               5                   10                  15

Leu His Glu Tyr Trp Ala Arg Leu Trp Asn Tyr Leu Tyr Ala Val Ala
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Pro Arg Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Pro Arg Arg Pro Arg Cys Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Pro Arg Arg Pro Arg Cys Pro Gly Asp Asp Ala Ser Val Glu Asp
1               5                   10                  15

Leu His Glu Tyr Trp Ala Arg Leu Trp Asn Tyr Leu Tyr Ala Val Ala
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Pro Arg Arg Pro Arg Cys Pro Gly Asp Asp Ala Ser Thr Glu Asp
1               5                   10                  15

Leu His Ala Tyr Trp Ala Arg Leu Trp Asn Tyr Leu Tyr Ala Val Ala
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Pro Arg Arg Pro Arg Cys Pro Gly Asp Asp Ala Ser Val Glu Asp
1               5                   10                  15

Leu His Ala Tyr Trp Ala Lys Leu Trp Asn Tyr Leu Tyr Ala Val Ala
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Pro Arg Arg Pro Arg Cys Pro Gly Asp Asp Ala Ser Thr Glu Asp
1               5                   10                  15

Leu His Ala Tyr Trp Ala Lys Leu Trp Asn Tyr Leu Tyr Ala Val Ala
            20                  25                  30

<210> SEQ ID NO 75
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Cys Gly Gly Pro Arg Arg Pro Arg Tyr Pro Gly Asp Asp Ala Ser
1               5                   10                  15

Ile Glu Asp Leu His Glu Tyr Trp Ala Arg Leu Trp Ala Tyr Leu Tyr
            20                  25                  30

Ala Val Ala
        35

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Trp Ala Arg Leu Trp Asn
            20                  25                  30

Tyr Leu Tyr Ala Val Ala
        35

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Cys Gly Gly Pro Arg Arg Pro Ala Arg Pro Arg Tyr Pro Gly Asp
1               5                   10                  15

Asp Ala Ser Ile Glu Asp Leu His Glu Tyr Trp Ala Arg Leu Trp Asn
            20                  25                  30

Tyr Leu Tyr Ala Val Ala
        35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Cys Gly Gly Pro Arg Arg Pro Arg Arg Pro Ala Tyr Pro Gly Asp
1               5                   10                  15

Asp Ala Ser Ile Glu Asp Leu His Glu Tyr Trp Ala Arg Leu Trp Asn
            20                  25                  30

Tyr Leu Tyr Ala Val Ala
        35

<210> SEQ ID NO 79
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Cys Gly Gly Pro Arg Arg Pro Arg Arg Pro Arg Tyr Pro Gly Asp
1               5                   10                  15

Ala Ala Ser Ile Glu Asp Leu His Glu Tyr Trp Ala Arg Leu Trp Asn
            20                  25                  30

Tyr Leu Tyr Ala Val Ala

35

<210> SEQ ID NO 80
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Cys Gly Gly Pro Arg Arg Pro Arg Arg Pro Arg Tyr Pro Gly Asp
1               5                   10                  15

Asp Ala Ser Ala Glu Asp Leu His Glu Tyr Trp Ala Arg Leu Trp Asn
            20                  25                  30

Tyr Leu Tyr Ala Val Ala
        35

<210> SEQ ID NO 81
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Cys Gly Gly Pro Arg Arg Pro Arg Arg Pro Arg Tyr Pro Gly Asp
1               5                   10                  15

Asp Ala Ser Ile Glu Asp Leu Ala Glu Tyr Trp Ala Arg Leu Trp Asn
            20                  25                  30

Tyr Leu Tyr Ala Val Ala
        35

<210> SEQ ID NO 82
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Ala Ala Arg Leu Trp Asn
            20                  25                  30

Tyr Leu Tyr Ala Val Ala
        35

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Trp Ala Arg Leu Ala Asn
            20                  25                  30

Tyr Leu Tyr Ala Val Ala
        35

<210> SEQ ID NO 84
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Trp Ala Arg Leu Trp Ala
            20                  25                  30

Tyr Leu Tyr Ala Val Ala
        35

<210> SEQ ID NO 85
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Cys Gly Gly Pro Arg Arg Pro Arg Arg Pro Arg Tyr Pro Gly Asp
1               5                   10                  15

Asp Ala Ser Ile Glu Asp Leu His Glu Tyr Trp Ala Arg Leu Trp Asn
            20                  25                  30

Tyr Leu Ala Ala Val Ala
        35

<210> SEQ ID NO 86
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any naturally occurring amino acid encoded by
      an "nnk" codon

<400> SEQUENCE: 86

Xaa Xaa Arg Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any naturally occurring amino acid encoded by
      an "nnk" codon -continued

```
<400> SEQUENCE: 87

Gly Xaa Xaa Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(4)
<223> OTHER INFORMATION: Any naturally occurring amino acid encoded by
      an "nnk" codon

<400> SEQUENCE: 88

Gly Pro Xaa Xaa Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(5)
<223> OTHER INFORMATION: Any naturally occurring amino acid encoded by
      an "nnk" codon

<400> SEQUENCE: 89

Gly Pro Arg Xaa Xaa Arg Tyr Pro Gly Asp Asp Ala Ser Ile Glu Asp
1               5                   10                  15

Leu His Glu Tyr Trp Ala Arg Leu Trp Asn Tyr Leu Tyr Ala Val Ala
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(32)
<223> OTHER INFORMATION: Any naturally occurring amino acid encoded by
      an "nnk" codon

<400> SEQUENCE: 90

Gly Pro Arg Arg Pro Arg Tyr Pro Gly Asp Asp Ala Ser Ile Glu Asp
1               5                   10                  15

Leu His Glu Tyr Trp Ala Arg Leu Trp Asn Tyr Leu Tyr Ala Xaa Xaa
            20                  25                  30

<210> SEQ ID NO 91
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 91

Ile Glu Asp Leu His Glu Tyr Trp Ala Arg Leu Trp Asn Tyr Leu Tyr
1               5                   10                  15

Ala

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Asp Leu His Glu Tyr Trp Ala Arg Leu Trp Asn Tyr Leu Tyr Ala
1               5                   10                  15

Val

<210> SEQ ID NO 93
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(3)
<223> OTHER INFORMATION: This region may encompass 1-2 residues
<220> FEATURE:
<221> NAME/KEY: MOD_RES
<222> LOCATION: (17)..(17)
<223> OTHER INFORMATION: Any naturally occurring amino acid encoded by
      an "nnk" codon
<220> FEATURE:
<221> NAME/KEY: MOD_RES
<222> LOCATION: (21)..(26)
<223> OTHER INFORMATION: Any naturally occurring amino acid encoded by
      an "nnk" codon
<220> FEATURE:
<221> NAME/KEY: MISC_FEATURE
<222> LOCATION: (21)..(26)
<223> OTHER INFORMATION: This region may encompass 4-6 residues
<220> FEATURE:
<221> NAME/KEY: MOD_RES
<222> LOCATION: (29)..(29)
<223> OTHER INFORMATION: Any naturally occurring amino acid encoded by
      an "nnk" codon
<220> FEATURE:
<221> NAME/KEY: MISC_FEATURE
<222> LOCATION: (44)..(45)
<223> OTHER INFORMATION: This region may encompass 1-2 residues
<220> FEATURE:
<223> OTHER INFORMATION: See specification as filed for detailed
      description of substitutions and preferred embodiments

<400> SEQUENCE: 93

Cys Gly Gly Ile Glu Asp Ala His Glu Ala Trp Ala Arg Leu Trp Asn
1               5                   10                  15

Xaa Leu Tyr Ala Xaa Xaa Xaa Xaa Xaa Xaa Glu Asp Xaa His Glu Ala
                20                  25                  30

Trp Ala Arg Leu Trp Asn Ala Leu Tyr Ala Val Gly Gly Cys
            35                  40                  45

<210> SEQ ID NO 94
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Ser Leu Glu Phe Ile Ala Ser Lys Leu Ala
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Gly Gly Ser Gly Gly Gly Gly Ser Gly Gly Gly Gly
1               5                   10

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Arg, any amino acid capable of cross-
      linking the peptide with another peptide or absent
<220> FEATURE:
<221> NAME/KEY: MOD_RES
<222> LOCATION: (3)..(4)
<223> OTHER INFORMATION: Any charged amino acid
<220> FEATURE:
<221> NAME/KEY: MOD_RES
<222> LOCATION: (6)..(6)
<223> OTHER INFORMATION: Any charged amino acid
<220> FEATURE:
<221> NAME/KEY: MOD_RES
<222> LOCATION: (7)..(7)
<223> OTHER INFORMATION: Tyr or any amino acid capable of cross-linking
      the peptide with another peptide
<220> FEATURE:
<221> NAME/KEY: MOD_RES
<222> LOCATION: (11)..(11)
<223> OTHER INFORMATION: Any charged amino acid or any amino acid
      capable of cross-linking the peptide with another peptide
<220> FEATURE:
<221> NAME/KEY: MOD_RES
<222> LOCATION: (13)..(13)
<223> OTHER INFORMATION: Ser or any amino acid capable of cross-linking
      the peptide with another peptide
<220> FEATURE:
<221> NAME/KEY: MOD_RES
<222> LOCATION: (14)..(14)
<223> OTHER INFORMATION: Ile or Glu
<220> FEATURE:
<221> NAME/KEY: MOD_RES
<222> LOCATION: (15)..(15)
<223> OTHER INFORMATION: Glu, Asp, Gln or Gly
<220> FEATURE:
<221> NAME/KEY: MOD_RES
<222> LOCATION: (18)..(18)
<223> OTHER INFORMATION: Any aromatic or hydrophobic amino acid
<220> FEATURE:
<221> NAME/KEY: MOD_RES
<222> LOCATION: (19)..(19)
<223> OTHER INFORMATION: Glu, Asp, Gln, Ala or Trp
<220> FEATURE:
```

```
<221> NAME/KEY: MOD_RES
<222> LOCATION: (21)..(21)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (22)..(22)
<223> OTHER INFORMATION: Ala, Gly, Ser or Val
<220> FEATURE:
<221> NAME/KEY: MOD_RES
<222> LOCATION: (25)..(25)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (26)..(26)
<223> OTHER INFORMATION: Asn, Leu, Ile or His
<220> FEATURE:
<221> NAME/KEY: MOD_RES
<222> LOCATION: (29)..(29)
<223> OTHER INFORMATION: Tyr, Phe, Trp, His or any amino acid with a
      cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (30)..(30)
<223> OTHER INFORMATION: Ala or Arg
<220> FEATURE:
<223> OTHER INFORMATION: See specification as filed for detailed
      description of substitutions and preferred embodiments

<400> SEQUENCE: 96

Xaa Pro Xaa Xaa Pro Xaa Xaa Pro Gly Asp Xaa Ala Xaa Xaa Xaa Asp
1               5                   10                  15

Leu Xaa Xaa Tyr Xaa Xaa Arg Leu Xaa Xaa Tyr Leu Xaa Xaa Val Ala
            20                  25                  30

<210> SEQ ID NO 97
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Cys or Selenocysteine
<220> FEATURE:
<221> NAME/KEY: MOD_RES
<222> LOCATION: (5)..(5)
<223> OTHER INFORMATION: Pro, Cys, Selenocysteine or Gly
<220> FEATURE:
<221> NAME/KEY: MOD_RES
<222> LOCATION: (6)..(6)
<223> OTHER INFORMATION: Arg or Gly
<220> FEATURE:
<221> NAME/KEY: MOD_RES
<222> LOCATION: (7)..(7)
<223> OTHER INFORMATION: Gly, Arg or any amino acid capable of cross-
      linking the peptide with another peptide
<220> FEATURE:
<221> NAME/KEY: MOD_RES
<222> LOCATION: (9)..(10)
<223> OTHER INFORMATION: Any neutral or charged amino acid
<220> FEATURE:
<221> NAME/KEY: MOD_RES
<222> LOCATION: (12)..(12)
<223> OTHER INFORMATION: Any charged amino acid or any amino acid
      capable of cross-linking the peptide with another peptide
<220> FEATURE:
<221> NAME/KEY: MOD_RES
<222> LOCATION: (13)..(13)
<223> OTHER INFORMATION: Tyr, His or any amino acid capable of cross-
```

```
      linking the peptide with another peptide
<220> FEATURE:
<221> NAME/KEY: MOD_RES
<222> LOCATION: (16)..(16)
<223> OTHER INFORMATION: Pro, any charged amino acid or any amino acid
      capable of cross-linking the peptide with another peptide
<220> FEATURE:
<221> NAME/KEY: MOD_RES
<222> LOCATION: (17)..(17)
<223> OTHER INFORMATION: Ala, Ser, any neutral or charged amino acid or
      any amino acid capable of cross-linking the peptide with another
      peptide
<220> FEATURE:
<221> NAME/KEY: MOD_RES
<222> LOCATION: (19)..(19)
<223> OTHER INFORMATION: Ser, Pro, Thr or any amino acid capable of
      cross-linking the peptide with another peptide
<220> FEATURE:
<221> NAME/KEY: MOD_RES
<222> LOCATION: (20)..(20)
<223> OTHER INFORMATION: Ile, Glu, Val, Leu or any amino acid capable of
      cross-linking the peptide with another peptide
<220> FEATURE:
<221> NAME/KEY: MOD_RES
<222> LOCATION: (21)..(21)
<223> OTHER INFORMATION: Glu, Lys, Arg, Ala, Ser, Asp, Gln or Gly
<220> FEATURE:
<221> NAME/KEY: MOD_RES
<222> LOCATION: (22)..(22)
<223> OTHER INFORMATION: Asp, Glu, Gln, Ala or Ser
<220> FEATURE:
<221> NAME/KEY: MOD_RES
<222> LOCATION: (24)..(24)
<223> OTHER INFORMATION: Any aromatic or hydrophobic amino acid
<220> FEATURE:
<221> NAME/KEY: MOD_RES
<222> LOCATION: (25)..(25)
<223> OTHER INFORMATION: Glu, Lys, Leu, Met, His, Asp, Gln, Ala, Ser,
      Trp or Arg
<220> FEATURE:
<221> NAME/KEY: MOD_RES
<222> LOCATION: (26)..(26)
<223> OTHER INFORMATION: Tyr or Phe
<220> FEATURE:
<221> NAME/KEY: MOD_RES
<222> LOCATION: (27)..(27)
<223> OTHER INFORMATION: Gln, Tyr, Phe, Trp, His or any amino acid with
      a cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (28)..(28)
<223> OTHER INFORMATION: Ala, Gln, Trp, Leu, Tyr, Gly, Ser, Val or Asn
<220> FEATURE:
<221> NAME/KEY: MOD_RES
<222> LOCATION: (29)..(29)
<223> OTHER INFORMATION: Arg, Asp, Leu or Ala
<220> FEATURE:
<221> NAME/KEY: MOD_RES
<222> LOCATION: (31)..(31)
<223> OTHER INFORMATION: Gln, Tyr, Phe, Trp, His, Asp or any amino acid
      with a cyclohexyl side chain, wherein Tyr, Phe, Trp,
      cyclohexyl side chain can be substituted with
      one or more fluorines
<220> FEATURE:
<221> NAME/KEY: MOD_RES
<222> LOCATION: (32)..(32)
<223> OTHER INFORMATION: Asn, Ala, Leu, Arg, Phe, Ile, His or Gln
<220> FEATURE:
<221> NAME/KEY: MOD_RES
<222> LOCATION: (35)..(35)
<223> OTHER INFORMATION: Ala, Leu, Glu, Asn, Gln, Tyr, Phe, Trp, His or
      any amino acid with a cyclohexyl side chain, wherein Tyr, Phe,
      Trp, cyclohexyl side chain can be substituted with one or
      more fluorines
<220> FEATURE:
<221> NAME/KEY: MOD_RES
<222> LOCATION: (36)..(36)
<223> OTHER INFORMATION: Ala, Arg or Val
```

-continued

```
<220> FEATURE:
<221> NAME/KEY: MOD_RES
<222> LOCATION: (37)..(37)
<223> OTHER INFORMATION: Val or any amino acid capable of cross-linking
      the peptide with another peptide
<220> FEATURE:
<221> NAME/KEY: MOD_RES
<222> LOCATION: (38)..(38)
<223> OTHER INFORMATION: Val, Ala, Arg, Ser or any amino acid capable of
      cross-linking the peptide with another peptide
<220> FEATURE:
<221> NAME/KEY: MISC_FEATURE
<222> LOCATION: (1)..(38)
<223> OTHER INFORMATION: Wherein the peptide comprises one to two amino
      acids capable of cross-linking the peptide with another peptide
<220> FEATURE:
<223> OTHER INFORMATION: See specification as filed for detailed
      description of substitutions and preferred embodiments

<400> SEQUENCE: 97

Gly Xaa Gly Gly Xaa Xaa Xaa Pro Xaa Xaa Pro Xaa Xaa Pro Gly Xaa
1               5                   10                  15

Xaa Ala Xaa Xaa Xaa Xaa Leu Xaa Xaa Xaa Xaa Xaa Leu Xaa Xaa
            20                  25                  30

Tyr Leu Xaa Xaa Xaa Xaa
        35

<210> SEQ ID NO 98
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any neutral or charged amino acid
<220> FEATURE:
<221> NAME/KEY: MOD_RES
<222> LOCATION: (5)..(5)
<223> OTHER INFORMATION: Any charged amino acid or any amino acid
      capable of cross-linking the peptide with another peptide
<220> FEATURE:
<221> NAME/KEY: MOD_RES
<222> LOCATION: (6)..(6)
<223> OTHER INFORMATION: Tyr, His or any amino acid capable of cross-
      linking the peptide with another peptide
<220> FEATURE:
<221> NAME/KEY: MOD_RES
<222> LOCATION: (9)..(9)
<223> OTHER INFORMATION: Pro, any charged amino acid or any amino acid
      capable of cross-linking the peptide with another peptide
<220> FEATURE:
<221> NAME/KEY: MOD_RES
<222> LOCATION: (10)..(10)
<223> OTHER INFORMATION: Ala, Ser, any neutral or charged amino acid or
      any amino acid capable of cross-linking the peptide with another
      peptide
<220> FEATURE:
<221> NAME/KEY: MOD_RES
<222> LOCATION: (12)..(12)
<223> OTHER INFORMATION: Ser, Pro, Thr or any amino acid capable of
      cross-linking the peptide with another peptide
<220> FEATURE:
<221> NAME/KEY: MOD_RES
<222> LOCATION: (13)..(13)
<223> OTHER INFORMATION: Ile, Glu, Val, Leu or any amino acid capable of
      cross-linking the peptide with another peptide
<220> FEATURE:
<221> NAME/KEY: MOD_RES
<222> LOCATION: (14)..(14)
<223> OTHER INFORMATION: Glu, Lys, Arg, Ala, Ser, Asp, Gln or Gly
<220> FEATURE:
<221> NAME/KEY: MOD_RES
```

```
<222> LOCATION: (15)..(15)
<223> OTHER INFORMATION: Asp, Glu, Gln, Ala or Ser
<220> FEATURE:
<221> NAME/KEY: MOD_RES
<222> LOCATION: (17)..(17)
<223> OTHER INFORMATION: Any aromatic or hydrophobic amino acid
<220> FEATURE:
<221> NAME/KEY: MOD_RES
<222> LOCATION: (18)..(18)
<223> OTHER INFORMATION: Glu, Lys, Leu, Met, His, Asp, Gln, Ala, Ser,
      Trp or Arg
<220> FEATURE:
<221> NAME/KEY: MOD_RES
<222> LOCATION: (19)..(19)
<223> OTHER INFORMATION: Tyr or Phe
<220> FEATURE:
<221> NAME/KEY: MOD_RES
<222> LOCATION: (20)..(20)
<223> OTHER INFORMATION: Gln, Tyr, Phe, Trp, His or any amino acid with
      a cyclohexyl side chain, wherein Tyr, Phe, Trp, cyclohexyl side
      chain can be substituted with one or more fluorines
<220> FEATURE:
<221> NAME/KEY: MOD_RES
<222> LOCATION: (21)..(21)
<223> OTHER INFORMATION: Ala, Gln, Trp, Leu, Tyr, Gly, Ser, Val or Asn
<220> FEATURE:
<221> NAME/KEY: MOD_RES
<222> LOCATION: (22)..(22)
<223> OTHER INFORMATION: Arg, Asp, Leu or Ala
<220> FEATURE:
<221> NAME/KEY: MOD_RES
<222> LOCATION: (24)..(24)
<223> OTHER INFORMATION: Gln, Tyr, Phe, Trp, His, Asp or any amino acid
      with a cyclohexyl side chain, wherein Tyr, Phe, Trp,
      cyclohexyl side chain can be substituted with
      one or more fluorines
<220> FEATURE:
<221> NAME/KEY: MOD_RES
<222> LOCATION: (25)..(25)
<223> OTHER INFORMATION: Asn, Ala, Leu, Arg, Phe, Ile, His or Gln
<220> FEATURE:
<221> NAME/KEY: MOD_RES
<222> LOCATION: (28)..(28)
<223> OTHER INFORMATION: Ala, Leu, Glu, Asn, Gln, Tyr, Phe, Trp, His or
      any amino acid with a cyclohexyl side chain, wherein Tyr, Phe,
      Trp, cyclohexyl side chain can be substituted with one or
      more fluorines
<220> FEATURE:
<221> NAME/KEY: MOD_RES
<222> LOCATION: (29)..(29)
<223> OTHER INFORMATION: Ala, Arg or Val
<220> FEATURE:
<221> NAME/KEY: MOD_RES
<222> LOCATION: (30)..(30)
<223> OTHER INFORMATION: Val or any amino acid capable of cross-linking
      the peptide with another peptide
<220> FEATURE:
<221> NAME/KEY: MOD_RES
<222> LOCATION: (31)..(31)
<223> OTHER INFORMATION: Val, Ala, Arg, Ser or any amino acid capable of
      cross-linking the peptide with another peptide
<220> FEATURE:
<221> NAME/KEY: MISC_FEATURE
<222> LOCATION: (1)..(31)
<223> OTHER INFORMATION: Wherein the peptide comprises one to two amino
      acids capable of cross-linking the peptide with another peptide
<220> FEATURE:
<223> OTHER INFORMATION: See specification as filed for detailed
      description of substitutions and preferred embodiments

<400> SEQUENCE: 98

Pro Xaa Xaa Pro Xaa Xaa Pro Gly Xaa Xaa Ala Xaa Xaa Xaa Xaa Leu
1               5                   10                  15

Xaa Xaa Xaa Xaa Xaa Xaa Leu Xaa Xaa Tyr Leu Xaa Xaa Xaa Xaa
            20                  25                  30
```

-continued

```
<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid except Pro
<220> FEATURE:
<221> NAME/KEY: MOD_RES
<222> LOCATION: (5)..(6)
<223> OTHER INFORMATION: Any amino acid capable of cross-linking the
      peptide with a second peptide
<220> FEATURE:
<223> OTHER INFORMATION: See specification as filed for detailed
      description of substitutions and preferred embodiments

<400> SEQUENCE: 99

Pro Xaa Xaa Pro Xaa Xaa Pro
1               5

<210> SEQ ID NO 100
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Pro, Thr or any amino acid capable of
      cross-linking the peptide with another peptide
<220> FEATURE:
<221> NAME/KEY: MOD_RES
<222> LOCATION: (2)..(2)
<223> OTHER INFORMATION: Ile, Glu, Val, Leu, or any amino acid capable
      of cross-linking the peptide with another peptide
<220> FEATURE:
<221> NAME/KEY: MOD_RES
<222> LOCATION: (3)..(3)
<223> OTHER INFORMATION: Glu, Lys, Arg, Ala, Ser, Asp, Gln or Gly
<220> FEATURE:
<221> NAME/KEY: MOD_RES
<222> LOCATION: (6)..(6)
<223> OTHER INFORMATION: Any aromatic or hydrophobic amino acid
<220> FEATURE:
<221> NAME/KEY: MOD_RES
<222> LOCATION: (7)..(7)
<223> OTHER INFORMATION: Glu, Lys, Leu, Met, His, Asp, Gln, Ala, Ser,
      Trp, or Arg
<220> FEATURE:
<221> NAME/KEY: MOD_RES
<222> LOCATION: (9)..(9)
<223> OTHER INFORMATION: Gln, Tyr, Phe, Trp, His or any amino acid with
      a cyclohexyl side chain, wherein Tyr, Phe, Trp, or the cyclohexyl
      side chain can be substituted with one or more fluorines
<220> FEATURE:
<221> NAME/KEY: MOD_RES
<222> LOCATION: (10)..(10)
<223> OTHER INFORMATION: Ala, Gln, Trp, Leu, Tyr, Gly, Ser, Val, or Asn
<220> FEATURE:
<221> NAME/KEY: MOD_RES
<222> LOCATION: (13)..(13)
<223> OTHER INFORMATION: Gln, Tyr, Phe, Trp, His, Asp or any amino acid
      with a cyclohexyl side chain, wherein Tyr, Phe, Trp, or the
      cyclohexyl side chain can be substituted with one or
      more fluorines
<220> FEATURE:
<221> NAME/KEY: MOD_RES
<222> LOCATION: (14)..(14)
<223> OTHER INFORMATION: Asn, Ala, Leu, Arg, Phe, Ile, His, or Gln
<220> FEATURE:
<221> NAME/KEY: MOD_RES
```

-continued

```
<222> LOCATION: (17)..(17)
<223> OTHER INFORMATION: Ala, Leu, Glu, Asn, Gln, Tyr, Phe, Trp, His or
      any amino acid with a cyclohexyl side chain, wherein Tyr, Phe,
      Trp, or the cyclohexyl side chain can be substituted with one
      or more fluorines
<220> FEATURE:
<221> NAME/KEY: MOD_RES
<222> LOCATION: (18)..(18)
<223> OTHER INFORMATION: Ala, Arg or Val
<220> FEATURE:
<221> NAME/KEY: MISC_FEATURE
<222> LOCATION: (1)..(20)
<223> OTHER INFORMATION: Wherein the peptide comprises one to two amino
      acids capable of cross-linking the peptide with another
      peptide

<400> SEQUENCE: 100

Xaa Xaa Xaa Asp Leu Xaa Xaa Tyr Xaa Xaa Arg Leu Xaa Xaa Tyr Leu
1               5                   10                  15

Xaa Xaa Val Ala
            20
```